(12) United States Patent
Le Page et al.

(10) Patent No.: US 8,632,784 B2
(45) Date of Patent: Jan. 21, 2014

(54) **NUCLEIC ACIDS AND PROTEINS FROM *STREPTOCOCCUS PNEUMONIAE***

(75) Inventors: Richard William Falla Le Page, Cambridge (GB); Jeremy Mark Wells, Cambridge (GB); Sean Bosco Hanniffy, Cambridge (GB); Philip Michael Hansbro, Cambridge (GB)

(73) Assignee: Sanofi Pasteur Limited, Toronto, Ontario (CA)

( * ) Notice: Subject to any disclaimer, the term of this patent is extended or adjusted under 35 U.S.C. 154(b) by 665 days.

(21) Appl. No.: 11/448,101

(22) Filed: Jun. 7, 2006

(65) Prior Publication Data

US 2006/0263378 A1 Nov. 23, 2006

Related U.S. Application Data

(63) Continuation of application No. 09/769,744, filed on Jan. 26, 2001, now abandoned, which is a continuation of application No. PCT/GB99/02452, filed on Jul. 27, 1999.

(60) Provisional application No. 60/125,329, filed on Mar. 19, 1999.

(30) Foreign Application Priority Data

Jul. 27, 1998 (GB) .................................. 9816336.3

(51) Int. Cl.
| | | |
|---|---|---|
| *A61K 39/09* | (2006.01) | |
| *A61K 39/02* | (2006.01) | |
| *A61K 39/00* | (2006.01) | |
| *A61K 38/00* | (2006.01) | |
| *C07K 1/00* | (2006.01) | |

(52) U.S. Cl.
USPC ................. 424/244.1; 424/234.1; 424/190.1; 424/192.1; 424/184.1; 514/1.1; 530/350; 530/825

(58) Field of Classification Search
USPC ...................... 530/350, 300, 825, 806; 514/2; 424/234.1, 244.1, 190.1, 184.1
See application file for complete search history.

(56) References Cited

U.S. PATENT DOCUMENTS 6,800,744 B1   10/2004   Doucette-Stamm et al.   536/23.1

FOREIGN PATENT DOCUMENTS

| WO | WO 95/06732 | 3/1995 |
|---|---|---|
| WO | WO 97/37026 | 10/1997 |
| WO | WO 97/43303 | 11/1997 |
| WO | WO 98/18930 | 5/1998 |
| WO | WO 98/18931 | 5/1998 |
| WO | WO 98/26072 | 6/1998 |
| WO | WO 98/31786 | 7/1998 |
| WO | WO 00/37105 | 6/2000 |
| WO | WO 00/39299 | 7/2000 |

OTHER PUBLICATIONS

Lazar et al. Mol. Cellular Biol. 8: 1247-1252, 1988.*
Rudinger et al. In: Peptide Hormones. (Ed) JA Parsons, University Park Press, pp. 1-7, 1976.*
Skolnick et al. Trends in Biotechnology 18: 34-39, 2000.*
Anderson et al. (1996) "Immune Response in mice following immunization with DNA encoding fragment C of tetanus toxin." *Infection and Immunity* 64: 3168-3173.
Breiman et al. (1990) Arch. Intern. Med. 150: 1401.
Breiman et al. (1994) J. Am. Med. Assoc. 271: 1831.
Donnelly et al. (1997) Ann. Rev. Immunol. 15: 617-648.
Dougall et al. (Sep. 1994) Tibtech 12: 372-379.
Ellis (1988) Vaccines Chapter 29: 568-575.
Houghten et al. (1986) Vaccines 86: 21-25.
Kohler & Milstein (1975) Nature 256.
Kolkman et al. (1996) 178: 3736-3741.
Kovacevic et al. (1985) J. Bacteriol. 162: 521-528.
Kurar and Splitter (1997) Vaccine 15: 1851-57.
Le Loir et al. (1994) J. Bacteriol. 176: 5135-5139.
LeBlanc et al. (1978) PNAS USA 75: 3484-3487.
Li et al. (1997) PNAS 94: 13251-13256.
Liebl et al. (1992) J. Bacteriol. 174: 1854-1861.
Marck (1988) Nucleic Acids Research 16: 1829-1836.
Miller et al. (1987) J. Bacteriol. 169: 3508-3514.
Morrison et al. (1984) PNAS 81: 6851-6855.
Oultram and Klaenhammer (1985) FEMS Microbiological Letters 27: 129-134.
Poquet et al. (1998) J. Bacteriol. 180: 1904-1912.
Schappert (1992) Vital and Health Statistics of the Centres for Disease Control/National Centre for Health Statistics 214: 1.
Shortle (1983) Gene 22: 181-189.
Simon and Chopin (1988) Biochimie 70: 559-567.
Takeda et al. (1985) Nature 314: 452-454.
van der Vossen, et al. (1985) Applied and Environmental Microbiology 50: 540-542.
Waterfield et al. (1995) Gene 165: 9-15.
Wells and Schoefield (1996) in Current advances in metabolism, genetics, and applications—NATO ADI Series H 98: 37-62.
Wells et al. (1993) J. Appl. Bacteriol. 74: 629-636.
Zhang et al. (1997) Infection and Immunity 176: 1035-1040.
George R. Siber, "Pneumococcal Disease: Prospects for a New Generation of Vaccines" Science, Sep. 1994, vol. 265, pp. 1385-1387.
Berry, et al. (Feb. 1992) "Effect of insertional inactivation of the genes encoding pneumolysin and autolysin on the virulence of *Streptococcus pneumoniae* type 3." Microbial Pathogenesis 12(2): 87-93.
Poquet, et al. (Apr. 1998) "An export-specific reporter designed for gram-positive bacteria: application to *Lactococcus lactis*."
Siber (Sep. 2, 1994) "Penumocccal disease: prospects for a new generation of vaccines." Science 265(5177): 1385-1387.

* cited by examiner

*Primary Examiner* — S. Devi

(74) *Attorney, Agent, or Firm* — Hunton & Williams LLP

(57) ABSTRACT

Novel proteins from *Streptococcus pneumoniae* are described, together with nucleic acid sequences encoding them. Their use in vaccines and in screening methods is also described.

23 Claims, 2 Drawing Sheets

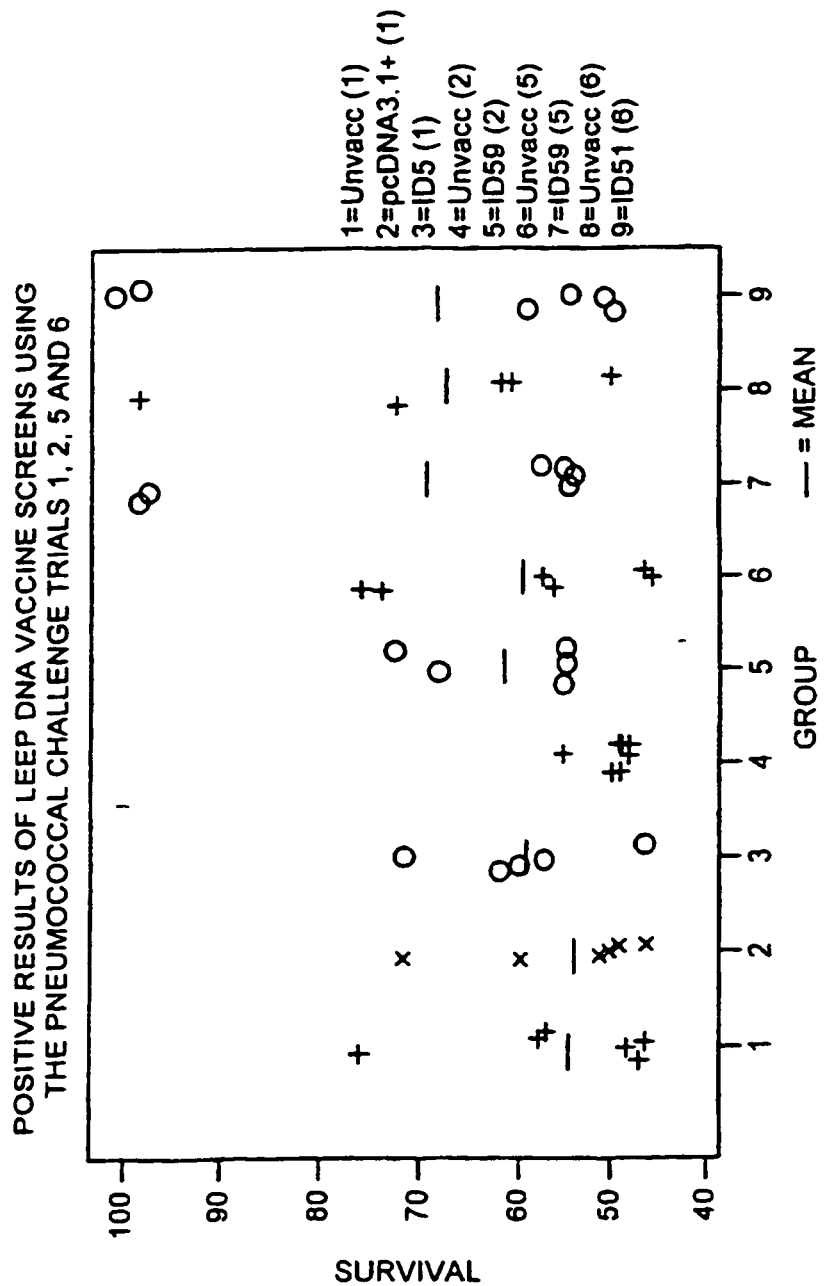

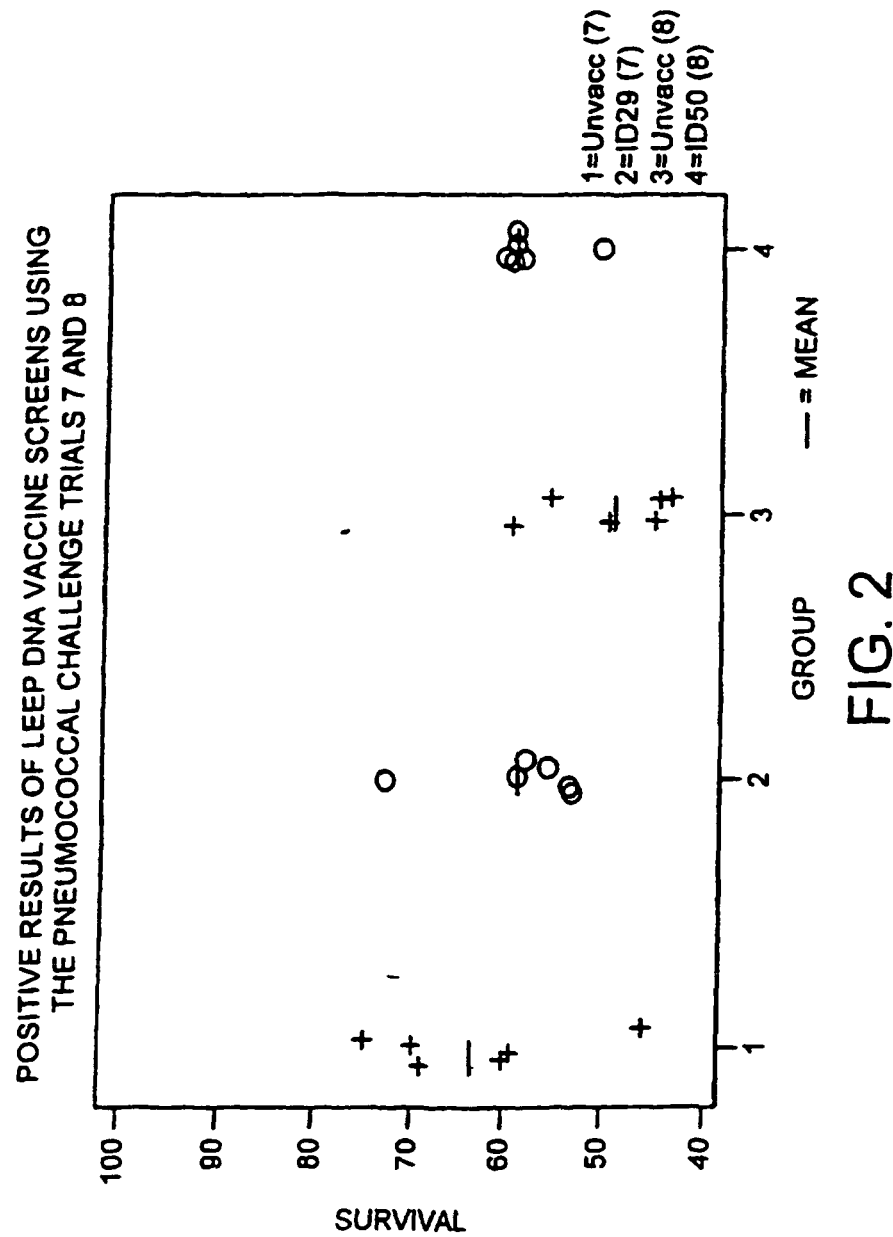

SEQUENCE LISTING

<160> NUMBER OF SEQ ID NOS: 196

<210> SEQ ID NO 1
<211> LENGTH: 1200
<212> TYPE: DNA
<213> ORGANISM: Streptococcus pneumoniae

<400> SEQUENCE: 1

```
atgagaaata tgtgggttgt aatcaaggaa acctatcttc gacatgtcga gtcatggagt      60
ttcttcttta tggtgatttc gccgttcctc tttttaggaa tctctgtagg aattgggcat     120
ctccaaggtt cttctatggc taaaaataat aaagtggcag tagtgacaac agtgccatct     180
gtagcagaag gactgaagaa tgtaaatggt gttaacttcg actataaaga cgaagcaagt     240
gccaaagaag caattaaaga agaaaaatta aaaggttatt tgaccattga tcaagaagat     300
agtgttctaa aggcagtttta tcatggcgaa acatcgcttg aaaatggaat taaatttgag     360
gttacaggta cactcaatga actgcaaaat cagcttaatc gttcaactgc ttccttgtct     420
caagagcagg aaaacgcttt agcgcagaca attcaattca cagaaaagat tgatgaagcc     480
aaggaaaata aaaagtttat tcaaacaatt gcagcaggtg ccttaggatt ctttctttat     540
atgattctga ttacctatgc gggtgtaaca gctcaggaag ttgccagtga aaaaggcacc     600
aaaattatgg aagtcgtttt tctagcata agggcaagtc actatttcta tgcgcggatg     660
atggctctgt ttctagtgat tttaacgcat attgggatct atgttgtagg tggtctggct     720
gccgttttgc tctttaaaga tttgccattc ttggctcagt ctggtatttt ggatcacttg     780
ggagatgcta tctcactgaa taccttgctc tttattttga tcagtctttt catgtacgta     840
gtcttggcag ccttcctagg atctatggtt tctcgtcctg aggactcagg gaaagccttg     900
tcgcctttga tgattttgat tatgggtggt ttttttggag tgacagctct aggtgcagct     960
ggtgacaatc tcctcttgaa gattggttct tatattccct ttatttcgac cttctttatg    1020
ccgtttcgaa cgattaatga ctatgcgggg ggagcagaag catggatttc acttgctatt    1080
acagtgattt tgcggtggt agcaacagga tttatcggac gcatgtatgc tagtctcgtt    1140
cttcaaacgg atgatttagg gatttggaaa acctttaaac gtgccttatc ttataaatag    1200
```

<210> SEQ ID NO 2
<211> LENGTH: 399
<212> TYPE: PRT
<213> ORGANISM: Streptococcus pneumoniae

<400> SEQUENCE: 2

```
Met Arg Asn Met Trp Val Val Ile Lys Glu Thr Tyr Leu Arg His Val
  1               5                  10                  15

Glu Ser Trp Ser Phe Phe Phe Met Val Ile Ser Pro Phe Leu Phe Leu
             20                  25                  30

Gly Ile Ser Val Gly Ile Gly His Leu Gln Gly Ser Ser Met Ala Lys
         35                  40                  45

Asn Asn Lys Val Ala Val Val Thr Thr Val Pro Ser Val Ala Glu Gly
     50                  55                  60

Leu Lys Asn Val Asn Gly Val Asn Phe Asp Tyr Lys Asp Glu Ala Ser
 65                  70                  75                  80

Ala Lys Glu Ala Ile Lys Glu Glu Lys Leu Lys Gly Tyr Leu Thr Ile
                 85                  90                  95

Asp Gln Glu Asp Ser Val Leu Lys Ala Val Tyr His Gly Glu Thr Ser
            100                 105                 110
```

```
Leu Glu Asn Gly Ile Lys Phe Glu Val Thr Gly Thr Leu Asn Glu Leu
            115                 120                 125

Gln Asn Gln Leu Asn Arg Ser Thr Ala Ser Leu Ser Gln Glu Gln Glu
        130                 135                 140

Lys Arg Leu Ala Gln Thr Ile Gln Phe Thr Lys Ile Asp Glu Ala
145                 150                 155                 160

Lys Glu Asn Lys Lys Phe Ile Gln Thr Ile Ala Ala Gly Ala Leu Gly
                165                 170                 175

Phe Phe Leu Tyr Met Ile Leu Ile Thr Tyr Ala Gly Val Thr Ala Gln
            180                 185                 190

Glu Val Ala Ser Glu Lys Gly Thr Lys Ile Met Glu Val Val Phe Ser
        195                 200                 205

Ser Ile Arg Ala Ser His Tyr Phe Tyr Ala Arg Met Met Ala Leu Phe
    210                 215                 220

Leu Val Ile Leu Thr His Ile Gly Ile Tyr Val Val Gly Gly Leu Ala
225                 230                 235                 240

Ala Val Leu Leu Phe Lys Asp Leu Pro Phe Leu Ala Gln Ser Gly Ile
                245                 250                 255

Leu Asp His Leu Gly Asp Ala Ile Ser Leu Asn Thr Leu Leu Phe Ile
            260                 265                 270

Leu Ile Ser Leu Phe Met Tyr Val Val Leu Ala Ala Phe Leu Gly Ser
        275                 280                 285

Met Val Ser Arg Pro Glu Asp Ser Gly Lys Ala Leu Ser Pro Leu Met
    290                 295                 300

Ile Leu Ile Met Gly Gly Phe Phe Gly Val Thr Ala Leu Gly Ala Ala
305                 310                 315                 320

Gly Asp Asn Leu Leu Lys Ile Gly Ser Tyr Ile Pro Phe Ile Ser
                325                 330                 335

Thr Phe Phe Met Pro Phe Arg Thr Ile Asn Asp Tyr Ala Gly Gly Ala
            340                 345                 350

Glu Ala Trp Ile Ser Leu Ala Ile Thr Val Ile Phe Ala Val Val Ala
        355                 360                 365

Thr Gly Phe Ile Gly Arg Met Tyr Ala Ser Leu Val Leu Gln Thr Asp
    370                 375                 380

Asp Leu Gly Ile Trp Lys Thr Phe Lys Arg Ala Leu Ser Tyr Lys
385                 390                 395

<210> SEQ ID NO 3
<211> LENGTH: 1125
<212> TYPE: DNA
<213> ORGANISM: Streptococcus pneumoniae

<400> SEQUENCE: 3
cctgggaaag tcttgaaaat tatgatagaa tggtggaagg aaaaattcag gagagtagta      60
gtgactcaaa atgttgaaag tcttctcgta tccattgtaa tcagtgcata caatgaagaa     120
aaatatctgc ctggtctaat tgaagactta aaaaatcaaa cctatcctaa agaggatatt     180
gaaattctat ttataaatgc tatgtccaca gatgggacca cagctatcat tcagcaattt     240
ataaaggaag atacagagtt taactcaatt agattgtata acaatcctaa gaaaaatcaa     300
gctagtggtt ttaacctggg agttaaacat tctgtagggg accttatttt aaaaattgat     360
gctcattcaa aagttactga ctttttgta atgaacaatg tggctattat tcaacaaggt     420
gaatttgtct gtgggggggcc tagaccgacg attgtcgaag aaaaggaaa atgggcagag     480 accttgcatc ttgttgagga aaatatgttt ggcagtagca ttgccaatta tcgaaatagt     540
```

-continued

```
tctgaggata gatatgtttc ttctattttt catggaatgt ataaacgaga ggttttccag      600
aaggttggtt tagtaaatga gcaacttggc cgaactgaag ataatgatat tcattataga      660
attcgagaat atggttataa aatccgctat agcccaagta ttctatctta tcagtatatt      720
cgaccaacat tcaagaaaat gctgcatcaa agtattcaa atggtttgtg gattggcttg       780
acaagtcatg ttcagtttaa gtgtttatca ttatttcact atgttccttg tttatttgtt      840
ttgagtcttg tgtttagtct agcattgtta ccgatcacat tcgtattcat aactttacta      900
ttaggtgcct atttctact tttgtcatta ctcactttgc tgactttatt aaaacataaa       960
aatggatttc taattgtgat gccctttatt ttattttcca ttcactttgc ttatggcctt     1020
gggacgattg taggtttaat tagaggattt aaatggaaga aggagtacaa gagaacaata     1080
atttatttgg ataaaataag ccaaataaat caaaatatgc tataa                    1125
```

<210> SEQ ID NO 4
<211> LENGTH: 374
<212> TYPE: PRT
<213> ORGANISM: Streptococcus pneumoniae

<400> SEQUENCE: 4

```
Pro Gly Lys Val Leu Lys Ile Met Ile Glu Trp Trp Lys Glu Lys Phe
 1               5                  10                  15

Arg Arg Val Val Val Thr Gln Asn Val Glu Ser Leu Leu Val Ser Ile
            20                  25                  30

Val Ile Ser Ala Tyr Asn Glu Glu Lys Tyr Leu Pro Gly Leu Ile Glu
        35                  40                  45

Asp Leu Lys Asn Gln Thr Tyr Pro Lys Glu Asp Ile Glu Ile Leu Phe
    50                  55                  60

Ile Asn Ala Met Ser Thr Asp Gly Thr Thr Ala Ile Ile Gln Gln Phe
65                  70                  75                  80

Ile Lys Glu Asp Thr Glu Phe Asn Ser Ile Arg Leu Tyr Asn Asn Pro
                85                  90                  95

Lys Lys Asn Gln Ala Ser Gly Phe Asn Leu Gly Val Lys His Ser Val
            100                 105                 110

Gly Asp Leu Ile Leu Lys Ile Asp Ala His Ser Lys Val Thr Glu Thr
        115                 120                 125

Phe Val Met Asn Asn Val Ala Ile Ile Gln Gln Gly Glu Phe Val Cys
    130                 135                 140

Gly Gly Pro Arg Pro Thr Ile Val Glu Gly Lys Gly Lys Trp Ala Glu
145                 150                 155                 160

Thr Leu His Leu Val Glu Glu Asn Met Phe Gly Ser Ser Ile Ala Asn
                165                 170                 175

Tyr Arg Asn Ser Ser Glu Asp Arg Tyr Val Ser Ile Phe His Gly
            180                 185                 190

Met Tyr Lys Arg Glu Val Phe Gln Lys Val Gly Leu Val Asn Glu Gln
        195                 200                 205

Leu Gly Arg Thr Glu Asp Asn Asp Ile His Tyr Arg Ile Arg Glu Tyr
    210                 215                 220

Gly Tyr Lys Ile Arg Tyr Ser Pro Ser Ile Leu Ser Tyr Gln Tyr Ile
225                 230                 235                 240

Arg Pro Thr Phe Lys Lys Met Leu His Gln Lys Tyr Ser Asn Gly Leu
                245                 250                 255

Trp Ile Gly Leu Thr Ser His Val Gln Phe Lys Cys Leu Ser Leu Phe
            260                 265                 270
```

```
His Tyr Val Pro Cys Leu Phe Val Leu Ser Leu Val Phe Ser Leu Ala
        275                 280                 285

Leu Leu Pro Ile Thr Phe Val Phe Ile Thr Leu Leu Leu Gly Ala Tyr
        290                 295                 300

Phe Leu Leu Ser Leu Leu Thr Leu Thr Leu Leu Lys His Lys
305                 310                 315                 320

Asn Gly Phe Leu Ile Val Met Pro Phe Ile Leu Phe Ser Ile His Phe
                325                 330                 335

Ala Tyr Gly Leu Gly Thr Ile Val Gly Leu Ile Arg Gly Phe Lys Trp
                340                 345                 350

Lys Lys Glu Tyr Lys Arg Thr Ile Ile Tyr Leu Asp Lys Ile Ser Gln
        355                 360                 365

Ile Asn Gln Asn Met Leu
        370
```

<210> SEQ ID NO 5
<211> LENGTH: 696
<212> TYPE: DNA
<213> ORGANISM: Streptococcus pneumoniae

<400> SEQUENCE: 5

```
atgatgaaag aacaaaatac gatagaaatc gatgtatttc aattagttaa aagcttgtgg      60
aaacgcaagc taatgatttt aatagtggca cttgtgacag gtgcgggggc ttttgcatat    120
agcactttta ttgttaagcc agaatatacg gtaccacgc gaatttacgt agtgaatcgc     180
aatcaaggag acaagccggg gttgacaaat caggatttgc aggcaggaac ttatctggta    240
aaagactacc gtgagattat cctttcgcag gatgtttggg aggaagttgt ttctgatttg    300
aaactagatt tgacgccaaa aggtttggct aataaaatta aagtgacagt accagttgat    360
acccgtattg tctctatttc agttaatgat cgagttcctg aagaggcaag ccgtatcgct    420
aactctttga gaagtagcag tgctcaaaaa attatcagta ttactcgtgt ttctgacgtg    480
acaacactgg aggaggcaag gccggcgata tccccgtctt cgccaaatat taaacgcaat    540
acactaattg tttttttggc aggggtgatt ggaactagtg ttatagttct tcatcttgaa    600
cttttggata tcgtgtgaa acgtccggaa gatatcgaaa atacattgca gatgacactt    660
ttgggagttg tgccaaactt gggtaagttg aaatag                              696
```

<210> SEQ ID NO 6
<211> LENGTH: 231
<212> TYPE: PRT
<213> ORGANISM: Streptococcus pneumoniae

<400> SEQUENCE: 6

```
Met Met Lys Glu Gln Asn Thr Ile Glu Ile Asp Val Phe Gln Leu Val
  1               5                  10                  15

Lys Ser Leu Trp Lys Arg Lys Leu Met Ile Leu Ile Val Ala Leu Val
             20                  25                  30

Thr Gly Ala Gly Ala Phe Ala Tyr Ser Thr Phe Ile Val Lys Pro Glu
         35                  40                  45

Tyr Thr Ser Thr Thr Arg Ile Tyr Val Val Asn Arg Asn Gln Gly Asp
     50                  55                  60

Lys Pro Gly Leu Thr Asn Gln Asp Leu Gln Ala Gly Thr Tyr Leu Val
 65                  70                  75                  80

Lys Asp Tyr Arg Glu Ile Ile Leu Ser Gln Asp Val Leu Glu Glu Val
                 85                  90                  95

Val Ser Asp Leu Lys Leu Asp Leu Thr Pro Lys Gly Leu Ala Asn Lys
```

```
                   100                 105                 110
Ile Lys Val Thr Val Pro Val Asp Thr Arg Ile Val Ser Ile Ser Val
            115                 120                 125

Asn Asp Arg Val Pro Glu Glu Ala Ser Arg Ile Ala Asn Ser Leu Arg
130                 135                 140

Glu Val Ala Ala Gln Lys Ile Ile Ser Ile Thr Arg Val Ser Asp Val
145                 150                 155                 160

Thr Thr Leu Glu Glu Ala Arg Pro Ala Ile Ser Pro Ser Pro Asn
                165                 170                 175

Ile Lys Arg Asn Thr Leu Ile Gly Phe Leu Ala Gly Val Ile Gly Thr
            180                 185                 190

Ser Val Ile Val Leu His Leu Glu Leu Leu Asp Thr Arg Val Lys Arg
            195                 200                 205

Pro Glu Asp Ile Glu Asn Thr Leu Gln Met Thr Leu Leu Gly Val Val
            210                 215                 220

Pro Asn Leu Gly Lys Leu Lys
225                 230

<210> SEQ ID NO 7
<211> LENGTH: 555
<212> TYPE: DNA
<213> ORGANISM: Streptococcus pneumoniae

<400> SEQUENCE: 7
atggtaaaag tagcagttat attagctcag ggctttgaag aaattgaagc cttgacagtt      60
gtagatgtct tgcgtcgagc caatatcaca tgtgatatgg ttggttttga agagcaagta     120
acgggttcgc atgcaatcca agtaagagca gatcatgtct ttgatggaga tttatcagac     180
tatgatatga ttgttcttcc tggaggtatg cctggttctg cacatttacg tgataatcag     240
accttgattc aagaattgca aagcttcgag caagaaggga gaaaactagc agccatttgt     300
gcggcaccaa ttgccctcaa tcaagcagag atattgaaaa ataagcgata cacttgttat     360
gacggcgttc aagagcaaat ccttgatggt cactacgtca aggaaacagt agtggtagat     420
ggtcagttga caaccagtcg gggtccttca acagcccttg cctttgccta cgagttggtg     480
gagcaactag gagggacgc agagagttta cgaacaggaa tgctctatcg agatgtcttt     540
ggtaaaaatc agtaa                                                      555

<210> SEQ ID NO 8
<211> LENGTH: 184
<212> TYPE: PRT
<213> ORGANISM: Streptococcus pneumoniae

<400> SEQUENCE: 8

Met Val Lys Val Ala Val Ile Leu Ala Gln Gly Phe Glu Glu Ile Glu
1               5                   10                  15

Ala Leu Thr Val Val Asp Val Leu Arg Arg Ala Asn Ile Thr Cys Asp
                20                  25                  30

Met Val Gly Phe Glu Glu Gln Val Thr Gly Ser His Ala Ile Gln Val
            35                  40                  45

Arg Ala Asp His Val Phe Asp Gly Asp Leu Ser Asp Tyr Asp Met Ile
        50                  55                  60

Val Leu Pro Gly Gly Met Pro Gly Ser Ala His Leu Arg Asp Asn Gln
65                  70                  75                  80

Thr Leu Ile Gln Glu Leu Gln Ser Phe Glu Gln Glu Gly Lys Lys Leu
                85                  90                  95
```

```
Ala Ala Ile Cys Ala Ala Pro Ile Ala Leu Asn Gln Ala Glu Ile Leu
            100                 105                 110

Lys Asn Lys Arg Tyr Thr Cys Tyr Asp Gly Val Gln Glu Gln Ile Leu
        115                 120                 125

Asp Gly His Tyr Val Lys Glu Thr Val Val Val Asp Gly Gln Leu Thr
    130                 135                 140

Thr Ser Arg Gly Pro Ser Thr Ala Leu Ala Phe Ala Tyr Glu Leu Val
145                 150                 155                 160

Glu Gln Leu Gly Gly Asp Ala Glu Ser Leu Arg Thr Gly Met Leu Tyr
                165                 170                 175

Arg Asp Val Phe Gly Lys Asn Gln
            180

<210> SEQ ID NO 9
<211> LENGTH: 306
<212> TYPE: DNA
<213> ORGANISM: Streptococcus pneumoniae

<400> SEQUENCE: 9
gtggtaggga tggtagaacc aaacctagaa agccttataa aagatcttta caatcatgct      60
cgacatgatt tgagtgaaga tttagttgct gctctcctag agactactaa aaaactgcct     120
actacaaatg agcaattgca ggcagttcgt ctctcaggcc tggtcaatcg tgaattgctc     180
ctaaatccca acatccagc acctgagttg ctcaacttgg ctcgctttgt caaaagagaa      240
gaagccaagt acagaggaac tgcgacttct gcgcttatgt atgaggaact ctttaaaatg     300
ctttga                                                               306

<210> SEQ ID NO 10
<211> LENGTH: 101
<212> TYPE: PRT
<213> ORGANISM: Streptococcus pneumoniae

<400> SEQUENCE: 10

Met Val Gly Met Val Glu Pro Asn Leu Glu Ser Leu Ile Lys Asp Leu
1               5                   10                  15

Tyr Asn His Ala Arg His Asp Leu Ser Glu Asp Leu Val Ala Ala Leu
            20                  25                  30

Leu Glu Thr Thr Lys Lys Leu Pro Thr Thr Asn Glu Gln Leu Gln Ala
        35                  40                  45

Val Arg Leu Ser Gly Leu Val Asn Arg Glu Leu Leu Asn Pro Lys
    50                  55                  60

His Pro Ala Pro Glu Leu Leu Asn Leu Ala Arg Phe Val Lys Arg Glu
65                  70                  75                  80

Glu Ala Lys Tyr Arg Gly Thr Ala Thr Ser Ala Leu Met Tyr Glu Glu
                85                  90                  95

Leu Phe Lys Met Leu
            100

<210> SEQ ID NO 11
<211> LENGTH: 945
<212> TYPE: DNA
<213> ORGANISM: Streptococcus pneumoniae

<400> SEQUENCE: 11
ttgttcttaa aaaggaaag agaggtaatc agcatgcgta aatggacaaa aggatttctc       60
atctttggtg tggtgactac cgttatcggc tttatcctgc ttttttgtagg tatccaatct    120 gacgggatta agagcctact ttccatgtcc aagaacctg tctatgatag ccgtacggaa     180
```

-continued

```
aagctaacct tggcaagga agtcgaaaac ctagaaatta ctctccacca acacacgctc    240
accatcacag actctttcga tgatcaaatc cacatttctt accatccatc tctttctgct    300
caccatgatc ttatcaccaa tcagaacgat agaactctga gtctcactga taagaaactg    360
tctgaaactc cgtttctctc ttctggaatt ggtgggattc ttcatatcgc aagtagctac    420
tctagtcgtt ttgaagaagt tattctccga ctaccaaaag ggagaactct aaaagggatc    480
aacatctcag ccaatcgcgg acaaaccacc atcataaatg ctagccttga aaatgcgacc    540
ctcaatacaa acagctatat cctccgaatt gaaggaagtc gtatcaaaaa cagtaaactc    600
acaacgccca atatcgttaa tatctttgat acagttctta cagatagtca gctagagtca    660
acagagaatc acttccacgc tgaaaatatc caagtccatg gcaaggttga actgactgcc    720
aaagattatc tcagaatcat cctagaccag aaagaaagcc aacgaattaa ctgggacatc    780
tcaagcaact atggttctat cttccaattc acaagagaaa agcctgaatc aagaggtacg    840
gaattaagca acccttacaa aactgaaaaa accgatgtca aggatcaact cattgcgaga    900
tctgatgata atattgatct aatatccaca ccaagcagac gttga                    945
```

```
<210> SEQ ID NO 12
<211> LENGTH: 314
<212> TYPE: PRT
<213> ORGANISM: Streptococcus pneumoniae

<400> SEQUENCE: 12

Met Phe Leu Lys Lys Glu Arg Glu Val Ile Ser Met Arg Lys Trp Thr
 1               5                  10                  15

Lys Gly Phe Leu Ile Phe Gly Val Val Thr Thr Val Ile Gly Phe Ile
                20                  25                  30

Leu Leu Phe Val Gly Ile Gln Ser Asp Gly Ile Lys Ser Leu Leu Ser
            35                  40                  45

Met Ser Lys Glu Pro Val Tyr Asp Ser Arg Thr Glu Lys Leu Thr Phe
        50                  55                  60

Gly Lys Glu Val Glu Asn Leu Glu Ile Thr Leu His Gln His Thr Leu
 65                  70                  75                  80

Thr Ile Thr Asp Ser Phe Asp Asp Gln Ile His Ile Ser Tyr His Pro
                85                  90                  95

Ser Leu Ser Ala His His Asp Leu Ile Thr Asn Gln Asn Asp Arg Thr
            100                 105                 110

Leu Ser Leu Thr Asp Lys Lys Leu Ser Glu Thr Pro Phe Leu Ser Ser
        115                 120                 125

Gly Ile Gly Gly Ile Leu His Ile Ala Ser Ser Tyr Ser Ser Arg Phe
    130                 135                 140

Glu Glu Val Ile Leu Arg Leu Pro Lys Gly Arg Thr Leu Lys Gly Ile
145                 150                 155                 160

Asn Ile Ser Ala Asn Arg Gly Gln Thr Thr Ile Ile Asn Ala Ser Leu
                165                 170                 175

Glu Asn Ala Thr Leu Asn Thr Asn Ser Tyr Ile Leu Arg Ile Glu Gly
            180                 185                 190

Ser Arg Ile Lys Asn Ser Lys Leu Thr Thr Pro Asn Ile Val Asn Ile
        195                 200                 205

Phe Asp Thr Val Leu Thr Asp Ser Gln Leu Glu Ser Thr Glu Asn His
    210                 215                 220

Phe His Ala Glu Asn Ile Gln Val His Gly Lys Val Glu Leu Thr Ala
225                 230                 235                 240
```

```
Lys Asp Tyr Leu Arg Ile Ile Leu Asp Gln Lys Glu Ser Gln Arg Ile
                245                 250                 255

Asn Trp Asp Ile Ser Ser Asn Tyr Gly Ser Ile Phe Gln Phe Thr Arg
            260                 265                 270

Glu Lys Pro Glu Ser Arg Gly Thr Glu Leu Ser Asn Pro Tyr Lys Thr
        275                 280                 285

Glu Lys Thr Asp Val Lys Asp Gln Leu Ile Ala Arg Ser Asp Asp Asn
    290                 295                 300

Ile Asp Leu Ile Ser Thr Pro Ser Arg Arg
305                 310

<210> SEQ ID NO 13
<211> LENGTH: 879
<212> TYPE: DNA
<213> ORGANISM: Streptococcus pneumoniae

<400> SEQUENCE: 13
atgaaacaag aatggtttga agtaatgat tttgtaaaaa caacaagcaa gaacaagcct      60
gaagagcaag ctcaagaggt tgcagacaag gctgaagaaa cgatagccga tctcgataca    120
ccaattgaaa aaatactca gttagaggag gaagtccctc aagctgaagt cgaattggaa     180
agccagcaag aagagaaaat tgaagctcct gaagacagtg aagcgagaac agaaatagaa    240
gaaaagaagg catctaattc tactgaagaa gagccagacc tttctaaaga aacagaaaaa    300
gtcactatag ctgaagagag ccaagaagct cttcctcagc aaaaagcaac cacgaaagag    360
ccacttctta tcagtaaatc tttagaaagt ccttatatcc ccgaccaagc tccaaaatct    420
agggataaat ggaaagagca agtgcttgat ttttggtctt ggctagtgga agcgatcaaa    480
tctcctacaa gtaagttgga aacaagtatc acacacagtt acacagcctt ctctcttgctc    540 attctgtttt ctgcatcttc ctttttcttt agtatctatc acatcaaaca tgcttactat     600
ggacatatag caagcattaa cagtcgcttc cctgagcagc tagctccttt aactcttttt     660
tctatcatct ctatcctagt agcgacaaca ctcttcttct tttcattcct cttgggtagt    720
ttcgttgtga gacgatttat ccaccaggaa aaggactgga cgctagacaa ggttctccaa    780
caatatagtc aactcttggc aattccaatc tcctcactgc tattgctagt ttctttgctt    840
tctttgatag cctacgattt acagccctct tgtgtgtga                           879

<210> SEQ ID NO 14
<211> LENGTH: 292
<212> TYPE: PRT
<213> ORGANISM: Streptococcus pneumoniae

<400> SEQUENCE: 14

Met Lys Gln Glu Trp Phe Glu Ser Asn Asp Phe Val Lys Thr Thr Ser
  1               5                  10                  15

Lys Asn Lys Pro Glu Glu Gln Ala Gln Glu Val Ala Asp Lys Ala Glu
             20                  25                  30

Glu Thr Ile Ala Asp Leu Asp Thr Pro Ile Glu Lys Asn Thr Gln Leu
         35                  40                  45

Glu Glu Glu Val Pro Gln Ala Glu Val Glu Leu Glu Ser Gln Gln Glu
     50                  55                  60

Glu Lys Ile Glu Ala Pro Glu Asp Ser Glu Ala Arg Thr Glu Ile Glu
 65                  70                  75                  80

Glu Lys Lys Ala Ser Asn Ser Thr Glu Glu Glu Pro Asp Leu Ser Lys
                 85                  90                  95

Glu Thr Glu Lys Val Thr Ile Ala Glu Glu Ser Gln Glu Ala Leu Pro
```

|   |   |   | 100 |   |   |   | 105 |   |   |   | 110 |   |
|---|---|---|---|---|---|---|---|---|---|---|---|---|

Gln Gln Lys Ala Thr Thr Lys Glu Pro Leu Leu Ile Ser Lys Ser Leu
             115                     120                    125

Glu Ser Pro Tyr Ile Pro Asp Gln Ala Pro Lys Ser Arg Asp Lys Trp
130                   135                     140

Lys Glu Gln Val Leu Asp Phe Trp Ser Trp Leu Val Glu Ala Ile Lys
145                 150                   155                  160

Ser Pro Thr Ser Lys Leu Glu Ser Ile Thr His Ser Tyr Thr Ala
             165                     170                     175

Phe Leu Leu Leu Ile Leu Phe Ser Ala Ser Phe Phe Phe Ser Ile
             180                     185                     190

Tyr His Ile Lys His Ala Tyr Tyr Gly His Ile Ala Ser Ile Asn Ser
             195                     200                     205

Arg Phe Pro Glu Gln Leu Ala Pro Leu Thr Leu Phe Ser Ile Ile Ser
          210                     215                     220

Ile Leu Val Ala Thr Thr Leu Phe Phe Phe Ser Phe Leu Leu Gly Ser
225                 230                     235                  240

Phe Val Val Arg Arg Phe Ile His Gln Glu Lys Asp Trp Thr Leu Asp
               245                     250                     255

Lys Val Leu Gln Gln Tyr Ser Gln Leu Leu Ala Ile Pro Ile Ser Ser
          260                     265                     270

Leu Leu Leu Val Ser Leu Leu Ser Leu Ile Ala Tyr Asp Leu Gln
             275                     280                     285

Pro Ser Cys Val
    290

<210> SEQ ID NO 15
<211> LENGTH: 990
<212> TYPE: DNA
<213> ORGANISM: Streptococcus pneumoniae

<400> SEQUENCE: 15

```
atgcaactcg cttcttcggt ctactcattg ttcgtctggt acaatttgtt cttaaaaaag    60
gaaagagagg taatcagcat gcgtaaatgg acaaaaggat tctcatctt tggtgtggtg   120
actaccgtta tcggctttat cctgctttt gtaggtatcc aatctgacgg gattaagagc   180
ctactttcca tgtccaaaga acctgtctat gatagccgta cggaaaagct aacctttggc   240
aaggaagtcg aaaacctaga aattactctc caccaacaca cgctcaccat cacagactct   300
ttcgatgatc aaatccacat ttcttaccat ccatctcttt ctgctcacca tgatcttatc   360
accaatcaga acgatagaac tctgagtctc actgataaga aactgtctga aactccgttt   420
ctctcttctg gaattggtgg gattcttcat atcgcaagta gctactctag tcgttttgaa   480
gaagttattc tccgactacc aaaagggaga actctaaaag ggatcaacat ctcagccaat   540
cgcggacaaa ccaccatcat aaatgctagc cttgaaaatg cgaccctcaa tacaaacagc   600
tatatcctcc gaattgaagg aagtcgtatc aaaaacagta aactcacaac gcccaatatc   660
gttaatatct tgatacagt tcttacagat agtcagctag agtcaacaga gaatcacttc   720
cacgctgaaa atatccaagt ccatggcaag gttgaactga ctgccaaaga ttatctcaga   780
atcatcctag accagaaaga aagccaacga attaactggg acatctcaag caactatggt   840
tctatcttcc aattcacaag agaaaagcct gaatcaagag gtacggaatt aagcaaccct   900
tacaaaactg aaaaaaccga tgtcaaggat caactcattg cgagatctga tgataatatt   960
gatctaatat ccacaccaag cagacgttga                                    990
```

<210> SEQ ID NO 16
<211> LENGTH: 329
<212> TYPE: PRT
<213> ORGANISM: Streptococcus pneumoniae

<400> SEQUENCE: 16

```
Met Gln Leu Ala Ser Ser Val Tyr Ser Leu Phe Val Trp Tyr Asn Leu
  1               5                  10                  15

Phe Leu Lys Lys Glu Arg Glu Val Ile Ser Met Arg Lys Trp Thr Lys
             20                  25                  30

Gly Phe Leu Ile Phe Gly Val Val Thr Thr Val Ile Gly Phe Ile Leu
         35                  40                  45

Leu Phe Val Gly Ile Gln Ser Asp Gly Ile Lys Ser Leu Leu Ser Met
     50                  55                  60

Ser Lys Glu Pro Val Tyr Asp Ser Arg Thr Glu Lys Leu Thr Phe Gly
 65                  70                  75                  80

Lys Glu Val Glu Asn Leu Glu Ile Thr Leu His Gln His Thr Leu Thr
                 85                  90                  95

Ile Thr Asp Ser Phe Asp Asp Gln Ile His Ile Ser Tyr His Pro Ser
            100                 105                 110

Leu Ser Ala His His Asp Leu Ile Thr Asn Gln Asn Asp Arg Thr Leu
        115                 120                 125

Ser Leu Thr Asp Lys Lys Leu Ser Glu Thr Pro Phe Leu Ser Ser Gly
    130                 135                 140

Ile Gly Gly Ile Leu His Ile Ala Ser Ser Tyr Ser Ser Arg Phe Glu
145                 150                 155                 160

Glu Val Ile Leu Arg Leu Pro Lys Gly Arg Thr Leu Lys Gly Ile Asn
                165                 170                 175

Ile Ser Ala Asn Arg Gly Gln Thr Thr Ile Ile Asn Ala Ser Leu Glu
            180                 185                 190

Asn Ala Thr Leu Asn Thr Asn Ser Tyr Ile Leu Arg Ile Glu Gly Ser
        195                 200                 205

Arg Ile Lys Asn Ser Lys Leu Thr Thr Pro Asn Ile Val Asn Ile Phe
    210                 215                 220

Asp Thr Val Leu Thr Asp Ser Gln Leu Glu Ser Thr Glu Asn His Phe
225                 230                 235                 240

His Ala Glu Asn Ile Gln Val His Gly Lys Val Glu Leu Thr Ala Lys
                245                 250                 255

Asp Tyr Leu Arg Ile Ile Leu Asp Gln Lys Glu Ser Gly Arg Ile Asn
            260                 265                 270

Trp Asp Ile Ser Ser Asn Tyr Gly Ser Ile Phe Gln Phe Thr Arg Glu
        275                 280                 285

Lys Pro Glu Ser Arg Gly Thr Glu Leu Ser Asn Pro Tyr Lys Thr Glu
    290                 295                 300

Lys Thr Asp Val Lys Asp Gln Leu Ile Ala Arg Ser Asp Asn Ile
305                 310                 315                 320

Asp Leu Ile Ser Thr Pro Ser Arg Arg
                325
```

<210> SEQ ID NO 17
<211> LENGTH: 79
<212> TYPE: DNA
<213> ORGANISM: Streptococcus pneumoniae

<400> SEQUENCE: 17
atgatatgta aaatgaagca gggagggagc agggcgtgct ggggatggag agtgggggag        60

```
ggacgctgct attttaatc                                                  79
```

<210> SEQ ID NO 18
<211> LENGTH: 26
<212> TYPE: PRT
<213> ORGANISM: Streptococcus pneumoniae

<400> SEQUENCE: 18

```
Met Ile Cys Lys Met Lys Gln Gly Gly Ser Arg Ala Cys Trp Gly Trp
 1               5                  10                  15

Arg Val Gly Glu Gly Arg Cys Tyr Phe Asn
             20                  25
```

<210> SEQ ID NO 19
<211> LENGTH: 715
<212> TYPE: DNA
<213> ORGANISM: Streptococcus pneumoniae

<400> SEQUENCE: 19

```
cgataaagag gccttgagta atctcaattt gcagattgaa aatggagaga ttatgggctt    60
gattggtcat aatggggctg gaaaatcgac cactataaaa tccctagtca gtatcatttc   120
acccagcagt ggtcgtattt tggtagacgg tcaggagtta tcggaaaatc gcttggctat   180
taaacgaaag attggctacg tagcagactc gcctgactta ttttacgct aacggccaa    240
tgaattttgg gaattgatcg cctcatccta tgatctgagt agatctgact ggaggctag   300
tctagctagg ctattgaacg ttttgattt tgctgaaaat cgctatcagg ttattgaaac   360
tctttctcac ggaatgcgtc agaaagtctt tgtcatcgga gcactcttgt ctgatcccga   420
tatttgggtt ttggacgaac ccttgactgg tttggatccc caggctgcct tgatttgaa    480
acagatgatg aaggaacatg cacaaaaagg aagacagtc ttgttttcaa ctcatgtcct   540
agaggtggca gagcaagtct gtgatcggat tgccattttg aaaaagggc atttgattta   600
ttgtggtaag gtagaggact tgaggaaaga ccacccagac cagtctttgg aaagtatcta   660
ccttagtctt gctggtagaa agaggaggt tgcggatgcg tctcaaggtc attaa         715
```

<210> SEQ ID NO 20
<211> LENGTH: 237
<212> TYPE: PRT
<213> ORGANISM: Streptococcus pneumoniae

<400> SEQUENCE: 20

```
Asp Lys Glu Ala Leu Ser Asn Leu Asn Leu Gln Ile Glu Asn Gly Glu
 1               5                  10                  15

Ile Met Gly Leu Ile Gly His Asn Gly Ala Gly Lys Ser Thr Thr Ile
             20                  25                  30

Lys Ser Leu Val Ser Ile Ile Ser Pro Ser Ser Gly Arg Ile Leu Val
         35                  40                  45

Asp Gly Gln Glu Leu Ser Glu Asn Arg Leu Ala Ile Lys Arg Lys Ile
     50                  55                  60

Gly Tyr Val Ala Asp Ser Pro Asp Leu Phe Leu Arg Leu Thr Ala Asn
 65                  70                  75                  80

Glu Phe Trp Glu Leu Ile Ala Ser Ser Tyr Asp Leu Ser Arg Ser Asp
                 85                  90                  95

Leu Glu Ala Ser Leu Ala Arg Leu Leu Asn Val Phe Asp Phe Ala Glu
            100                 105                 110

Asn Arg Tyr Gln Val Ile Glu Thr Leu Ser His Gly Met Arg Gln Lys
        115                 120                 125
```

Val Phe Val Ile Gly Ala Leu Leu Ser Asp Pro Asp Ile Trp Val Leu
            130                 135                 140

Asp Glu Pro Leu Thr Gly Leu Asp Pro Gln Ala Ala Phe Asp Leu Lys
145                 150                 155                 160

Gln Met Met Lys Glu His Ala Gln Lys Gly Lys Thr Val Leu Phe Ser
                165                 170                 175

Thr His Val Leu Glu Val Ala Glu Gln Val Cys Asp Arg Ile Ala Ile
            180                 185                 190

Leu Lys Lys Gly His Leu Ile Tyr Cys Gly Lys Val Glu Asp Leu Arg
        195                 200                 205

Lys Asp His Pro Asp Gln Ser Leu Glu Ser Ile Tyr Leu Ser Leu Ala
210                 215                 220

Gly Arg Lys Glu Glu Val Ala Asp Ala Ser Gln Gly His
225                 230                 235

<210> SEQ ID NO 21
<211> LENGTH: 360
<212> TYPE: DNA
<213> ORGANISM: Streptococcus pneumoniae

<400> SEQUENCE: 21
atggctttgt tttcagagag aggagcagta cggaagacac caatggcaag tccaataatg      60
agacctatga tggttccgac gatagagatt aaaagagtga taccagcacc acgcaagagt     120
tgttgccagt tttcagaaag aattttagca acttggctaa agaaactact gctagtctct     180
tcagttgttg tagcttcggc aggttgttcc ttgatcatac gatccatcaa ggcaacttgg     240
tcatcttttg aaatggtttc aatgctggca ttgatttggc taatacgatt gtcatttta      300 cgaagcccga tagcgatagc tgtatcttct tccccagttt tgaaaccagg ttctacttga     360

<210> SEQ ID NO 22
<211> LENGTH: 119
<212> TYPE: PRT
<213> ORGANISM: Streptococcus pneumoniae

<400> SEQUENCE: 22

Met Ala Leu Phe Ser Glu Arg Gly Ala Val Arg Lys Thr Pro Met Ala
1               5                   10                  15

Ser Pro Ile Met Arg Pro Met Met Val Pro Thr Ile Glu Ile Lys Arg
            20                  25                  30

Val Ile Pro Ala Pro Arg Lys Ser Cys Cys Gln Phe Ser Glu Arg Ile
        35                  40                  45

Leu Ala Thr Trp Leu Lys Lys Leu Leu Leu Val Ser Ser Val Val Val
    50                  55                  60

Ala Ser Ala Gly Cys Ser Leu Ile Ile Arg Ser Ile Lys Ala Thr Trp
65                  70                  75                  80

Ser Ser Phe Glu Met Val Ser Met Leu Ala Leu Ile Trp Leu Ile Arg
                85                  90                  95

Leu Ser Phe Leu Arg Ser Pro Ile Ala Ile Ala Val Ser Ser Ser Pro
            100                 105                 110

Val Leu Lys Pro Gly Ser Thr
        115

<210> SEQ ID NO 23
<211> LENGTH: 1455
<212> TYPE: DNA
<213> ORGANISM: Streptococcus pneumoniae

<400> SEQUENCE: 23

```
atgaaattta gtaaaaaata tatagcagct ggatcagctg ttatcgtatc cttgagtcta    60
tgtgcctatg cactaaacca gcatcgttcg caggaaaata aggacaataa tcgtgtctct   120
tatgtggatg gcagccagtc aagtcagaaa agtgaaaact tgacaccaga ccaggttagc   180
cagaaagaag gaattcaggc tgagcaaatt gtaatcaaaa ttacagatca gggctatgta   240
acgtcacacg gtgaccacta tcattactat aatgggaaag ttccttatga tgccctcttt   300
agtgaagaac tcttgatgaa ggatccaaac tatcaactta agacgctga tattgtcaat   360
gaagtcaagg gtggttatat catcaaggtc gatggaaaat attatgtcta cctgaaagat   420
gcagctcatg ctgataatgt tcgaactaaa gatgaaatca atcgtcaaaa acaagaacat   480
gtcaaagata tgagaaggt taactctaat gttgctgtag caaggtctca gggacgatat   540
acgacaaatg atggttatgt cttaatcca gctgatatta tcgaagatac gggtaatgct   600
tatatcgttc ctcatggagg tcactatcac tacattccca aaagcgattt atctgctagt   660
gaattagcag cagctaaagc acatctggct ggaaaaaata tgcaaccgag tcagttaagc   720
tattcttcaa cagctagtga caataacacg caatctgtag caaaaggatc aactagcaag   780
ccagcaaata aatctgaaaa tctccagagt cttttgaagg aactctatga ttcacctagc   840
gcccaacgtt acagtgaatc agatggcctg gtctttgacc ctgctaagat tatcagtcgt   900
acaccaaatg gagttgcgat tccgcatggc gaccattacc actttattcc ttacagcaag   960
ctttctgcct tagaagaaaa gattgccaga atggtgccta tcagtggaac tggttctaca  1020
gtttctacaa atgcaaaacc taatgaagta gtgtctagtc taggcagtct ttcaagcaat  1080
ccttcttctt taacgacaag taaggagctc tcttcagcat ctgatggtta tatttttaat  1140
ccaaaagata tcgttgaaga aacggctaca gcttatattg taagacatgg tgatcatttc  1200
cattacattc caaaatcaaa tcaaattggg caaccgactc ttccaaacaa tagtctagca  1260
acaccttctc catctcttcc aatcaatcca ggaacttcac atgagaaaca tgaagaagat  1320
ggatacggat ttgatgctaa tcgtattatc gctgaagatg aatcaggttt tgtcatgagt  1380
cacggagacc acaatcatta tttcttcaag aaggacttga cagaagagca aattaaggtg  1440
cgcaaaaaca tttag                                                   1455
```

<210> SEQ ID NO 24
<211> LENGTH: 484
<212> TYPE: PRT
<213> ORGANISM: Streptococcus pneumoniae

<400> SEQUENCE: 24

```
Met Lys Phe Ser Lys Lys Tyr Ile Ala Ala Gly Ser Ala Val Ile Val
  1               5                  10                  15
Ser Leu Ser Leu Cys Ala Tyr Ala Leu Asn Gln His Arg Ser Gln Glu
                 20                  25                  30
Asn Lys Asp Asn Asn Arg Val Ser Tyr Val Asp Gly Ser Gln Ser Ser
             35                  40                  45
Gln Lys Ser Glu Asn Leu Thr Pro Asp Gln Val Ser Gln Lys Glu Gly
         50                  55                  60
Ile Gln Ala Glu Gln Ile Val Ile Lys Ile Thr Asp Gln Gly Tyr Val
 65                  70                  75                  80
Thr Ser His Gly Asp His Tyr His Tyr Tyr Asn Gly Lys Val Pro Tyr
                 85                  90                  95
Asp Ala Leu Phe Ser Glu Glu Leu Leu Met Lys Asp Pro Asn Tyr Gln
                100                 105                 110
```

Leu Lys Asp Ala Asp Ile Val Asn Glu Val Lys Gly Gly Tyr Ile Ile
            115                 120                 125

Lys Val Asp Gly Lys Tyr Tyr Val Tyr Leu Lys Asp Ala Ala His Ala
        130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
            260                 265                 270

Lys Glu Leu Tyr Asp Ser Pro Ser Ala Gln Arg Tyr Ser Glu Ser Asp
        275                 280                 285

Gly Leu Val Phe Asp Pro Ala Lys Ile Ile Ser Arg Thr Pro Asn Gly
    290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
                325                 330                 335

Thr Gly Ser Thr Val Ser Thr Asn Ala Lys Pro Asn Glu Val Val Ser
            340                 345                 350

Ser Leu Gly Ser Leu Ser Ser Asn Pro Ser Ser Leu Thr Thr Ser Lys
        355                 360                 365

Glu Leu Ser Ser Ala Ser Asp Gly Tyr Ile Phe Asn Pro Lys Asp Ile
    370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
                405                 410                 415

Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
        435                 440                 445

Ile Ile Ala Glu Asp Glu Ser Gly Phe Val Met Ser His Gly Asp His
    450                 455                 460

Asn His Tyr Phe Phe Lys Lys Asp Leu Thr Glu Glu Gln Ile Lys Val
465                 470                 475                 480

Arg Lys Asn Ile

<210> SEQ ID NO 25
<211> LENGTH: 840
<212> TYPE: DNA
<213> ORGANISM: Streptococcus pneumoniae

<400> SEQUENCE: 25

```
atgggaattg ctctagaaaa tgtgaatttt acatatcaag aaggtactcc cttagcttca    60
gcagctttgt cggatgtttc tttgacgatt gaagatggct cttatacagc tttaattggg   120
cacacaggta gtggtaaatc aactatttta caactcttaa atggtttatt ggtgccaagt   180
caagggagtg tgagggtttt tgatacctta atcacctcga cttctaaaaa taaagatatt   240
cgtcaaatta gaaaacaggt tggcttggta tttcagtttg ctgaaaatca gattttttgaa   300 gaaacggttt tgaaggacgt tgcttttgga ccgcaaaatt ttggagtttc tgaagaagat   360
gctgtgaaga ctgcgcgtga aaactggctc tggttggaa ttgatgaatc acttttttgat   420 cgtagtccgt ttgagctgtc aggggggacaa atgagacgtg ttgccattgc aggcatactt   480
gccatggagc cagctatatt agtcttagat gagccaacag ctggtctaga tcctctaggg   540
agaaaagagt tgatgaccct gttcaaaaaa ctccaccagt cagggatgac catcgtcttg   600
gtaacgcatt tgatggatga tgttgctgaa tatgcgaatc aagtctatgt aatggaaaag   660
ggacgtttag taaagggggg caaaccaagt gatgtctttc aagacgttgt ttttatggaa   720
gaagttcagt tgggagtacc taaaattacg gccttttgta acgattggc tgatagaggc   780 gtgtcattta acgattacc gattaagata gaggagttca aggagtcgct aaatggatag   840
```

<210> SEQ ID NO 26
<211> LENGTH: 279
<212> TYPE: PRT
<213> ORGANISM: Streptococcus pneumoniae

<400> SEQUENCE: 26

```
Met Gly Ile Ala Leu Glu Asn Val Asn Phe Thr Tyr Gln Glu Gly Thr
  1               5                  10                  15

Pro Leu Ala Ser Ala Ala Leu Ser Asp Val Ser Leu Thr Ile Glu Asp
                 20                  25                  30

Gly Ser Tyr Thr Ala Leu Ile Gly His Thr Gly Ser Gly Lys Ser Thr
             35                  40                  45

Ile Leu Gln Leu Leu Asn Gly Leu Leu Val Pro Ser Gln Gly Ser Val
         50                  55                  60

Arg Val Phe Asp Thr Leu Ile Thr Ser Thr Ser Lys Asn Lys Asp Ile
 65                  70                  75                  80

Arg Gln Ile Arg Lys Gln Val Gly Leu Val Phe Gln Phe Ala Glu Asn
                 85                  90                  95

Gln Ile Phe Glu Glu Thr Val Leu Lys Asp Val Ala Phe Gly Pro Gln
                100                 105                 110

Asn Phe Gly Val Ser Glu Glu Asp Ala Val Lys Thr Ala Arg Glu Lys
            115                 120                 125

Leu Ala Leu Val Gly Ile Asp Glu Ser Leu Phe Asp Arg Ser Pro Phe
        130                 135                 140

Glu Leu Ser Gly Gly Gln Met Arg Arg Val Ala Ile Ala Gly Ile Leu
145                 150                 155                 160

Ala Met Glu Pro Ala Ile Leu Val Leu Asp Glu Pro Thr Ala Gly Leu
                165                 170                 175

Asp Pro Leu Gly Arg Lys Glu Leu Met Thr Leu Phe Lys Lys Leu His
            180                 185                 190

Gln Ser Gly Met Thr Ile Val Leu Val Thr His Leu Met Asp Asp Val
        195                 200                 205

Ala Glu Tyr Ala Asn Gln Val Tyr Val Met Glu Lys Gly Arg Leu Val
    210                 215                 220

Lys Gly Gly Lys Pro Ser Asp Val Phe Gln Asp Val Val Phe Met Glu
225                 230                 235                 240
```

Glu Val Gln Leu Gly Val Pro Lys Ile Thr Ala Phe Cys Lys Arg Leu
            245                 250                 255

Ala Asp Arg Gly Val Ser Phe Lys Arg Leu Pro Ile Lys Ile Glu Glu
            260                 265                 270

Phe Lys Glu Ser Leu Asn Gly
        275

<210> SEQ ID NO 27
<211> LENGTH: 6360
<212> TYPE: DNA
<213> ORGANISM: Streptococcus pneumoniae

<400> SEQUENCE: 27

```
tacccggtag tcttagcaga cacatctagc tctgaagatg ctttaaacat ctctgataaa      60
gaaaaagtag cagaaaataa agagaaacat gaaaatatcc atagtgctat ggaaacttca     120
caggatttta agagaagaa acagcagtc attaaggaaa agaagttgt tagtaaaaat        180
cctgtgatag acaataacac tagcaatgaa gaagcaaaaa tcaaagaaga aaattccaat    240
aaatcccaag gagattatac ggactcattt gtgaataaaa acacagaaaa tcccaaaaaa    300
gaagataaag ttgtctatat tgctgaattt aaagataaag aatctggaga aaaagcaatc    360
aaggaactat ccagtcttaa gaatacaaaa gttttatata cttatgatag aattttttaac   420
ggtagtgcca tagaaacaac tccagataac ttggacaaaa ttaaacaaat agaaggtatt    480
tcatcggttg aaagggcaca aaagtccaa cccatgatga atcatgccag aaaggaaatt     540
ggagttgagg aagctattga ttacctaaag tctatcaatg ctccgtttgg gaaaaatttt    600
gatggtagag gtatggtcat ttcaaatatc gatactggaa cagattatag acataaggct    660
atgagaatcg atgatgatgc caaagcctca atgagattta aaaagaaga cttaaaaggc    720
actgataaaa attattggtt gagtgataaa atccctcatg cgttcaatta ttataatggt    780
ggcaaaatca ctgtagaaaa atatgatgat ggaagggatt atttttgaccc acatgggatg   840
catattgcag ggattcttgc tggaaatgat actgaacaag acatcaaaaa ctttaacggc    900
atagatggaa ttgcacctaa tgcacaaatt ttctcttaca aatgtattc tgacgcagga    960
tctgggtttg cgggtgatga acaatgtttt catgctattg aagattctat caaacacaac  1020
gttgatgttg tttcggtatc atctggtttt acaggaacag gtcttgtagg tgagaaatat   1080
tggcaagcta ttcgggcatt aagaaaagca ggcattccaa tggttgtcgc tacgggtaac  1140
tatgcgactt ctgcttcaag ttcttcatgg gatttagtag caaataatca tctgaaaatg   1200
accgacactg gaaatgtaac acgaactgca gcacatgaag atgcgatagc ggtcgcttct  1260
gctaaaaatc aaacagttga gtttgataaa gttaacatag gtggagaaag ttttaaatac   1320
agaaatatag gggcctttttt cgataagagt aaaatcacaa caaatgaaga tggaacaaaa  1380
gctcctagta aattaaaatt tgtatatata ggcaagggc aagaccaaga tttgataggt    1440
ttggatctta ggggcaaaat tgcagtaatg gatagaattt atacaaagga tttaaaaaat   1500
gcttttaaaa aagctatgga taagggtgca cgcgccatta tggttgtaaa tactgtaaat   1560
tactacaata gagataattg gacagagctt ccagctatgg gatatgaagc ggatgaaggt  1620
actaaaagtc aagtgttttc aatttcagga tgatgatggtg taaagctatg gaacatgatt  1680
aatcctgata aaaaaactga agtcaaaaga aataataaag aagatttaa agataaattg    1740
gagcaatact atccaattga tatggaaagt tttaattcca acaaaccgaa tgtaggtgac   1800
gaaaaagaga ttgactttaa gtttgcacct gacacagaca aagaactcta taagaagat   1860
```

```
atcatcgttc cagcaggatc tacatcttgg gggccaagaa tagatttact tttaaaaccc    1920
gatgtttcag cacctggtaa aaatattaaa tccacgctta atgttattaa tggcaaatca    1980
acttatggct atatgtcagg aactagtatg gcgactccaa tcgtggcagc ttctactgtt    2040
ttgattagac cgaaattaaa ggaaatgctt gaaagacctg tattgaaaaa tcttaaggga    2100
gatgacaaaa tagatcttac aagtcttaca aaaattgccc tacaaaatac tgcgcgacct    2160
atgatggatg caacttcttg gaaagaaaaa agtcaatact ttgcatcacc tagacaacag    2220
ggagcaggcc taattaatgt ggccaatgct ttgagaaatg aagttgtagc aactttcaaa    2280
aacactgatt ctaaaggttt ggtaaactca tatggttcca tttctcttaa agaaataaaa    2340
ggtgataaaa aatactttac aatcaagctt cacaatacat caaacagacc tttgactttt    2400
aaagtttcag catcagcgat aactacagat tctctaactg acagattaaa acttgatgaa    2460
acatataaag atgaaaaatc tccagatggt aagcaaattg ttccagaaat tcacccagaa    2520
aaagtcaaag gagcaaatat cacatttgag catgatactt tcactatagg cgcaaattct    2580
agctttgatt tgaatgcggt tataaatgtt ggagaggcca aaaacaaaaa taaatttgta    2640
gaatcattta ttcattttga gtcagtggaa gcgatggaag ctctaaactc cagcgggaag    2700
aaaataaact tccaaccttc tttgtcgatg cctctaatgg gatttgctgg gaattggaac    2760
cacgaaccaa tccttgataa atgggcttgg gaagaagggt caagatcaaa aacactggga    2820
ggttatgatg atgatggtaa accgaaaatt ccaggaacct taaataaggg aattggtgga    2880
gaacatggta tagataaatt taatccagca ggagttatac aaaatagaaa agataaaaat    2940
acaacatccc tggatcaaaa tccagaatta tttgctttca ataacgaagg gatcaacgct    3000
ccatcatcaa gtggttctaa gattgctaac atttatcctt tagattcaaa tggaaatcct    3060
caagatgctc aacttgaaag aggattaaca ccttctccac ttgtattaag aagtgcagaa    3120
gaaggattga tttcaatagt aaatacaaat aaagagggag aaaatcaaag agacttaaaa    3180
gtcatttcga gagaacactt tattagagga attttaaatt ctaaaagcaa tgatgcaaag    3240
ggaatcaaat catctaaact aaaagtttgg ggtgacttga agtgggatgg actcatctat    3300
aatcctagag gtagagaaga aaatgcacca gaaagtaagg ataatcaaga tcctgctact    3360
aagataagag gtcaatttga accgattgcg gaaggtcaat atttctataa atttaaatat    3420
agattaacta aagattaccc atggcaggtt tcctatattc ctgtaaaaat tgataacacc    3480
gcccctaaga ttgtttcggt tgatttttca aatcctgaaa aaattaagtt gattacaaag    3540
gatacttatc ataaggtaaa agatcagtat aagaatgaaa cgctatttgc gagagatcaa    3600
aaagaacatc ctgaaaaatt tgacgagatt gcgaacgaag tttggtatgc tggcgccgct    3660
cttgttaatg aagatggaga ggttgaaaaa atcttgaag taacttacgc aggtgagggt    3720
caaggaagaa atagaaaact tgataaagac ggaaatacca tttatgaaat taaaggtgcg    3780
ggagatttaa ggggaaaaat cattgaagtc attgcattag atggttctag caatttcaca    3840
aagattcata gaattaaatt tgctaatcag gctgatgaaa agggatgat ttcctattat    3900 ctagtagatc ctgatcaaga ttcatctaaa tatcaaaagc ttggcgagat tgcagaatct    3960
aaatttaaaa atttaggaaa tggaaaagag ggtagtctaa aaaagatac aactggggta    4020 gaacatcatc atcaagaaaa tgaagagtct attaaagaaa aatctagttt tactattgat    4080
agaaatattt caacaattag agactttgaa aataaagact aaagaaact cattaaaaag    4140 aaatttagag aagttgatga ttttacaagt gaaactggta agagaatgga ggaatacgat    4200
tataaatacg atgataaagg aaatataata gcctacgatg atgggactga tctagaatat    4260
```

-continued

```
gaaactgaga aacttgacga aatcaaatca aaaatttatg gtgttctaag tccgtctaaa      4320
gatggacact ttgaaattct tggaaagata agtaatgttt ctaaaaatgc caaggtatat      4380
tatgggaata actataaatc tatagaaatc aaagcgacca agtatgattt ccactcaaaa      4440
acgatgacat ttgatctata cgctaatatt aatgatattg tggatggatt agcttttgca      4500
ggagatatga gattatttgt taaagataat gatcagaaaa aagctgaaat taaaattaga      4560
atgcctgaaa aaattaagga aactaaatca gaatatccct atgtatcaag ttatgggaat      4620
gtcatagaat taggggaagg agatctttca aaaaacaaac cagacaattt aactaaaatg      4680
gaatctggta aaatctattc tgattcagaa aaacaacaat atctgttaaa ggataatatc      4740
attctaagaa aaggctatgc actaaaagtg actacctata atcctggaaa aacggatatg      4800
ttagaaggaa atggagtcta tagcaaggaa gatatagcaa aaatacaaaa ggccaatcct      4860
aatctaagag cccttttcaga aacaacaatt tatgctgata gtagaaatgt tgaagatgga      4920
agaagtaccc aatctgtatt aatgtcggct ttggacggct ttaacattat aaggtatcaa      4980
gtgtttacat ttaaaatgaa cgataaaggg gaagctatcg ataaagacgg aaatcttgtg      5040
acagattctt ctaaacttgt attatttggt aaggatgata agaatacac tggagaggat       5100 aagttcaatg tagaagctat aaaagaagat ggctccatgt tatttattga taccaaacca      5160
gtaaaccttt caatggataa gaactacttt aatccatcta aatctaataa aatttatgta      5220
cgaaatccag aattttattt aagaggtaag atttctgata agggtggttt taactgggaa      5280
ttgagagtta atgaatcggt tgtagataat tatttaatct acggagattt acacattgat      5340
aacactagag attttaatat taagctgaat gttaaagacg gtgacatcat ggactgggga      5400
atgaaagact ataaagcaaa cggatttcca gataaggtaa cagatatgga tggaaatgtt      5460
tatcttcaaa ctggctatag cgatttgaat gctaaagcag ttggagtcca ctatcagttt      5520
ttatatgata atgttaaacc cgaagtaaac attgatccta agggaaatac tagtatcgaa      5580
tatgctgatg gaaaatctgt agtctttaac atcaatgata aagagaataa tggattcgat      5640
ggtgagattc aagaacaaca tatttatata aatggaaaag aatatacatc atttaatgat      5700
attaaacaaa taatagacaa gacactaaac attaagattg ttgtaaaaga ttttgcaaga      5760
aatacaaccg taaagaatt cattttaaat aaagatacgg gagaggtaag tgaattaaaa       5820
cctcataggg taactgtgac cattcaaaat ggaaaagaaa tgagttcaac gatagtgtcg      5880
gaagaagatt ttatttacc tgtttataag ggtgaattag aaaaaggata ccaatttgat        5940
ggttgggaaa tttctggttt cgaaggtaaa aaagacgctg gctatgttat taatctatca      6000
aaagatacct ttataaaacc tgtattcaag aaaatagagg agaaaaagga ggaagaaaat      6060
aaacctactt ttgatgtatc gaaaagaaa gataacccac aagtaaacca tagtcaatta       6120
aatgaaagtc acagaaaaga ggatttacaa agagaagagc attcacaaaa atctgattca      6180
actaaggatg ttacagctac agttcttgat aaaaacaata tcagtagtaa atcaactact      6240
aacaatccta ataagttgcc aaaaactgga acagcaagcg gagcccagac actattagct      6300
gccggaataa tgtttatagt aggaattttt cttggattga agaaaaaaaa tcaagattaa      6360
```

<210> SEQ ID NO 28
<211> LENGTH: 2119
<212> TYPE: PRT
<213> ORGANISM: Streptococcus pneumoniae

<400> SEQUENCE: 28

Tyr Pro Val Val Leu Ala Asp Thr Ser Ser Ser Glu Asp Ala Leu Asn
 1               5                  10                  15

```
Ile Ser Asp Lys Glu Lys Val Ala Glu Asn Lys Glu Lys His Glu Asn
            20                  25                  30
Ile His Ser Ala Met Glu Thr Ser Gln Asp Phe Lys Glu Lys Lys Thr
        35                  40                  45
Ala Val Ile Lys Glu Lys Val Val Ser Lys Asn Pro Val Ile Asp
 50                  55                  60
Asn Asn Thr Ser Asn Glu Glu Ala Lys Ile Lys Glu Asn Ser Asn
 65                  70                  75                  80
Lys Ser Gln Gly Asp Tyr Thr Asp Ser Phe Val Asn Lys Asn Thr Glu
            85                  90                  95
Asn Pro Lys Lys Glu Asp Lys Val Val Tyr Ile Ala Glu Phe Lys Asp
                100                 105                 110
Lys Glu Ser Gly Glu Lys Ala Ile Lys Glu Leu Ser Ser Leu Lys Asn
            115                 120                 125
Thr Lys Val Leu Tyr Thr Tyr Asp Arg Ile Phe Asn Gly Ser Ala Ile
        130                 135                 140
Glu Thr Thr Pro Asp Asn Leu Asp Lys Ile Lys Gln Ile Glu Gly Ile
145                 150                 155                 160
Ser Ser Val Glu Arg Ala Gln Lys Val Gln Pro Met Met Asn His Ala
                165                 170                 175
Arg Lys Glu Ile Gly Val Glu Glu Ala Ile Asp Tyr Leu Lys Ser Ile
            180                 185                 190
Asn Ala Pro Phe Gly Lys Asn Phe Asp Gly Arg Gly Met Val Ile Ser
        195                 200                 205
Asn Ile Asp Thr Gly Thr Asp Tyr Arg His Lys Ala Met Arg Ile Asp
    210                 215                 220
Asp Asp Ala Lys Ala Ser Met Arg Phe Lys Lys Glu Asp Leu Lys Gly
225                 230                 235                 240
Thr Asp Lys Asn Tyr Trp Leu Ser Asp Lys Ile Pro His Ala Phe Asn
                245                 250                 255
Tyr Tyr Asn Gly Gly Lys Ile Thr Val Glu Lys Tyr Asp Asp Gly Arg
            260                 265                 270
Asp Tyr Phe Asp Pro His Gly Met His Ile Ala Gly Ile Leu Ala Gly
        275                 280                 285
Asn Asp Thr Glu Gln Asp Ile Lys Asn Phe Asn Gly Ile Asp Gly Ile
    290                 295                 300
Ala Pro Asn Ala Gln Ile Phe Ser Tyr Lys Met Tyr Ser Asp Ala Gly
305                 310                 315                 320
Ser Gly Phe Ala Gly Asp Glu Thr Met Phe His Ala Ile Glu Asp Ser
                325                 330                 335
Ile Lys His Asn Val Asp Val Val Ser Val Ser Ser Gly Phe Thr Gly
            340                 345                 350
Thr Gly Leu Val Gly Glu Lys Tyr Trp Gln Ala Ile Arg Ala Leu Arg
        355                 360                 365
Lys Ala Gly Ile Pro Met Val Val Ala Thr Gly Asn Tyr Ala Thr Ser
    370                 375                 380
Ala Ser Ser Ser Ser Trp Asp Leu Val Ala Asn His Leu Lys Met
385                 390                 395                 400
Thr Asp Thr Gly Asn Val Thr Arg Thr Ala His Glu Asp Ala Ile
                405                 410                 415
Ala Val Ala Ser Ala Lys Asn Gln Thr Val Glu Phe Asp Lys Val Asn
            420                 425                 430
Ile Gly Gly Glu Ser Phe Lys Tyr Arg Asn Ile Gly Ala Phe Phe Asp
```

-continued

```
                435                 440                 445
Lys Ser Lys Ile Thr Thr Asn Glu Asp Gly Thr Lys Ala Pro Ser Lys
450                 455                 460
Leu Lys Phe Val Tyr Ile Gly Lys Gly Gln Asp Gln Asp Leu Ile Gly
465                 470                 475                 480
Leu Asp Leu Arg Gly Lys Ile Ala Val Met Asp Arg Ile Tyr Thr Lys
                485                 490                 495
Asp Leu Lys Asn Ala Phe Lys Lys Ala Met Asp Lys Gly Ala Arg Ala
                500                 505                 510
Ile Met Val Val Asn Thr Val Asn Tyr Tyr Asn Arg Asp Asn Trp Thr
                515                 520                 525
Glu Leu Pro Ala Met Gly Tyr Glu Ala Asp Glu Gly Thr Lys Ser Gln
530                 535                 540
Val Phe Ser Ile Ser Gly Asp Asp Gly Val Lys Leu Trp Asn Met Ile
545                 550                 555                 560
Asn Pro Asp Lys Lys Thr Glu Val Lys Arg Asn Asn Lys Glu Asp Phe
                565                 570                 575
Lys Asp Lys Leu Glu Gln Tyr Tyr Pro Ile Asp Met Glu Ser Phe Asn
                580                 585                 590
Ser Asn Lys Pro Asn Val Gly Asp Glu Lys Glu Ile Asp Phe Lys Phe
                595                 600                 605
Ala Pro Asp Thr Asp Lys Glu Leu Tyr Lys Glu Asp Ile Ile Val Pro
                610                 615                 620
Ala Gly Ser Thr Ser Trp Gly Pro Arg Ile Asp Leu Leu Lys Pro
625                 630                 635                 640
Asp Val Ser Ala Pro Gly Lys Asn Ile Lys Ser Thr Leu Asn Val Ile
                645                 650                 655
Asn Gly Lys Ser Thr Tyr Gly Tyr Met Ser Gly Thr Ser Met Ala Thr
                660                 665                 670
Pro Ile Val Ala Ala Ser Thr Val Leu Ile Arg Pro Lys Leu Lys Glu
                675                 680                 685
Met Leu Glu Arg Pro Val Leu Lys Asn Leu Lys Gly Asp Asp Lys Ile
690                 695                 700
Asp Leu Thr Ser Leu Thr Lys Ile Ala Leu Gln Asn Thr Ala Arg Pro
705                 710                 715                 720
Met Met Asp Ala Thr Ser Trp Lys Glu Lys Ser Gln Tyr Phe Ala Ser
                725                 730                 735
Pro Arg Gln Gln Gly Ala Gly Leu Ile Asn Val Ala Asn Ala Leu Arg
                740                 745                 750
Asn Glu Val Val Ala Thr Phe Lys Asn Thr Asp Ser Lys Gly Leu Val
                755                 760                 765
Asn Ser Tyr Gly Ser Ile Ser Leu Lys Glu Ile Lys Gly Asp Lys Lys
                770                 775                 780
Tyr Phe Thr Ile Lys Leu His Asn Thr Ser Asn Arg Pro Leu Thr Phe
785                 790                 795                 800
Lys Val Ser Ala Ser Ala Ile Thr Thr Asp Ser Leu Thr Asp Arg Leu
                805                 810                 815
Lys Leu Asp Glu Thr Tyr Lys Asp Glu Lys Ser Pro Asp Gly Lys Gln
                820                 825                 830
Ile Val Pro Glu Ile His Pro Glu Lys Val Lys Gly Ala Asn Ile Thr
                835                 840                 845
Phe Glu His Asp Thr Phe Thr Ile Gly Ala Asn Ser Ser Phe Asp Leu
850                 855                 860
```

```
Asn Ala Val Ile Asn Val Gly Glu Ala Lys Asn Lys Asn Lys Phe Val
865                 870                 875                 880

Glu Ser Phe Ile His Phe Glu Ser Val Glu Ala Met Glu Ala Leu Asn
            885                 890                 895

Ser Ser Gly Lys Lys Ile Asn Phe Gln Pro Ser Leu Ser Met Pro Leu
        900                 905                 910

Met Gly Phe Ala Gly Asn Trp Asn His Glu Pro Ile Leu Asp Lys Trp
        915                 920                 925

Ala Trp Glu Glu Gly Ser Arg Ser Lys Thr Leu Gly Gly Tyr Asp Asp
        930                 935                 940

Asp Gly Lys Pro Lys Ile Pro Gly Thr Leu Asn Lys Gly Ile Gly Gly
945                 950                 955                 960

Glu His Gly Ile Asp Lys Phe Asn Pro Ala Gly Val Ile Gln Asn Arg
            965                 970                 975

Lys Asp Lys Asn Thr Thr Ser Leu Asp Gln Asn Pro Glu Leu Phe Ala
        980                 985                 990

Phe Asn Asn Glu Gly Ile Asn Ala Pro Ser Ser Gly Ser Lys Ile
            995                 1000                1005

Ala Asn Ile Tyr Pro Leu Asp Ser Asn Gly Asn Pro Gln Asp Ala Gln
    1010                1015                1020

Leu Glu Arg Gly Leu Thr Pro Ser Pro Leu Val Leu Arg Ser Ala Glu
1025                1030                1035                1040

Glu Gly Leu Ile Ser Ile Val Asn Thr Asn Lys Glu Gly Glu Asn Gln
        1045                1050                1055

Arg Asp Leu Lys Val Ile Ser Arg Glu His Phe Ile Arg Gly Ile Leu
            1060                1065                1070

Asn Ser Lys Ser Asn Asp Ala Lys Gly Ile Lys Ser Ser Lys Leu Lys
    1075                1080                1085

Val Trp Gly Asp Leu Lys Trp Asp Gly Leu Ile Tyr Asn Pro Arg Gly
    1090                1095                1100

Arg Glu Glu Asn Ala Pro Glu Ser Lys Asp Asn Gln Asp Pro Ala Thr
1105                1110                1115                1120

Lys Ile Arg Gly Gln Phe Glu Pro Ile Ala Glu Gly Gln Tyr Phe Tyr
            1125                1130                1135

Lys Phe Lys Tyr Arg Leu Thr Lys Asp Tyr Pro Trp Gln Val Ser Tyr
        1140                1145                1150

Ile Pro Val Lys Ile Asp Asn Thr Ala Pro Lys Ile Val Ser Val Asp
        1155                1160                1165

Phe Ser Asn Pro Glu Lys Ile Lys Leu Ile Thr Lys Asp Thr Tyr His
    1170                1175                1180

Lys Val Lys Asp Gln Tyr Lys Asn Glu Thr Leu Phe Ala Arg Asp Gln
1185                1190                1195                1200

Lys Glu His Pro Glu Lys Phe Asp Glu Ile Ala Asn Glu Val Trp Tyr
        1205                1210                1215

Ala Gly Ala Ala Leu Val Asn Glu Asp Gly Glu Val Glu Lys Asn Leu
        1220                1225                1230

Glu Val Thr Tyr Ala Gly Glu Gly Gln Gly Arg Asn Arg Lys Leu Asp
        1235                1240                1245

Lys Asp Gly Asn Thr Ile Tyr Glu Ile Lys Gly Ala Gly Asp Leu Arg
    1250                1255                1260

Gly Lys Ile Ile Glu Val Ile Ala Leu Asp Gly Ser Ser Asn Phe Thr
1265                1270                1275                1280

Lys Ile His Arg Ile Lys Phe Ala Asn Gln Ala Asp Glu Lys Gly Met
            1285                1290                1295
```

```
Ile Ser Tyr Tyr Leu Val Asp Pro Asp Gln Asp Ser Ser Lys Tyr Gln
        1300                1305                1310

Lys Leu Gly Glu Ile Ala Glu Ser Lys Phe Lys Asn Leu Gly Asn Gly
    1315                1320                1325

Lys Glu Gly Ser Leu Lys Lys Asp Thr Thr Gly Val Glu His His His
1330                1335                1340

Gln Glu Asn Glu Glu Ser Ile Lys Glu Lys Ser Ser Phe Thr Ile Asp
1345                1350                1355                1360

Arg Asn Ile Ser Thr Ile Arg Asp Phe Glu Asn Lys Asp Leu Lys Lys
            1365                1370                1375

Leu Ile Lys Lys Lys Phe Arg Glu Val Asp Asp Phe Thr Ser Glu Thr
        1380                1385                1390

Gly Lys Arg Met Glu Glu Tyr Asp Tyr Lys Tyr Asp Lys Gly Asn
    1395                1400                1405

Ile Ile Ala Tyr Asp Asp Gly Thr Asp Leu Glu Tyr Glu Thr Glu Lys
        1410                1415                1420

Leu Asp Glu Ile Lys Ser Lys Ile Tyr Gly Val Leu Ser Pro Ser Lys
1425                1430                1435                1440

Asp Gly His Phe Glu Ile Leu Gly Lys Ile Ser Asn Val Ser Lys Asn
            1445                1450                1455

Ala Lys Val Tyr Tyr Gly Asn Asn Tyr Lys Ser Ile Glu Ile Lys Ala
        1460                1465                1470

Thr Lys Tyr Asp Phe His Ser Lys Thr Met Thr Phe Asp Leu Tyr Ala
    1475                1480                1485

Asn Ile Asn Asp Ile Val Asp Gly Leu Ala Phe Ala Gly Asp Met Arg
    1490                1495                1500

Leu Phe Val Lys Asp Asn Asp Gln Lys Lys Ala Glu Ile Lys Ile Arg
1505                1510                1515                1520

Met Pro Glu Lys Ile Lys Glu Thr Lys Ser Glu Tyr Pro Tyr Val Ser
            1525                1530                1535

Ser Tyr Gly Asn Val Ile Glu Leu Gly Glu Gly Asp Leu Ser Lys Asn
        1540                1545                1550

Lys Pro Asp Asn Leu Thr Lys Met Glu Ser Gly Lys Ile Tyr Ser Asp
    1555                1560                1565

Ser Glu Lys Gln Gln Tyr Leu Leu Lys Asp Asn Ile Ile Leu Arg Lys
    1570                1575                1580

Gly Tyr Ala Leu Lys Val Thr Thr Tyr Asn Pro Gly Lys Thr Asp Met
1585                1590                1595                1600

Leu Glu Gly Asn Gly Val Tyr Ser Lys Glu Asp Ile Ala Lys Ile Gln
            1605                1610                1615

Lys Ala Asn Pro Asn Leu Arg Ala Leu Ser Glu Thr Thr Ile Tyr Ala
        1620                1625                1630

Asp Ser Arg Asn Val Glu Asp Gly Arg Ser Thr Gln Ser Val Leu Met
    1635                1640                1645

Ser Ala Leu Asp Gly Phe Asn Ile Ile Arg Tyr Gln Val Phe Thr Phe
1650                1655                1660

Lys Met Asn Asp Lys Gly Glu Ala Ile Asp Lys Asp Gly Asn Leu Val
1665                1670                1675                1680

Thr Asp Ser Ser Lys Leu Val Leu Phe Gly Lys Asp Lys Glu Tyr
            1685                1690                1695

Thr Gly Glu Asp Lys Phe Asn Val Glu Ala Ile Lys Glu Asp Gly Ser
    1700                1705                1710

Met Leu Phe Ile Asp Thr Lys Pro Val Asn Leu Ser Met Asp Lys Asn
```

```
                  1715                1720                1725
Tyr Phe Asn Pro Ser Lys Ser Asn Lys Ile Tyr Val Arg Asn Pro Glu
         1730                1735                1740
Phe Tyr Leu Arg Gly Lys Ile Ser Asp Lys Gly Gly Phe Asn Trp Glu
1745                1750                1755                1760
Leu Arg Val Asn Glu Ser Val Val Asp Asn Tyr Leu Ile Tyr Gly Asp
              1765                1770                1775
Leu His Ile Asp Asn Thr Arg Asp Phe Asn Ile Lys Leu Asn Val Lys
         1780                1785                1790
Asp Gly Asp Ile Met Asp Trp Gly Met Lys Asp Tyr Lys Ala Asn Gly
    1795                1800                1805
Phe Pro Asp Lys Val Thr Asp Met Asp Gly Asn Val Tyr Leu Gln Thr
   1810                1815                1820
Gly Tyr Ser Asp Leu Asn Ala Lys Ala Val Gly Val His Tyr Gln Phe
1825                1830                1835                1840
Leu Tyr Asp Asn Val Lys Pro Glu Val Asn Ile Asp Pro Lys Gly Asn
              1845                1850                1855
Thr Ser Ile Glu Tyr Ala Asp Gly Lys Ser Val Val Phe Asn Ile Asn
         1860                1865                1870
Asp Lys Arg Asn Asn Gly Phe Asp Gly Glu Ile Gln Glu Gln His Ile
    1875                1880                1885
Tyr Ile Asn Gly Lys Glu Tyr Thr Ser Phe Asn Asp Ile Lys Gln Ile
   1890                1895                1900
Ile Asp Lys Thr Leu Asn Ile Lys Ile Val Lys Asp Phe Ala Arg
1905                1910                1915                1920
Asn Thr Thr Val Lys Glu Phe Ile Leu Asn Lys Asp Thr Gly Glu Val
              1925                1930                1935
Ser Glu Leu Lys Pro His Arg Val Thr Val Thr Ile Gln Asn Gly Lys
         1940                1945                1950
Glu Met Ser Ser Thr Ile Val Ser Glu Asp Phe Ile Leu Pro Val
    1955                1960                1965
Tyr Lys Gly Glu Leu Glu Lys Gly Tyr Gln Phe Asp Gly Trp Glu Ile
   1970                1975                1980
Ser Gly Phe Glu Gly Lys Lys Asp Ala Gly Tyr Val Ile Asn Leu Ser
1985                1990                1995                2000
Lys Asp Thr Phe Ile Lys Pro Val Phe Lys Lys Ile Glu Glu Lys Lys
              2005                2010                2015
Glu Glu Glu Asn Lys Pro Thr Phe Asp Val Ser Lys Lys Lys Asp Asn
         2020                2025                2030
Pro Gln Val Asn His Ser Gln Leu Asn Glu Ser His Arg Lys Glu Asp
    2035                2040                2045
Leu Gln Arg Glu Glu His Ser Gln Lys Ser Asp Ser Thr Lys Asp Val
   2050                2055                2060
Thr Ala Thr Val Leu Asp Lys Asn Asn Ile Ser Ser Lys Ser Thr Thr
2065                2070                2075                2080
Asn Asn Pro Asn Lys Leu Pro Lys Thr Gly Thr Ala Ser Gly Ala Gln
              2085                2090                2095
Thr Leu Leu Ala Ala Gly Ile Met Phe Ile Val Gly Ile Phe Leu Gly
         2100                2105                2110
Leu Lys Lys Lys Asn Gln Asp
         2115

<210> SEQ ID NO 29
<211> LENGTH: 597
```

<212> TYPE: DNA
<213> ORGANISM: Streptococcus pneumoniae

<400> SEQUENCE: 29

```
cttgaattaa ataaaaaacg tcatgcgact aagcatttta ctgataagct tgttgatccc      60
aaagatgtgc gtacggctat cgaaattgca accttagcgc aagcgccca caacagccag     120
ccttggaaat tgtggtggt acgtgagaaa aatgctgaac tggcaaagtt agcttatggt     180
tccaattttg aacaggtatc atcagcgcct gtaaccattg ccttgtttac agatacggac    240
ttagccaaac gtgctcgtaa gattgcccgt gttggtggtg ctaataactt ttctgaagag    300
caacttcaat attttatgaa aaatctgcca gctgagtttg cccgttacag tgagcaacaa    360
gtcagcgact acctagctct caatgcaggt ttggttgcca tgaacttggt tcttgcattg    420
acagaccaag gaattggttc taacattatt cttggttttg acaaatcaaa agttaatgaa    480
gttttggaaa tcgaagaccg tttccgccca gaactcttga tcacagtggg ttatacagac    540
gaaaaattgg aaccaagcta ccgcttgcca gtagatgaaa tcatcgagaa aagatag      597
```

<210> SEQ ID NO 30
<211> LENGTH: 198
<212> TYPE: PRT
<213> ORGANISM: Streptococcus pneumoniae

<400> SEQUENCE: 30

```
Leu Glu Leu Asn Lys Lys Arg His Ala Thr Lys His Phe Thr Asp Lys
  1               5                  10                  15
Leu Val Asp Pro Lys Asp Val Arg Thr Ala Ile Glu Ile Ala Thr Leu
             20                  25                  30
Ala Pro Ser Ala His Asn Ser Gln Pro Trp Lys Phe Val Val Val Arg
         35                  40                  45
Glu Lys Asn Ala Glu Leu Ala Lys Leu Ala Tyr Gly Ser Asn Phe Glu
     50                  55                  60
Gln Val Ser Ser Ala Pro Val Thr Ile Ala Leu Phe Thr Asp Thr Asp
 65                  70                  75                  80
Leu Ala Lys Arg Ala Arg Lys Ile Ala Arg Val Gly Gly Ala Asn Asn
                 85                  90                  95
Phe Ser Glu Glu Gln Leu Gln Tyr Phe Met Lys Asn Leu Pro Ala Glu
            100                 105                 110
Phe Ala Arg Tyr Ser Glu Gln Gln Val Ser Asp Tyr Leu Ala Leu Asn
        115                 120                 125
Ala Gly Leu Val Ala Met Asn Leu Val Leu Ala Thr Asp Gln Gly
    130                 135                 140
Ile Gly Ser Asn Ile Ile Leu Gly Phe Asp Lys Ser Lys Val Asn Glu
145                 150                 155                 160
Val Leu Glu Ile Glu Asp Arg Phe Arg Pro Glu Leu Leu Ile Thr Val
                165                 170                 175
Gly Tyr Thr Asp Glu Lys Leu Glu Pro Ser Tyr Arg Leu Pro Val Asp
            180                 185                 190
Glu Ile Ile Glu Lys Arg
        195
```

<210> SEQ ID NO 31
<211> LENGTH: 1401
<212> TYPE: DNA
<213> ORGANISM: Streptococcus pneumoniae

<400> SEQUENCE: 31

```
atgacagcaa ttgattttac agcagaagta gaaaaacgca agaagaccct cttggctgac      60
ttgtttagcc ttttggaaat caattcagaa cgtgatgaca gcaaggctga tgcccagcat     120
ccatttgggc ctggtccagt aaaagccttg gagaaattcc ttgaaatcgc agaccgcgat     180
ggctacccaa ctaagaatgt tgataactat gcaggacatt ttgagtttgg tgatggagaa     240
gaagttctcg gaatctttgc ccatatggat gtggtgcctg ctggtagcgg ttgggacaca     300
gacccttaca caccaactat caaagatggt cgcctttatg cgcgcgggc ttcggacgat      360
aagggtccta acagcttg ttactatggt ttgaaaatca tcaaagaatt gggtcttcca       420
acttctaaga aagttcgctt catcgttgga acagacgaag aatcaggctg gcagacatg      480
gactactact ttgagcacgt aggacttgcc aaaccagatt tcggtttctc accagatgct     540
gaatttccaa tcatcaatgg tgaaaaagga aatatcacgg aatacctcca ctttgcagga     600
gaaaatacag gtgttgcccg tcttcacagc tttacaggtg gtttacgtga aatatggta      660
ccagaatcag caacagcagt cgtttcaggt gacttggctg acttgcaagc taaactagat     720
gcctttgttg cagaacacaa acttagagga gaactccaag aagaagctgg caaatacaag     780
gtgacgatca ttggtaaatc agcccacggt gctatgcctg cttcaggtgt caatggcgca     840
acttaccttg ccctcttcct cagccagttt ggctttgctg gtccagccaa agactacctt     900
gacatcgcag gtaaaattct cttgaacgat catgagggtg aaaatcttaa gattgctcat     960
gtggatgaaa agatgggtgc tctttctatg aatgccggcg tcttccactt cgatgaaaca    1020
agtgctgata taccattgcc cctcaacatc cgctatccaa aggaacaag tccagaacaa     1080
atcaagtcaa tccttgaaaa cttgccagtt gtttctgtta gcctgtctga acacggtcac    1140
acgcctcact atgtgccaat ggaagatcca cttgtgcaaa ccttgttgaa tatctatgaa    1200
aaacaaactg gctttaaagg tcatgaacaa gtcatcggtg gtggaacctt tggtcgcttg    1260
ctagaacgcg gagttgccta cggtgctatg ttcccagact cgattgatac catgcaccaa    1320
gccaatgaat ttatcgcctt ggatgatctt ttccgagcag cagcaattta tgccgaagct    1380
atttacgaat tgatcaaata a                                              1401
```

<210> SEQ ID NO 32
<211> LENGTH: 466
<212> TYPE: PRT
<213> ORGANISM: Streptococcus pneumoniae

<400> SEQUENCE: 32

```
Met Thr Ala Ile Asp Phe Thr Ala Glu Val Glu Lys Arg Lys Glu Asp
  1               5                  10                  15

Leu Leu Ala Asp Leu Phe Ser Leu Leu Glu Ile Asn Ser Glu Arg Asp
                 20                  25                  30

Asp Ser Lys Ala Asp Ala Gln His Pro Phe Gly Pro Gly Pro Val Lys
             35                  40                  45

Ala Leu Glu Lys Phe Leu Glu Ile Ala Asp Arg Asp Gly Tyr Pro Thr
         50                  55                  60

Lys Asn Val Asp Asn Tyr Ala Gly His Phe Glu Phe Gly Asp Gly Glu
 65                  70                  75                  80

Glu Val Leu Gly Ile Phe Ala His Met Asp Val Val Pro Ala Gly Ser
                 85                  90                  95

Gly Trp Asp Thr Asp Pro Tyr Thr Pro Thr Ile Lys Asp Gly Arg Leu
            100                 105                 110

Tyr Ala Arg Gly Ala Ser Asp Asp Lys Gly Pro Thr Thr Ala Cys Tyr
            115                 120                 125
```

```
Tyr Gly Leu Lys Ile Ile Lys Glu Leu Gly Leu Pro Thr Ser Lys Lys
            130                 135                 140

Val Arg Phe Ile Val Gly Thr Asp Glu Glu Ser Gly Trp Ala Asp Met
145                 150                 155                 160

Asp Tyr Tyr Phe Glu His Val Gly Leu Ala Lys Pro Asp Phe Gly Phe
                165                 170                 175

Ser Pro Asp Ala Glu Phe Pro Ile Ile Asn Gly Glu Lys Gly Asn Ile
            180                 185                 190

Thr Glu Tyr Leu His Phe Ala Gly Glu Asn Thr Gly Val Ala Arg Leu
        195                 200                 205

His Ser Phe Thr Gly Gly Leu Arg Glu Asn Met Val Pro Glu Ser Ala
210                 215                 220

Thr Ala Val Val Ser Gly Asp Leu Ala Asp Leu Gln Ala Lys Leu Asp
225                 230                 235                 240

Ala Phe Val Ala Glu His Lys Leu Arg Gly Glu Leu Gln Glu Glu Ala
                245                 250                 255

Gly Lys Tyr Lys Val Thr Ile Ile Gly Lys Ser Ala His Gly Ala Met
            260                 265                 270

Pro Ala Ser Gly Val Asn Gly Ala Thr Tyr Leu Ala Leu Phe Leu Ser
        275                 280                 285

Gln Phe Gly Phe Ala Gly Pro Ala Lys Asp Tyr Leu Asp Ile Ala Gly
290                 295                 300

Lys Ile Leu Leu Asn Asp His Glu Gly Glu Asn Leu Lys Ile Ala His
305                 310                 315                 320

Val Asp Glu Lys Met Gly Ala Leu Ser Met Asn Ala Gly Val Phe His
                325                 330                 335

Phe Asp Glu Thr Ser Ala Asp Asn Thr Ile Ala Leu Asn Ile Arg Tyr
            340                 345                 350

Pro Lys Gly Thr Ser Pro Glu Gln Ile Lys Ser Ile Leu Glu Asn Leu
        355                 360                 365

Pro Val Val Ser Val Ser Leu Ser Glu His Gly His Thr Pro His Tyr
370                 375                 380

Val Pro Met Glu Asp Pro Leu Val Gln Thr Leu Leu Asn Ile Tyr Glu
385                 390                 395                 400

Lys Gln Thr Gly Phe Lys Gly His Glu Gln Val Ile Gly Gly Thr
                405                 410                 415

Phe Gly Arg Leu Leu Glu Arg Gly Val Ala Tyr Gly Ala Met Phe Pro
            420                 425                 430

Asp Ser Ile Asp Thr Met His Gln Ala Asn Glu Phe Ile Ala Leu Asp
        435                 440                 445

Asp Leu Phe Arg Ala Ala Ala Ile Tyr Ala Glu Ala Ile Tyr Glu Leu
450                 455                 460

Ile Lys
465

<210> SEQ ID NO 33
<211> LENGTH: 1617
<212> TYPE: DNA
<213> ORGANISM: Streptococcus pneumoniae

<400> SEQUENCE: 33
gtgtatacta ttataaaatc aaatataaaa aaatttagtt tattaacgat atttattgtt    60
gctggtcaat tattgctaat ttatgcagca actattaatg ctctggtgtt gaatgaatta   120
attgcgatga atttagagcg gttttgaaa ttgtcaatct accaaatgat tgtctggtgt    180
```

```
gggataatat tccttgactg ggtagtgaaa aattatcagg ttgaagtgat ccaagagttt    240
aatctagaga ttcgaaatag agttgccaca gacatctcta actctaccta tcaagaattt    300
catagtaaat catcaggaac atatctttcg tggctaaata atgatgttca gactttaaat    360
gatcaggcgt ttaaacaact tttttagta ataaaaggaa tttctggtac tatatttgca     420
gttgtgactc ttaatcacta tcattggtca ttgactgtag ccaccttgtt ttcattaatg    480
attatgctac ttgtaccaaa aatctttgca tcgaaaatgc gagaagttag tctaaattta    540
actaaccaaa atgaagcttt tttaaaatct agtgagacta tattgaatgg atttgatgtg    600
ttagcgtcct tgaatctttt atatgtattg cctaagaaaa ttaaagaagc aggaattta     660
ttaaagatgg ttatacaaag aaagacaact gtagaaacgt tagcaggcgc tattagcttc    720
tttctcaata ttttttttca gatatctctc gttttttaa caggctatct tgcaataaaa     780
ggaatagtga aaattggtac tattgaagca ataggagcac taacaggtgt tattttttaca  840
gcgctaggtg aattaggagg tcaattatcc tctattattg gtacgaagcc tattttttta   900
aaattgtatt caattaatcc aattgagtca aataaaatga atgatatcga accaaatgag    960
gtgaatagag attttccgtt tatatgaagca aaaaatattt gctataagta tggagataaa  1020
gaaatattaa aaaacttaaa ttttttgtttt caacgtaatg aaaagtattt aattttaggt   1080
gaaagtggaa gcgggaaatc tacattatta aaattattga atggcttttt gagagattat   1140
agtggagaat tgcgattctg cggggatgat ataaaaaaaa cctcctattt aaatatggtt   1200
tcgaatgttc tatatgtaga tcaaaaagct tatttgtttg aaggtacgat tagagataat   1260
atttttattgg aagaaaatta tactgatgaa gaaatactac agtctttaga gcaagttggt  1320
ttgagtgtaa aagatttttcc taataacatt ttagattatt atgttggtga tgatgggaga  1380
ttactgtcag gagggcagaa acaaaaaatt actttagcta gagggctaat tagaaataag   1440
aaaatagtat taattgacga gggaacttct gctatcgata ggagaacttc gttagcgatt   1500
gaacgtaaga tattagatag agaggatttg actgtcatta ttgttaccca tgctccgcat   1560
ccggaactta acaatatttt tactaagata tatcaatttc caaggatttt tatttaa       1617
```

<210> SEQ ID NO 34
<211> LENGTH: 538
<212> TYPE: PRT
<213> ORGANISM: Streptococcus pneumoniae

<400> SEQUENCE: 34

```
Met Tyr Thr Ile Ile Lys Ser Asn Ile Lys Lys Phe Ser Leu Leu Thr
 1               5                  10                  15

Ile Phe Ile Val Ala Gly Gln Leu Leu Leu Ile Tyr Ala Ala Thr Ile
             20                  25                  30

Asn Ala Leu Val Leu Asn Glu Leu Ile Ala Met Asn Leu Glu Arg Phe
         35                  40                  45

Leu Lys Leu Ser Ile Tyr Gln Met Ile Val Trp Cys Gly Ile Ile Phe
     50                  55                  60

Leu Asp Trp Val Val Lys Asn Tyr Gln Val Glu Val Ile Gln Glu Phe
 65                  70                  75                  80

Asn Leu Glu Ile Arg Asn Arg Val Ala Thr Asp Ile Ser Asn Ser Thr
                 85                  90                  95

Tyr Gln Glu Phe His Ser Lys Ser Ser Gly Thr Tyr Leu Ser Trp Leu
            100                 105                 110

Asn Asn Asp Val Gln Thr Leu Asn Asp Gln Ala Phe Lys Gln Leu Phe
        115                 120                 125
```

```
Leu Val Ile Lys Gly Ile Ser Gly Thr Ile Phe Ala Val Val Thr Leu
        130             135                 140
Asn His Tyr His Trp Ser Leu Thr Val Ala Thr Leu Phe Ser Leu Met
145                 150                 155                 160
Ile Met Leu Leu Val Pro Lys Ile Phe Ala Ser Lys Met Arg Glu Val
                    165                 170                 175
Ser Leu Asn Leu Thr Asn Gln Asn Glu Ala Phe Leu Lys Ser Ser Glu
            180                 185                 190
Thr Ile Leu Asn Gly Phe Asp Val Leu Ala Ser Leu Asn Leu Leu Tyr
            195                 200                 205
Val Leu Pro Lys Lys Ile Lys Glu Ala Gly Ile Leu Leu Lys Met Val
210                 215                 220
Ile Gln Arg Lys Thr Thr Val Glu Thr Leu Ala Gly Ala Ile Ser Phe
225                 230                 235                 240
Phe Leu Asn Ile Phe Phe Gln Ile Ser Leu Val Phe Leu Thr Gly Tyr
                245                 250                 255
Leu Ala Ile Lys Gly Ile Val Lys Ile Gly Thr Ile Glu Ala Ile Gly
                260                 265                 270
Ala Leu Thr Gly Val Ile Phe Thr Ala Leu Gly Glu Leu Gly Gly Gln
            275                 280                 285
Leu Ser Ser Ile Ile Gly Thr Lys Pro Ile Phe Leu Lys Leu Tyr Ser
        290                 295                 300
Ile Asn Pro Ile Glu Ser Asn Lys Met Asn Asp Ile Glu Pro Asn Glu
305                 310                 315                 320
Val Asn Arg Asp Phe Pro Leu Tyr Glu Ala Lys Asn Ile Cys Tyr Lys
                325                 330                 335
Tyr Gly Asp Lys Glu Ile Leu Lys Asn Leu Asn Phe Cys Phe Gln Arg
            340                 345                 350
Asn Glu Lys Tyr Leu Ile Leu Gly Glu Ser Gly Ser Gly Lys Ser Thr
        355                 360                 365
Leu Leu Lys Leu Leu Asn Gly Phe Leu Arg Asp Tyr Ser Gly Glu Leu
        370                 375                 380
Arg Phe Cys Gly Asp Asp Ile Lys Lys Thr Ser Tyr Leu Asn Met Val
385                 390                 395                 400
Ser Asn Val Leu Tyr Val Asp Gln Lys Ala Tyr Leu Phe Glu Gly Thr
                405                 410                 415
Ile Arg Asp Asn Ile Leu Leu Glu Glu Asn Tyr Thr Asp Glu Glu Ile
            420                 425                 430
Leu Gln Ser Leu Glu Gln Val Gly Leu Ser Val Lys Asp Phe Pro Asn
        435                 440                 445
Asn Ile Leu Asp Tyr Tyr Val Gly Asp Asp Gly Arg Leu Leu Ser Gly
    450                 455                 460
Gly Gln Lys Gln Lys Ile Thr Leu Ala Arg Gly Leu Ile Arg Asn Lys
465                 470                 475                 480
Lys Ile Val Leu Ile Asp Glu Gly Thr Ser Ala Ile Asp Arg Arg Thr
                485                 490                 495
Ser Leu Ala Ile Glu Arg Lys Ile Leu Asp Arg Glu Asp Leu Thr Val
            500                 505                 510
Ile Ile Val Thr His Ala Pro His Pro Glu Leu Lys Gln Tyr Phe Thr
            515                 520                 525
Lys Ile Tyr Gln Phe Pro Lys Asp Phe Ile
        530                 535

<210> SEQ ID NO 35
```

```
<211> LENGTH: 705
<212> TYPE: DNA
<213> ORGANISM: Streptococcus pneumoniae

<400> SEQUENCE: 35
ataacagtta aacagattat ggacgaaata gccgtttcag atatgactgc aaggcgctat      60
ttacaggaat tagctgataa agatttgctg attcgtgtgc atggtggagc tgaaaaactt     120
cgaaccaact cccttttgac taatgagcga tcaaatattg aaaaacaagc cctccaaacg     180
gcagaaaaac aagaaatagc ccattttgca ggcagtctag tagaagaaag agaaactatt     240
ttcattggac caggaacaac attagagttt tttgcgcgtg agttgcctat tgacaatatc     300
cgcgtcgtaa ccaacagtct acctgttttt ctgattttaa gcgaacgaaa attaacagat     360
ttgattttaa taggtggaaa ttatcgcgat attacaggtg cttttgttgg tacattgacc     420
ctacaaaatc tctctaatct ccaattttct aaagctttcg ttagctgtaa tggtattcaa     480
aacggagctc tagctacttt tagcgaggaa gagggagagg ctcaacgcat cgctttaaat     540
aattctaata aaaatatttt actcgcagat catagcaagt caataagtt tgattttat      600 acttttata atgtatcaaa tcttgatact attgttcag attctaaact aagtgattca      660
atccttttta agctatctaa acacattaaa gtcatcaagc cttaa                    705

<210> SEQ ID NO 36
<211> LENGTH: 234
<212> TYPE: PRT
<213> ORGANISM: Streptococcus pneumoniae

<400> SEQUENCE: 36

Ile Thr Val Lys Gln Ile Met Asp Glu Ile Ala Val Ser Asp Met Thr
  1               5                  10                  15

Ala Arg Arg Tyr Leu Gln Glu Leu Ala Asp Lys Asp Leu Leu Ile Arg
             20                  25                  30

Val His Gly Gly Ala Glu Lys Leu Arg Thr Asn Ser Leu Leu Thr Asn
         35                  40                  45

Glu Arg Ser Asn Ile Glu Lys Gln Ala Leu Gln Thr Ala Glu Lys Gln
     50                  55                  60

Glu Ile Ala His Phe Ala Gly Ser Leu Val Glu Glu Arg Glu Thr Ile
 65                  70                  75                  80

Phe Ile Gly Pro Gly Thr Thr Leu Glu Phe Phe Ala Arg Glu Leu Pro
                 85                  90                  95

Ile Asp Asn Ile Arg Val Val Thr Asn Ser Leu Pro Val Phe Leu Ile
            100                 105                 110

Leu Ser Glu Arg Lys Leu Thr Asp Leu Ile Leu Ile Gly Gly Asn Tyr
        115                 120                 125

Arg Asp Ile Thr Gly Ala Phe Val Gly Thr Leu Thr Leu Gln Asn Leu
    130                 135                 140

Ser Asn Leu Gln Phe Ser Lys Ala Phe Val Ser Cys Asn Gly Ile Gln
145                 150                 155                 160

Asn Gly Ala Leu Ala Thr Phe Ser Glu Glu Gly Glu Ala Gln Arg
                165                 170                 175

Ile Ala Leu Asn Asn Ser Asn Lys Lys Tyr Leu Leu Ala Asp His Ser
            180                 185                 190

Lys Phe Asn Lys Phe Asp Phe Tyr Thr Phe Tyr Asn Val Ser Asn Leu
        195                 200                 205

Asp Thr Ile Val Ser Asp Ser Leu Ser Asp Ser Ile Leu Phe Lys
    210                 215                 220
```

Leu Ser Lys His Ile Lys Val Ile Lys Pro
225                 230

<210> SEQ ID NO 37
<211> LENGTH: 483
<212> TYPE: DNA
<213> ORGANISM: Streptococcus pneumoniae

<400> SEQUENCE: 37

```
atgactgagt tttcgttaga tcttcttcta gaagccatta aactagctcg ttggacctac      60
tactatcact tgaaacagct agacaaaaca gataaagacc aagagcttaa aactgaaatt     120
caatccatct ttatcgaaca caagggaaat tatgcttatc gccgggttca tttagaacta     180
agaaatcgtg gttatctggt aaatcataaa agagttcaag cttgatgaa agtactcaat     240
ttacaagcta aaatgcgaaa gaaacgaaaa tattcttctc ataaaggaga cgttggtaag     300
aaggcagaga tctcattca gcccaatttt gaaggctcta aaacaatgga aaagtgctac     360
acagatgtga ctgaatttgc cattccagca agtactcaaa gctttactt atcaccagtt     420
ttagatggct ttaacagcga aattattgct tttaatcttt cttgttcgcc taatttagaa     480
taa                                                                   483
```

<210> SEQ ID NO 38
<211> LENGTH: 160
<212> TYPE: PRT
<213> ORGANISM: Streptococcus pneumoniae

<400> SEQUENCE: 38

Met Thr Glu Phe Ser Leu Asp Leu Leu Glu Ala Ile Lys Leu Ala
 1               5                  10                  15

Arg Trp Thr Tyr Tyr His Leu Lys Gln Leu Asp Lys Thr Asp Lys
                20                  25                  30

Asp Gln Glu Leu Lys Thr Glu Ile Gln Ser Ile Phe Ile Glu His Lys
            35                  40                  45

Gly Asn Tyr Ala Tyr Arg Arg Val His Leu Glu Leu Arg Asn Arg Gly
        50                  55                  60

Tyr Leu Val Asn His Lys Arg Val Gln Gly Leu Met Lys Val Leu Asn
65                  70                  75                  80

Leu Gln Ala Lys Met Arg Lys Lys Arg Lys Tyr Ser Ser His Lys Gly
                85                  90                  95

Asp Val Gly Lys Lys Ala Glu Asn Leu Ile Gln Ala Gln Phe Glu Gly
            100                 105                 110

Ser Lys Thr Met Glu Lys Cys Tyr Thr Asp Val Thr Glu Phe Ala Ile
        115                 120                 125

Pro Ala Ser Thr Gln Lys Leu Tyr Leu Ser Pro Val Leu Asp Gly Phe
    130                 135                 140

Asn Ser Glu Ile Ile Ala Phe Asn Leu Ser Cys Ser Pro Asn Leu Glu
145                 150                 155                 160

<210> SEQ ID NO 39
<211> LENGTH: 1266
<212> TYPE: DNA
<213> ORGANISM: Streptococcus pneumoniae

<400> SEQUENCE: 39

```
ccaggatttg gtaccgttgc aagtggtgtg cctttcctcc taaaggaaaa tggaggaaaa      60
atcaatcaat cagcacattc agatatcaaa gttgctaagg tattggtcaa ggatgaagat     120
gaaaaaaatc gcttgcttgc agcagggaat gactttaact ttgtaaccaa tgtggatgat     180
```

```
attttatcag accaggatat tactatcgta gtggaattga tggggcgtat tgagcctgct    240
aaaaccttta tcactcgtgc cttggaagct ggaaaacacg ttgttactgc taacaaggac    300
cttttagctg tccatggcgc agaattgcta gaaatcgctc aagctaacaa ggtagcactt    360
tactacgaag cagcagttgc tggtgggatt ccaattcttc gtactttagc aaattccttg    420
gcttctgata aaattacgcg cgtgcttgga gtagtcaacg gaacttccaa cttcatggtg    480
accaagatgg tggaagaagg ctggtcttac gatgatgctc ttgcggaagc acaacgtcta    540
ggatttgcag aaagcgatcc gacgaatgac gtagatggga ttgatgcagc ctacaagatg    600
gttattttga gccaatttgc ctttggcatg aagattgcct ttgatgatgt agcccacaag    660
ggaatccgca atatcacacc agaagacgta gctgtagctc aagagcttgg ttacgtagtg    720
aaattggttg ttctattga ggaaacttct tcaggtattg ctgcagaagt gactccaacc    780
ttcctaccta aagcgcaccc acttgctagt gtgaatggcg taatgaacgc tgtctttgta    840
gaatctatcg gtattggtga gtctatgtac tacggaccag gtgcgggtca aaaaccaact    900
gcaacaagtg ttgtagctga tattgtccgt atcgttcgtc gtttgaatga tggtactatt    960
ggcaaagact tcaacgaata tagccgtgac ttggtcttgg caaatcctga agatgtcaaa    1020
gcaaactact atttctcaat cttggctcta gactcaaaag gtcaggtctt gaagttggct    1080
gaaatcttca atgctcaaga tatttccttt aagcaaatcc ttcaagatgg caagagggt    1140 gacaaggcgc gtgtcgttat catcacacac aagattaata aagcccagct tgaaaatgtc    1200
tcagctgaat tgaagaaggt ttcagaattc gacctcttga ataccttcaa ggtgctagga    1260
gaataa                                                              1266
```

<210> SEQ ID NO 40
<211> LENGTH: 421
<212> TYPE: PRT
<213> ORGANISM: Streptococcus pneumoniae

<400> SEQUENCE: 40

```
Pro Gly Phe Gly Thr Val Ala Ser Gly Val Pro Phe Leu Leu Lys Glu
 1               5                  10                  15

Asn Gly Gly Lys Ile Asn Gln Ser Ala His Ser Asp Ile Lys Val Ala
             20                  25                  30

Lys Val Leu Val Lys Asp Glu Asp Glu Lys Asn Arg Leu Leu Ala Ala
         35                  40                  45

Gly Asn Asp Phe Asn Phe Val Thr Asn Val Asp Ile Leu Ser Asp
     50                  55                  60

Gln Asp Ile Thr Ile Val Val Glu Leu Met Gly Arg Ile Glu Pro Ala
 65                  70                  75                  80

Lys Thr Phe Ile Thr Arg Ala Leu Glu Ala Gly Lys His Val Val Thr
                 85                  90                  95

Ala Asn Lys Asp Leu Leu Ala Val His Gly Ala Glu Leu Leu Glu Ile
             100                 105                 110

Ala Gln Ala Asn Lys Val Ala Leu Tyr Tyr Glu Ala Ala Val Ala Gly
         115                 120                 125

Gly Ile Pro Ile Leu Arg Thr Leu Ala Asn Ser Leu Ala Ser Asp Lys
     130                 135                 140

Ile Thr Arg Val Leu Gly Val Val Asn Gly Thr Ser Asn Phe Met Val
145                 150                 155                 160

Thr Lys Met Val Glu Glu Gly Trp Ser Tyr Asp Asp Ala Leu Ala Glu
                 165                 170                 175
```

-continued

```
Ala Gln Arg Leu Gly Phe Ala Glu Ser Asp Pro Thr Asn Asp Val Asp
            180                 185                 190

Gly Ile Asp Ala Ala Tyr Lys Met Val Ile Leu Ser Gln Phe Ala Phe
        195                 200                 205

Gly Met Lys Ile Ala Phe Asp Asp Val Ala His Lys Gly Ile Arg Asn
    210                 215                 220

Ile Thr Pro Glu Asp Val Ala Val Ala Gln Glu Leu Gly Tyr Val Val
225                 230                 235                 240

Lys Leu Val Gly Ser Ile Glu Glu Thr Ser Ser Gly Ile Ala Ala Glu
                245                 250                 255

Val Thr Pro Thr Phe Leu Pro Lys Ala His Pro Leu Ala Ser Val Asn
            260                 265                 270

Gly Val Met Asn Ala Val Phe Val Glu Ser Ile Gly Ile Gly Glu Ser
        275                 280                 285

Met Tyr Tyr Gly Pro Gly Ala Gly Gln Lys Pro Thr Ala Thr Ser Val
    290                 295                 300

Val Ala Asp Ile Val Arg Ile Val Arg Arg Leu Asn Asp Gly Thr Ile
305                 310                 315                 320

Gly Lys Asp Phe Asn Glu Tyr Ser Arg Asp Leu Val Leu Ala Asn Pro
                325                 330                 335

Glu Asp Val Lys Ala Asn Tyr Tyr Phe Ser Ile Leu Ala Leu Asp Ser
            340                 345                 350

Lys Gly Gln Val Leu Lys Leu Ala Glu Ile Phe Asn Ala Gln Asp Ile
        355                 360                 365

Ser Phe Lys Gln Ile Leu Gln Asp Gly Lys Glu Gly Asp Lys Ala Arg
    370                 375                 380

Val Val Ile Ile Thr His Lys Ile Asn Lys Ala Gln Leu Glu Asn Val
385                 390                 395                 400

Ser Ala Glu Leu Lys Lys Val Ser Glu Phe Asp Leu Leu Asn Thr Phe
                405                 410                 415

Lys Val Leu Gly Glu
            420
```

<210> SEQ ID NO 41
<211> LENGTH: 1725
<212> TYPE: DNA
<213> ORGANISM: Streptococcus pneumoniae

<400> SEQUENCE: 41

```
atgaaacacc tattatctta cttcaaaccc tacatcaagg aatcaatttt agccccttg       60
ttcaagctgt tagaagctgt ttttgagctc ttggttccca tggtgattgc tgggattgtt     120
gaccaatctt tacctcaggg agatcaaggt catctctgga tgcagattgg cctgctcctt     180
atctttgcag taattggcgt tttagtggcc ttgatagctc aattttactc agcaaaggca     240
gcagtaggtt ctgctaagga attgacaaac gatctttatc gtcatattct ttccttgccc     300
aaggacagca gagaccgtct gacaacttct agtttggtca ctcgcttgac ttcggatacc     360
taccagattc agactggtat caatcaattc ctgcgtctct ttttacgagc gcccattatc     420
gtttttggtg ccatttttat ggcttatcga atctcagctg agttgacttt ctggttctta     480
gtcttggttg ccattttgac cattgtcatt gtagggttat ctcgattggt caatcctttc     540
tacagtagtc tcagaaagaa aacggaccaa ctggttcagg aaacgcgcca gcaattgcaa     600
gggatgcggg ttattcgtgc ttttggtcaa gaaaaacgag agttacagat ttttcaaacc     660
cttaaccaag tttatgctag attacaagaa aagacaggtt tctggtctag tttattaaca     720
```

-continued

```
cctctgacct atctgattgt caatggaact cttctcgtta ttatctggca aggctatatt    780
tcaattcaag gaggagtgct cagtcaaggt gctctcattg ctcttatcaa ttacctctta    840
cagattttgg tggaattggt caagctagcc atgttgatca attccctcaa ccagtcctat    900
atctcagtca agcgaatcga ggaagtcttt gttgaggctc cagaggatat ccattcagag    960
ttagaacaaa agcaagctac cagagataag gttttacaag tccaagaatt gacctttacc   1020
tatcctgatg cggcccagcc ttctctgaga tacatttcct ttgatatgac tcaaggacaa   1080
attctaggta tcatcggggg aactggttct ggtaaatcaa gcttggtgca actcttactt   1140
ggactttatc cagtagacaa ggggaacatt gacctttatc aaaatggacg tagtcctctt   1200
aatttggagc agtggcggtc ttggattgcc tatgtacctc aaaaggtcga actctttaaa   1260
ggaaccattc gttccaactt gactctaggt ttcaatcaag aagtatctga ccaggaactc   1320
tggcaggcct tggagattgc gcaagctaag gattttgtca gtgaaaagga aggactcttg   1380
gatgctctag ttgaggcagg ggggcgaaat ttctcaggtg acaaaaaca aagattgtct   1440 atcgcccgag cagtcttgcg ccaggctccg tttctcatcc tagatgatgc aacctcggca   1500
ctggatacca ttacagagtc caagctcttg aaagctatta gagaaaattt tccaaacacg   1560
agcttaattt tgatctctca acgaacctca actttacaga tggcggacca gattctcctc   1620
ttggaaaaag gtgagttgct agctgttggc aagcacgatg acttgatgaa atccagccaa   1680
gtctattgtg aaatcaatgc atcccaacat ggaaaggagg actag                   1725
```

<210> SEQ ID NO 42
<211> LENGTH: 574
<212> TYPE: PRT
<213> ORGANISM: Streptococcus pneumoniae

<400> SEQUENCE: 42

```
Met Lys His Leu Leu Ser Tyr Phe Lys Pro Tyr Ile Lys Glu Ser Ile
  1               5                  10                  15

Leu Ala Pro Leu Phe Lys Leu Leu Glu Ala Val Phe Glu Leu Leu Val
                 20                  25                  30

Pro Met Val Ile Ala Gly Ile Val Asp Gln Ser Leu Pro Gln Gly Asp
             35                  40                  45

Gln Gly His Leu Trp Met Gln Ile Gly Leu Leu Leu Ile Phe Ala Val
         50                  55                  60

Ile Gly Val Leu Val Ala Leu Ile Ala Gln Phe Tyr Ser Ala Lys Ala
 65                  70                  75                  80

Ala Val Gly Ser Ala Lys Glu Leu Thr Asn Asp Leu Tyr Arg His Ile
                 85                  90                  95

Leu Ser Leu Pro Lys Asp Ser Arg Asp Arg Leu Thr Thr Ser Ser Leu
                100                 105                 110

Val Thr Arg Leu Thr Ser Asp Thr Tyr Gln Ile Gln Thr Gly Ile Asn
            115                 120                 125

Gln Phe Leu Arg Leu Phe Leu Arg Ala Pro Ile Ile Val Phe Gly Ala
        130                 135                 140

Ile Phe Met Ala Tyr Arg Ile Ser Ala Glu Leu Thr Phe Trp Phe Leu
145                 150                 155                 160

Val Leu Val Ala Ile Leu Thr Ile Val Ile Val Gly Leu Ser Arg Leu
                165                 170                 175

Val Asn Pro Phe Tyr Ser Ser Leu Arg Lys Lys Thr Asp Gln Leu Val
            180                 185                 190

Gln Glu Thr Arg Gln Gln Leu Gln Gly Met Arg Val Ile Arg Ala Phe
        195                 200                 205
```

Gly Gln Glu Lys Arg Glu Leu Gln Ile Phe Gln Thr Leu Asn Gln Val
210                 215                 220

Tyr Ala Arg Leu Gln Glu Lys Thr Gly Phe Trp Ser Ser Leu Leu Thr
225                 230                 235                 240

Pro Leu Thr Tyr Leu Ile Val Asn Gly Thr Leu Leu Val Ile Ile Trp
                245                 250                 255

Gln Gly Tyr Ile Ser Ile Gln Gly Gly Val Leu Ser Gln Gly Ala Leu
                260                 265                 270

Ile Ala Leu Ile Asn Tyr Leu Leu Gln Ile Leu Val Glu Leu Val Lys
            275                 280                 285

Leu Ala Met Leu Ile Asn Ser Leu Asn Gln Ser Tyr Ile Ser Val Lys
290                 295                 300

Arg Ile Glu Glu Val Phe Val Glu Ala Pro Glu Asp Ile His Ser Glu
305                 310                 315                 320

Leu Glu Gln Lys Gln Ala Thr Arg Asp Lys Val Leu Gln Val Gln Glu
                325                 330                 335

Leu Thr Phe Thr Tyr Pro Asp Ala Ala Gln Pro Ser Leu Arg Tyr Ile
                340                 345                 350

Ser Phe Asp Met Thr Gln Gly Gln Ile Leu Gly Ile Gly Gly Thr
            355                 360                 365

Gly Ser Gly Lys Ser Ser Leu Val Gln Leu Leu Leu Gly Leu Tyr Pro
370                 375                 380

Val Asp Lys Gly Asn Ile Asp Leu Tyr Gln Asn Gly Arg Ser Pro Leu
385                 390                 395                 400

Asn Leu Glu Gln Trp Arg Ser Trp Ile Ala Tyr Val Pro Gln Lys Val
                405                 410                 415

Glu Leu Phe Lys Gly Thr Ile Arg Ser Asn Leu Thr Leu Gly Phe Asn
                420                 425                 430

Gln Glu Val Ser Asp Gln Glu Leu Trp Gln Ala Leu Glu Ile Ala Gln
            435                 440                 445

Ala Lys Asp Phe Val Ser Glu Lys Glu Gly Leu Leu Asp Ala Leu Val
450                 455                 460

Glu Ala Gly Gly Arg Asn Phe Ser Gly Gly Gln Lys Gln Arg Leu Ser
465                 470                 475                 480

Ile Ala Arg Ala Val Leu Arg Gln Ala Pro Phe Leu Ile Leu Asp Asp
                485                 490                 495

Ala Thr Ser Ala Leu Asp Thr Ile Thr Glu Ser Lys Leu Leu Lys Ala
                500                 505                 510

Ile Arg Glu Asn Phe Pro Asn Thr Ser Leu Ile Leu Ile Ser Gln Arg
            515                 520                 525

Thr Ser Thr Leu Gln Met Ala Asp Gln Ile Leu Leu Glu Lys Gly
530                 535                 540

Glu Leu Leu Ala Val Gly Lys His Asp Asp Leu Met Lys Ser Ser Gln
545                 550                 555                 560

Val Tyr Cys Glu Ile Asn Ala Ser Gln His Gly Lys Glu Asp
                565                 570

<210> SEQ ID NO 43
<211> LENGTH: 1224
<212> TYPE: DNA
<213> ORGANISM: Streptococcus pneumoniae

<400> SEQUENCE: 43
atgaaacgtt ctctcgactc aagagtcgat tacagtttgc tcttgccagt attttttcta    60

-continued

```
ctggtcatcg gtgtggtggc tatctatata gccgttagtc atgattatcc caataatatt    120
ctgcccattt tagggcagca ggtcgcctgg attgccttgg ggcttgtgat tggttttgtg    180
gtcatgctct ttaatacaga atttctttgg aaggtgaccc cctttctata tattttaggc    240
ttgggactta tgatcttgcc gattgtattt tataatccaa gcttagttgc atcaacgggt    300
gccaaaaact gggtatcaat aaatggaatt accctattcc aaccgtcaga atttatgaag    360
atatcctata tcctcatgtt ggctcgtgtc attgtccaat ttacaaagaa acataaggaa    420
tggagacgca cggttccgct ggacttttg ttaatttct ggatgattct ctttaccatt      480
ccagtcctag ttcttttagc acttcaaagt gacttgggga cggctttggt ttttgtagcc    540
attttctcag gaatcgtttt attatcaggg gtttcttgga aaattattat cccagtattt    600
gtgactgctg taacaggagt tgctggtttc ttagctatct ttattagcaa ggacggacga    660
gcttttcttc accagattgg aatgccgacc taccaaatta tcggatttt ggcttggctc     720
aatccctttg agtttgccca acaacgact taccagcagg ctcaagggca gattgccatt     780
gggagtggtg gcttatttgg tcagggattt aatgcttcga atctgcttat cccagttcga    840
gagtcagata tgatttttac ggttattgca gaagatttg ctttattgg ctctgtcctg      900
gttattgccc tctatctcat gttgatttac cgtatgttga agattactct taaatcaaat    960
aaccagttct acacttatat ttccacaggt ttgattatga tgttgctctt ccacatcttt    1020
gagaatatcg gtgctgtgac tggactactt cctttgacgg ggattcctt gcctttcatt     1080
tcgcaagggg gatcagctat tatcagtaat ctgattggtg ttggttgct ttatcgatg      1140
agttaccaga ctaatctagc tgaagaaaag agcggaaaag tcccattcaa acggaaaaag    1200
gttgtattaa acaaattaa ataa                                            1224
```

<210> SEQ ID NO 44
<211> LENGTH: 407
<212> TYPE: PRT
<213> ORGANISM: Streptococcus pneumoniae

<400> SEQUENCE: 44

```
Met Lys Arg Ser Leu Asp Ser Arg Val Asp Tyr Ser Leu Leu Leu Pro
  1               5                  10                  15

Val Phe Pro Leu Leu Val Ile Gly Val Val Ala Ile Tyr Ile Ala Val
                 20                  25                  30

Ser His Asp Tyr Pro Asn Asn Ile Leu Pro Ile Leu Gly Gln Gln Val
             35                  40                  45

Ala Trp Ile Ala Leu Gly Leu Val Ile Gly Phe Val Val Met Leu Phe
         50                  55                  60

Asn Thr Glu Phe Leu Trp Lys Val Thr Pro Phe Leu Tyr Ile Leu Gly
 65                  70                  75                  80

Leu Gly Leu Met Ile Leu Pro Ile Val Phe Tyr Asn Pro Ser Leu Val
                 85                  90                  95

Ala Ser Thr Gly Ala Lys Asn Trp Val Ser Ile Asn Gly Ile Thr Leu
            100                 105                 110

Phe Gln Pro Ser Glu Phe Met Lys Ile Ser Tyr Ile Leu Met Leu Ala
        115                 120                 125

Arg Val Ile Val Gln Phe Thr Lys Lys His Lys Glu Trp Arg Arg Thr
    130                 135                 140

Val Pro Leu Asp Phe Leu Leu Ile Phe Trp Met Ile Leu Phe Thr Ile
145                 150                 155                 160

Pro Val Leu Val Leu Leu Ala Leu Gln Ser Asp Leu Gly Thr Ala Leu
                165                 170                 175
```

```
Val Phe Val Ala Ile Phe Ser Gly Ile Val Leu Leu Ser Gly Val Ser
            180                 185                 190

Trp Lys Ile Ile Ile Pro Val Phe Val Thr Ala Val Thr Gly Val Ala
        195                 200                 205

Gly Phe Leu Ala Ile Phe Ile Ser Lys Asp Gly Arg Ala Phe Leu His
210                 215                 220

Gln Ile Gly Met Pro Thr Tyr Gln Ile Asn Arg Ile Leu Ala Trp Leu
225                 230                 235                 240

Asn Pro Phe Glu Phe Ala Gln Thr Thr Thr Tyr Gln Gln Ala Gln Gly
                245                 250                 255

Gln Ile Ala Ile Gly Ser Gly Leu Phe Gly Gln Gly Phe Asn Ala
            260                 265                 270

Ser Asn Leu Leu Ile Pro Val Arg Glu Ser Asp Met Ile Phe Thr Val
            275                 280                 285

Ile Ala Glu Asp Phe Gly Phe Ile Gly Ser Val Leu Val Ile Ala Leu
        290                 295                 300

Tyr Leu Met Leu Ile Tyr Arg Met Leu Lys Ile Thr Leu Lys Ser Asn
305                 310                 315                 320

Asn Gln Phe Tyr Thr Tyr Ile Ser Thr Gly Leu Ile Met Met Leu Leu
                325                 330                 335

Phe His Ile Phe Glu Asn Ile Gly Ala Val Thr Gly Leu Leu Pro Leu
            340                 345                 350

Thr Gly Ile Pro Leu Pro Phe Ile Ser Gln Gly Gly Ser Ala Ile Ile
            355                 360                 365

Ser Asn Leu Ile Gly Val Gly Leu Leu Leu Ser Met Ser Tyr Gln Thr
370                 375                 380

Asn Leu Ala Glu Glu Lys Ser Gly Lys Val Pro Phe Lys Arg Lys Lys
385                 390                 395                 400

Val Val Leu Lys Gln Ile Lys
                405

<210> SEQ ID NO 45
<211> LENGTH: 1104
<212> TYPE: DNA
<213> ORGANISM: Streptococcus pneumoniae

<400> SEQUENCE: 45
atggtggcta agaaaaaaat cttatttttt atgtggtctt tttctcttgg aggtggtgca      60
gagaagattc tatcaaccat tgtttcaaat ctggatccag aaaagtatga tattgatatt     120
cttgaaatgg agcactttga aagggatat gaatctgttc caaagcatgt acgcatttta     180
aaatcccttc aagattatcg ccaaaccaga tggttacgag cttttttgtg agaaatgaga     240 atttatttc caagactgac tcgtcgtttg cttgtaaaag atgattatga tgttgaagtt     300
tcttttacca ttatgaatcc accactgttg ttctctaaaa aagagaagt caagaagata     360 tcttggattc atggaagtat tgaagaactt cttaaggata gctctaaaag agaatcacat     420
agaagccagt tggatgctgc gaatacaatt gtagggattt caaaaaagac cagcaattct     480
atcaaggaag tttatccaga ttatacttct aaattacaga caatctacaa tggatatgat     540
tttcagacta ttctagaaaa atctcaagag aagatcgata tcgagattgc tcctcaaagt     600
atctgtacta tcggacggat tgaggaaaat aagggttctg accgtgtagt ggaagtgata     660
cgattattac accaagaggg aaaaaactat catctctatt ttatcggggc tggtgatatg     720
gaagaggaac tgaaaaaacg agtcaaagag tatgggattg aggactatgt acatttcctt     780
```

```
ggttatcaaa aaaatcctta tcagtatcta tctcagacga aagttctttt gtctatgtct    840
aaacaagaag gttttcctgg agtgtatgtg gaggccttga gtctgggact ccctttatc     900 tctacggacg ttggagggggc tgaggaatta tcccaagaag gacgatttgg acaaatcatt  960
gagagcaatc aagaggcagc tcaggcgatt actaattaca tgacttctgc ctcaaacttt   1020
gatgtcgatg aggctagcca attcattcaa caatttacaa ttacaaaaca aatcgaacaa   1080
gtagaaaaac tattagagga gtag                                          1104
```

<210> SEQ ID NO 46
<211> LENGTH: 367
<212> TYPE: PRT
<213> ORGANISM: Streptococcus pneumoniae

<400> SEQUENCE: 46

Met Val Ala Lys Lys Ile Leu Phe Phe Met Trp Ser Phe Ser Leu
1               5                   10                  15

Gly Gly Gly Ala Glu Lys Ile Leu Ser Thr Ile Val Ser Asn Leu Asp
            20                  25                  30

Pro Glu Lys Tyr Asp Ile Asp Ile Leu Glu Met Glu His Phe Asp Lys
        35                  40                  45

Gly Tyr Glu Ser Val Pro Lys His Val Arg Ile Leu Lys Ser Leu Gln
    50                  55                  60

Asp Tyr Arg Gln Thr Arg Trp Leu Arg Ala Phe Leu Trp Arg Met Arg
65                  70                  75                  80

Ile Tyr Phe Pro Arg Leu Thr Arg Arg Leu Leu Val Lys Asp Asp Tyr
                85                  90                  95

Asp Val Glu Val Ser Phe Thr Ile Met Asn Pro Pro Leu Leu Phe Ser
            100                 105                 110

Lys Arg Arg Glu Val Lys Lys Ile Ser Trp Ile His Gly Ser Ile Glu
        115                 120                 125

Glu Leu Leu Lys Asp Ser Ser Lys Arg Glu Ser His Arg Ser Gln Leu
    130                 135                 140

Asp Ala Ala Asn Thr Ile Val Gly Ile Ser Lys Lys Thr Ser Asn Ser
145                 150                 155                 160

Ile Lys Glu Val Tyr Pro Asp Tyr Thr Ser Lys Leu Gln Thr Ile Tyr
                165                 170                 175

Asn Gly Tyr Asp Phe Gln Thr Ile Leu Glu Lys Ser Gln Glu Lys Ile
            180                 185                 190

Asp Ile Glu Ile Ala Pro Gln Ser Ile Cys Thr Ile Gly Arg Ile Glu
        195                 200                 205

Glu Asn Lys Gly Ser Asp Arg Val Val Glu Val Ile Arg Leu Leu His
    210                 215                 220

Gln Glu Gly Lys Asn Tyr His Leu Tyr Phe Ile Gly Ala Gly Asp Met
225                 230                 235                 240

Glu Glu Glu Leu Lys Lys Arg Val Lys Glu Tyr Gly Ile Glu Asp Tyr
                245                 250                 255

Val His Phe Leu Gly Tyr Gln Lys Asn Pro Tyr Gln Tyr Leu Ser Gln
            260                 265                 270

Thr Lys Val Leu Leu Ser Met Ser Lys Gln Glu Gly Phe Pro Gly Val
        275                 280                 285

Tyr Val Glu Ala Leu Ser Leu Gly Leu Pro Phe Ile Ser Thr Asp Val
    290                 295                 300

Gly Gly Ala Glu Glu Leu Ser Gln Glu Gly Arg Phe Gly Gln Ile Ile
305                 310                 315                 320

Glu Ser Asn Gln Glu Ala Ala Gln Ala Ile Thr Asn Tyr Met Thr Ser
            325                 330                 335

Ala Ser Asn Phe Asp Val Asp Glu Ala Ser Gln Phe Ile Gln Gln Phe
        340                 345                 350

Thr Ile Thr Lys Gln Ile Glu Gln Val Glu Lys Leu Leu Glu Glu
        355                 360                 365

<210> SEQ ID NO 47
<211> LENGTH: 987
<212> TYPE: DNA
<213> ORGANISM: Streptococcus pneumoniae

<400> SEQUENCE: 47

```
atggaaactg cattaattag tgtgattgtg ccagtctata atgtggcgca gtacctagaa    60
aaatcgatag cttccattca gaagcagacc tatcaaaatc tggaaattat tcttgttgat   120
gatggtgcaa cagatgaaag tggtcgcttg tgtgattcaa tcgctgaaca agatgacagg   180
gtgtcagtgc ttcataaaaa gaacgaagga ttgtcgcaag cacgaaatga tgggatgaag   240
caggctcacg gggattatct gatttttatt gactcagatg attatatcca tccagaaatg   300
attcagagct tatatgagca attagttcaa gaagatgcgg atgtttcgag ctgtggtgtc   360
atgaatgtct atgctaatga tgaaagccca cagtcagcca atcaggatga ctattttgtc   420
tgtgattctc aaacatttct aaaggaatac ctcataggtg aaaaaatacc tgggacgatt   480
tgcaataagc taatcaagag acagattgca actgccctat cctttcctaa ggggttgatt   540
tacgaagatg cctattacca ttttgattta atcaagttgg ccaagaagta tgtggttaat   600
actaaaccct attattacta tttccataga ggggatagta ttacgaccaa accctatgca   660
gagaaggatt tagcctatat tgatatctac caaaagtttt ataatgaagt tgtgaaaaac   720
tatcctgact tgaaagaggt cgcttttttc agattggcct atgcccactt ctttattctg   780
gataagatgt tgctagatga tcagtataaa cagtttgaag cctattctca gattcatcgt   840
ttttttaaaag gccatgcctt tgctatttct aggaatccaa ttttccgtaa ggggagaaga   900
attagtgctt tggccctatt cataaatatt tccttatatc gattcttatt actgaaaaat   960
attgaaaaat ctaaaaaatt acattag                                       987
```

<210> SEQ ID NO 48
<211> LENGTH: 328
<212> TYPE: PRT
<213> ORGANISM: Streptococcus pneumoniae

<400> SEQUENCE: 48

Met Glu Thr Ala Leu Ile Ser Val Ile Val Pro Val Tyr Asn Val Ala
 1               5                  10                  15

Gln Tyr Leu Glu Lys Ser Ile Ala Ser Ile Gln Lys Gln Thr Tyr Gln
            20                  25                  30

Asn Leu Glu Ile Ile Leu Val Asp Asp Gly Ala Thr Asp Glu Ser Gly
        35                  40                  45

Arg Leu Cys Asp Ser Ile Ala Glu Gln Asp Asp Arg Val Ser Val Leu
    50                  55                  60

His Lys Lys Asn Glu Gly Leu Ser Gln Ala Arg Asn Asp Gly Met Lys
65                  70                  75                  80

Gln Ala His Gly Asp Tyr Leu Ile Phe Ile Asp Ser Asp Asp Tyr Ile
                85                  90                  95

His Pro Glu Met Ile Gln Ser Leu Tyr Glu Gln Leu Val Gln Glu Asp
            100                 105                 110

-continued

```
Ala Asp Val Ser Ser Cys Gly Val Met Asn Val Tyr Ala Asn Asp Glu
            115                 120                 125

Ser Pro Gln Ser Ala Asn Gln Asp Asp Tyr Phe Val Cys Asp Ser Gln
        130                 135                 140

Thr Phe Leu Lys Glu Tyr Leu Ile Gly Glu Lys Ile Pro Gly Thr Ile
145                 150                 155                 160

Cys Asn Lys Leu Ile Lys Arg Gln Ile Ala Thr Ala Leu Ser Phe Pro
                165                 170                 175

Lys Gly Leu Ile Tyr Glu Asp Ala Tyr Tyr His Phe Asp Leu Ile Lys
            180                 185                 190

Leu Ala Lys Lys Tyr Val Val Asn Thr Lys Pro Tyr Tyr Tyr Tyr Phe
        195                 200                 205

His Arg Gly Asp Ser Ile Thr Thr Lys Pro Tyr Ala Glu Lys Asp Leu
    210                 215                 220

Ala Tyr Ile Asp Ile Tyr Gln Lys Phe Tyr Asn Glu Val Val Lys Asn
225                 230                 235                 240

Tyr Pro Asp Leu Lys Glu Val Ala Phe Phe Arg Leu Ala Tyr Ala His
                245                 250                 255

Phe Phe Ile Leu Asp Lys Met Leu Leu Asp Asp Gln Tyr Lys Gln Phe
            260                 265                 270

Glu Ala Tyr Ser Gln Ile His Arg Phe Leu Lys Gly His Ala Phe Ala
        275                 280                 285

Ile Ser Arg Asn Pro Ile Phe Arg Lys Gly Arg Arg Ile Ser Ala Leu
    290                 295                 300

Ala Leu Phe Ile Asn Ile Ser Leu Tyr Arg Phe Leu Leu Leu Lys Asn
305                 310                 315                 320

Ile Glu Lys Ser Lys Lys Leu His
                325

<210> SEQ ID NO 49
<211> LENGTH: 735
<212> TYPE: DNA
<213> ORGANISM: Streptococcus pneumoniae

<400> SEQUENCE: 49
atgagaatca aagagaaaac caataatatt aatggaggaa taaaaaatgt aagtaagcat      60
tatggtcatt caatcattct caaagatata aattttgcac ttaacaaggg tgaaattgtt     120
ggtctagcag ggagaaatgg agttggtaag agtacgttga tgaaaattct tgttcagaat     180
aatcaaccga cttcaggtaa tattataagc agtgataatg ttgggtattt aatcgaagaa     240
ccaaaattat ttttatctaa aacaggttta gagaatttaa atatttgtc aaatttatat      300 ggtgttgact acaatcaaga aagatttaga tgtttgatcc aagagttaga tttgactcag     360
tctattaata aaaagtaaa gacctattct ttgggtacaa acaaaaatt agctttgctt      420 ctaactctcg ttacggaacc tgatatattg attttagatg aaccgactaa tggtttagat      480
attgaatcat cacaaatagt tttagcggtt ctaaaaaaat tagctttaca tgaaaatgtg     540
ggaattttaa tatcgagtca taaattagaa gacattgaag aaatttgtga gagagttctt      600
ttcttggaga acgggctttt gacatttcaa aaagtaggaa agatagtca taatttcttg      660 tttgagatag cttttttcatc agctacagat agagacattt tcattaccaa acaagaattt      720
tgggatattg tttag                                                        735

<210> SEQ ID NO 50
<211> LENGTH: 244
<212> TYPE: PRT
```

<213> ORGANISM: Streptococcus pneumoniae

<400> SEQUENCE: 50

```
Met Arg Ile Lys Glu Lys Thr Asn Asn Ile Asn Gly Gly Ile Lys Asn
 1               5                  10                  15
Val Ser Lys His Tyr Gly His Ser Ile Ile Leu Lys Asp Ile Asn Phe
                20                  25                  30
Ala Leu Asn Lys Gly Glu Ile Val Gly Leu Ala Gly Arg Asn Gly Val
            35                  40                  45
Gly Lys Ser Thr Leu Met Lys Ile Leu Val Gln Asn Asn Gln Pro Thr
        50                  55                  60
Ser Gly Asn Ile Ile Ser Ser Asp Asn Val Gly Tyr Leu Ile Glu Glu
 65                  70                  75                  80
Pro Lys Leu Phe Leu Ser Lys Thr Gly Leu Glu Asn Leu Lys Tyr Leu
                85                  90                  95
Ser Asn Leu Tyr Gly Val Asp Tyr Asn Gln Glu Arg Phe Arg Cys Leu
               100                 105                 110
Ile Gln Glu Leu Asp Leu Thr Gln Ser Ile Asn Lys Lys Val Lys Thr
           115                 120                 125
Tyr Ser Leu Gly Thr Lys Gln Lys Leu Ala Leu Leu Thr Leu Val
       130                 135                 140
Thr Glu Pro Asp Ile Leu Ile Leu Asp Glu Pro Thr Asn Gly Leu Asp
145                 150                 155                 160
Ile Glu Ser Ser Gln Ile Val Leu Ala Val Leu Lys Lys Leu Ala Leu
               165                 170                 175
His Glu Asn Val Gly Ile Leu Ile Ser Ser His Lys Leu Glu Asp Ile
           180                 185                 190
Glu Glu Ile Cys Glu Arg Val Leu Phe Leu Glu Asn Gly Leu Leu Thr
       195                 200                 205
Phe Gln Lys Val Gly Lys Asp Ser His Asn Phe Leu Phe Glu Ile Ala
   210                 215                 220
Phe Ser Ser Ala Thr Asp Arg Asp Ile Phe Ile Thr Lys Gln Glu Phe
225                 230                 235                 240
Trp Asp Ile Val
```

<210> SEQ ID NO 51
<211> LENGTH: 1704
<212> TYPE: DNA
<213> ORGANISM: Streptococcus pneumoniae

<400> SEQUENCE: 51

```
atgactgaat tagataaacg tcaccgcagt agcatttatg acagcatggt taaatcacct    60
aaccgtgcta tgcttcgtgc gactggtatg acagataagg actttgaaac atcgattgtg   120
ggagtgattt cgacttgggc ggaaaataca ccatgtaaca ttcacttgca tgatttcggg   180
aaactggcta agaaggtgt caaatctgca ggcgcttggc ctgtacagtt tggaaccatt   240
accgtagcgg acgggatcgc tatgggaacg cctggtatgc gtttctctct aacatctcgt   300
gacatcatcg cggactccat cgaggcggct atgagtggtc acaacgtgga tgccttcgtc   360
gctatcggtg gctgtgacaa gaacatgcct ggatctatga ttgctattgc taatatggat   420
atcccagcta ttttcgccta tggtggaact attgcaccgg aaatcttga tggtaaagat   480
atcgacttgg tttctgtctt tgaaggtatc ggaaaatgga accacggtga catgacagct   540
gaggacgtga acgtcttga atgtaatgcc tgccctggcc ctggtggttg tggtggtatg   600
tatactgcta ataccatggc aactgctatc gaagttctag ggatgagttt gccagggtca   660
```

-continued

```
tcctctcacc cagctgaatc agctgataag aaagaagata tcgaagcagc aggacgtgct    720
gttgttaaga tgttggaact tggtctcaaa ccatcagata tcttgactcg tgaagccttt    780
gaagatgcta tcactgtaac gatggctctc ggtggttcta caaacgccac tcttcacttg    840
ctcgccattg cccatgccgc aaatgttgac ttgtcacttg aggacttcaa tacgattcaa    900
gaacgtgtgc ctcacttggc cgacttgaaa ccatctggtc agtatgtctt ccaagacctc    960
tacgaagtcg gtggtgtccc tgcggttatg aagtatttgt tggcaaatgg tttccttcac   1020
ggagatcgca tcacatgtac tggtaagact gtagctgaaa acttggctga ctttgcagac   1080
ttgactccag gccaaaaagt tatcatgcca cttgaaaatc aaaacgtgc ggatggtccg    1140
cttatcatct tgaacgggaa ccttgctcct gacggtgcag ttgccaaggt atcaggtgtt   1200
aaagtgcgtc gtcacgttgg gccagctaag gtctttgact cagaagaaga tgcgattcag   1260
gccgttctga cagatgaaat cgttgatggc gatgtagtcg ttgttcgttt tgttggacct   1320
aaaggtggtc ctggtatgcc tgagatgcta tcactttctt caatgattgt tggtaaaggt   1380
cagggagata aggtggccct cttgacggac ggacgtttct ctggtggtac ttatggtctg   1440
gttgttggac atatcgctcc tgaagctcag gatggtggac caattgccta tctccgtacc   1500
ggcgatatcg ttacggttga ccaagatacc aaagaaattt ctatggccgt atccgaagaa   1560
gaacttgaaa aacgcaaggc agaaacaacc ttgccaccac tttacagccg tggtgtcctc   1620
ggtaaatatg cccacatcgt atcatctgct tcacgcggag ccgtgacaga cttctggaat   1680
atggacaagt caggtaaaaa ataa                                           1704
```

<210> SEQ ID NO 52
<211> LENGTH: 567
<212> TYPE: PRT
<213> ORGANISM: Streptococcus pneumoniae

<400> SEQUENCE: 52

```
Met Thr Glu Leu Asp Lys Arg His Arg Ser Ser Ile Tyr Asp Ser Met
 1               5                  10                  15

Val Lys Ser Pro Asn Arg Ala Met Leu Arg Ala Thr Gly Met Thr Asp
            20                  25                  30

Lys Asp Phe Glu Thr Ser Ile Val Gly Val Ile Ser Thr Trp Ala Glu
        35                  40                  45

Asn Thr Pro Cys Asn Ile His Leu His Asp Phe Gly Lys Leu Ala Lys
    50                  55                  60

Glu Gly Val Lys Ser Ala Gly Ala Trp Pro Val Gln Phe Gly Thr Ile
65                  70                  75                  80

Thr Val Ala Asp Gly Ile Ala Met Gly Thr Pro Gly Met Arg Phe Ser
                85                  90                  95

Leu Thr Ser Arg Asp Ile Ile Ala Asp Ser Ile Glu Ala Ala Met Ser
            100                 105                 110

Gly His Asn Val Asp Ala Phe Val Ala Ile Gly Gly Cys Asp Lys Asn
        115                 120                 125

Met Pro Gly Ser Met Ile Ala Ile Ala Asn Met Asp Ile Pro Ala Ile
    130                 135                 140

Phe Ala Tyr Gly Gly Thr Ile Ala Pro Gly Asn Leu Asp Gly Lys Asp
145                 150                 155                 160

Ile Asp Leu Val Ser Val Phe Glu Gly Ile Gly Lys Trp Asn His Gly
                165                 170                 175

Asp Met Thr Ala Glu Asp Val Lys Arg Leu Glu Cys Asn Ala Cys Pro
            180                 185                 190
```

Gly Pro Gly Gly Cys Gly Gly Met Tyr Thr Ala Asn Thr Met Ala Thr
            195                 200                 205

Ala Ile Glu Val Leu Gly Met Ser Leu Pro Gly Ser Ser His Pro
210                 215                 220

Ala Glu Ser Ala Asp Lys Lys Glu Asp Ile Glu Ala Ala Gly Arg Ala
225                 230                 235                 240

Val Val Lys Met Leu Glu Leu Gly Leu Lys Pro Ser Asp Ile Leu Thr
            245                 250                 255

Arg Glu Ala Phe Glu Asp Ala Ile Thr Val Thr Met Ala Leu Gly Gly
            260                 265                 270

Ser Thr Asn Ala Thr Leu His Leu Leu Ala Ile Ala His Ala Ala Asn
            275                 280                 285

Val Asp Leu Ser Leu Glu Asp Phe Asn Thr Ile Gln Glu Arg Val Pro
            290                 295                 300

His Leu Ala Asp Leu Lys Pro Ser Gly Gln Tyr Val Phe Gln Asp Leu
305                 310                 315                 320

Tyr Glu Val Gly Gly Val Pro Ala Val Met Lys Tyr Leu Leu Ala Asn
            325                 330                 335

Gly Phe Leu His Gly Asp Arg Ile Thr Cys Thr Gly Lys Thr Val Ala
            340                 345                 350

Glu Asn Leu Ala Asp Phe Ala Asp Leu Thr Pro Gly Gln Lys Val Ile
            355                 360                 365

Met Pro Leu Glu Asn Pro Lys Arg Ala Asp Gly Pro Leu Ile Ile Leu
            370                 375                 380

Asn Gly Asn Leu Ala Pro Asp Gly Ala Val Ala Lys Val Ser Gly Val
385                 390                 395                 400

Lys Val Arg Arg His Val Gly Pro Ala Lys Val Phe Asp Ser Glu Glu
            405                 410                 415

Asp Ala Ile Gln Ala Val Leu Thr Asp Glu Ile Val Asp Gly Asp Val
            420                 425                 430

Val Val Val Arg Phe Val Gly Pro Lys Gly Gly Pro Gly Met Pro Glu
            435                 440                 445

Met Leu Ser Leu Ser Ser Met Ile Val Gly Lys Gly Gln Gly Asp Lys
            450                 455                 460

Val Ala Leu Leu Thr Asp Gly Arg Phe Ser Gly Gly Thr Tyr Gly Leu
465                 470                 475                 480

Val Val Gly His Ile Ala Pro Glu Ala Gln Asp Gly Gly Pro Ile Ala
            485                 490                 495

Tyr Leu Arg Thr Gly Asp Ile Val Thr Val Asp Gln Asp Thr Lys Glu
            500                 505                 510

Ile Ser Met Ala Val Ser Glu Glu Leu Glu Lys Arg Lys Ala Glu
            515                 520                 525

Thr Thr Leu Pro Pro Leu Tyr Ser Arg Gly Val Leu Gly Lys Tyr Ala
530                 535                 540

His Ile Val Ser Ser Ala Ser Arg Gly Ala Val Thr Asp Phe Trp Asn
545                 550                 555                 560

Met Asp Lys Ser Gly Lys Lys
            565

<210> SEQ ID NO 53
<211> LENGTH: 274
<212> TYPE: DNA
<213> ORGANISM: Streptococcus pneumoniae

<400> SEQUENCE: 53

```
atgttataat aaaaataaag aatttaagga gaaatacaat atgtcaattt ttattggagg    60
agcatggcca tatgcaaacg gttcgttaca tattggtcac gcggcagcgc ttttaccggg   120
ggatattctt gcaagatact atcgtcagaa gggagaggaa gttttatatg tttctggaag   180
tgattgtaat ggaaccccta tttctatcag agctaaaaaa gaaataagt ctgtgaaaga    240 aattgctgat ttttatcata aggaatttaa tcca                               274
```

<210> SEQ ID NO 54
<211> LENGTH: 91
<212> TYPE: PRT
<213> ORGANISM: Streptococcus pneumoniae

<400> SEQUENCE: 54

```
Cys Tyr Asn Lys Asn Lys Glu Phe Lys Glu Lys Tyr Asn Met Ser Ile
  1               5                  10                  15

Phe Ile Gly Gly Ala Trp Pro Tyr Ala Asn Gly Ser Leu His Ile Gly
             20                  25                  30

His Ala Ala Leu Leu Pro Gly Asp Ile Leu Ala Arg Tyr Tyr Arg
         35                  40                  45

Gln Lys Gly Glu Glu Val Leu Tyr Val Ser Gly Ser Asp Cys Asn Gly
     50                  55                  60

Thr Pro Ile Ser Ile Arg Ala Lys Lys Glu Asn Lys Ser Val Lys Glu
 65                  70                  75                  80

Ile Ala Asp Phe Tyr His Lys Glu Phe Asn Pro
             85                  90
```

<210> SEQ ID NO 55
<211> LENGTH: 1065
<212> TYPE: DNA
<213> ORGANISM: Streptococcus pneumoniae

<400> SEQUENCE: 55

```
atgacaacat tattttcaaa aattaagaa gtaacagaac ttgctgcagt ctcaggtcat     60
gaagcgcctg tccgtgctta tcttcgtgaa aagttgacac cgcatgtgga tgaagtggtg   120
acagatggct ggttggtat ttttggtatc aaacattcag aagctgtgga tgcaccgcgc    180
gtcttggtcg cttctcatat ggacgaagtt ggttttatgg tcagcgaaat caagccagat   240
ggtaccttcc gtgtcgtaga atcggtggc tggaacccca tggtggttag cagccaacgt    300
ttcaaactct tgactcgtga tggtcatgaa attcctgtga tttcaggttc tgttcctccg   360
catttgactc gtggaaaggg gggaccaacc atgccagcca ttgccgatat cgttttttgat  420 ggtggttttg cggacaaggc tgaggcagaa agttttggca tccgtcctgg tgataccatt   480
gtaccagata gttctgcaat tttgacagcc aatgaaaaaa atatcatctc aaaagcttgg   540
gataaccgct acggtgtcct catggtaagc gagctagctg aagctttatc gggtcaaaaa   600
ctcggcaatg aactctatct gggttctaac gtccaagaag aagttggtct gcgtggcgct   660
catacctcta caaccaagtt tgacccagaa gtcttcctcg cagttgattg ctcaccagca   720
ggtgatgtct acggtggtca aggcaagatt ggagatggaa ccttgattcg tttctatgat   780
ccaggtcact tgcttctccc agggatgaag gatttccttt tgacaacggc tgaagaagct   840
ggtatcaagt accaatacta ctgtggtaaa gcggaacag atgcaggtgc agctcatctg    900
aaaaatggtg gtgtcccatc aacaactatc ggtgtctgcg ctcgttatat ccattctcac   960
caaaccctct atgcaatgga tgacttccta gaagcgcaag ctttcttaca agccttggtg  1020
aagaaattgg atcgttcaac ggttgatttg attaaacatt attaa                  1065
```

<210> SEQ ID NO 56
<211> LENGTH: 354
<212> TYPE: PRT
<213> ORGANISM: Streptococcus pneumoniae

<400> SEQUENCE: 56

```
Met Thr Thr Leu Phe Ser Lys Ile Lys Glu Val Thr Glu Leu Ala Ala
  1               5                  10                  15

Val Ser Gly His Glu Ala Pro Val Arg Ala Tyr Leu Arg Glu Lys Leu
                 20                  25                  30

Thr Pro His Val Asp Glu Val Val Thr Asp Gly Leu Gly Gly Ile Phe
             35                  40                  45

Gly Ile Lys His Ser Glu Ala Val Asp Ala Pro Arg Val Leu Val Ala
         50                  55                  60

Ser His Met Asp Glu Val Gly Phe Met Val Ser Glu Ile Lys Pro Asp
 65                  70                  75                  80

Gly Thr Phe Arg Val Val Glu Ile Gly Gly Trp Asn Pro Met Val Val
                 85                  90                  95

Ser Ser Gln Arg Phe Lys Leu Leu Thr Arg Asp Gly His Glu Ile Pro
                100                 105                 110

Val Ile Ser Gly Ser Val Pro Pro His Leu Thr Arg Gly Lys Gly Gly
            115                 120                 125

Pro Thr Met Pro Ala Ile Ala Asp Ile Val Phe Asp Gly Gly Phe Ala
        130                 135                 140

Asp Lys Ala Glu Ala Ser Phe Gly Ile Arg Pro Gly Asp Thr Ile
145                 150                 155                 160

Val Pro Asp Ser Ser Ala Ile Leu Thr Ala Asn Glu Lys Asn Ile Ile
                165                 170                 175

Ser Lys Ala Trp Asp Asn Arg Tyr Gly Val Leu Met Val Ser Glu Leu
                180                 185                 190

Ala Glu Ala Leu Ser Gly Gln Lys Leu Gly Asn Glu Leu Tyr Leu Gly
            195                 200                 205

Ser Asn Val Gln Glu Val Gly Leu Arg Gly Ala His Thr Ser Thr
        210                 215                 220

Thr Lys Phe Asp Pro Glu Val Phe Leu Ala Val Asp Cys Ser Pro Ala
225                 230                 235                 240

Gly Asp Val Tyr Gly Gly Gln Gly Lys Ile Gly Asp Gly Thr Leu Ile
                245                 250                 255

Arg Phe Tyr Asp Pro Gly His Leu Leu Pro Gly Met Lys Asp Phe
                260                 265                 270

Leu Leu Thr Thr Ala Glu Glu Ala Gly Ile Lys Tyr Gln Tyr Tyr Cys
        275                 280                 285

Gly Lys Gly Gly Thr Asp Ala Gly Ala Ala His Leu Lys Asn Gly Gly
    290                 295                 300

Val Pro Ser Thr Thr Ile Gly Val Cys Ala Arg Tyr Ile His Ser His
305                 310                 315                 320

Gln Thr Leu Tyr Ala Met Asp Asp Phe Leu Glu Ala Gln Ala Phe Leu
                325                 330                 335

Gln Ala Leu Val Lys Lys Leu Asp Arg Ser Thr Val Asp Leu Ile Lys
            340                 345                 350

His Tyr
```

<210> SEQ ID NO 57
<211> LENGTH: 1182

```
<212> TYPE: DNA
<213> ORGANISM: Streptococcus pneumoniae

<400> SEQUENCE: 57 atggaattttt ctatgaaatc agtcaaagga ctactcttta tcatagctag ttttatcttg      60
actcttttga cttggatgaa cacttctccc caattcatga ttccaggact agctttaaca     120
agcctatctc tgactttat  cctagccact cgtctcccac tactagaaag ctggtttcac     180
agtttggaga aggtctacac cgtccacaaa ttcacagcct ttctctcaat catcctacta     240
atctttcata actttagtat gggcggtttg tggggctctc gcttagctgc tcagtttggc     300
aatcttgcca tctatatctt tgccagcatc atccttgtcg cctatttagg caaatacatc     360
caatacgaag cttggcgatg gattcaccgc ctggtttacc tagcctatat tttaggactc     420
tttcacatct acatgataat gggcaatcgt ctccttacat taatcttct  aagttttctt     480
gttggtagct atgccctttt aggcttacta gctggttttt atatcatttt tctatatcaa     540
aagatttcct tcccctatct agggaaaatt acccatctca aacgcttaaa tcacgatact     600
agagaaattc aaatccatct tagcagacct ttcaactatc aatcaggaca atttgccttt     660
ctaaagattt tccaagaagg ctttgaaagt gctccgcatc ccttttctat ctcaggaggt     720
catggtcaaa ctctttactt tactgttaaa acttcaggcg accataccaa gaatatctat     780
gataatcttc aagccggcag caaagtaacc ctagacagag cttacggaca catgatcata     840
gaagaaggac gagaaaatca ggtttggatt gctggaggta ttgggatcac cccttcatc     900
tcttacatcc gtgaacatcc tattttagat aaacaggttc acttctacta tagcttccgt     960
ggagatgaaa atgcagtcta cctagattta ctccgtaact atgctcagaa aaatcctaat    1020
tttgaactcc atctaatcga cagtacgaaa gacggctatc ttaatttga  acaaaaagaa    1080
gtgcccgaac atgcaaccgt ctatatgtgt ggtcctattt ctatgatgaa ggcacttgcc    1140
aaacagatta agaaacaaaa tccaaaaaca gagcatattt ac                       1182

<210> SEQ ID NO 58
<211> LENGTH: 394
<212> TYPE: PRT
<213> ORGANISM: Streptococcus pneumoniae

<400> SEQUENCE: 58

Met Glu Phe Ser Met Lys Ser Val Lys Gly Leu Leu Phe Ile Ile Ala
  1               5                  10                  15

Ser Phe Ile Leu Thr Leu Leu Thr Trp Met Asn Thr Ser Pro Gln Phe
             20                  25                  30

Met Ile Pro Gly Leu Ala Leu Thr Ser Leu Ser Leu Thr Phe Ile Leu
         35                  40                  45

Ala Thr Arg Leu Pro Leu Leu Glu Ser Trp Phe His Ser Leu Glu Lys
     50                  55                  60

Val Tyr Thr Val His Lys Phe Thr Ala Phe Leu Ser Ile Ile Leu Leu
 65                  70                  75                  80

Ile Phe His Asn Phe Ser Met Gly Gly Leu Trp Gly Ser Arg Leu Ala
                 85                  90                  95

Ala Gln Phe Gly Asn Leu Ala Ile Tyr Ile Phe Ala Ser Ile Ile Leu
            100                 105                 110

Val Ala Tyr Leu Gly Lys Tyr Ile Gln Tyr Glu Ala Trp Arg Trp Ile
        115                 120                 125

His Arg Leu Val Tyr Leu Ala Tyr Ile Leu Gly Leu Phe His Ile Tyr
    130                 135                 140
```

```
Met Ile Met Gly Asn Arg Leu Leu Thr Phe Asn Leu Leu Ser Phe Leu
145                 150                 155                 160

Val Gly Ser Tyr Ala Leu Leu Gly Leu Leu Ala Gly Phe Tyr Ile Ile
                165                 170                 175

Phe Leu Tyr Gln Lys Ile Ser Phe Pro Tyr Leu Gly Lys Ile Thr His
            180                 185                 190

Leu Lys Arg Leu Asn His Asp Thr Arg Glu Ile Gln Ile His Leu Ser
        195                 200                 205

Arg Pro Phe Asn Tyr Gln Ser Gly Gln Phe Ala Phe Leu Lys Ile Phe
    210                 215                 220

Gln Glu Gly Phe Glu Ser Ala Pro His Pro Phe Ser Ile Ser Gly Gly
225                 230                 235                 240

His Gly Gln Thr Leu Tyr Phe Thr Val Lys Thr Ser Gly Asp His Thr
                245                 250                 255

Lys Asn Ile Tyr Asp Asn Leu Gln Ala Gly Ser Lys Val Thr Leu Asp
            260                 265                 270

Arg Ala Tyr Gly His Met Ile Ile Glu Glu Gly Arg Glu Asn Gln Val
        275                 280                 285

Trp Ile Ala Gly Ile Gly Ile Thr Pro Phe Ile Ser Tyr Ile Arg
    290                 295                 300

Glu His Pro Ile Leu Asp Lys Gln Val His Phe Tyr Ser Phe Arg
305                 310                 315                 320

Gly Asp Glu Asn Ala Val Tyr Leu Asp Leu Leu Arg Asn Tyr Ala Gln
                325                 330                 335

Lys Asn Pro Asn Phe Glu Leu His Leu Ile Asp Ser Thr Lys Asp Gly
            340                 345                 350

Tyr Leu Asn Phe Glu Gln Lys Glu Val Pro Glu His Ala Thr Val Tyr
        355                 360                 365

Met Cys Gly Pro Ile Ser Met Met Lys Ala Leu Ala Lys Gln Ile Lys
    370                 375                 380

Lys Gln Asn Pro Lys Thr Glu His Ile Tyr
385                 390
```

<210> SEQ ID NO 59
<211> LENGTH: 900
<212> TYPE: DNA
<213> ORGANISM: Streptococcus pneumoniae

<400> SEQUENCE: 59

```
atgactttta aatcaggctt tgtagccatt ttaggacgtc ccaatgttgg gaagtcaacc      60
ttttaaatc acgttatggg gcaaaagatt gccatcatga gtgacaaggc gcagacaacg     120
cgcaataaaa tcatgggaat ttacacgact gataaggagc aaattgtctt tatcgacaca     180
ccagggattc acaagcctaa aacagctctc ggagatttca tggttgagtc tgcctacagt     240
acccttcgcg aagtggacac tgttcttttc atggtgcctg ctgatgaagc gcgtggtaag     300
ggggacgata tgattatcga gcgtctcaag gctgccaagg ttcctgtgat tttggtggtg     360
aataaaatcg ataaggtcca tccagaccag ctcttgtctc agattgatga cttccgtaat     420
caaatggact taaggaaat tgttccaatc tcagcccttc agggaaataa cgtgtctcgt     480
ctagtggata ttttgagtga aaatctggat gaaggtttcc aatatttccc gtctgatcaa     540
atcacagacc atccagaacg tttcttggtt tcagaaatgg ttcgcgagaa agtcttgcac     600
ctaactcgtg aagagattcc gcattctgta gcagtagttg ttgactctat gaaacgagac     660
gaagagacag acaaggttca catccgtgca accatcatgg tcgagcgcga tagccaaaaa     720
```

```
gggattatca tcggtaaagg tggcgctatg cttaagaaaa tcggtagcat ggcccgtcgt      780
gatatcgaac tcatgctagg agacaaggtc ttcctagaaa cctgggtcaa ggtcaagaaa      840
aactggcgcg ataaaaagct agatttggct gactttggct ataatgaaag agaatactaa      900
```

<210> SEQ ID NO 60
<211> LENGTH: 299
<212> TYPE: PRT
<213> ORGANISM: Streptococcus pneumoniae

<400> SEQUENCE: 60

```
Met Thr Phe Lys Ser Gly Phe Val Ala Ile Leu Gly Arg Pro Asn Val
  1               5                  10                  15

Gly Lys Ser Thr Phe Leu Asn His Val Met Gly Gln Lys Ile Ala Ile
             20                  25                  30

Met Ser Asp Lys Ala Gln Thr Thr Arg Asn Lys Ile Met Gly Ile Tyr
         35                  40                  45

Thr Thr Asp Lys Glu Gln Ile Val Phe Ile Asp Thr Pro Gly Ile His
     50                  55                  60

Lys Pro Lys Thr Ala Leu Gly Asp Phe Met Val Glu Ser Ala Tyr Ser
 65                  70                  75                  80

Thr Leu Arg Glu Val Asp Thr Val Leu Phe Met Val Pro Ala Asp Glu
                 85                  90                  95

Ala Arg Gly Lys Gly Asp Asp Met Ile Ile Glu Arg Leu Lys Ala Ala
            100                 105                 110

Lys Val Pro Val Ile Leu Val Val Asn Lys Ile Asp Lys Val His Pro
        115                 120                 125

Asp Gln Leu Leu Ser Gln Ile Asp Asp Phe Arg Asn Gln Met Asp Phe
    130                 135                 140

Lys Glu Ile Val Pro Ile Ser Ala Leu Gln Gly Asn Asn Val Ser Arg
145                 150                 155                 160

Leu Val Asp Ile Leu Ser Glu Asn Leu Asp Glu Gly Phe Gln Tyr Phe
                165                 170                 175

Pro Ser Asp Gln Ile Thr Asp His Pro Glu Arg Phe Leu Val Ser Glu
            180                 185                 190

Met Val Arg Glu Lys Val Leu His Leu Thr Arg Glu Glu Ile Pro His
        195                 200                 205

Ser Val Ala Val Val Asp Ser Met Lys Arg Asp Glu Glu Thr Asp
    210                 215                 220

Lys Val His Ile Arg Ala Thr Ile Met Val Glu Arg Asp Ser Gln Lys
225                 230                 235                 240

Gly Ile Ile Ile Gly Lys Gly Ala Met Leu Lys Lys Ile Gly Ser
                245                 250                 255

Met Ala Arg Arg Asp Ile Glu Leu Met Leu Gly Asp Lys Val Phe Leu
            260                 265                 270

Glu Thr Trp Val Lys Val Lys Lys Asn Trp Arg Asp Lys Lys Leu Asp
        275                 280                 285

Leu Ala Asp Phe Gly Tyr Asn Glu Arg Glu Tyr
    290                 295
```

<210> SEQ ID NO 61
<211> LENGTH: 855
<212> TYPE: DNA
<213> ORGANISM: Streptococcus pneumoniae

<400> SEQUENCE: 61

```
ctgcttcttg tttttacaga aggaggactt atgcctgaat tacctgaggt tgaaaccgtt       60
```

```
tgtcgtggct tagaaaaatt gattatagga aagaagattt cgagtataga aattcgctac    120
cccaagatga ttaagacgga tttggaagag tttcaaaggg aattgcctag tcagattatc    180
gagtcaatgg gacgtcgtgg aaaatatttg cttttttatc tgacagacaa ggtcttgatt    240
tcccatttgc ggatggaggg caagtatttt tactatccag accaaggacc tgaacgcaag    300
catgcccatg ttttctttca ttttgaagat ggtggcacgc ttgtttatga ggatgttcgc    360
aagtttggaa ccatggaact cttggtgcct gaccttttag acgtctactt tatttctaaa    420
aaattaggtc ctgaaccaag cgaacaagac tttgatttac aggtctttca atctgccctt    480
gccaagtcca aaaagcctat caaatcccat ctcctagacc agaccttggt agctggactt    540
ggcaatatct atgtggatga ggttctctgg cgagctcagg ttcatccagc tagaccttcc    600
cagactttga cagcagaaga agcgactgcc attcatgacc agaccattgc tgttttgggc    660
caggctgttg aaaaaggtgg ctccaccatt cggacttata ccaatgcctt tggggaagat    720
ggaagcatgc aggactttca tcaggtctat gataagactg gtcaagaatg tgtacgctgt    780
ggtaccatca ttgagaaaat tcaactaggc ggacgtggaa cccacttttg tccaaactgt    840
caaaggaggg actga                                                   855
```

<210> SEQ ID NO 62
<211> LENGTH: 284
<212> TYPE: PRT
<213> ORGANISM: Streptococcus pneumoniae

<400> SEQUENCE: 62

```
Met Leu Leu Val Phe Thr Glu Gly Gly Leu Met Pro Glu Leu Pro Glu
  1               5                  10                  15

Val Glu Thr Val Cys Arg Gly Leu Glu Lys Leu Ile Ile Gly Lys Lys
             20                  25                  30

Ile Ser Ser Ile Glu Ile Arg Tyr Pro Lys Met Ile Lys Thr Asp Leu
         35                  40                  45

Glu Glu Phe Gln Arg Glu Leu Pro Ser Gln Ile Ile Glu Ser Met Gly
     50                  55                  60

Arg Arg Gly Lys Tyr Leu Leu Phe Tyr Leu Thr Asp Lys Val Leu Ile
 65                  70                  75                  80

Ser His Leu Arg Met Glu Gly Lys Tyr Phe Tyr Tyr Pro Asp Gln Gly
                 85                  90                  95

Pro Glu Arg Lys His Ala His Val Phe Phe His Phe Glu Asp Gly Gly
            100                 105                 110

Thr Leu Val Tyr Glu Asp Val Arg Lys Phe Gly Thr Met Glu Leu Leu
        115                 120                 125

Val Pro Asp Leu Leu Asp Val Tyr Phe Ile Ser Lys Lys Leu Gly Pro
    130                 135                 140

Glu Pro Ser Glu Gln Asp Phe Asp Leu Gln Val Phe Gln Ser Ala Leu
145                 150                 155                 160

Ala Lys Ser Lys Lys Pro Ile Lys Ser His Leu Leu Asp Gln Thr Leu
                165                 170                 175

Val Ala Gly Leu Gly Asn Ile Tyr Val Asp Glu Val Leu Trp Arg Ala
            180                 185                 190

Gln Val His Pro Ala Arg Pro Ser Gln Thr Leu Thr Ala Glu Glu Ala
        195                 200                 205

Thr Ala Ile His Asp Gln Thr Ile Ala Val Leu Gly Gln Ala Val Glu
    210                 215                 220

Lys Gly Gly Ser Thr Ile Arg Thr Tyr Thr Asn Ala Phe Gly Glu Asp
```

```
225                 230                 235                 240
Gly Ser Met Gln Asp Phe His Gln Val Tyr Asp Lys Thr Gly Gln Glu
                245                 250                 255
Cys Val Arg Cys Gly Thr Ile Ile Glu Lys Ile Gln Leu Gly Gly Arg
            260                 265                 270
Gly Thr His Phe Cys Pro Asn Cys Gln Arg Arg Asp
        275                 280

<210> SEQ ID NO 63
<211> LENGTH: 633
<212> TYPE: DNA
<213> ORGANISM: Streptococcus pneumoniae

<400> SEQUENCE: 63
ttgtccaaac tgtcaaagga gggactgatg gaaaaaatca tcggaatcac tgggggaatt      60
gcctctggta agtcaactgt gacaaatttt ctaagacagc aaggctttca agtagtggat     120
gccgacgcag tcgtccacca actacagaaa cctggtggtc gtctgtttga ggctctagta     180
cagcactttg gcaagaaat cattcttgaa acggagaac tcaatcgccc tctcctagct      240
agtctcatct tttcaaatcc tgatgaacga gaatggtcta agcaaattca aggggagatt     300
atccgtgagg aactggctac tttgagagaa cagttggctc agacagaaga gattttcttc     360
atggatattc ccctactttt tgagcaggac tacagcgatt ggtttgctga cttggttg      420 gtctatgtgg accgagatgc ccaagtggaa cgcttaatga aagggaccag ttgtccaaa      480 gatgaagctg agtctcgtct ggcagcccag tggccttag aaaaaaagaa agatttggcc     540
agccaggttc ttgataataa tggcaatcag aaccagcttc ttaatcaagt gcatatcctt     600
cttgagggag gtaggcaaga tgacagagat taa                                 633

<210> SEQ ID NO 64
<211> LENGTH: 210
<212> TYPE: PRT
<213> ORGANISM: Streptococcus pneumoniae

<400> SEQUENCE: 64

Met Ser Lys Leu Ser Lys Glu Gly Leu Met Gly Lys Ile Ile Gly Ile
  1               5                  10                  15

Thr Gly Gly Ile Ala Ser Gly Lys Ser Thr Val Thr Asn Phe Leu Arg
             20                  25                  30

Gln Gln Gly Phe Gln Val Val Asp Ala Asp Ala Val Val His Gln Leu
         35                  40                  45

Gln Lys Pro Gly Gly Arg Leu Phe Glu Ala Leu Val Gln His Phe Gly
     50                  55                  60

Gln Glu Ile Ile Leu Glu Asn Gly Glu Leu Asn Arg Pro Leu Leu Ala
 65                  70                  75                  80

Ser Leu Ile Phe Ser Asn Pro Asp Glu Arg Glu Trp Ser Lys Gln Ile
                 85                  90                  95

Gln Gly Glu Ile Ile Arg Glu Glu Leu Ala Thr Leu Arg Glu Gln Leu
            100                 105                 110

Ala Gln Thr Glu Glu Ile Phe Phe Met Asp Ile Pro Leu Leu Phe Glu
        115                 120                 125

Gln Asp Tyr Ser Asp Trp Phe Ala Glu Thr Trp Leu Val Tyr Val Asp
    130                 135                 140

Arg Asp Ala Gln Val Glu Arg Leu Met Lys Arg Asp Gln Leu Ser Lys
145                 150                 155                 160

Asp Glu Ala Glu Ser Arg Leu Ala Ala Gln Trp Pro Leu Glu Lys Lys
```

```
                165                 170                 175
Lys Asp Leu Ala Ser Gln Val Leu Asp Asn Asn Gly Asn Gln Asn Gln
        180                 185                 190

Leu Leu Asn Gln Val His Ile Leu Glu Gly Gly Arg Gln Asp Asp
        195                 200                 205

Arg Asp
    210

<210> SEQ ID NO 65
<211> LENGTH: 1269
<212> TYPE: DNA
<213> ORGANISM: Streptococcus pneumoniae

<400> SEQUENCE: 65
ttgataataa tggcaatcag aaccagcttc ttaatcaagt gcatatcctt cttgagggag        60
gtaggcaaga tgacagagat taactggaag gataatctgc gcattgcctg gtttggtaat       120
tttctgacag gagccagtat ttctttggtt gtaccttta tgcccatctt cgtggaaaat        180
ctaggtgtag ggagtcagca agtcgctttt tatgcaggct tagcaatttc tgtctctgct       240
atttccgcgg cgctcttttc tcctatttgg ggtattcttg ctgacaaata cggccgaaaa       300
cccatgatga ttcgggcagg tcttgctatg actatcacta tgggaggctt ggcctttgtc       360
ccaaatatct attggttaat ctttcttcgt ttactaaacg tgtatttgc aggttttgtt        420 cctaatgcaa cggcactgat agccagtcag gttccaaagg agaaatcagg ctctgcctta       480
ggtactttgt ctacaggcgt agttgcaggt actctaactg gtcccttat tggtggcttt        540 atcgcagaat tatttggcat tcgtacagtt ttcttactgg ttggtagttt tctattttta       600 gctgctatt tgactatttg ctttatcaag gaagattttc aaccagtagc caaggaaaag        660
gctattccaa caaaggaatt atttacctcg gttaaatatc cctatctttt gctcaatctc       720 ttttaacca gttttgtcat ccaatttca gctcaatcga ttggccctat tttggctctt        780
tatgtacgcg acttagggca gacagagaat cttcttttg tctctggttt gattgtgtcc       840
agtatgggct tttccagcat gatgagtgca ggagtcatgg gcaagctagg tgacaaggtg       900
ggcaatcatc gtctcttggt tgtcgcccag ttttattcag tcatcatcta tctcctctgt       960
gccaatgcct ctagcccct tcaactagga ctctatcgtt tcctctttgg attgggaacc       1020
ggtgccttga ttcccggggt taatgcccta ctcagcaaaa tgactcccaa agccggcatt      1080
tcgagggtct ttgccttcaa tcaggtattc ttttatctgg gaggtgttgt tggtcccatg      1140
gcaggttctg cagtagcagg tcaatttggc taccatgctg tcttttatgc gacaagcctt      1200
tgtgttgcct ttagttgtct ctttaacctg attcaattc gaacattatt aaaagtaaag      1260
gaaatctag                                                              1269

<210> SEQ ID NO 66
<211> LENGTH: 422
<212> TYPE: PRT
<213> ORGANISM: Streptococcus pneumoniae

<400> SEQUENCE: 66

Met Ile Ile Met Ala Ile Arg Thr Ser Phe Leu Ile Lys Cys Ile Ser
  1               5                  10                  15

Phe Leu Arg Glu Val Gly Lys Met Thr Glu Ile Asn Trp Lys Asp Asn
             20                  25                  30

Leu Arg Ile Ala Trp Phe Gly Asn Phe Leu Thr Gly Ala Ser Ile Ser
         35                  40                  45
```

| | | | | | | | | | | | |
|---|---|---|---|---|---|---|---|---|---|---|---|
|Leu|Val|Val|Pro|Phe|Met|Pro|Ile|Phe|Val|Glu|Asn|Leu|Gly|Val|Gly|
|50| | | | |55| | | | |60| | | | | |

Ser Gln Gln Val Ala Phe Tyr Ala Gly Leu Ala Ile Ser Val Ser Ala
65          70              75              80

Ile Ser Ala Ala Leu Phe Ser Pro Ile Trp Gly Ile Leu Ala Asp Lys
        85              90              95

Tyr Gly Arg Lys Pro Met Met Ile Arg Ala Gly Leu Ala Met Thr Ile
            100             105             110

Thr Met Gly Gly Leu Ala Phe Val Pro Asn Ile Tyr Trp Leu Ile Phe
        115             120             125

Leu Arg Leu Leu Asn Gly Val Phe Ala Gly Phe Val Pro Asn Ala Thr
130             135             140

Ala Leu Ile Ala Ser Gln Val Pro Lys Glu Lys Ser Gly Ser Ala Leu
145             150             155             160

Gly Thr Leu Ser Thr Gly Val Val Ala Gly Thr Leu Thr Gly Pro Phe
            165             170             175

Ile Gly Gly Phe Ile Ala Glu Leu Phe Gly Ile Arg Thr Val Phe Leu
            180             185             190

Leu Val Gly Ser Phe Leu Phe Leu Ala Ala Ile Leu Thr Ile Cys Phe
            195             200             205

Ile Lys Glu Asp Phe Gln Pro Val Ala Lys Glu Lys Ala Ile Pro Thr
210             215             220

Lys Glu Leu Phe Thr Ser Val Lys Tyr Pro Tyr Leu Leu Asn Leu
225             230             235             240

Phe Leu Thr Ser Phe Val Ile Gln Phe Ser Ala Gln Ser Ile Gly Pro
            245             250             255

Ile Leu Ala Leu Tyr Val Arg Asp Leu Gly Gln Thr Glu Asn Leu Leu
            260             265             270

Phe Val Ser Gly Leu Ile Val Ser Ser Met Gly Phe Ser Ser Met Met
            275             280             285

Ser Ala Gly Val Met Gly Lys Leu Gly Asp Lys Val Gly Asn His Arg
            290             295             300

Leu Leu Val Val Ala Gln Phe Tyr Ser Val Ile Ile Tyr Leu Leu Cys
305             310             315             320

Ala Asn Ala Ser Ser Pro Leu Gln Leu Gly Leu Tyr Arg Phe Leu Phe
            325             330             335

Gly Leu Gly Thr Gly Ala Leu Ile Pro Gly Val Asn Ala Leu Leu Ser
            340             345             350

Lys Met Thr Pro Lys Ala Gly Ile Ser Arg Val Phe Ala Phe Asn Gln
            355             360             365

Val Phe Phe Tyr Leu Gly Gly Val Val Gly Pro Met Ala Gly Ser Ala
            370             375             380

Val Ala Gly Gln Phe Gly Tyr His Ala Val Phe Tyr Ala Thr Ser Leu
385             390             395             400

Cys Val Ala Phe Ser Cys Leu Phe Asn Leu Ile Gln Phe Arg Thr Leu
            405             410             415

Leu Lys Val Lys Glu Ile
            420

<210> SEQ ID NO 67
<211> LENGTH: 1311
<212> TYPE: DNA
<213> ORGANISM: Streptococcus pneumoniae

<400> SEQUENCE: 67

```
atggccctac caactattgc cattgtagga cgtcccaatg ttgggaaatc aaccctattt      60
aatcggatcg ctggtgagcg aatctccatt gtagaagatg tcgaaggagt gacacgtgac     120
cgtatttatg caacgggtga gtggctcaat cgttctttta gcatgattga tacaggagga     180
attgatgatg tcgatgctcc tttcatggaa caaatcaagc accaggcaga aattgccatg     240
gaagaagcag atgttatcgt ttttgtcgtg tctggtaagg aaggaattac tgatgcagac     300
gaatacgtag ctcgtaagct ttataagacc cacaaaccag ttatcctcgc agtcaacaag     360
gtggacaacc ctgagatgag aaatgatata tatgatttct atgctctcgg tttgggtgaa     420
ccattgccta tctcatctgt ccatggaatc ggtacagggg atgtgctaga tgcgatcgta     480
gaaaatcttc caaatgaata tgaggaagaa atccagatg tcattaagtt tagcttgatt      540
ggtcgtccta acgttggaaa atcaagcttg atcaatgcta tcttgggaga agaccgtgtt     600
attgctagtc ctgttgctgg aacaactcgt gatgccattg atacccactt tacagataca     660
gatggtcaag agtttaccat gattgatacg gctggtatgc gtaagtctgg taaggtttat     720
gaaaatactg agaaatactc tgttatgcgt gccatgcgtg ctattgaccg ttcagatgtg     780
gtcttgatgg tcatcaatgc ggaagaaggc attcgtgagt acgacaagcg tatcgcagga     840
tttgcccatg aagctggtaa agggatgatt atcgtggtca acaagtggga tacgcttgaa     900
aaagataacc acactatgaa aaactgggaa gaagatatcc gtgagcagtt ccaatacctg     960
ccttacgcac cgattatctt tgtatcagct ttaaccaagc aacgtctcca caaacttcct    1020
gagatgatta gcaaatcag cgaaagtcaa aatacacgta ttccatcagc tgtcttgaac    1080
gatgtcatca tggatgccat tgccatcaac ccaacaccga cagacaaagg aaaacgtctc    1140
aagattttct atgcgaccca gtggcaacc aaaccaccaa cctttgtcat ctttgtcaat     1200
gaagaagaac tcatgcactt tcttacctg cgtttcttgg aaaatcaaat ccgcaaggcc     1260
tttgttttg agggaacacc gattcatctc atcgcaagaa aacgcaaata a              1311
```

```
<210> SEQ ID NO 68
<211> LENGTH: 436
<212> TYPE: PRT
<213> ORGANISM: Streptococcus pneumoniae

<400> SEQUENCE: 68
```

Met Ala Leu Pro Thr Ile Ala Ile Val Gly Arg Pro Asn Val Gly Lys
1               5                   10                  15

Ser Thr Leu Phe Asn Arg Ile Ala Gly Glu Arg Ile Ser Ile Val Glu
            20                  25                  30

Asp Val Glu Gly Val Thr Arg Asp Arg Ile Tyr Ala Thr Gly Glu Trp
        35                  40                  45

Leu Asn Arg Ser Phe Ser Met Ile Asp Thr Gly Gly Ile Asp Asp Val
    50                  55                  60

Asp Ala Pro Phe Met Glu Gln Ile Lys His Gln Ala Glu Ile Ala Met
65                  70                  75                  80

Glu Glu Ala Asp Val Ile Val Phe Val Val Ser Gly Lys Glu Gly Ile
                85                  90                  95

Thr Asp Ala Asp Glu Tyr Val Ala Arg Lys Leu Tyr Lys Thr His Lys
            100                 105                 110

Pro Val Ile Leu Ala Val Asn Lys Val Asp Asn Pro Glu Met Arg Asn
        115                 120                 125

Asp Ile Tyr Asp Phe Tyr Ala Leu Gly Leu Gly Glu Pro Leu Pro Ile
    130                 135                 140

Ser Ser Val His Gly Ile Gly Thr Gly Asp Val Leu Asp Ala Ile Val

```
                145                 150                 155                 160
Glu Asn Leu Pro Asn Glu Tyr Glu Glu Asn Pro Asp Val Ile Lys
                    165                 170                 175
Phe Ser Leu Ile Gly Arg Pro Asn Val Gly Lys Ser Ser Leu Ile Asn
                    180                 185                 190
Ala Ile Leu Gly Glu Asp Arg Val Ile Ala Ser Pro Val Ala Gly Thr
                    195                 200                 205
Thr Arg Asp Ala Ile Asp Thr His Phe Thr Asp Thr Gly Gln Glu
    210                 215                 220
Phe Thr Met Ile Asp Thr Ala Gly Met Arg Lys Ser Gly Lys Val Tyr
225                 230                 235                 240
Glu Asn Thr Glu Lys Tyr Ser Val Met Arg Ala Met Arg Ala Ile Asp
                245                 250                 255
Arg Ser Asp Val Val Leu Met Val Ile Asn Ala Glu Glu Gly Ile Arg
                260                 265                 270
Glu Tyr Asp Lys Arg Ile Ala Gly Phe Ala His Glu Ala Gly Lys Gly
                275                 280                 285
Met Ile Ile Val Val Asn Lys Trp Asp Thr Leu Glu Lys Asp Asn His
    290                 295                 300
Thr Met Lys Asn Trp Glu Glu Asp Ile Arg Glu Gln Phe Gln Tyr Leu
305                 310                 315                 320
Pro Tyr Ala Pro Ile Ile Phe Val Ser Ala Leu Thr Lys Gln Arg Leu
                325                 330                 335
His Lys Leu Pro Glu Met Ile Lys Gln Ile Ser Glu Ser Gln Asn Thr
                340                 345                 350
Arg Ile Pro Ser Ala Val Leu Asn Asp Val Ile Met Asp Ala Ile Ala
                355                 360                 365
Ile Asn Pro Thr Pro Thr Asp Lys Gly Lys Arg Leu Lys Ile Phe Tyr
    370                 375                 380
Ala Thr Gln Val Ala Thr Lys Pro Pro Thr Phe Val Ile Phe Val Asn
385                 390                 395                 400
Glu Glu Glu Leu Met His Phe Ser Tyr Leu Arg Phe Leu Glu Asn Gln
                405                 410                 415
Ile Arg Lys Ala Phe Val Phe Glu Gly Thr Pro Ile His Leu Ile Ala
                420                 425                 430
Arg Lys Arg Lys
    435

<210> SEQ ID NO 69
<211> LENGTH: 714
<212> TYPE: DNA
<213> ORGANISM: Streptococcus pneumoniae

<400> SEQUENCE: 69
atgacagaaa ccattaaatt gatgaaggct catacttcag tgcgcaggtt taaagagcaa      60
gaaattcccc aagtagactt aaatgagatt ttgacagcag cccagatggc atcatcttgg     120
aagaatttcc aatcctactc tgtgattgtg gtacgaagtc aagagaagaa agatgccttg     180
tatgaattgg tacctcaaga agccattcgc cagtctgctg ttttccttct ctttgtcgga     240
gatttgaacc gagcagaaaa gggagcccga cttcataccg acaccttcca accccaaggt     300
gtggaaggtc tcttgattag ttcggtcgat gcagctcttg ctggacaaaa cgccttgttg     360
gcagctgaaa gctgggcta tgtggtgtg attatcggtt tggttcgata caagtctgaa     420
gaagtggcag agctctttaa cctacctgac tacacctatt ctgtctttgg gatggcactg     480
```

| | | |
|---|---|---|
| ggtgtgccaa atcaacatca tgatatgaaa ccgagactgc cactagagaa tgttgtcttt | 540 | |
| gaggaagaat accaagaaca gtcaactgag gcaatccaag cttatgaccg tgttcaggct | 600 | |
| gactatgctg gggcgcgtgc gaccacaagc tggagtcagc gcctagcaga acagtttggt | 660 | |
| caagctgaac caagctcaac tagaaaaaat cttgaacaga agaaattatt gtag | 714 | |

<210> SEQ ID NO 70
<211> LENGTH: 237
<212> TYPE: PRT
<213> ORGANISM: Streptococcus pneumoniae

<400> SEQUENCE: 70

Met Thr Glu Thr Ile Lys Leu Met Lys Ala His Thr Ser Val Arg Arg
1               5                   10                  15

Phe Lys Glu Gln Glu Ile Pro Gln Val Asp Leu Asn Glu Ile Leu Thr
            20                  25                  30

Ala Ala Gln Met Ala Ser Ser Trp Lys Asn Phe Gln Ser Tyr Ser Val
        35                  40                  45

Ile Val Val Arg Ser Gln Glu Lys Lys Asp Ala Leu Tyr Glu Leu Val
    50                  55                  60

Pro Gln Glu Ala Ile Arg Gln Ser Ala Val Phe Leu Leu Phe Val Gly
65                  70                  75                  80

Asp Leu Asn Arg Ala Glu Lys Gly Ala Arg Leu His Thr Asp Thr Phe
                85                  90                  95

Gln Pro Gln Gly Val Glu Gly Leu Leu Ile Ser Ser Val Asp Ala Ala
            100                 105                 110

Leu Ala Gly Gln Asn Ala Leu Leu Ala Ala Glu Ser Leu Gly Tyr Gly
        115                 120                 125

Gly Val Ile Ile Gly Leu Val Arg Tyr Lys Ser Glu Glu Val Ala Glu
    130                 135                 140

Leu Phe Asn Leu Pro Asp Tyr Thr Tyr Ser Val Phe Gly Met Ala Leu
145                 150                 155                 160

Gly Val Pro Asn Gln His His Asp Met Lys Pro Arg Leu Pro Leu Glu
                165                 170                 175

Asn Val Phe Glu Glu Glu Tyr Gln Glu Gln Ser Thr Glu Ala Ile
            180                 185                 190

Gln Ala Tyr Asp Arg Val Gln Ala Asp Tyr Ala Gly Ala Arg Ala Thr
        195                 200                 205

Thr Ser Trp Ser Gln Arg Leu Ala Glu Gln Phe Gly Gln Ala Glu Pro
    210                 215                 220

Ser Ser Thr Arg Lys Asn Leu Glu Gln Lys Lys Leu Leu
225                 230                 235

<210> SEQ ID NO 71
<211> LENGTH: 729
<212> TYPE: DNA
<213> ORGANISM: Streptococcus pneumoniae

<400> SEQUENCE: 71

| | | |
|---|---|---|
| atgacagaaa ttagactaga gcacgtcagt tatgcctatg gtcaggagag gattttagag | 60 | |
| gatatcaacc tacaggtgac ttcaggcgaa gtggttttcca tcctaggccc aagtggtgtt | 120 | |
| ggaaagacca ccctctcttaa tctaatcgct gggattttag aagttcagtc agggagaatt | 180 | |
| gtccttgatg gtgaagaaaa tcccaagggg cgcgtgagtt atatgttgca aaaggatctg | 240 | |
| ctcttggagc acaagacggt gcttggaaat atcattctgc ccctcttgat tcaaaaggtg | 300 | |
| gataaggcag aagctatttc ccgagcggat aaaattcttg cgaccttcca gctgacagct | 360 | |

```
gtaagagaca agtatcctca tgaacttagc ggtgggatgc gccagcgtgt agccttactc    420
cggacctacc tttttgggca caagctcttt ctcttagatg aggcctttag cgccttggat    480
gagatgacaa agatggaact ccacgcttgg tatcttgaga ttcacaagca gttgcagcta    540
acaaccctga tcatcacgca tagtattgag gaggccctca atctcagcga ccgtatctat    600
atcttgaaaa atcgcctgg gcagattgtt tcagaaatta aactagattg gtctgaagat    660
gaggacaagg aagtccaaaa gattgcctac aaacgtcaaa ttttggcgga attaggctta    720
gataagtag                                                            729
```

<210> SEQ ID NO 72
<211> LENGTH: 242
<212> TYPE: PRT
<213> ORGANISM: Streptococcus pneumoniae

<400> SEQUENCE: 72

```
Met Thr Glu Ile Arg Leu Glu His Val Ser Tyr Ala Tyr Gly Gln Glu
 1               5                  10                  15

Arg Ile Leu Glu Asp Ile Asn Leu Gln Val Thr Ser Gly Glu Val Val
             20                  25                  30

Ser Ile Leu Gly Pro Ser Gly Val Gly Lys Thr Thr Leu Phe Asn Leu
         35                  40                  45

Ile Ala Gly Ile Leu Glu Val Gln Ser Gly Arg Ile Val Leu Asp Gly
     50                  55                  60

Glu Glu Asn Pro Lys Gly Arg Val Ser Tyr Met Leu Gln Lys Asp Leu
 65                  70                  75                  80

Leu Leu Glu His Lys Thr Val Leu Gly Asn Ile Ile Leu Pro Leu Leu
                 85                  90                  95

Ile Gln Lys Val Asp Lys Ala Glu Ala Ile Ser Arg Ala Asp Lys Ile
            100                 105                 110

Leu Ala Thr Phe Gln Leu Thr Ala Val Arg Asp Lys Tyr Pro His Glu
        115                 120                 125

Leu Ser Gly Gly Met Arg Gln Arg Val Ala Leu Leu Arg Thr Tyr Leu
    130                 135                 140

Phe Gly His Lys Leu Phe Leu Leu Asp Glu Ala Phe Ser Ala Leu Asp
145                 150                 155                 160

Glu Met Thr Lys Met Glu Leu His Ala Trp Tyr Leu Glu Ile His Lys
                165                 170                 175

Gln Leu Gln Leu Thr Thr Leu Ile Ile Thr His Ser Ile Glu Glu Ala
            180                 185                 190

Leu Asn Leu Ser Asp Arg Ile Tyr Ile Leu Lys Asn Arg Pro Gly Gln
        195                 200                 205

Ile Val Ser Glu Ile Lys Leu Asp Trp Ser Glu Asp Glu Asp Lys Glu
    210                 215                 220

Val Gln Lys Ile Ala Tyr Lys Arg Gln Ile Leu Ala Glu Leu Gly Leu
225                 230                 235                 240

Asp Lys
```

<210> SEQ ID NO 73
<211> LENGTH: 2433
<212> TYPE: DNA
<213> ORGANISM: Streptococcus pneumoniae

<400> SEQUENCE: 73

```
atgaactatt caaaagcatt gaatgaatgt atcgaaagtg cctacatggt tgctggacat    60
```

```
tttggagctc gttatctaga gtcgtggcac ttgttgattg ccatgtctaa tcacagttat    120
agtgtagcag gggcaacttt aaatgattat ccgtatgaga tggaccgttt agaagaggtg    180
gctttggaac tgactgaaac ggactatagc caggatgaaa cctttacgga attgccgttc    240
tcccgtcgtt tgcaggttct ttttgatgaa gcagagtatg tagcgtcagt ggtccatgct    300
aaggtactag ggacagagca cgtcctctat gcgattttgc atgatagcaa tgccttggcg    360
actcgtatct tggagagggc tggttttttct tatgaagaca agaaagatca ggtcaagatt    420
gctgctcttc gtcgaaattt agaagaacgg gcaggctgga ctcgtgaaga tctcaaggct    480
ttacgccaac gccatcgtac agtagctgac aagcaaaatt ctatggccaa tatgatgggc    540
atgccgcaga ctcctagtgg tggtctcgag gattatacgc atgatttgac agagcaagcg    600
cgttctggca gttagaaacc agtcatcggt cgggacaagg aaatctcacg tatgattcaa    660
atcttgagcc ggaagactaa gaacaaccct gtcttggttg gggatgctgg tgtcgggaaa    720
acagctctgg cgcttggtct tgcccagcgt attgctagtg gtgacgtgcc tgcggaaatg    780
gctaagatgc gcgtgttaga acttgatttg atgaatgtcg ttgcagggac acgcttccgt    840
ggtgactttg aagaacgcat gaataatatc atcaaggata ttgaagaaga tggccaagtc    900 atcctctttta tcgatgaact ccacaccatc atgggttctg gtagcgggat tgattcgact    960
ctggatgcgg ccaatatctt gaaaccagcc ttggcgcgtg aactttgag aacggttggt   1020 gccactactc aggaagaata tcaaaaacat atcgaaaaag atgcggcact ttctcgtcgt   1080
ttcgctaaag tgacgattga agaaccaagt gtggcagata gtatgactat tttacaaggt   1140
ttgaaggcga cttatgagaa acatcaccgt gtacaaatca cagatgaagc ggttgaaaca   1200
gcggttaaga tggctcatcg ttatttaacc agtcgtcact tgccagactc tgctatcgat   1260
ctcttggatg aggcggcagc aacagtgcaa aataaggcaa agcatgtaaa agcagacgat   1320
tcagatttga gtccagctga caaggccctg atggatggca gtggaaaca ggcagcccag   1380 ctaatcgcaa aagaagagga agtacctgtc tacaaagact tggtgacaga gtctgatatt   1440
ttgaccacct tgagtcgctt gtcaggaatc ccagttcaaa aactgactca aacggatgct   1500
aagaagtatt taaatcttga agcagaactc cataaacggg ttatcggtca agatcaagct   1560
gtttcaagca ttagccgtgc cattcgccgc aaccagtcag ggattcgcag tcataagcgt   1620
ccgattggtt cctttatgtt cctagggcct acaggtgtcg ggaaaactga attagccaag   1680
gctctggcag aagttctttt tgacgacgaa tcagccctta tccgctttga tatgagtgag   1740
tatatggaga aatttgcagc tagtcgtctc aacggagctc ctccaggcta tgtaggatat   1800
gaagaaggtg gggagttgac agagaaggtt cgcaataaac cctattccgt tctcctctttt  1860 gatgaggtag agaaggccca cccagatatc tttaatgttc tcttgcaggt tctgatgac    1920 ggtgtcttga cagatagcaa gggacgcaag gtcgatttt caaataccat tatcattatg    1980
acatcgaatc taggtgcgac tgcccttcgt gatgataaga ctgttggttt tggggctaag   2040
gatattcgtt ttgaccagga aaatatggaa aaacgcatgt ttgaagaact gaaaaaagct   2100
tatagaccgg aattcatcaa ccgtattgat gagaaggtgg tcttccatag cctatctagt   2160
gatcatatgc aggaagtggt gaagattatg gtcaagcctt agtggcaag tttgactgaa   2220 aaaggcattg acttgaaatt acaagcttca gctctgaaat tgttagcaaa tcaaggatat   2280
gacccagaga tgggagctcg cccacttcgc agaaccctgc aaacagaagt ggaggacaag   2340
ttggcagaac ttcttctcaa gggagattta gtgcaggca gcacacttaa gattggtgtc    2400
aaagcaggcc agttaaaatt tgatattgca taa                                2433
```

<210> SEQ ID NO 74
<211> LENGTH: 810
<212> TYPE: PRT
<213> ORGANISM: Streptococcus pneumoniae

<400> SEQUENCE: 74

```
Met Asn Tyr Ser Lys Ala Leu Asn Glu Cys Ile Glu Ser Ala Tyr Met
  1               5                  10                  15

Val Ala Gly His Phe Gly Ala Arg Tyr Leu Glu Ser Trp His Leu Leu
                 20                  25                  30

Ile Ala Met Ser Asn His Ser Tyr Ser Val Ala Gly Ala Thr Leu Asn
             35                  40                  45

Asp Tyr Pro Tyr Glu Met Asp Arg Leu Glu Glu Val Ala Leu Glu Leu
         50                  55                  60

Thr Glu Thr Asp Tyr Ser Gln Asp Glu Thr Phe Thr Glu Leu Pro Phe
 65                  70                  75                  80

Ser Arg Arg Leu Gln Val Leu Phe Asp Glu Ala Glu Tyr Val Ala Ser
                 85                  90                  95

Val Val His Ala Lys Val Leu Gly Thr Glu His Val Leu Tyr Ala Ile
                100                 105                 110

Leu His Asp Ser Asn Ala Leu Ala Thr Arg Ile Leu Glu Arg Ala Gly
            115                 120                 125

Phe Ser Tyr Glu Asp Lys Lys Asp Gln Val Lys Ile Ala Ala Leu Arg
        130                 135                 140

Arg Asn Leu Glu Glu Arg Ala Gly Trp Thr Arg Glu Asp Leu Lys Ala
145                 150                 155                 160

Leu Arg Gln Arg His Arg Thr Val Ala Asp Lys Gln Asn Ser Met Ala
                165                 170                 175

Asn Met Met Gly Met Pro Gln Thr Pro Ser Gly Gly Leu Glu Asp Tyr
            180                 185                 190

Thr His Asp Leu Thr Glu Gln Ala Arg Ser Gly Lys Leu Glu Pro Val
        195                 200                 205

Ile Gly Arg Asp Lys Glu Ile Ser Arg Met Ile Gln Ile Leu Ser Arg
    210                 215                 220

Lys Thr Lys Asn Asn Pro Val Leu Val Gly Asp Ala Gly Val Gly Lys
225                 230                 235                 240

Thr Ala Leu Ala Leu Gly Leu Ala Gln Arg Ile Ala Ser Gly Asp Val
                245                 250                 255

Pro Ala Glu Met Ala Lys Met Arg Val Leu Glu Leu Asp Leu Met Asn
            260                 265                 270

Val Val Ala Gly Thr Arg Phe Arg Gly Asp Phe Glu Glu Arg Met Asn
        275                 280                 285

Asn Ile Ile Lys Asp Ile Glu Glu Asp Gly Gln Val Ile Leu Phe Ile
    290                 295                 300

Asp Glu Leu His Thr Ile Met Gly Ser Gly Ser Gly Ile Asp Ser Thr
305                 310                 315                 320

Leu Asp Ala Ala Asn Ile Leu Lys Pro Ala Leu Ala Arg Gly Thr Leu
                325                 330                 335

Arg Thr Val Gly Ala Thr Thr Gln Glu Glu Tyr Gln Lys His Ile Glu
            340                 345                 350

Lys Asp Ala Ala Leu Ser Arg Arg Phe Ala Lys Val Thr Ile Glu Glu
        355                 360                 365

Pro Ser Val Ala Asp Ser Met Thr Ile Leu Gln Gly Leu Lys Ala Thr
    370                 375                 380
```

-continued

```
Tyr Glu Lys His His Arg Val Gln Ile Thr Asp Glu Ala Val Glu Thr
385                 390                 395                 400

Ala Val Lys Met Ala His Arg Tyr Leu Thr Ser Arg His Leu Pro Asp
                405                 410                 415

Ser Ala Ile Asp Leu Leu Asp Glu Ala Ala Thr Val Gln Asn Lys
            420                 425                 430

Ala Lys His Val Lys Ala Asp Ser Asp Leu Ser Pro Ala Asp Lys
        435                 440                 445

Ala Leu Met Asp Gly Lys Trp Lys Gln Ala Gln Leu Ile Ala Lys
    450                 455                 460

Glu Glu Glu Val Pro Val Tyr Lys Asp Leu Val Thr Glu Ser Asp Ile
465                 470                 475                 480

Leu Thr Thr Leu Ser Arg Leu Ser Gly Ile Pro Val Gln Lys Leu Thr
                485                 490                 495

Gln Thr Asp Ala Lys Lys Tyr Leu Asn Leu Glu Ala Glu Leu His Lys
            500                 505                 510

Arg Val Ile Gly Gln Asp Gln Ala Val Ser Ser Ile Ser Arg Ala Ile
        515                 520                 525

Arg Arg Asn Gln Ser Gly Ile Arg Ser His Lys Arg Pro Ile Gly Ser
530                 535                 540

Phe Met Phe Leu Gly Pro Thr Gly Val Gly Lys Thr Glu Leu Ala Lys
545                 550                 555                 560

Ala Leu Ala Glu Val Leu Phe Asp Asp Glu Ser Ala Leu Ile Arg Phe
                565                 570                 575

Asp Met Ser Glu Tyr Met Glu Lys Phe Ala Ala Ser Arg Leu Asn Gly
            580                 585                 590

Ala Pro Pro Gly Tyr Val Gly Tyr Glu Glu Gly Gly Glu Leu Thr Glu
        595                 600                 605

Lys Val Arg Asn Lys Pro Tyr Ser Val Leu Leu Phe Asp Glu Val Glu
610                 615                 620

Lys Ala His Pro Asp Ile Phe Asn Val Leu Leu Gln Val Leu Asp Asp
625                 630                 635                 640

Gly Val Leu Thr Asp Ser Lys Gly Arg Lys Val Asp Phe Ser Asn Thr
                645                 650                 655

Ile Ile Ile Met Thr Ser Asn Leu Gly Ala Thr Ala Leu Arg Asp Asp
            660                 665                 670

Lys Thr Val Gly Phe Gly Ala Lys Asp Ile Arg Phe Asp Gln Glu Asn
        675                 680                 685

Met Glu Lys Arg Met Phe Glu Leu Lys Lys Ala Tyr Arg Pro Glu
    690                 695                 700

Phe Ile Asn Arg Ile Asp Glu Lys Val Val Phe His Ser Leu Ser Ser
705                 710                 715                 720

Asp His Met Gln Glu Val Val Lys Ile Met Val Lys Pro Leu Val Ala
                725                 730                 735

Ser Leu Thr Glu Lys Gly Ile Asp Leu Lys Leu Gln Ala Ser Ala Leu
            740                 745                 750

Lys Leu Leu Ala Asn Gln Gly Tyr Asp Pro Glu Met Gly Ala Arg Pro
        755                 760                 765

Leu Arg Arg Thr Leu Gln Thr Glu Val Glu Asp Lys Leu Ala Glu Leu
770                 775                 780

Leu Leu Lys Gly Asp Leu Val Ala Gly Ser Thr Leu Lys Ile Gly Val
785                 790                 795                 800

Lys Ala Gly Gln Leu Lys Phe Asp Ile Ala
                805                 810
```

<210> SEQ ID NO 75
<211> LENGTH: 1008
<212> TYPE: DNA
<213> ORGANISM: Streptococcus pneumoniae

<400> SEQUENCE: 75

```
atgaagaaaa catggaaagt gttttttaacg cttgtaacag ctcttgtagc tgttgtgctt    60
gtggcctgtg gtcaaggaac tgcttctaaa gacaacaaag aggcagaact taagaaggtt   120
gactttatcc tagactggac accaaatacc aaccacacag gctttatgt tgccaaggaa    180
aaaggttatt tcaaagaagc tggagtggat gttgatttga attgccacc agaagaaagt    240
tcttctgact tggttatcaa cggaaaggca ccatttgcag tgtatttcca agactacatg   300
gctaagaaat tggaaaaagg agcaggaatc actgccgttg cagctattgt tgaacacaat   360
acatcaggaa tcatctctcg taaatctgat aatgtaagca gtccaaaaga cttggttggt   420
aagaaatatg gacatggaa tgacccaact gaacttgcta tgttgaaaac cttggtagaa   480
tctcaaggtg agactttga aaggttgaa aaagtaccaa ataacgactc aaactcaatc   540
acaccgattg ccaatggcgt ctttgatact gcttggattt actacggttg ggatggtatc   600
cttgctaaat ctcaaggtgt agatgctaac ttcatgtact tgaaagacta tgtcaaggag   660
tttgactact attcaccagt tatcatcgca acaacgact atctgaaaga taacaaagaa   720
gaagctcgca aagtcatcca agccatcaaa aaaggctacc aatatgccat ggaacatcca   780
gaagaagctg cagatattct catcaagaat gcacctgaac tcaaggaaaa acgtgacttt   840
gtcatcgaat ctcaaaaata cttgtcaaaa gaatacgcaa gcgacaagga aaatgggt    900
caatttgacg cagctcgctg gaatgctttc tacaaatggg ataagaaaa tggtatcctt   960
aaagaagact tgacagacaa aggcttcacc aacgaatttg tgaaataa              1008
```

<210> SEQ ID NO 76
<211> LENGTH: 335
<212> TYPE: PRT
<213> ORGANISM: Streptococcus pneumoniae

<400> SEQUENCE: 76

```
Met Lys Lys Thr Trp Lys Val Phe Leu Thr Leu Val Thr Ala Leu Val
  1               5                  10                  15

Ala Val Val Leu Val Ala Cys Gly Gln Gly Thr Ala Ser Lys Asp Asn
                 20                  25                  30

Lys Glu Ala Glu Leu Lys Lys Val Asp Phe Ile Leu Asp Trp Thr Pro
             35                  40                  45

Asn Thr Asn His Thr Gly Leu Tyr Val Ala Lys Glu Lys Gly Tyr Phe
         50                  55                  60

Lys Glu Ala Gly Val Asp Val Asp Leu Lys Leu Pro Pro Glu Glu Ser
 65                  70                  75                  80

Ser Ser Asp Leu Val Ile Asn Gly Lys Ala Pro Phe Ala Val Tyr Phe
                 85                  90                  95

Gln Asp Tyr Met Ala Lys Lys Leu Glu Lys Gly Ala Gly Ile Thr Ala
            100                 105                 110

Val Ala Ala Ile Val Glu His Asn Thr Ser Gly Ile Ile Ser Arg Lys
        115                 120                 125

Ser Asp Asn Val Ser Ser Pro Lys Asp Leu Val Gly Lys Lys Tyr Gly
    130                 135                 140

Thr Trp Asn Asp Pro Thr Glu Leu Ala Met Leu Lys Thr Leu Val Glu
145                 150                 155                 160
```

Ser Gln Gly Gly Asp Phe Glu Lys Val Glu Lys Val Pro Asn Asn Asp
            165                 170                 175

Ser Asn Ser Ile Thr Pro Ile Ala Asn Gly Val Phe Asp Thr Ala Trp
        180                 185                 190

Ile Tyr Tyr Gly Trp Asp Gly Ile Leu Ala Lys Ser Gln Gly Val Asp
            195                 200                 205

Ala Asn Phe Met Tyr Leu Lys Asp Tyr Val Lys Glu Phe Asp Tyr Tyr
210                 215                 220

Ser Pro Val Ile Ile Ala Asn Asn Asp Tyr Leu Lys Asp Asn Lys Glu
225                 230                 235                 240

Glu Ala Arg Lys Val Ile Gln Ala Ile Lys Lys Gly Tyr Gln Tyr Ala
                245                 250                 255

Met Glu His Pro Glu Ala Ala Asp Ile Leu Ile Lys Asn Ala Pro
            260                 265                 270

Glu Leu Lys Glu Lys Arg Asp Phe Val Ile Glu Ser Gln Lys Tyr Leu
        275                 280                 285

Ser Lys Glu Tyr Ala Ser Asp Lys Glu Lys Trp Gly Gln Phe Asp Ala
            290                 295                 300

Ala Arg Trp Asn Ala Phe Tyr Lys Trp Asp Lys Glu Asn Gly Ile Leu
305                 310                 315                 320

Lys Glu Asp Leu Thr Asp Lys Gly Phe Thr Asn Glu Phe Val Lys
                325                 330                 335

<210> SEQ ID NO 77
<211> LENGTH: 762
<212> TYPE: DNA
<213> ORGANISM: Streptococcus pneumoniae

<400> SEQUENCE: 77
ttgatgagaa acttgagaag tatactgaga cgacacatta gtctattggg ctttctcgga      60
gtattgtcaa tctggcagtt agcaggtttt cttaaacttc tccccaagtt tatcctgccg     120
acacctcttg aaattctcca gcccttttgtt cgtgacagag aatttctctg caccatagc     180 tgggcgacct tgagagtggc tttactgggg ctgattttgg gagttttgat tgcctgtctt     240
atggctgtgc tcatggatag tttgacttgg ctcaatgacc tgatttaccc tatgatggtg     300
gtcattcaga ccattccgac cattgccata gctcctatcc tggtcttgtg ctaggttat      360 gggattttgc ccaagattgt cttgattatc ttaacgacaa cctttcccat catcgttagt     420
attttggacg ttttaggca ttgcgacaag gatatgctga ccttgtttag tctgatgcgg     480
gccaagcctt ggcaaatcct gtggcatttt aaaatcccag ttagcctgcc ttactttat     540 gcaggtctga gggtcagtgt ctcctacgcc tttatcacaa ctgtggtatc tgagtggttg     600
ggaggttttg aaggtcttgg tgtttatatg attcagtcta aaaaactgtt tcagtatgat     660
accatgtttg ccattattat tctggtgtcg attatcagtc ttttgggtat gaagctggtc     720
gatatcagtg aaaaatatgt gattaaatgg aaacgttcgt ag                        762

<210> SEQ ID NO 78
<211> LENGTH: 253
<212> TYPE: PRT
<213> ORGANISM: Streptococcus pneumoniae

<400> SEQUENCE: 78

Met Met Arg Asn Leu Arg Ser Ile Leu Arg Arg His Ile Ser Leu Leu
1               5                   10                  15

Gly Phe Leu Gly Val Leu Ser Ile Trp Gln Leu Ala Gly Phe Leu Lys

```
                 20                  25                  30

Leu Leu Pro Lys Phe Ile Leu Pro Thr Pro Leu Glu Ile Leu Gln Pro
             35                  40                  45

Phe Val Arg Asp Arg Glu Phe Leu Trp His His Ser Trp Ala Thr Leu
         50                  55                  60

Arg Val Ala Leu Leu Gly Leu Ile Leu Gly Val Leu Ile Ala Cys Leu
 65                  70                  75                  80

Met Ala Val Leu Met Asp Ser Leu Thr Trp Leu Asn Asp Leu Ile Tyr
                 85                  90                  95

Pro Met Met Val Val Ile Gln Thr Ile Pro Thr Ile Ala Ile Ala Pro
            100                 105                 110

Ile Leu Val Leu Trp Leu Gly Tyr Gly Ile Leu Pro Lys Ile Val Leu
        115                 120                 125

Ile Ile Leu Thr Thr Thr Phe Pro Ile Ile Val Ser Ile Leu Asp Gly
130                 135                 140

Phe Arg His Cys Asp Lys Asp Met Leu Thr Leu Phe Ser Leu Met Arg
145                 150                 155                 160

Ala Lys Pro Trp Gln Ile Leu Trp His Phe Lys Ile Pro Val Ser Leu
                165                 170                 175

Pro Tyr Phe Tyr Ala Gly Leu Arg Val Ser Val Ser Tyr Ala Phe Ile
            180                 185                 190

Thr Thr Val Val Ser Glu Trp Leu Gly Gly Phe Glu Gly Leu Gly Val
        195                 200                 205

Tyr Met Ile Gln Ser Lys Lys Leu Phe Gln Tyr Asp Thr Met Phe Ala
    210                 215                 220

Ile Ile Ile Leu Val Ser Ile Ser Leu Leu Gly Met Lys Leu Val
225                 230                 235                 240

Asp Ile Ser Glu Lys Tyr Val Ile Lys Trp Lys Arg Ser
                245                 250

<210> SEQ ID NO 79
<211> LENGTH: 372
<212> TYPE: DNA
<213> ORGANISM: Streptococcus pneumoniae

<400> SEQUENCE: 79 ttgatttta atcctatttg ctgtatgata agggaaaaga aaggggacag agatatggct      60
tttaccaata cccacatgcg atctgctagt tttggtattg ttaccagctt gcctgatgac     120
atcattgact cttttggta tatcatcgac catttcttaa aaaatgtctt tgaattggaa     180
gaagaactcg agtttcaatt gcttaataac caaggaaaga ttaccttcca ctttcaagt     240 caacacctcc ctacagccat tgattttgac tttaaccatc ctttcgaccc tcgttatccc    300
ccaagagtac tggttttaga catggacggt agagaaacta tcctcctccc agaagaaaat   360
gacctatttt aa                                                       372

<210> SEQ ID NO 80
<211> LENGTH: 123
<212> TYPE: PRT
<213> ORGANISM: Streptococcus pneumoniae

<400> SEQUENCE: 80

Met Ile Phe Asn Pro Ile Cys Cys Met Ile Arg Glu Lys Lys Gly Asp
  1               5                  10                  15

Arg Asp Met Ala Phe Thr Asn Thr His Met Arg Ser Ala Ser Phe Gly
             20                  25                  30
```

```
Ile Val Thr Ser Leu Pro Asp Asp Ile Ile Asp Ser Phe Trp Tyr Ile
         35                  40                  45

Ile Asp His Phe Leu Lys Asn Val Phe Glu Leu Glu Glu Leu Glu
 50                  55                  60

Phe Gln Leu Leu Asn Asn Gln Gly Lys Ile Thr Phe His Phe Ser Ser
 65                  70                  75                  80

Gln His Leu Pro Thr Ala Ile Asp Phe Asp Phe Asn His Pro Phe Asp
             85                  90                  95

Pro Arg Tyr Pro Pro Arg Val Leu Val Leu Asp Met Asp Gly Arg Glu
            100                 105                 110

Thr Ile Leu Leu Pro Glu Glu Asn Asp Leu Phe
        115                 120

<210> SEQ ID NO 81
<211> LENGTH: 1645
<212> TYPE: DNA
<213> ORGANISM: Streptococcus pneumoniae

<400> SEQUENCE: 81
acagcggtgt cattctatct attttaagaa aagtaataat caattgttaa aaatagtaaa      60
aaaattggag gttctgatga atatttttgt tcctaatgag gtattcagta ttcgtaaatt     120
aaaggtgggg acttgctcgg tactattggc aatttcaatt ttgggaagcc aaggtatttt     180
atcggatgaa gttgttacta gttcttcacc gatggctaca aaagagtctt ctaatgcaat     240
tactaatgat ttagataatt caccaactgt taatcagaat cgttctgctg aaatgattgc     300
ctctaattca accactaatg gtttagataa ttcgttaagt gttaatagca tcagctctaa     360
tggtactatt cgttccaatt cacaattaga caacagaaca gttgaatcta cagtaacatc     420
tactaatgaa aataagagtt ataaggaaga tgttataagt gacagaatta tcaaaaaaga     480
atttgaagat actgctttaa gtgtaaaaga ttatggtgca gtaggtgatg ggattcatga     540
tgatcgacaa gcaattcaag atgcaataga tgctgcagct caagggctag gtggaggaaa     600
tgtatatttt cctgaaggaa cttatttagt aaaagaaatt gttttttttaa aaagtcatac     660 acacttagaa ttgaatgaga aagctacaat tctaaatggt ataaaatatta agaatcaccc     720 ttccattgtt tttatgacag gtttattttac ggatgatggt gcgcaagtag aatggggccc     780
aacagaagat attagttatt ctggtggtac gattgatatg aacggtgctt gaatgaagaa     840
aggaactaaa gcaaaaaatc taccacttat aaattcttca ggtgcatttg ctattgggaa     900
ttcaaataac gtaactataa aaaatgtaac attcaaggat agttatcaag gcatgctat    960 tcaaattgca ggttcgaaaa atgtattagt tgataattct cgttttcttg ggcaagcctt    1020
acccaaaacg atgaaggatg gcaaatcat agtaaggag agcattcaga ttgaaccatt    1080
aactagaaaa ggttttcctt atgccttgaa tgatgatggg aaaaaatctg aaaatgtgac    1140
tattcaaaat tcctattttg gcaaaagtga taaatctggg gaattagtaa cagcaattgg    1200
cacacactat caaacattgt cgacacagaa cccctctaat attaaaattc aaaataatca    1260
ttttgataac atgatgtatg caggtgtacg ttttacagga ttcactgatg tattaatcaa    1320
aggaaatcgc tttgataaga aagttaaagg agagagtgta cattatcgag aaagcggagc    1380
agctttagta aatgcttata gctataaaaa cactaaagac ctattagatt taaataaaca    1440
ggtggttatc gccgaaaata tatttaatat tgccgatcct aaaacaaaag cgatacgagt    1500
tgcaaaagat agtgcagaat gtttaggaaa agtatcagat attactgtaa caaaaaatgt    1560
aattaataat aattctaagg aaacagaaca accaaatatt gaattattac gagttagtga    1620
```
taatttagta gtctcagaga atagt 1645

<210> SEQ ID NO 82
<211> LENGTH: 548
<212> TYPE: PRT
<213> ORGANISM: Streptococcus pneumoniae

<400> SEQUENCE: 82

Gln Arg Cys His Ser Ile Tyr Phe Lys Lys Ser Asn Asn Gln Leu Leu
1               5                   10                  15

Lys Ile Val Lys Lys Leu Glu Val Leu Met Lys Tyr Phe Val Pro Asn
            20                  25                  30

Glu Val Phe Ser Ile Arg Lys Leu Lys Val Gly Thr Cys Ser Val Leu
        35                  40                  45

Leu Ala Ile Ser Ile Leu Gly Ser Gln Gly Ile Leu Ser Asp Glu Val
    50                  55                  60

Val Thr Ser Ser Pro Met Ala Thr Lys Glu Ser Ser Asn Ala Ile
65                  70                  75                  80

Thr Asn Asp Leu Asp Asn Ser Pro Thr Val Asn Gln Asn Arg Ser Ala
                85                  90                  95

Glu Met Ile Ala Ser Asn Ser Thr Thr Asn Gly Leu Asp Asn Ser Leu
            100                 105                 110

Ser Val Asn Ser Ile Ser Ser Asn Gly Thr Ile Arg Ser Asn Ser Gln
        115                 120                 125

Leu Asp Asn Arg Thr Val Glu Ser Thr Val Thr Ser Thr Asn Glu Asn
    130                 135                 140

Lys Ser Tyr Lys Glu Asp Val Ile Ser Asp Arg Ile Ile Lys Lys Glu
145                 150                 155                 160

Phe Glu Asp Thr Ala Leu Ser Val Lys Asp Tyr Gly Ala Val Gly Asp
                165                 170                 175

Gly Ile His Asp Asp Arg Gln Ala Ile Gln Asp Ala Ile Asp Ala Ala
            180                 185                 190

Ala Gln Gly Leu Gly Gly Gly Asn Val Tyr Phe Pro Glu Gly Thr Tyr
        195                 200                 205

Leu Val Lys Glu Ile Val Phe Leu Lys Ser His Thr His Leu Glu Leu
    210                 215                 220

Asn Glu Lys Ala Thr Ile Leu Asn Gly Ile Asn Ile Lys Asn His Pro
225                 230                 235                 240

Ser Ile Val Phe Met Thr Gly Leu Phe Thr Asp Asp Gly Ala Gln Val
                245                 250                 255

Glu Trp Gly Pro Thr Glu Asp Ile Ser Tyr Ser Gly Gly Thr Ile Asp
            260                 265                 270

Met Asn Gly Ala Leu Asn Glu Gly Thr Lys Ala Lys Asn Leu Pro
        275                 280                 285

Leu Ile Asn Ser Ser Gly Ala Phe Ala Ile Gly Asn Ser Asn Val
    290                 295                 300

Thr Ile Lys Asn Val Thr Phe Lys Asp Ser Tyr Gln Gly His Ala Ile
305                 310                 315                 320

Gln Ile Ala Gly Ser Lys Asn Val Leu Val Asp Asn Ser Arg Phe Leu
                325                 330                 335

Gly Gln Ala Leu Pro Lys Thr Met Lys Asp Gly Gln Ile Ile Ser Lys
            340                 345                 350

Glu Ser Ile Gln Ile Glu Pro Leu Thr Arg Lys Gly Phe Pro Tyr Ala
        355                 360                 365

Leu Asn Asp Asp Gly Lys Lys Ser Glu Asn Val Thr Ile Gln Asn Ser

```
                370              375              380
Tyr Phe Gly Lys Ser Asp Lys Ser Gly Glu Leu Val Thr Ala Ile Gly
385              390              395              400

Thr His Tyr Gln Thr Leu Ser Thr Gln Asn Pro Ser Asn Ile Lys Ile
            405              410              415

Gln Asn Asn His Phe Asp Asn Met Met Tyr Ala Gly Val Arg Phe Thr
        420              425              430

Gly Phe Thr Asp Val Leu Ile Lys Gly Asn Arg Phe Asp Lys Lys Val
            435              440              445

Lys Gly Glu Ser Val His Tyr Arg Glu Ser Gly Ala Ala Leu Val Asn
    450              455              460

Ala Tyr Ser Tyr Lys Asn Thr Lys Asp Leu Leu Asp Leu Asn Lys Gln
465              470              475              480

Val Val Ile Ala Glu Asn Ile Phe Asn Ile Ala Asp Pro Lys Thr Lys
                485              490              495

Ala Ile Arg Val Ala Lys Asp Ser Ala Glu Cys Leu Gly Lys Val Ser
            500              505              510

Asp Ile Thr Val Thr Lys Asn Val Ile Asn Asn Ser Lys Glu Thr
            515              520              525

Glu Gln Pro Asn Ile Glu Leu Leu Arg Val Ser Asp Asn Leu Val Val
530              535              540

Ser Glu Asn Ser
545

<210> SEQ ID NO 83
<211> LENGTH: 324
<212> TYPE: DNA
<213> ORGANISM: Streptococcus pneumoniae

<400> SEQUENCE: 83
gtgatgaaag aaactcagct attaaaaggt gttcttgaag ttgtgtcttt ggatatgatt       60
ggtcaaaaag agcggtatgg ttatgagttg gttcagactt tgcgagaggc tggatttgat      120
actatcgttc caggaactat ttatcctttg ttgcaaaagt tagaaaaaaa tcaatggata      180
agaggcgaca tgcgcccgtc gccagatggt ccagatcgga agtattttttc attaatgaaa     240 gaaggagaag agcgtgtctc agtctttttgg caacaatggg acgatttgag tcaaaaagta    300
gaagggatta agaatggggg ttaa                                             324

<210> SEQ ID NO 84
<211> LENGTH: 107
<212> TYPE: PRT
<213> ORGANISM: Streptococcus pneumoniae

<400> SEQUENCE: 84

Met Met Lys Glu Thr Gln Leu Leu Lys Gly Val Leu Glu Gly Cys Val
1               5                   10                  15

Leu Asp Met Ile Gly Gln Lys Glu Arg Tyr Gly Tyr Glu Leu Val Gln
            20                  25                  30

Thr Leu Arg Glu Ala Gly Phe Asp Thr Ile Val Pro Gly Thr Ile Tyr
        35                  40                  45

Pro Leu Leu Gln Lys Leu Glu Lys Asn Gln Trp Ile Arg Gly Asp Met
    50                  55                  60

Arg Pro Ser Pro Asp Gly Pro Asp Arg Lys Tyr Phe Ser Leu Met Lys
65                  70                  75                  80

Glu Gly Glu Glu Arg Val Ser Val Phe Trp Gln Gln Trp Asp Asp Leu
                85                  90                  95
```

Ser Gln Lys Val Glu Gly Ile Lys Asn Gly Gly
              100                 105

<210> SEQ ID NO 85
<211> LENGTH: 816
<212> TYPE: DNA
<213> ORGANISM: Streptococcus pneumoniae

<400> SEQUENCE: 85

```
atgaagaaaa tgaagtatta cgaagaaaca agcgctttgc tacatgagtt ttctgaggag      60
aatcaaaagt attttgagga gttgtgggaa agttttaatc ttgctggatt tctctatgat     120
gaagactatc tcagagagca gatctatttg atgatgctag atttctcaga agcagaacga     180
gatggcatga gtgcagagga ttatctaggt aagaatccta aaaaaataat gaaagagatt     240
ctcaagggag cacctcgcag ttctatcaaa gagtcccttt tgacgccaat tcttgtcctg     300
gcggtattac gttattatca actactaagt gattttcta aaggtcctct cttaacagtc      360
aatttgctca cattttagg gcaacttctt attttttctga ttggatttgg acttgtggcc     420
acaattttac gaagaagttt agtccaagat tctcctaaaa tgaaaattgg cacttacatt     480
gttgttggga ctatagttct tctagttgtt ttaggatatg taggaatggc aagcttcata     540
caagaaggag cctttatat tccggctccc tgggatagtt tgtctgtctt tacgatttcg      600
ctagttatcg gtatttggaa ttggaaagaa gcggtctttc gtccatttgt cagtatgatt     660
attgcccatc ttgtggtggg ttctctgctc cgttattatg agtggatggg aatttcaaat     720
gttttcctta caaaagttat tcctttagct gtcctcttta ttggaatctt tgtcttgttc     780
cgtgggttta agaagataaa atggagtgaa gtatag                               816
```

<210> SEQ ID NO 86
<211> LENGTH: 271
<212> TYPE: PRT
<213> ORGANISM: Streptococcus pneumoniae

<400> SEQUENCE: 86

Met Lys Lys Met Lys Tyr Tyr Glu Glu Thr Ser Ala Leu Leu His Glu
1               5                   10                  15

Phe Ser Glu Glu Asn Gln Lys Tyr Phe Glu Glu Leu Trp Glu Ser Phe
            20                  25                  30

Asn Leu Ala Gly Phe Leu Tyr Asp Glu Asp Tyr Leu Arg Glu Gln Ile
        35                  40                  45

Tyr Leu Met Met Leu Asp Phe Ser Glu Ala Glu Arg Asp Gly Met Ser
    50                  55                  60

Ala Glu Asp Tyr Leu Gly Lys Asn Pro Lys Lys Ile Met Lys Glu Ile
65                  70                  75                  80

Leu Lys Gly Ala Pro Arg Ser Ser Ile Lys Glu Ser Leu Leu Thr Pro
                85                  90                  95

Ile Leu Val Leu Ala Val Leu Arg Tyr Tyr Gln Leu Leu Ser Asp Phe
            100                 105                 110

Ser Lys Gly Pro Leu Leu Thr Val Asn Leu Leu Thr Phe Leu Gly Gln
        115                 120                 125

Leu Leu Ile Phe Leu Ile Gly Phe Gly Leu Val Ala Thr Ile Leu Arg
    130                 135                 140

Arg Ser Leu Val Gln Asp Ser Pro Lys Met Lys Ile Gly Thr Tyr Ile
145                 150                 155                 160

Val Val Gly Thr Ile Val Leu Leu Val Val Leu Gly Tyr Val Gly Met
                165                 170                 175

```
Ala Ser Phe Ile Gln Glu Gly Ala Phe Tyr Ile Pro Ala Pro Trp Asp
            180                 185                 190

Ser Leu Ser Val Phe Thr Ile Ser Leu Val Ile Gly Ile Trp Asn Trp
            195                 200                 205

Lys Glu Ala Val Phe Arg Pro Phe Val Ser Met Ile Ile Ala His Leu
            210                 215                 220

Val Val Gly Ser Leu Leu Arg Tyr Tyr Glu Trp Met Gly Ile Ser Asn
225                 230                 235                 240

Val Phe Leu Thr Lys Val Ile Pro Leu Ala Val Leu Phe Ile Gly Ile
            245                 250                 255

Phe Val Leu Phe Arg Gly Phe Lys Lys Ile Lys Trp Ser Glu Val
            260                 265                 270

<210> SEQ ID NO 87
<211> LENGTH: 348
<212> TYPE: DNA
<213> ORGANISM: Streptococcus pneumoniae

<400> SEQUENCE: 87
ctgttttttt atttatactc aatgaaaatc aaagagcaaa ctaggaagct agccgcaggt    60
tgctcaaaac actgttttga ggttgtagac gaaactgacg aagtcagctc aaaacatgtt   120
tttgaggttg tagatgaaac tgacgaagtc agctcaaaac actgttttga ggttgtagat   180
gaaactgacg aagtcagctc aaaacactgt ttgaggttg tagatgaaac tgacgaagtc   240
agctcaaaac atgttttga ggttgtagat gaaactgacg aagtcagtaa ccatacatac   300
ggtagggcga cgctgacgtg gtttgaagag atttttcgaag agtattaa               348

<210> SEQ ID NO 88
<211> LENGTH: 115
<212> TYPE: PRT
<213> ORGANISM: Streptococcus pneumoniae

<400> SEQUENCE: 88

Met Phe Phe Tyr Leu Tyr Ser Met Lys Ile Lys Glu Gln Thr Arg Lys
  1                 5                  10                  15

Leu Ala Ala Gly Cys Ser Lys His Cys Phe Glu Val Val Asp Glu Thr
             20                  25                  30

Asp Glu Val Ser Ser Lys His Val Phe Glu Val Val Asp Glu Thr Asp
         35                  40                  45

Glu Val Ser Ser Lys His Cys Phe Glu Val Val Asp Glu Thr Asp Glu
     50                  55                  60

Val Ser Ser Lys His Cys Phe Glu Val Val Asp Glu Thr Asp Glu Val
 65                  70                  75                  80

Ser Ser Lys His Val Phe Glu Val Val Asp Glu Thr Asp Glu Val Ser
             85                  90                  95

Asn His Thr Tyr Gly Arg Ala Thr Leu Thr Trp Phe Glu Glu Ile Phe
            100                 105                 110

Glu Glu Tyr
        115

<210> SEQ ID NO 89
<211> LENGTH: 1260
<212> TYPE: DNA
<213> ORGANISM: Streptococcus pneumoniae

<400> SEQUENCE: 89
atgcagaatc tgaaatttgc ctttcatct atcatggctc acaagatgcg ttctttgctt    60
```

```
actatgattg ggattattat cggtgtttca tcagttgttg tgattatggc tttgggtgat      120
tccctatctc gtcaagtcaa taaagatatg actaaatctc agaaaaatat tagcgtcttt      180
ttctctccta aaaaagtaa agacgggtct tttactcaga acaatcagc ttttacggtt        240 tctggaaagg aagaggaagt tcctgttgaa ccgccaaaac cgcaagaatc ctgggtccaa      300
gaggcagcta aactgaaggg agtggatagt tactatgtaa ccaattcaac gaatgccatc      360
ttgacctatc aagataaaaa ggttgagaat gctaatttga caggtggaaa cagaacttac      420
atggacgctg ttaagaatga aattattgca ggtcgtagtc tgagagagca agatttcaaa      480
gagtttgcaa gtgtcatttt gctagatgag gaattgtcca ttagtttatt tgaatctcct      540
caagaggcta ttaacaaggt tgtagaagtc aatggattta gttaccgggt cattggggtt      600
tatactagtc cggaggctaa aagatcaaaa atatatgggt ttggtggctt gcctattact      660
accaatatct cccttgctgc gaattttaat gtagatgaaa tagctaatat tgtctttcga      720
gtgaatgata ccagtttaac cccaactctg ggtccagaac tggcacgaaa aatgacagag      780
cttgcaggct acaacaggg agaataccag gtggcagatg agtccgttgt atttgcagaa      840
attcaacaat cgtttagttt tatgacgacg attattagtt ccatcgcagg gatttctctc      900
tttgttggag gaactggtgt catgaacatc atgctggttt cggtgacaga gcgcactcgt      960
gagattggtc ttcgtaaggc tttgggtgca acacgtgcca atattttaat tcagttttg     1020 attgaatcca tgattttgac cttgttaggt ggcttaattg gcttgacaat gcaagtggt     1080 ttaactgcct tagcaggttt gttactgcaa ggtttaatag aaggtataga agttggagta     1140
tcaatcccag tcgccctatt tagtcttgca gtttcggcta gtgttggtat gattttggga    1200
gtcttgccag ccaacaaggc atcgaaactt gatccaattg aagcccttcg ttatgaatga    1260
```

<210> SEQ ID NO 90
<211> LENGTH: 419
<212> TYPE: PRT
<213> ORGANISM: Streptococcus pneumoniae

<400> SEQUENCE: 90

```
Met Gln Asn Leu Lys Phe Ala Phe Ser Ser Ile Met Ala His Lys Met
  1               5                  10                  15

Arg Ser Leu Leu Thr Met Ile Gly Ile Ile Gly Val Ser Ser Val
             20                  25                  30

Val Val Ile Met Ala Leu Gly Asp Ser Leu Ser Arg Gln Val Asn Lys
         35                  40                  45

Asp Met Thr Lys Ser Gln Lys Asn Ile Ser Val Phe Phe Ser Pro Lys
     50                  55                  60

Lys Ser Lys Asp Gly Ser Phe Thr Gln Lys Gln Ser Ala Phe Thr Val
 65                  70                  75                  80

Ser Gly Lys Glu Glu Glu Val Pro Val Glu Pro Pro Lys Pro Gln Glu
                 85                  90                  95

Ser Trp Val Gln Glu Ala Ala Lys Leu Lys Gly Val Asp Ser Tyr Tyr
            100                 105                 110

Val Thr Asn Ser Thr Asn Ala Ile Leu Thr Tyr Gln Asp Lys Lys Val
        115                 120                 125

Glu Asn Ala Asn Leu Thr Gly Gly Asn Arg Thr Tyr Met Asp Ala Val
    130                 135                 140

Lys Asn Glu Ile Ile Ala Gly Arg Ser Leu Arg Glu Gln Asp Phe Lys
145                 150                 155                 160

Glu Phe Ala Ser Val Ile Leu Leu Asp Glu Glu Leu Ser Ile Ser Leu
```

```
              165                 170                 175
Phe Glu Ser Pro Gln Glu Ala Ile Asn Lys Val Glu Val Asn Gly
            180                 185                 190

Phe Ser Tyr Arg Val Ile Gly Val Tyr Thr Ser Pro Glu Ala Lys Arg
        195                 200                 205

Ser Lys Ile Tyr Gly Phe Gly Gly Leu Pro Ile Thr Thr Asn Ile Ser
    210                 215                 220

Leu Ala Ala Asn Phe Asn Val Asp Glu Ile Ala Asn Ile Val Phe Arg
225                 230                 235                 240

Val Asn Asp Thr Ser Leu Thr Pro Thr Leu Gly Pro Glu Leu Ala Arg
                245                 250                 255

Lys Met Thr Glu Leu Ala Gly Leu Gln Gln Gly Glu Tyr Gln Val Ala
            260                 265                 270

Asp Glu Ser Val Val Phe Ala Glu Ile Gln Gln Ser Phe Ser Phe Met
        275                 280                 285

Thr Thr Ile Ile Ser Ser Ile Ala Gly Ile Ser Leu Phe Val Gly Gly
    290                 295                 300

Thr Gly Val Met Asn Ile Met Leu Val Ser Val Thr Glu Arg Thr Arg
305                 310                 315                 320

Glu Ile Gly Leu Arg Lys Ala Leu Gly Ala Thr Arg Ala Asn Ile Leu
                325                 330                 335

Ile Gln Phe Leu Ile Glu Ser Met Ile Leu Thr Leu Leu Gly Gly Leu
            340                 345                 350

Ile Gly Leu Thr Ile Ala Ser Gly Leu Thr Ala Leu Ala Gly Leu Leu
        355                 360                 365

Leu Gln Gly Leu Ile Glu Gly Ile Glu Val Gly Val Ser Ile Pro Val
    370                 375                 380

Ala Leu Phe Ser Leu Ala Val Ser Ala Ser Val Gly Met Ile Phe Gly
385                 390                 395                 400

Val Leu Pro Ala Asn Lys Ala Ser Lys Leu Asp Pro Ile Glu Ala Leu
                405                 410                 415

Arg Tyr Glu

<210> SEQ ID NO 91
<211> LENGTH: 705
<212> TYPE: DNA
<213> ORGANISM: Streptococcus pneumoniae

<400> SEQUENCE: 91
ctgatgaagc aactaattag tctaaaaaat atcttcagaa gttaccgtaa tggtgaccaa      60
gaactgcagg ttctcaaaaa tatcaatcta gaagtgaatg agggtgaatt tgtagccatc    120
atgggaccat ctgggtctgg taagtccact ctgatgaata cgattggcat gttggataca    180
ccaaccagtg gagaatatta tcttgaaggt caagaagtgg ctgggcttgg tgaaaaacaa    240
ctagctaagg tccgtaacca acaaatcggt tttgtctttc agcagttctt tcttctatcg    300
aagctcaatg ctctgcaaaa tgtagaattg cccttgattt acgcaggagt ttcgtcttca    360
aaacgtcgca agttggctga ggaatattta gacaaggtta aattgacaga acgtagtcac    420
catttacctt cagaattatc tggtggtcaa aagcaacgtg tagccattgc gcgtgccttg    480
gtaaacaatc cttctattat cctagcggat gaaccgacag gagccttgga taccaaaaca    540
ggtaaccaaa ttatgcaatt attggttgat ttgaataaag aaggaaaaac cattatcatg    600
gtaacgcatg agcctgagat tgctgccgtat gccaaacgtc agattgtcat tcgggatggg    660
gtcatttcgt ctgacagtgc tcagttagga aaggaggaaa actaa                   705
```

<210> SEQ ID NO 92
<211> LENGTH: 234
<212> TYPE: PRT
<213> ORGANISM: Streptococcus pneumoniae

<400> SEQUENCE: 92

Met Met Lys Gln Leu Ile Ser Leu Lys Asn Ile Phe Arg Ser Tyr Arg
1               5                   10                  15

Asn Gly Asp Gln Glu Leu Gln Val Leu Lys Asn Ile Asn Leu Glu Val
            20                  25                  30

Asn Glu Gly Glu Phe Val Ala Ile Met Gly Pro Ser Gly Ser Gly Lys
        35                  40                  45

Ser Thr Leu Met Asn Thr Ile Gly Met Leu Asp Thr Pro Thr Ser Gly
    50                  55                  60

Glu Tyr Tyr Leu Glu Gly Gln Glu Val Ala Gly Leu Gly Lys Gln
65                  70                  75                  80

Leu Ala Lys Val Arg Asn Gln Gln Ile Gly Phe Val Phe Gln Gln Phe
                85                  90                  95

Phe Leu Leu Ser Lys Leu Asn Ala Leu Gln Asn Val Glu Leu Pro Leu
            100                 105                 110

Ile Tyr Ala Gly Val Ser Ser Lys Arg Arg Lys Leu Ala Glu Glu
        115                 120                 125

Tyr Leu Asp Lys Val Glu Leu Thr Glu Arg Ser His His Leu Pro Ser
    130                 135                 140

Glu Leu Ser Gly Gly Gln Lys Gln Arg Val Ala Ile Ala Arg Ala Leu
145                 150                 155                 160

Val Asn Asn Pro Ser Ile Ile Leu Ala Asp Glu Pro Thr Gly Ala Leu
                165                 170                 175

Asp Thr Lys Thr Gly Asn Gln Ile Met Gln Leu Leu Val Asp Leu Asn
            180                 185                 190

Lys Glu Gly Lys Thr Ile Ile Met Val Thr His Glu Pro Glu Ile Ala
        195                 200                 205

Ala Tyr Ala Lys Arg Gln Ile Val Ile Arg Asp Gly Val Ile Ser Ser
    210                 215                 220

Asp Ser Ala Gln Leu Gly Lys Glu Glu Asn
225                 230

<210> SEQ ID NO 93
<211> LENGTH: 1200
<212> TYPE: DNA
<213> ORGANISM: Streptococcus pneumoniae

<400> SEQUENCE: 93
atgaagaaaa agaatggtaa agctaaaaag tggcaactgt atgcagcaat cggtgctgcg      60
agtgtagttg tattgggtgc tggggggatt ttactcttta caaccttc tcagactgct       120 ctaaaagatg agcctactca tcttgttgtt gccaaggaag gaagcgtggc ctcctctgtt      180
ttattgtcag ggacagtaac agcaaaaaat gaacaatatg tttattttga tgctagtaag      240
ggtgatttag atgaaatcct tgtttctgtg ggcgataagg tcagcgaagg caggcttta      300 gtcaagtaca gtagttcaga agcgcaggcg gcctatgatt cagctagtcg agcagtagct      360
agggcagatc gtcatatcaa tgaactcaat caagcacgaa atgaagccgc ttcagctccg      420
gctccacagt taccagcgcc agtaggagga gaagatgcaa cggtgcaaag cccaactcca      480
gtggctggaa attctgttgc ttctattgac gctcaattgg gtgatgcccg tgatgcgcgt      540

-continued

```
gcagatgctg cggcgcaatt aagcaaggct caaagtcaat tggatgcaac aactgttctc    600
agtaccctag agggaactgt ggtcgaagtc aatagcaatg tttctaaatc tccaacaggg    660
gcgagtcaag ttatggttca tattgtcagc aatgaaaatt tacaagtcaa gggagaattg    720
tctgagtaca atctagccaa cctttctgta ggtcaagaag taagctttac ttctaaagtg    780
tatcctgata aaaatggac tgggaaatta agctatattt ctgactatcc taaaaacaat     840
ggtgaagcag ctagtccagc agccgggaat aatacaggtt ctaaataccc ttatactatt    900
gatgtgacag gcgaggttgg tgatttgaaa caaggttttt ctgtcaacat tgaggttaaa    960
agcaaaacta aggctattct tgttcctgtt agcagtctag taatggatga tagtaaaaat   1020
tatgtctgga ttgtggatga acaacaaaag gctaaaaaag ttgaggtttc attgggaaat   1080
gctgacgcag aaaatcaaga aatcacttct ggtttaacga acggtgctaa ggtcatcagt   1140
aatccaacat cttccttgga agaaggaaaa gaggtgaagg ctgatgaagc aactaattag   1200
```

<210> SEQ ID NO 94
<211> LENGTH: 399
<212> TYPE: PRT
<213> ORGANISM: Streptococcus pneumoniae

<400> SEQUENCE: 94

```
Met Lys Lys Lys Asn Gly Lys Ala Lys Lys Trp Gln Leu Tyr Ala Ala
 1               5                  10                  15

Ile Gly Ala Ala Ser Val Val Leu Gly Ala Gly Ile Leu Leu
                20                  25                  30

Phe Arg Gln Pro Ser Gln Thr Ala Leu Lys Asp Glu Pro Thr His Leu
                35                  40                  45

Val Val Ala Lys Glu Gly Ser Val Ala Ser Ser Val Leu Leu Ser Gly
         50                  55                  60

Thr Val Thr Ala Lys Asn Glu Gln Tyr Val Tyr Phe Asp Ala Ser Lys
 65                  70                  75                  80

Gly Asp Leu Asp Glu Ile Leu Val Ser Val Gly Asp Lys Val Ser Glu
                 85                  90                  95

Gly Gln Ala Leu Val Lys Tyr Ser Ser Ser Glu Ala Gln Ala Ala Tyr
                100                 105                 110

Asp Ser Ala Ser Arg Ala Val Ala Arg Ala Asp Arg His Ile Asn Glu
             115                 120                 125

Leu Asn Gln Ala Arg Asn Glu Ala Ser Ala Pro Ala Pro Gln Leu
         130                 135                 140

Pro Ala Pro Val Gly Gly Glu Asp Ala Thr Val Gln Ser Pro Thr Pro
145                 150                 155                 160

Val Ala Gly Asn Ser Val Ala Ser Ile Asp Ala Gln Leu Gly Asp Ala
                165                 170                 175

Arg Asp Ala Arg Ala Asp Ala Ala Gln Leu Ser Lys Ala Gln Ser
             180                 185                 190

Gln Leu Asp Ala Thr Thr Val Leu Ser Thr Leu Glu Gly Thr Val Val
         195                 200                 205

Glu Val Asn Ser Asn Val Ser Lys Ser Pro Thr Gly Ala Ser Gln Val
     210                 215                 220

Met Val His Ile Val Ser Asn Glu Asn Leu Gln Val Lys Gly Glu Leu
225                 230                 235                 240

Ser Glu Tyr Asn Leu Ala Asn Leu Ser Val Gly Gln Glu Val Ser Phe
                245                 250                 255

Thr Ser Lys Val Tyr Pro Asp Lys Lys Trp Thr Gly Lys Leu Ser Tyr
                260                 265                 270
```

```
Ile Ser Asp Tyr Pro Lys Asn Asn Gly Glu Ala Ala Ser Pro Ala Ala
        275                 280                 285

Gly Asn Asn Thr Gly Ser Lys Tyr Pro Tyr Thr Ile Asp Val Thr Gly
    290                 295                 300

Glu Val Gly Asp Leu Lys Gln Gly Phe Ser Val Asn Ile Glu Val Lys
305                 310                 315                 320

Ser Lys Thr Lys Ala Ile Leu Val Pro Val Ser Ser Leu Val Met Asp
                325                 330                 335

Asp Ser Lys Asn Tyr Val Trp Ile Val Asp Glu Gln Gln Lys Ala Lys
            340                 345                 350

Lys Val Glu Val Ser Leu Gly Asn Ala Asp Ala Glu Asn Gln Glu Ile
        355                 360                 365

Thr Ser Gly Leu Thr Asn Gly Ala Lys Val Ile Ser Asn Pro Thr Ser
    370                 375                 380

Ser Leu Glu Glu Gly Lys Glu Val Lys Ala Asp Glu Ala Thr Asn
385                 390                 395
```

<210> SEQ ID NO 95
<211> LENGTH: 759
<212> TYPE: DNA
<213> ORGANISM: Streptococcus pneumoniae

<400> SEQUENCE: 95

```
atgtcacgta aaccatttat cgctggtaac tggaaaatga caaaaatcc agaagaagct    60
aaagcattcg ttgaagcagt tgcatcaaaa cttccttcat cagatcttgt tgaagcaggt   120
atcgctgctc cagctcttga tttgacaact gttcttgctg ttgcaaaagg ctcaaacctt   180
aaagttgctg ctcaaaactg ctactttgaa aatgcaggtg cttttcactgg tgaaactagc   240
ccacaagttt tgaaagaaat cggtactgac tacgttgtta tcggtcactc agaacgccgt   300
gactacttcc atgaaactga tgaagatatc aacaaaaaag caaaagcaat ctttgcgaac   360
ggtatgcttc caatcatctg ttgtggtgaa tcacttgaaa cttacgaagc tggtaaagct   420
gctgaattcg taggtgctca agtatctgct gcattggctg gattgactgc tgaacaagtt   480
gctgcctcag ttatcgctta tgagccaatc tgggctatcg gtactggtaa atcagcttca   540
caagacgatg cacaaaaaat gtgtaaagtt gttcgtgacg ttgtagctgc tgactttggt   600
caagaagtcg cagacaaagt tcgtgttcaa tacggtggtt ctgttaaacc tgaaaatgtt   660
gcttcataca tggcttgccc agacgttgac ggtgcccttg taggtggtgc gtcacttgaa   720
gctgaaagct tcttggcttt gcttgacttt gtaaaataa                          759
```

<210> SEQ ID NO 96
<211> LENGTH: 252
<212> TYPE: PRT
<213> ORGANISM: Streptococcus pneumoniae

<400> SEQUENCE: 96

```
Met Ser Arg Lys Pro Phe Ile Ala Gly Asn Trp Lys Met Asn Lys Asn
  1               5                  10                  15

Pro Glu Glu Ala Lys Ala Phe Val Glu Ala Val Ala Ser Lys Leu Pro
                20                  25                  30

Ser Ser Asp Leu Val Glu Ala Gly Ile Ala Ala Pro Ala Leu Asp Leu
            35                  40                  45

Thr Thr Val Leu Ala Val Ala Lys Gly Ser Asn Leu Lys Val Ala Ala
        50                  55                  60

Gln Asn Cys Tyr Phe Glu Asn Ala Gly Ala Phe Thr Gly Glu Thr Ser
```

```
                65                  70                  75                  80
Pro Gln Val Leu Lys Glu Ile Gly Thr Asp Tyr Val Val Ile Gly His
                        85                  90                  95

Ser Glu Arg Arg Asp Tyr Phe His Glu Thr Asp Glu Asp Ile Asn Lys
                100                 105                 110

Lys Ala Lys Ala Ile Phe Ala Asn Gly Met Leu Pro Ile Ile Cys Cys
                115                 120                 125

Gly Glu Ser Leu Glu Thr Tyr Glu Ala Gly Lys Ala Ala Glu Phe Val
            130                 135                 140

Gly Ala Gln Val Ser Ala Ala Leu Ala Gly Leu Thr Ala Glu Gln Val
145                 150                 155                 160

Ala Ala Ser Val Ile Ala Tyr Glu Pro Ile Trp Ala Ile Gly Thr Gly
                165                 170                 175

Lys Ser Ala Ser Gln Asp Asp Ala Gln Lys Met Cys Lys Val Val Arg
                180                 185                 190

Asp Val Ala Ala Asp Phe Gly Gln Glu Val Ala Asp Lys Val Arg
                195                 200                 205

Val Gln Tyr Gly Gly Ser Val Lys Pro Glu Asn Val Ala Ser Tyr Met
            210                 215                 220

Ala Cys Pro Asp Val Asp Gly Ala Leu Val Gly Gly Ala Ser Leu Glu
225                 230                 235                 240

Ala Glu Ser Phe Leu Ala Leu Leu Asp Phe Val Lys
                245                 250

<210> SEQ ID NO 97
<211> LENGTH: 1473
<212> TYPE: DNA
<213> ORGANISM: Streptococcus pneumoniae

<400> SEQUENCE: 97
ttgaaaacaa aaattggatt agcaagtatc tgtttactag cttggcaac tagtcatgtc      60 gctgcaaatg aaactgaagt agcaaaaact tcgcaggata caacgacagc ttcaagtagt   120
tcagagcaaa atcagtcttc taataaaacg caaacgagcg cagaagtaca gactaatgct   180
gctgcccact gggatgggga ttattatgta aaggatgatg gttctaaagc tcaaagtgaa   240 tggattttg acaactacta taaggcttgg ttttatatta attcagatgg tcgttactcg    300
cagaatgaat ggcatggaaa ttactacctg aaatcaggtg atatatggc ccaaaacgag    360 tggatctatg acagtaatta caagagttgg ttttatctca agtcagatgg ggcttatgct   420
catcaagaat ggcaattgat tggaaataag tggtactact tcaagaagtg gggttacatg   480
gctaaaagcc aatggcaagg aagttatttc ttgaatggtc aaggagctat gatgcaaaat   540
gaatggctct atgatccagc ctattctgct tattttatc taaaatccga tggaacttat    600
gctaaccaag agtggcaaaa agtgggcggc aaatggtact atttcaagaa gtggggctat   660
atggctcgga tgagtggca aggcaactac tatttgactg gaagtggtgc catggcgact   720
gacgaagtga ttatggatgg tactcgctat atctttgcgg cctctggtga gctcaaagaa   780 aaaaagatt tgaatgtcgg ctgggttcac agagatggta gcgctatttt ctttaataat   840
agagaagaac aagtgggaac cgaacatgct aagaaagtca ttgatattag tgagcacaat   900
ggtcgtatca atgattggaa aaggttatt gatgagaacg aagtggatgg tgtcattgtt    960
cgtctaggtt atagcggtaa agaagacaag gaattggcgc ataacattaa ggagttaaac  1020
cgtctgggaa ttcctatgg tgtctatctc tataccctatg ctgaaaatga gaccgatgct  1080
gagagtgacg ctaaacagac cattgaactt ataaagaaat acaatatgaa cctgtcttac  1140
```

-continued

```
cctatctatt atgatgttga gaattgggaa tatgtaaata agagcaagag agctccaagt   1200
gatacaggca cttgggttaa atcatcaac aagtacatgg acacgatgaa gcaggcgggt   1260
tatcaaaatg tgtatgtcta tagctatcgt agtttattac agacgcgttt aaaacaccca   1320
gatattttaa aacatgtaaa ctgggtagcg gcctatacga atgctttaga atgggaaaac   1380
cctcattatt caggaaaaaa aggttggcaa tatcctctt ctgaatacat gaaaggaatc    1440
caagggcgcg tagatgtcag cgtttggtat taa                               1473
```

<210> SEQ ID NO 98
<211> LENGTH: 490
<212> TYPE: PRT
<213> ORGANISM: Streptococcus pneumoniae

<400> SEQUENCE: 98

```
Met Lys Thr Lys Ile Gly Leu Ala Ser Ile Cys Leu Leu Gly Leu Ala
  1               5                  10                  15

Thr Ser His Val Ala Ala Asn Glu Thr Glu Val Ala Lys Thr Ser Gln
             20                  25                  30

Asp Thr Thr Thr Ala Ser Ser Ser Glu Gln Asn Gln Ser Ser Asn
         35                  40                  45

Lys Thr Gln Thr Ser Ala Glu Val Gln Thr Asn Ala Ala His Trp
     50                  55                  60

Asp Gly Asp Tyr Tyr Val Lys Asp Gly Ser Lys Ala Gln Ser Glu
 65                  70                  75                  80

Trp Ile Phe Asp Asn Tyr Lys Ala Trp Phe Tyr Ile Asn Ser Asp
                 85                  90                  95

Gly Arg Tyr Ser Gln Asn Glu Trp His Gly Asn Tyr Leu Lys Ser
            100                 105                 110

Gly Gly Tyr Met Ala Gln Asn Glu Trp Ile Tyr Asp Ser Asn Tyr Lys
            115                 120                 125

Ser Trp Phe Tyr Leu Lys Ser Asp Gly Ala Tyr Ala His Gln Glu Trp
    130                 135                 140

Gln Leu Ile Gly Asn Lys Trp Tyr Tyr Phe Lys Lys Trp Gly Tyr Met
145                 150                 155                 160

Ala Lys Ser Gln Trp Gln Gly Ser Tyr Phe Leu Asn Gly Gln Gly Ala
                165                 170                 175

Met Met Gln Asn Glu Trp Leu Tyr Asp Pro Ala Tyr Ser Ala Tyr Phe
            180                 185                 190

Tyr Leu Lys Ser Asp Gly Thr Tyr Ala Asn Gln Glu Trp Gln Lys Val
            195                 200                 205

Gly Gly Lys Trp Tyr Tyr Phe Lys Lys Trp Gly Tyr Met Ala Arg Asn
        210                 215                 220

Glu Trp Gln Gly Asn Tyr Tyr Leu Thr Gly Ser Gly Ala Met Ala Thr
225                 230                 235                 240

Asp Glu Val Ile Met Asp Gly Thr Arg Tyr Ile Phe Ala Ala Ser Gly
                245                 250                 255

Glu Leu Lys Glu Lys Lys Asp Leu Asn Val Gly Trp Val His Arg Asp
            260                 265                 270

Gly Lys Arg Tyr Phe Phe Asn Asn Arg Glu Glu Gln Val Gly Thr Glu
        275                 280                 285

His Ala Lys Lys Val Ile Asp Ile Ser Glu His Asn Gly Arg Ile Asn
    290                 295                 300

Asp Trp Lys Lys Val Ile Asp Glu Asn Glu Val Asp Gly Val Ile Val
305                 310                 315                 320
```

Arg Leu Gly Tyr Ser Gly Lys Glu Asp Lys Glu Leu Ala His Asn Ile
                325                 330                 335

Lys Glu Leu Asn Arg Leu Gly Ile Pro Tyr Gly Val Tyr Leu Tyr Thr
            340                 345                 350

Tyr Ala Glu Asn Glu Thr Asp Ala Glu Ser Asp Ala Lys Gln Thr Ile
        355                 360                 365

Glu Leu Ile Lys Lys Tyr Asn Met Asn Leu Ser Tyr Pro Ile Tyr Tyr
    370                 375                 380

Asp Val Glu Asn Trp Glu Tyr Val Asn Lys Ser Lys Arg Ala Pro Ser
385                 390                 395                 400

Asp Thr Gly Thr Trp Val Lys Ile Ile Asn Lys Tyr Met Asp Thr Met
                405                 410                 415

Lys Gln Ala Gly Tyr Gln Asn Val Tyr Val Tyr Ser Tyr Arg Ser Leu
            420                 425                 430

Leu Gln Thr Arg Leu Lys His Pro Asp Ile Leu Lys His Val Asn Trp
        435                 440                 445

Val Ala Ala Tyr Thr Asn Ala Leu Glu Trp Glu Asn Pro His Tyr Ser
    450                 455                 460

Gly Lys Lys Gly Trp Gln Tyr Thr Ser Ser Glu Tyr Met Lys Gly Ile
465                 470                 475                 480

Gln Gly Arg Val Asp Val Ser Val Trp Tyr
                485                 490

<210> SEQ ID NO 99
<211> LENGTH: 774
<212> TYPE: DNA
<213> ORGANISM: Streptococcus pneumoniae

<400> SEQUENCE: 99
atgaaaaaat tgccaacct ttatctggga ctggtctttc tggtcctcta cctgcctatc        60
ttttacttga ttggctatgc ctttaatgct ggtgatgata tgaatagctt tacaggtttt      120
agctggactc actttgaaac catgtttgga gatgggagac tcatgctgat tttggctcag      180 acattttct tggccttcct atcagccttg atagcgacca ttatcgggac ttttggtgcc      240
atttacatct accagtctcg taagaaatac caagaagcct ttctatcact caataatatc      300
ctcatggttg cgcctgacgt tatgattggt gctagcttct tgattctctt tacccaactc      360 aagtttttcac ttggctttttt gaccgttcta tctagtcacg tggccttctc cattcctatc      420
gtggtcttga tggtcttgcc tcgactcaag gaaatgaatg cgacatgat tcatgcggcc      480 tatgacttgg gagctagtca atttcagatg ttcaaggaaa tcatgcttcc ttacctgact      540
ccgtctatca ttactggtta tttcatggcc ttcacctatt cgttagatga ctttgccgtg      600
accttctttg taacaggaaa tggcttttca accctatcag tcgagattta ctctcgtgct      660
cgcaagggga tttccttaga aatcaatgcc ctgtctgctc tagtcttct ctttagtatt      720 atcctagttg taggttatta ctttatctct cgtgagaagg aggagcaagc atga            774

<210> SEQ ID NO 100
<211> LENGTH: 257
<212> TYPE: PRT
<213> ORGANISM: Streptococcus pneumoniae

<400> SEQUENCE: 100

Met Lys Lys Phe Ala Asn Leu Tyr Leu Gly Leu Val Phe Leu Val Leu
1               5                   10                  15

Tyr Leu Pro Ile Phe Tyr Leu Ile Gly Tyr Ala Phe Asn Ala Gly Asp

```
                   20                  25                  30
Asp Met Asn Ser Phe Thr Gly Phe Ser Trp Thr His Phe Glu Thr Met
                35                  40                  45

Phe Gly Asp Gly Arg Leu Met Leu Ile Leu Ala Gln Thr Phe Phe Leu
    50                  55                  60

Ala Phe Leu Ser Ala Leu Ile Ala Thr Ile Ile Gly Thr Phe Gly Ala
65                  70                  75                  80

Ile Tyr Ile Tyr Gln Ser Arg Lys Lys Tyr Gln Glu Ala Phe Leu Ser
                85                  90                  95

Leu Asn Asn Ile Leu Met Val Ala Pro Asp Val Met Ile Gly Ala Ser
            100                 105                 110

Phe Leu Ile Leu Phe Thr Gln Leu Lys Phe Ser Leu Gly Phe Leu Thr
        115                 120                 125

Val Leu Ser Ser His Val Ala Phe Ser Ile Pro Ile Val Val Leu Met
    130                 135                 140

Val Leu Pro Arg Leu Lys Glu Met Asn Gly Asp Met Ile His Ala Ala
145                 150                 155                 160

Tyr Asp Leu Gly Ala Ser Gln Phe Gln Met Phe Lys Glu Ile Met Leu
                165                 170                 175

Pro Tyr Leu Thr Pro Ser Ile Ile Thr Gly Tyr Phe Met Ala Phe Thr
            180                 185                 190

Tyr Ser Leu Asp Asp Phe Ala Val Thr Phe Phe Val Thr Gly Asn Gly
        195                 200                 205

Phe Ser Thr Leu Ser Val Glu Ile Tyr Ser Arg Ala Arg Lys Gly Ile
    210                 215                 220

Ser Leu Glu Ile Asn Ala Leu Ser Ala Leu Val Phe Leu Phe Ser Ile
225                 230                 235                 240

Ile Leu Val Val Gly Tyr Tyr Phe Ile Ser Arg Glu Lys Glu Glu Gln
                245                 250                 255

Ala

<210> SEQ ID NO 101
<211> LENGTH: 1071
<212> TYPE: DNA
<213> ORGANISM: Streptococcus pneumoniae

<400> SEQUENCE: 101
atgaaaaaaa tctattcatt tttagcagga attgcagcga ttatccttgt cttgtgggga      60
attgcgactc atttagatag taaaatcaat agtcgagata gtcaaaaatt ggttatctat     120
aactggggag actatatcga tcctgaactc ttgactcagt ttacagaaga acaggaatt      180 caagttcagt acgagacttt tgactccaac gaagccatgt acactaagat aaagcagggt     240
ggaacgacct acgatattgc cattccaagt gaatacatga ttaacaagat gaaggacgaa     300
gacctcttgg ttccgcttga ttattcaaaa attgaaggaa tcgaaaatat cggaccagag     360
tttctcaacc agtcctttga cccaggtaat aaattctcca tcccttactt ctggggaacc     420
ttaggaattg tctacaacga aaccatggta gatgaagcgc tgagcattg ggatgacctt     480 tggaagccgg agtataagaa ttctatcatg ctctttgatg gggcgcgtga ggtgctggga     540
ctaggactca attccctcgg ctacagcctc aactccaagg atctgcagca gttggaagag     600
acagtggata agctctacaa actgactcca aatatcaagg ctatcgttgc ggacgagatg     660
aagggctata tgattcagaa taatgttgca atcggcgtga ccttctctgg tgaagccagc     720
caaatgttag aaaaaaatga aaatctacgt tatgtggtac cgacagaggc cagcaatctt     780
```

```
tggtttgaca atatggtcat tcccaaaaca gttaaaaacc aaaactcagc ctatgccttt      840
atcaacttta tgttgaaacc tgaaaatgct ctccaaaatg cggagtatgt cggctattca      900
acaccaaacc taccagcgaa ggaattgctc ccagaggaaa caaggaagat aaggccttc       960 tatcccgatg ttgaaaccat gaaacaccta gaagtttatg agaaatttga ccataaatgg     1020
acagggaaat atagcgacct cttcctacag tttaaaatgt atcggaagta g              1071
```

<210> SEQ ID NO 102
<211> LENGTH: 356
<212> TYPE: PRT
<213> ORGANISM: Streptococcus pneumoniae

<400> SEQUENCE: 102

```
Met Lys Lys Ile Tyr Ser Phe Leu Ala Gly Ile Ala Ala Ile Ile Leu
 1               5                  10                  15

Val Leu Trp Gly Ile Ala Thr His Leu Asp Ser Lys Ile Asn Ser Arg
            20                  25                  30

Asp Ser Gln Lys Leu Val Ile Tyr Asn Trp Gly Asp Tyr Ile Asp Pro
        35                  40                  45

Glu Leu Leu Thr Gln Phe Thr Glu Thr Gly Ile Gln Val Gln Tyr
    50                  55                  60

Glu Thr Phe Asp Ser Asn Glu Ala Met Tyr Thr Lys Ile Lys Gln Gly
 65                  70                  75                  80

Gly Thr Thr Tyr Asp Ile Ala Ile Pro Ser Glu Tyr Met Ile Asn Lys
                85                  90                  95

Met Lys Asp Glu Asp Leu Leu Val Pro Leu Asp Tyr Ser Lys Ile Glu
            100                 105                 110

Gly Ile Glu Asn Ile Gly Pro Glu Phe Leu Asn Gln Ser Phe Asp Pro
        115                 120                 125

Gly Asn Lys Phe Ser Ile Pro Tyr Phe Trp Gly Thr Leu Gly Ile Val
    130                 135                 140

Tyr Asn Glu Thr Met Val Asp Glu Ala Pro Glu His Trp Asp Asp Leu
145                 150                 155                 160

Trp Lys Pro Glu Tyr Lys Asn Ser Ile Met Leu Phe Asp Gly Ala Arg
                165                 170                 175

Glu Val Leu Gly Leu Gly Leu Asn Ser Leu Gly Tyr Ser Leu Asn Ser
            180                 185                 190

Lys Asp Leu Gln Gln Leu Glu Glu Thr Val Asp Lys Leu Tyr Lys Leu
        195                 200                 205

Thr Pro Asn Ile Lys Ala Ile Val Ala Asp Glu Met Lys Gly Tyr Met
    210                 215                 220

Ile Gln Asn Asn Val Ala Ile Gly Val Thr Phe Ser Gly Glu Ala Ser
225                 230                 235                 240

Gln Met Leu Glu Lys Asn Glu Asn Leu Arg Tyr Val Val Pro Thr Glu
                245                 250                 255

Ala Ser Asn Leu Trp Phe Asp Asn Met Val Ile Pro Lys Thr Val Lys
            260                 265                 270

Asn Gln Asn Ser Ala Tyr Ala Phe Ile Asn Phe Met Leu Lys Pro Glu
        275                 280                 285

Asn Ala Leu Gln Asn Ala Glu Tyr Val Gly Tyr Ser Thr Pro Asn Leu
    290                 295                 300

Pro Ala Lys Glu Leu Leu Pro Glu Glu Thr Lys Glu Asp Lys Ala Phe
305                 310                 315                 320

Tyr Pro Asp Val Glu Thr Met Lys His Leu Glu Val Tyr Glu Lys Phe
                325                 330                 335
```

Asp His Lys Trp Thr Gly Lys Tyr Ser Asp Leu Phe Leu Gln Phe Lys
        340                 345                 350

Met Tyr Arg Lys
    355

<210> SEQ ID NO 103
<211> LENGTH: 1851
<212> TYPE: DNA
<213> ORGANISM: Streptococcus pneumoniae

<400> SEQUENCE: 103

| | |
|---|---|
| atgaataaaa aactaacaga ttatgtgatt gatctggtgg aaattttaaa taaacaacaa | 60 |
| aagcaggttt tctggggaat atttgatatt ttcagtatgg tggtttccat cattgtatct | 120 |
| tatattttat tttatgggct gattaatcca gcacctgttg actacattat ctatacgagt | 180 |
| ttggccttcc tgttctatca attgatgatt ggttttgggg ggttgaacgc gagcattagt | 240 |
| cgttacagca agattacgga tttcatgaaa atcttttttg gtgtgactgc tagcagtgtc | 300 |
| ttgtcatata gtatctgtta tgccttcttg ccactcttct ccatccgttt catcattctc | 360 |
| tttatcttgt tgagtaccct cttgatttta ttgccacgga ttacttggca gttaatctac | 420 |
| tccagacgca aaaaggtag tggtgatgga aacaccgtc ggaccttctt gattggtgcc | 480 |
| ggtgatggtg gggctctttt tatggatagt taccaacatc aaccagtga attagaactg | 540 |
| gtcggtattt ggataagga ttctaagaaa aagggtcaaa acttggtgg tattcctgtt | 600 |
| ttgggctctt atgacaatct gcctgaatta gccaaacgcc atcaaatcga gcgtgtcatc | 660 |
| gttgcgattc cgtcgctgga tccgtcagaa tatgagcgta tcttgcagat gtgtaataag | 720 |
| ctgggtgtca atgttacaa gatgcctaag gttgaaactg ttgttcaggg ccttcaccaa | 780 |
| gcaggtactg cttccaaaa aattgatatt acggaccttt gggtcgtca ggaaatccgt | 840 |
| cttgacgaat cgcgtctggg tgcagaactg acaggtaaga ccatcttagt cacaggagct | 900 |
| ggaggttcaa tcggttctga atctgtcgt caagttagtc gcttcaatcc tgaacgcatt | 960 |
| gtcttgctcg tcatgggga aaactcaatc taccttgttt atcatgaatt gattcgtaag | 1020 |
| ttccaaggga ttgattatgt acctgtgatt gcggacattc aagactatga tcgtttgttg | 1080 |
| caagtctttg agcagtacaa acctgctatt gtttatcatg cggcagccca caagcatgtt | 1140 |
| cctatgatgg agcgcaatcc aaaagaagcc ttcaaaaaca atatccgtgg aacttacaat | 1200 |
| gttgctaagg ctgttgatga agctaaagtg tctaagatgg ttatgatttc gacagataag | 1260 |
| gcagtcaatc caccaaatgt tatgggagca accaagcgcg tggcggagtt gattgtcact | 1320 |
| ggctttaacc aacgtagcca atcaacctac tgtgcagttc gttttgggaa tgttcttggt | 1380 |
| agccgtggta gtgtcattcc agtctttgaa cgtcagattg ctgaaggtgg gcctgtaacg | 1440 |
| gtgacagact tccgtatgac ccgttacttt atgaccattc cagaagctag ccgtctggtt | 1500 |
| atccatgctg gtgcttatgc caaagatggg gaagtctta tccttgatat gggcaaacca | 1560 |
| gtcaagattt atgacttggc caagaagatg gtgcttctaa gtggccacac tgaaagtgaa | 1620 |
| attccaatcg ttgaagttgg aatccgccca ggtgaaaaac tctacgaaga actcttggta | 1680 |
| tcaaccgaac tcgttgataa tcaagttatg gataagattt cgttggtaa ggttaatgtc | 1740 |
| atgcctttag aatccatcaa tcaaaagatt ggagagttcc gcactctcag tggagatgag | 1800 |
| ttgaagcaag ctattatcgc ctttgctaat caaacaaccc acattgaata a | 1851 |

<210> SEQ ID NO 104
<211> LENGTH: 616

```
<212> TYPE: PRT
<213> ORGANISM: Streptococcus pneumoniae

<400> SEQUENCE: 104
```

Met Asn Lys Lys Leu Thr Asp Tyr Val Ile Asp Leu Val Glu Ile Leu
1               5                   10                  15

Asn Lys Gln Gln Lys Gln Val Phe Trp Gly Ile Phe Asp Ile Phe Ser
            20                  25                  30

Met Val Val Ser Ile Ile Val Ser Tyr Ile Leu Phe Tyr Gly Leu Ile
        35                  40                  45

Asn Pro Ala Pro Val Asp Tyr Ile Ile Tyr Thr Ser Leu Ala Phe Leu
    50                  55                  60

Phe Tyr Gln Leu Met Ile Gly Phe Trp Gly Leu Asn Ala Ser Ile Ser
65              70                  75                  80

Arg Tyr Ser Lys Ile Thr Asp Phe Met Lys Ile Phe Phe Gly Val Thr
                85                  90                  95

Ala Ser Ser Val Leu Ser Tyr Ser Ile Cys Tyr Ala Phe Leu Pro Leu
            100                 105                 110

Phe Ser Ile Arg Phe Ile Ile Leu Phe Ile Leu Leu Ser Thr Phe Leu
        115                 120                 125

Ile Leu Leu Pro Arg Ile Thr Trp Gln Leu Ile Tyr Ser Arg Arg Lys
130                 135                 140

Lys Gly Ser Gly Asp Gly Glu His Arg Arg Thr Phe Leu Ile Gly Ala
145                 150                 155                 160

Gly Asp Gly Gly Ala Leu Phe Met Asp Ser Tyr Gln His Pro Thr Ser
                165                 170                 175

Glu Leu Glu Leu Val Gly Ile Leu Asp Lys Asp Ser Lys Lys Lys Gly
            180                 185                 190

Gln Lys Leu Gly Gly Ile Pro Val Leu Gly Ser Tyr Asp Asn Leu Pro
        195                 200                 205

Glu Leu Ala Lys Arg His Gln Ile Glu Arg Val Ile Val Ala Ile Pro
210                 215                 220

Ser Leu Asp Pro Ser Glu Tyr Glu Arg Ile Leu Gln Met Cys Asn Lys
225                 230                 235                 240

Leu Gly Val Lys Cys Tyr Lys Met Pro Lys Val Glu Thr Val Val Gln
                245                 250                 255

Gly Leu His Gln Ala Gly Thr Gly Phe Gln Lys Ile Asp Ile Thr Asp
            260                 265                 270

Leu Leu Gly Arg Gln Glu Ile Arg Leu Asp Glu Ser Arg Leu Gly Ala
        275                 280                 285

Glu Leu Thr Gly Lys Thr Ile Leu Val Thr Gly Ala Gly Gly Ser Ile
290                 295                 300

Gly Ser Glu Ile Cys Arg Gln Val Ser Arg Phe Asn Pro Glu Arg Ile
305                 310                 315                 320

Val Leu Leu Gly His Gly Glu Asn Ser Ile Tyr Leu Val Tyr His Glu
                325                 330                 335

Leu Ile Arg Lys Phe Gln Gly Ile Asp Tyr Val Pro Val Ile Ala Asp
            340                 345                 350

Ile Gln Asp Tyr Asp Arg Leu Leu Gln Val Phe Glu Gln Tyr Lys Pro
        355                 360                 365

Ala Ile Val Tyr His Ala Ala Ala His Lys His Val Pro Met Met Glu
370                 375                 380

Arg Asn Pro Lys Glu Ala Phe Lys Asn Asn Ile Arg Gly Thr Tyr Asn
385                 390                 395                 400

```
Val Ala Lys Ala Val Asp Glu Ala Lys Val Ser Lys Met Val Met Ile
                405                 410                 415
Ser Thr Asp Lys Ala Val Asn Pro Pro Asn Val Met Gly Ala Thr Lys
            420                 425                 430
Arg Val Ala Glu Leu Ile Val Thr Gly Phe Asn Gln Arg Ser Gln Ser
        435                 440                 445
Thr Tyr Cys Ala Val Arg Phe Gly Asn Val Leu Gly Ser Arg Gly Ser
    450                 455                 460
Val Ile Pro Val Phe Glu Arg Gln Ile Ala Glu Gly Pro Val Thr
465                 470                 475                 480
Val Thr Asp Phe Arg Met Thr Arg Tyr Phe Met Thr Ile Pro Glu Ala
                485                 490                 495
Ser Arg Leu Val Ile His Ala Gly Ala Tyr Ala Lys Asp Gly Glu Val
            500                 505                 510
Phe Ile Leu Asp Met Gly Lys Pro Val Lys Ile Tyr Asp Leu Ala Lys
        515                 520                 525
Lys Met Val Leu Leu Ser Gly His Thr Glu Ser Glu Ile Pro Ile Val
    530                 535                 540
Glu Val Gly Ile Arg Pro Gly Glu Lys Leu Tyr Glu Glu Leu Leu Val
545                 550                 555                 560
Ser Thr Glu Leu Val Asp Asn Gln Val Met Asp Lys Ile Phe Val Gly
                565                 570                 575
Lys Val Asn Val Met Pro Leu Glu Ser Ile Asn Gln Lys Ile Gly Glu
            580                 585                 590
Phe Arg Thr Leu Ser Gly Asp Glu Leu Lys Gln Ala Ile Ile Ala Phe
        595                 600                 605
Ala Asn Gln Thr Thr His Ile Glu
    610                 615

<210> SEQ ID NO 105
<211> LENGTH: 1338
<212> TYPE: DNA
<213> ORGANISM: Streptococcus pneumoniae

<400> SEQUENCE: 105
atgattgaac tttatgatag ttacagtcaa gaaagtcgag atttacatga aagtctagtc      60
gctactggtc tttctcaact tggagtggtc atcgatgcag atggttttct gcctgatggt     120
ctgctttctc cttttaccta ttatctaggt tacgaggatg aaaacctct ctattttaat      180 caagttccg tttcagattt tgggaaatt ttaggagata tcagtctgc ttgtattgaa        240 gatgtgacgc aggagagggc tgtcattcat tatgctgatg aatgcaggc tcgcttggtt     300 aaacaggtag actggaaaga cctagaaggt cgagtacgtc aggttgacca ctacaatcgc     360
ttcggagctt gttttgctac aacgacttat agcgcagata gcgagccgat tatgacagtt     420
taccaagatg tcaatggtca acaagtttta ctggaaaacc atgtgacggg tgatatctta     480
ttgactttgc caggtcagtc catgcgttac tttgcaaata agttgaatt tatcaccttc     540 tttttgcaag atttggaaat agataccagt cagcttatct ttaatactct agcgactcct     600
ttcttggttt ccttccatca tccagataaa tctggctcgg atgtcttggt atggcaggaa     660
cctctctatg atgccattcc aggtaatatg cagttgattt tggaaagtga taatgtgcgt     720
actaagaaga tcatcattcc aaataaggcg acttatgagc gcgctttaga gttaactgac     780
gagaaatacc atgatcagtt tgtgcacttg ggttatcatt accagttcaa acgtgataat     840
ttcctaagac gagatgcctt aatcttgacc aattcagatc agattgagca gtagaagca      900
```

```
atcgcaggag ccttgcctga tgtcactttc cgtattgcag cggtgacaga gatgtcttct    960
aagctcttag acatgctttg ctatcctaat gtggcccttt accagaacgc tagtccacag   1020
aagattcagg agctgtatca actgtcggat atttacttgg atataaacca cagtaatgag   1080
ttgctacagg cagtgcgtca ggcctttgag cacaatctct tgattcttgg ctttaatcag   1140
acggtgcaca atagacttta tatcgctcca gaccatctat ttgaaagtag tgaagttgct   1200
gctttggttg agaccattaa attggccctt tcagatgttg atcaaatgcg tcaggcactt   1260
ggcaaacaag gccaacatgc aaattatgtt gacttggtga gatatcagga aaccatgcaa   1320
actgttttag gaggctaa                                                  1338
```

<210> SEQ ID NO 106
<211> LENGTH: 445
<212> TYPE: PRT
<213> ORGANISM: Streptococcus pneumoniae

<400> SEQUENCE: 106

```
Met Ile Glu Leu Tyr Asp Ser Tyr Ser Gln Glu Ser Arg Asp Leu His
  1               5                  10                  15

Glu Ser Leu Val Ala Thr Gly Leu Ser Gln Leu Gly Val Val Ile Asp
                 20                  25                  30

Ala Asp Gly Phe Leu Pro Asp Gly Leu Leu Ser Pro Phe Thr Tyr Tyr
             35                  40                  45

Leu Gly Tyr Glu Asp Gly Lys Pro Leu Tyr Phe Asn Gln Val Pro Val
         50                  55                  60

Ser Asp Phe Trp Glu Ile Leu Gly Asp Asn Gln Ser Ala Cys Ile Glu
 65                  70                  75                  80

Asp Val Thr Gln Glu Arg Ala Val Ile His Tyr Ala Asp Gly Met Gln
                 85                  90                  95

Ala Arg Leu Val Lys Gln Val Asp Trp Lys Asp Leu Glu Gly Arg Val
            100                 105                 110

Arg Gln Val Asp His Tyr Asn Arg Phe Gly Ala Cys Phe Ala Thr Thr
        115                 120                 125

Thr Tyr Ser Ala Asp Ser Glu Pro Ile Met Thr Val Tyr Gln Asp Val
    130                 135                 140

Asn Gly Gln Gln Val Leu Leu Glu Asn His Val Thr Gly Asp Ile Leu
145                 150                 155                 160

Leu Thr Leu Pro Gly Gln Ser Met Arg Tyr Phe Ala Asn Lys Val Glu
                165                 170                 175

Phe Ile Thr Phe Phe Leu Gln Asp Leu Glu Ile Asp Thr Ser Gln Leu
            180                 185                 190

Ile Phe Asn Thr Leu Ala Thr Pro Phe Leu Val Ser Phe His His Pro
        195                 200                 205

Asp Lys Ser Gly Ser Asp Val Leu Val Trp Gln Glu Pro Leu Tyr Asp
    210                 215                 220

Ala Ile Pro Gly Asn Met Gln Leu Ile Leu Glu Ser Asp Asn Val Arg
225                 230                 235                 240

Thr Lys Lys Ile Ile Pro Asn Lys Ala Thr Tyr Glu Arg Ala Leu
                245                 250                 255

Glu Leu Thr Asp Glu Lys Tyr His Asp Gln Phe Val His Leu Gly Tyr
            260                 265                 270

His Tyr Gln Phe Lys Arg Asp Asn Phe Leu Arg Arg Asp Ala Leu Ile
        275                 280                 285

Leu Thr Asn Ser Asp Gln Ile Glu Gln Val Glu Ala Ile Ala Gly Ala
    290                 295                 300
```

```
Leu Pro Asp Val Thr Phe Arg Ile Ala Ala Val Thr Glu Met Ser Ser
305                 310                 315                 320

Lys Leu Leu Asp Met Leu Cys Tyr Pro Asn Val Ala Leu Tyr Gln Asn
            325                 330                 335

Ala Ser Pro Gln Lys Ile Gln Glu Leu Tyr Gln Leu Ser Asp Ile Tyr
            340                 345                 350

Leu Asp Ile Asn His Ser Asn Glu Leu Leu Gln Ala Val Arg Gln Ala
        355                 360                 365

Phe Glu His Asn Leu Leu Ile Leu Gly Phe Asn Gln Thr Val His Asn
    370                 375                 380

Arg Leu Tyr Ile Ala Pro Asp His Leu Phe Glu Ser Ser Glu Val Ala
385                 390                 395                 400

Ala Leu Val Glu Thr Ile Lys Leu Ala Leu Ser Asp Val Asp Gln Met
            405                 410                 415

Arg Gln Ala Leu Gly Lys Gln Gly His Ala Asn Tyr Val Asp Leu
        420                 425                 430

Val Arg Tyr Gln Glu Thr Met Gln Thr Val Leu Gly Gly
        435                 440                 445

<210> SEQ ID NO 107
<211> LENGTH: 1512
<212> TYPE: DNA
<213> ORGANISM: Streptococcus pneumoniae

<400> SEQUENCE: 107
atgacaattt acaatataaa tttaggaatt ggttgggcta gtagcggtgt tgaatacgct      60
caagcctatc gtgctggtgt ttttcggaaa ttaaatctgt cctctaagtt tatctttaca     120
gatatgattt tagccgataa tattcagcac ttaacagcca atattggttt tgatgataat     180
caggttatct ggctttataa tcatttcaca gatatcaaaa ttgcacctac tagcgtgaca     240
gtggatgatg tcttggctta cttggtggt gaagaaagtc acagagaaaa aaatggcaag     300
gttttacgtg tattcttttt tgaccaagat aagtttgtaa cctgttattt ggttgatgag     360
aacaaggact tggttcaaca tgccgagtat gtttttaagg aaaacctgat tcggaaggat     420
tactttcctt atacgcgtta ttgtagcgag tattttgctc ccaaggacaa tgttgcagtc     480
ttataccaac gaactttta taatgaagac gggactccag tctatgatat cttgatgaat     540
caagggaagg aagaagttta tcatttcaag gataagattt tctatggaaa gcaagctttt     600
gtgcgtgcct ttatgaaatc tttgaatttg aataagtctg attggtcat tctcgatagg     660 gagacaggta ttggacaggt tgtgtttgag gaagcacaga cagcacatct agcggtagtt     720
gttcatgcgg agcattatag tgaaaatgct acaaatgagg actatatcct ttggaataac     780
tattatgact atcagtttac caatgcagat aaggttgact tctttatcgt gtctactgat     840
agacaaaatg aagttctaca agagcaattt gccaaatata tcagcatca gccaaagatt     900 gttaccattc ctgtaggcag tattgattcc ttgacagatt caagtcaagg cgcaaaacca     960
ttttcattga ttacggcttc acgtcttgcc aaagaaaagc acattgattg gcttgtgaaa    1020
gctgtgattg aagctcataa ggagttaccg gaactaacct tgatatcta tggtagtggt    1080 ggagaagatt ctctgcttag agaaattatt gcaaatcatc aggcagagga ctatatccaa    1140 ctcaagggc atgcggaact ttcgcagatt tatagccagt atgaggtcta cttaacggct    1200
tctaccagcg aaggatttgg tctgaccttg atggaagcta ttggttcagg tctacctcta    1260
attggttttg atgtgcctta tggtaatcag acctttatag aggatgggca aaatggttat    1320
```

```
ttgattccaa gttcatctga ccatgtagaa gaccaaatca agcaagctta tgccgctaag      1380
atttgtcaat tgtatcaaga aaatcgtttg gaagctatgc gtgcctattc ttaccaaatt      1440
gcagaaggct tcttgaccaa agaaattta gaaaagtgga gaaaacagt agaggaggtg        1500 ctccatgatt ga                                                         1512
```

<210> SEQ ID NO 108
<211> LENGTH: 503
<212> TYPE: PRT
<213> ORGANISM: Streptococcus pneumoniae

<400> SEQUENCE: 108

```
Met Thr Ile Tyr Asn Ile Asn Leu Gly Ile Gly Trp Ala Ser Ser Gly
  1               5                  10                  15

Val Glu Tyr Ala Gln Ala Tyr Arg Ala Gly Val Phe Arg Lys Leu Asn
                 20                  25                  30

Leu Ser Ser Lys Phe Ile Phe Thr Asp Met Ile Leu Ala Asp Asn Ile
             35                  40                  45

Gln His Leu Thr Ala Asn Ile Gly Phe Asp Asp Asn Gln Val Ile Trp
         50                  55                  60

Leu Tyr Asn His Phe Thr Asp Ile Lys Ile Ala Pro Thr Ser Val Thr
 65                  70                  75                  80

Val Asp Asp Val Leu Ala Tyr Phe Gly Gly Glu Glu Ser His Arg Glu
                 85                  90                  95

Lys Asn Gly Lys Val Leu Arg Val Phe Phe Asp Gln Asp Lys Phe
                100                 105                 110

Val Thr Cys Tyr Leu Val Asp Glu Asn Lys Asp Leu Val Gln His Ala
            115                 120                 125

Glu Tyr Val Phe Lys Gly Asn Leu Ile Arg Lys Asp Tyr Phe Ser Tyr
        130                 135                 140

Thr Arg Tyr Cys Ser Glu Tyr Phe Ala Pro Lys Asp Asn Val Ala Val
145                 150                 155                 160

Leu Tyr Gln Arg Thr Phe Tyr Asn Glu Asp Gly Thr Pro Val Tyr Asp
                165                 170                 175

Ile Leu Met Asn Gln Gly Lys Glu Glu Val Tyr His Phe Lys Asp Lys
            180                 185                 190

Ile Phe Tyr Gly Lys Gln Ala Phe Val Arg Ala Phe Met Lys Ser Leu
        195                 200                 205

Asn Leu Asn Lys Ser Asp Leu Val Ile Leu Asp Arg Glu Thr Gly Ile
    210                 215                 220

Gly Gln Val Val Phe Glu Glu Ala Gln Thr Ala His Leu Ala Val Val
225                 230                 235                 240

Val His Ala Glu His Tyr Ser Glu Asn Ala Thr Asn Glu Asp Tyr Ile
                245                 250                 255

Leu Trp Asn Asn Tyr Tyr Asp Tyr Gln Phe Thr Asn Ala Asp Lys Val
            260                 265                 270

Asp Phe Phe Ile Val Ser Thr Asp Arg Gln Asn Glu Val Leu Gln Glu
        275                 280                 285

Gln Phe Ala Lys Tyr Thr Gln His Gln Pro Lys Ile Val Thr Ile Pro
    290                 295                 300

Val Gly Ser Ile Asp Ser Leu Thr Asp Ser Ser Gln Gly Arg Lys Pro
305                 310                 315                 320

Phe Ser Leu Ile Thr Ala Ser Arg Leu Ala Lys Glu Lys His Ile Asp
                325                 330                 335

Trp Leu Val Lys Ala Val Ile Glu Ala His Lys Glu Leu Pro Glu Leu
```

```
                        340                 345                 350
Thr Phe Asp Ile Tyr Gly Ser Gly Gly Glu Asp Ser Leu Leu Arg Glu
            355                 360                 365
Ile Ile Ala Asn His Gln Ala Glu Asp Tyr Ile Gln Leu Lys Gly His
        370                 375                 380
Ala Glu Leu Ser Gln Ile Tyr Ser Gln Tyr Glu Val Tyr Leu Thr Ala
385                 390                 395                 400
Ser Thr Ser Glu Gly Phe Gly Leu Thr Leu Met Glu Ala Ile Gly Ser
                405                 410                 415
Gly Leu Pro Leu Ile Gly Phe Asp Val Pro Tyr Gly Asn Gln Thr Phe
            420                 425                 430
Ile Glu Asp Gly Gln Asn Gly Tyr Leu Ile Pro Ser Ser Ser Asp His
        435                 440                 445
Val Glu Asp Gln Ile Lys Gln Ala Tyr Ala Ala Lys Ile Cys Gln Leu
    450                 455                 460
Tyr Gln Glu Asn Arg Leu Glu Ala Met Arg Ala Tyr Ser Tyr Gln Ile
465                 470                 475                 480
Ala Glu Gly Phe Leu Thr Lys Glu Ile Leu Glu Lys Trp Lys Lys Thr
                485                 490                 495
Val Glu Glu Val Leu His Asp
            500

<210> SEQ ID NO 109
<211> LENGTH: 2292
<212> TYPE: DNA
<213> ORGANISM: Streptococcus pneumoniae

<400> SEQUENCE: 109
atgtcctctc tttcggatca agaattagta gctaaaacag tagagtttcg tcagcgtctt      60
tccgagggag aaagtctaga cgatattttg gttgaagctt ttgctgtggt gcgtgaagca     120
gataagcgga ttttagggat gtttccttat gatgttcaag tcatgggagc tattgtcatg     180
cactatggaa atgttgctga gatgaatacg ggggaaggta agaccttgac agctaccatg     240
cctgtctatt tgaacgcttt ttcaggagaa ggagtgatgg ttgtgactcc taatgagtat     300
ttatcaaagc gtgatgccga ggaaatgggt caagtttatc gttttctagg attgaccatt     360
ggtgtaccat ttacgaaaga tccaaagaag gagatgaaag ctgaagaaaa gaagcttatc     420
tatgcttcgg atatcatcta cacaaccaat agtaatttag gttttgatta tctaaatgat     480
aacctagcct cgaatgaaga aggtaagttt ttacgaccgt ttaactatgt gattattgat     540
gaaattgatg atatcttgct tgatagtgca caaactcctc tgattattgc gggttctcct     600
cgtgttcagt ctaattacta tgcgatcatt gatacacttg taacaacctt ggtcgaagga     660
gaggattata tctttaaaga ggagaaagag gaggtttggc tcactactaa gggggccaag     720
tctgctgaga atttcctagg gattgataat ttatacaagg aagagcatgc gtcttttgct     780
cgtcatttgg tttatgcgat tcgagctcat aagctcttta ctaaagataa ggactatatc     840
attcgtggaa atgagatggt actggttgat aagggaacag gcgtctctaat ggaaatgact     900 aaacttcaag gaggtctcca tcaggctatt gaagccaagg aacatgtcaa attatctcct     960
gagacgcggg ctatggcctc gatcacctat cagagtcttt ttaagatgtt taataagata    1020
tctggtatga cagggacagg taaggtcgcg gaaaaagagt ttattgaaac ttacaatatg    1080
tctgtagtac gcattccaac caatcgtccg agacaacgga ttgactatcc agataatcta    1140
tatatcactt tacctgaaaa agtgtatgca tccttggagt acatcaagca ataccatgct    1200
```

```
aagggaaatc ctttactcgt ttttgtaggc tcagttgaaa tgtctcaact ctattcgtct   1260
ctcttgtttc gtgaagggat tgcccataat gtcctaaatg ctaataatgc ggcgcgtgag   1320
gctcagatta tctccgagtc aggtcagatg ggggctgtga cagtggctac ctctatggca   1380
ggacgtggta cggatatcaa gcttggtaaa ggagtcgcag agcttggggg cttgattgtt   1440
attgggactg agcggatgga aagtcagcgg atcgacctac aaattcgtgg ccgttctggt   1500 cgtcaggag atcctggtat gagtaaattt tttgtatcct tagaggatga tgttatcaag    1560
aaatttggtc catcttgggt gcataaaaag tacaaagact atcaggttca agatatgact   1620
caaccggaag tattgaaagg tcgtaaatac cggaaactag tcgaaaaggc tcagcatgcc   1680
agtgatagtg ctggacgttc agcacgtcgt cagactctgg agtatgctga agtatgaat    1740 atacaacggg atatagtcta taagagaga atcgtctaa tagatggttc tcgtgactta     1800
gaggatgttg ttgtggatat cattgagaga tatacagaag aggtagcggc tgatcactat   1860
gctagtcgtg aattattgtt tcactttatt gtgaccaata ttagttttca tgttaaagag   1920
gttccagatt atatagatgt aactgacaaa actgcagttc gtagctttat gaagcaggtg   1980
attgataaag aactttctga aaagaaagaa ttacttaatc aacatgactt atatgaacag   2040 ttttacgac tttcactgct taaagccatt gatgacaact gggtagagca ggtagactat     2100
ctacaacagc tatccatggc tatcggtggt caatctgcta gtcagaaaaa tccaatcgta   2160
gagtactatc aagaagccta cgcgggcttt gaagctatga agaacagat tcatgcggat    2220 atggtgcgta atctcctgat ggggctggtt gaggtcactc caaaggtga atcgtgact     2280 cattttccat aa                                                       2292

<210> SEQ ID NO 110
<211> LENGTH: 763
<212> TYPE: PRT
<213> ORGANISM: Streptococcus pneumoniae

<400> SEQUENCE: 110

Met Ser Ser Leu Ser Asp Gln Glu Leu Val Ala Lys Thr Val Glu Phe
  1               5                  10                  15

Arg Gln Arg Leu Ser Glu Gly Glu Ser Leu Asp Asp Ile Leu Val Glu
                 20                  25                  30

Ala Phe Ala Val Val Arg Glu Ala Asp Lys Arg Ile Leu Gly Met Phe
             35                  40                  45

Pro Tyr Asp Val Gln Val Met Gly Ala Ile Val Met His Tyr Gly Asn
         50                  55                  60

Val Ala Glu Met Asn Thr Gly Glu Gly Lys Thr Leu Thr Ala Thr Met
 65                  70                  75                  80

Pro Val Tyr Leu Asn Ala Phe Ser Gly Glu Gly Val Met Val Val Thr
                 85                  90                  95

Pro Asn Glu Tyr Leu Ser Lys Arg Asp Ala Glu Glu Met Gly Gln Val
            100                 105                 110

Tyr Arg Phe Leu Gly Leu Thr Ile Gly Val Pro Phe Thr Glu Asp Pro
        115                 120                 125

Lys Lys Glu Met Lys Ala Glu Glu Lys Lys Leu Ile Tyr Ala Ser Asp
    130                 135                 140

Ile Ile Tyr Thr Thr Asn Ser Asn Leu Gly Phe Asp Tyr Leu Asn Asp
145                 150                 155                 160

Asn Leu Ala Ser Asn Glu Glu Gly Lys Phe Leu Arg Pro Phe Asn Tyr
                165                 170                 175

Val Ile Ile Asp Glu Ile Asp Asp Ile Leu Leu Asp Ser Ala Gln Thr
```

```
                180             185             190
Pro Leu Ile Ile Ala Gly Ser Pro Arg Val Gln Ser Asn Tyr Tyr Ala
            195                 200                 205

Ile Ile Asp Thr Leu Val Thr Thr Leu Val Glu Gly Glu Asp Tyr Ile
        210                 215                 220

Phe Lys Glu Glu Lys Glu Val Trp Leu Thr Thr Lys Gly Ala Lys
225                 230                 235                 240

Ser Ala Glu Asn Phe Leu Gly Ile Asp Asn Leu Tyr Lys Glu Glu His
                    245                 250                 255

Ala Ser Phe Ala Arg His Leu Val Tyr Ala Ile Arg Ala His Lys Leu
                260                 265                 270

Phe Thr Lys Asp Lys Asp Tyr Ile Ile Arg Gly Asn Glu Met Val Leu
            275                 280                 285

Val Asp Lys Gly Thr Gly Arg Leu Met Glu Met Thr Lys Leu Gln Gly
        290                 295                 300

Gly Leu His Gln Ala Ile Glu Ala Lys Glu His Val Lys Leu Ser Pro
305                 310                 315                 320

Glu Thr Arg Ala Met Ala Ser Ile Thr Tyr Gln Ser Leu Phe Lys Met
                325                 330                 335

Phe Asn Lys Ile Ser Gly Met Thr Gly Thr Gly Lys Val Ala Glu Lys
                340                 345                 350

Glu Phe Ile Glu Thr Tyr Asn Met Ser Val Val Arg Ile Pro Thr Asn
            355                 360                 365

Arg Pro Arg Gln Arg Ile Asp Tyr Pro Asp Asn Leu Tyr Ile Thr Leu
370                 375                 380

Pro Glu Lys Val Tyr Ala Ser Leu Glu Tyr Ile Lys Gln Tyr His Ala
385                 390                 395                 400

Lys Gly Asn Pro Leu Leu Val Phe Val Gly Ser Val Glu Met Ser Gln
                405                 410                 415

Leu Tyr Ser Ser Leu Leu Phe Arg Glu Gly Ile Ala His Asn Val Leu
                420                 425                 430

Asn Ala Asn Asn Ala Ala Arg Glu Ala Gln Ile Ile Ser Glu Ser Gly
            435                 440                 445

Gln Met Gly Ala Val Thr Val Ala Thr Ser Met Ala Gly Arg Gly Thr
        450                 455                 460

Asp Ile Lys Leu Gly Lys Gly Val Ala Glu Leu Gly Gly Leu Ile Val
465                 470                 475                 480

Ile Gly Thr Glu Arg Met Glu Ser Gln Arg Ile Asp Leu Gln Ile Arg
                485                 490                 495

Gly Arg Ser Gly Arg Gln Gly Asp Pro Gly Met Ser Lys Phe Phe Val
                500                 505                 510

Ser Leu Glu Asp Asp Val Ile Lys Lys Phe Gly Pro Ser Trp Val His
            515                 520                 525

Lys Lys Tyr Lys Asp Tyr Gln Val Gln Asp Met Thr Gln Pro Glu Val
            530                 535                 540

Leu Lys Gly Arg Lys Tyr Arg Lys Leu Val Glu Lys Ala Gln His Ala
545                 550                 555                 560

Ser Asp Ser Ala Gly Arg Ser Ala Arg Arg Gln Thr Leu Glu Tyr Ala
                565                 570                 575

Glu Ser Met Asn Ile Gln Arg Asp Ile Val Tyr Lys Glu Arg Asn Arg
                580                 585                 590

Leu Ile Asp Gly Ser Arg Asp Leu Glu Asp Val Val Asp Ile Ile
            595                 600                 605
```

```
Glu Arg Tyr Thr Glu Glu Val Ala Ala Asp His Tyr Ala Ser Arg Glu
    610                 615                 620

Leu Leu Phe His Phe Ile Val Thr Asn Ile Ser Phe His Val Lys Glu
625                 630                 635                 640

Val Pro Asp Tyr Ile Asp Val Thr Asp Lys Thr Ala Val Arg Ser Phe
                645                 650                 655

Met Lys Gln Val Ile Asp Lys Glu Leu Ser Glu Lys Lys Glu Leu Leu
                660                 665                 670

Asn Gln His Asp Leu Tyr Glu Gln Phe Leu Arg Leu Ser Leu Leu Lys
            675                 680                 685

Ala Ile Asp Asp Asn Trp Val Glu Gln Val Asp Tyr Leu Gln Gln Leu
    690                 695                 700

Ser Met Ala Ile Gly Gly Gln Ser Ala Ser Gln Lys Asn Pro Ile Val
705                 710                 715                 720

Glu Tyr Tyr Gln Glu Ala Tyr Ala Gly Phe Glu Ala Met Lys Glu Gln
                725                 730                 735

Ile His Ala Asp Met Val Arg Asn Leu Leu Met Gly Leu Val Glu Val
                740                 745                 750

Thr Pro Lys Gly Glu Ile Val Thr His Phe Pro
            755                 760
```

<210> SEQ ID NO 111
<211> LENGTH: 879
<212> TYPE: DNA
<213> ORGANISM: Streptococcus pneumoniae

<400> SEQUENCE: 111

```
atgaaacaag aatggtttga agtaatgat tttgtaaaaa caacaagcaa gaacaagcct      60
gaagagcaag ctcaagaggt tgcagacaag gctgaagaaa ggatacccga tctcgataca     120
ccaattgaaa aaatactca gttagaggag aagtctctc aagctgaagt cgaattggaa      180
agccagcaag aagagaaaat tgaagctcct gaagacagtg aagcgagaac agaaatagaa    240
gaaaagaagg catctaattc tactgaagaa gagccagacc tttctaaaga aacagaaaaa    300
gtcactatag ctgaagagag ccaagaagct cttcctcagc aaaaagcaac cacgaaagag    360
ccacttctta tcagtaaatc tttagaaagt ccttatatcc ccgaccaagc tccaaaatct    420
agggataaat ggaaagagca agtgcttgat ttttggtctt ggctagtgga agcgatcaaa    480
tctcctacaa gtaagttgga aacaagtatc acacacagtt acacagcctt tctcttgctc    540
attctgtttt ctgcatcttc cttttctttt agtatctatc acatcaaaca tgcttactat    600
ggacatatag caagcattaa cagtcgcttc cctgagcagc tagctccttt aactcttttt    660
tctatcatct ctatcctagt agcgacaaca ctcttcttct tttcattcct cttgggtagt    720
ttcgttgtga cgcgatttat ccaccaggaa aaggactgga cgctagacaa ggttctccaa    780
caatatagtc aactcttggc aattccaatc tcctcactgc tattgctagt ttctttgctt    840
tctttgatag cctacgattt acagccctct tgtgtgtga                           879
```

<210> SEQ ID NO 112
<211> LENGTH: 292
<212> TYPE: PRT
<213> ORGANISM: Streptococcus pneumoniae

<400> SEQUENCE: 112

```
Met Lys Gln Glu Trp Phe Glu Ser Asn Asp Phe Val Lys Thr Thr Ser
1               5                   10                  15

Lys Asn Lys Pro Glu Glu Gln Ala Gln Glu Val Ala Asp Lys Ala Glu
```

```
                20                  25                  30
Glu Arg Ile Pro Asp Leu Asp Thr Pro Ile Glu Lys Asn Thr Gln Leu
             35                  40                  45

Glu Glu Glu Val Ser Gln Ala Glu Val Glu Leu Glu Ser Gln Gln Glu
         50                  55                  60

Glu Lys Ile Glu Ala Pro Glu Asp Ser Glu Ala Arg Thr Glu Ile Glu
 65                  70                  75                  80

Glu Lys Lys Ala Ser Asn Ser Thr Glu Glu Pro Asp Leu Ser Lys
                 85                  90                  95

Glu Thr Glu Lys Val Thr Ile Ala Glu Glu Ser Gln Glu Ala Leu Pro
            100                 105                 110

Gln Gln Lys Ala Thr Thr Lys Glu Pro Leu Leu Ile Ser Lys Ser Leu
        115                 120                 125

Glu Ser Pro Tyr Ile Pro Asp Gln Ala Pro Lys Ser Arg Asp Lys Trp
    130                 135                 140

Lys Glu Gln Val Leu Asp Phe Trp Ser Trp Leu Val Glu Ala Ile Lys
145                 150                 155                 160

Ser Pro Thr Ser Lys Leu Glu Thr Ser Ile Thr His Ser Tyr Thr Ala
                165                 170                 175

Phe Leu Leu Leu Ile Leu Phe Ser Ala Ser Ser Phe Phe Ser Ile
            180                 185                 190

Tyr His Ile Lys His Ala Tyr Tyr Gly His Ile Ala Ser Ile Asn Ser
        195                 200                 205

Arg Phe Pro Glu Gln Leu Ala Pro Leu Thr Leu Phe Ser Ile Ile Ser
    210                 215                 220

Ile Leu Val Ala Thr Thr Leu Phe Phe Phe Ser Phe Leu Leu Gly Ser
225                 230                 235                 240

Phe Val Val Arg Arg Phe Ile His Gln Glu Lys Asp Trp Thr Leu Asp
                245                 250                 255

Lys Val Leu Gln Gln Tyr Ser Gln Leu Leu Ala Ile Pro Ile Ser Ser
            260                 265                 270

Leu Leu Leu Leu Val Ser Leu Leu Ser Leu Ile Ala Tyr Asp Leu Gln
        275                 280                 285

Pro Ser Cys Val
    290

<210> SEQ ID NO 113
<211> LENGTH: 327
<212> TYPE: DNA
<213> ORGANISM: Streptococcus pneumoniae

<400> SEQUENCE: 113
atgtactttc aacatcctc tgccttgatt gaatttctca tcttggctgt actggagcag      60
ggtgattctt atggttatga gattagccaa accattaagc tgatcgctaa tatcaaagaa    120
tccacactct atcccattct caaaaaattg gaaggcaata gctttctgac aacctattct    180
agagagttcc aagtcgcat gcgcaaatac tactccttga caaacggtgg tatagagcag    240
ctcttgaccc taaaagatga atgggcactc tatacagaca ccatcaatgg catcatagaa    300
gggagtatcc gccatgacaa gaactga                                          327

<210> SEQ ID NO 114
<211> LENGTH: 108
<212> TYPE: PRT
<213> ORGANISM: Streptococcus pneumoniae

<400> SEQUENCE: 114
```

```
Met Tyr Phe Pro Thr Ser Ser Ala Leu Ile Glu Phe Leu Ile Leu Ala
 1               5                  10                  15

Val Leu Glu Gln Gly Asp Ser Tyr Gly Tyr Glu Ile Ser Gln Thr Ile
            20                  25                  30

Lys Leu Ile Ala Asn Ile Lys Glu Ser Thr Leu Tyr Pro Ile Leu Lys
        35                  40                  45

Lys Leu Glu Gly Asn Ser Phe Leu Thr Thr Tyr Ser Arg Glu Phe Gln
 50                  55                  60

Gly Arg Met Arg Lys Tyr Tyr Ser Leu Thr Asn Gly Gly Ile Glu Gln
65                  70                  75                  80

Leu Leu Thr Leu Lys Asp Glu Trp Ala Leu Tyr Thr Asp Thr Ile Asn
                85                  90                  95

Gly Ile Ile Glu Gly Ser Ile Arg His Asp Lys Asn
            100                 105
```

<210> SEQ ID NO 115
<211> LENGTH: 954
<212> TYPE: DNA
<213> ORGANISM: Streptococcus pneumoniae

<400> SEQUENCE: 115

```
atggattttg aaaaaattga acaagcttat atctatttac tagagaatgt ccaagtcatc    60
caaagtgatt tggcgaccaa cttttatgac gccttggtgg agcaaaatag catctatctg   120
gatggtgaaa ctgagctaaa ccaggtcaaa gacaacaatc aggcccttaa gcgtttagca   180
ctacgcaaag aagaatggct caagacctac cagtttctct gatgaaggc tgggcaaaca    240
gaacccttgc aggccaatca ccagtttaca ccggatgcta ttgctttgct tttggtgttt   300
attgtggaag agttgtttaa agaggaggaa attactatcc tcgaaatggg ttctgggatg   360
ggaattctag cgctatttt cttgacctcg cttactaaaa aggtggatta cttgggaatg   420
gaagtggatg atttgctgat tgatctggca gctagcatgg cagatgtaat tggtttgcag   480
gctggctttg tccaaggaga tgccgttcgc ccacaaatgc tcaaagaaag cgatgtggtc   540
atcagtgact tgcctgtcgg ctattatcct gatgatgccg ttgcgtcgcg ccatcaagtt   600
gcttctagcc aagaacatac ttacgcccat cacttgctca tggaacaagg cttaagtac    660
ctcaagtcag acggatacgc tattttctca gctccgagtg atttgttgac cagtcctcaa   720
agtgatttgt taaagaatg gctgaaagaa gaggcgagtc tggttgctat gattagtctg   780
cctgaaaatc tctttgctaa tgccaaacaa tctaagacta tttttatctt acagaagaaa   840
aatgaaatag cagtagagcc ttttgtttat ccacttgcta gcttgcaaga tgcaagtgtt   900
ttaatgaaat ttaagaaaaa ttttcaaaaa tggactcaag gtactgaaat ataa          954
```

<210> SEQ ID NO 116
<211> LENGTH: 317
<212> TYPE: PRT
<213> ORGANISM: Streptococcus pneumoniae

<400> SEQUENCE: 116

```
Met Asp Phe Glu Lys Ile Glu Gln Ala Tyr Ile Tyr Leu Leu Glu Asn
 1               5                  10                  15

Val Gln Val Ile Gln Ser Asp Leu Ala Thr Asn Phe Tyr Asp Ala Leu
            20                  25                  30

Val Glu Gln Asn Ser Ile Tyr Leu Asp Gly Glu Thr Glu Leu Asn Gln
        35                  40                  45

Val Lys Asp Asn Asn Gln Ala Leu Lys Arg Leu Ala Leu Arg Lys Glu
```

```
                50                  55                  60
Glu Trp Leu Lys Thr Tyr Gln Phe Leu Leu Met Lys Ala Gly Gln Thr
 65                  70                  75                  80

Glu Pro Leu Gln Ala Asn His Gln Phe Thr Pro Asp Ala Ile Ala Leu
                 85                  90                  95

Leu Leu Val Phe Ile Val Glu Glu Leu Phe Lys Glu Glu Ile Thr
            100                 105                 110

Ile Leu Glu Met Gly Ser Gly Met Gly Ile Leu Gly Ala Ile Phe Leu
            115                 120                 125

Thr Ser Leu Thr Lys Lys Val Asp Tyr Leu Gly Met Glu Val Asp Asp
130                 135                 140

Leu Leu Ile Asp Leu Ala Ala Ser Met Ala Asp Val Ile Gly Leu Gln
145                 150                 155                 160

Ala Gly Phe Val Gln Gly Asp Ala Val Arg Pro Gln Met Leu Lys Glu
                165                 170                 175

Ser Asp Val Val Ile Ser Asp Leu Pro Val Gly Tyr Tyr Pro Asp Asp
            180                 185                 190

Ala Val Ala Ser Arg His Gln Val Ala Ser Gln Glu His Thr Tyr
            195                 200                 205

Ala His His Leu Leu Met Glu Gln Gly Leu Lys Tyr Leu Lys Ser Asp
210                 215                 220

Gly Tyr Ala Ile Phe Leu Ala Pro Ser Asp Leu Leu Thr Ser Pro Gln
225                 230                 235                 240

Ser Asp Leu Leu Lys Glu Trp Leu Lys Glu Glu Ala Ser Leu Val Ala
                245                 250                 255

Met Ile Ser Leu Pro Glu Asn Leu Phe Ala Asn Ala Lys Gln Ser Lys
            260                 265                 270

Thr Ile Phe Ile Leu Gln Lys Lys Asn Glu Ile Ala Val Glu Pro Phe
            275                 280                 285

Val Tyr Pro Leu Ala Ser Leu Gln Asp Ala Ser Val Leu Met Lys Phe
            290                 295                 300

Lys Glu Asn Phe Gln Lys Trp Thr Gln Gly Thr Glu Ile
305                 310                 315

<210> SEQ ID NO 117
<211> LENGTH: 1902
<212> TYPE: DNA
<213> ORGANISM: Streptococcus pneumoniae

<400> SEQUENCE: 117
atgattattt tacaagctaa taaaattgaa cgttcttttg caggagaggt tcttttcgat      60
aatatcaacc tgcaggttga tgaacgagat cggattgctc ttgttgggaa aaatggtgca    120
ggtaagtcta ctcttttgaa gattttagtt ggagaagagg agccaactag cggagaaatc    180
aataagaaaa aagatatttc tctgtcttac ctagcccaag atagccgttt tgagtctgaa    240
ataccatctc acgatgaaat gcttcatgtc tttaatgatt tgcgtcggac ggagagacaa    300
ctgcgtcaga tggagctgga gatgggtgaa aagtctggtg aggatttgga taaactgatg    360
tcagattatg accgcttatc tgagaatttt cgccaagcag gtggctttac ctatgaagct    420
gatattcgag cgattttgaa tggattcaag tttgacgagt ctatgtggca gatgaaaatt    480
gctgagcttt ctggtggtca aaatactcgt ttggcacttg ccaaaatgct ccttgaaaag    540
cccaatctct tggtcttgga cgagccaact aaccacttgg atattgaaac catcgcctgg    600
ctagagaatt acttggtaaa ctatagcggt gccctcatta tcgtcagcca cgaccgttat    660
```

```
ttcttggaca aggttgcgac aattacgcta gatttgacca agcattcctt ggatcgctat    720
gtggggaatt actctcgttt tgtcgaattg aaggagcaaa agctagttac tgaggcaaaa    780
aactatgaaa agcaacagaa ggaaatcgct gctctggaag actttgtcaa tcgcaatcta    840
gttcgtgctt caacgactaa acgtgctcaa tctcgccgta acaactaga aaaaatggag    900 cgtttggaca gcctgaagc tggcaagaaa gcagccaaca tgaccttcca gtctgaaaaa    960
acgtcgggca tgttgttttt gactgttgaa aatgcagctg ttggctatga cggggaagtc   1020
ttgtcacaac ctatcaacct agatcttcgt aagatgaatg ctgtcgctat cgttggtcca   1080
aatggtatcg gcaagtcaac ctttatcaag tctattgtgg accagattcc ttttatcaag   1140
ggagaaaagc gctttggcgc taatgttgag gttggttact atgaccaaac ccaaagcaag   1200
ctgacaccaa gtaataccggt gctggatgaa ctctggaatg atttcaaact gacaccagaa   1260
gttgaaatcc gcaaccgtct tggagccttc cttttctcag gagatgatgt taaaaaatca   1320
gtcggcatgc tatctggtgg cgaaaaagct cgtttgcttt tagctaaatt gtctatggaa   1380
aacaataact ttttgattct ggatgagccg accaaccact tggatattga tagtaaggaa   1440
gtgctagaaa atgccttgat tgactttgat ggaaccttgc tgtttgtcag tcatgatcgt   1500
tactttatca atcgtgtggc aactcatgtt ttggaattgt ctgagaatgg ttcaactctc   1560
taccttggag attacgacta ctatgttgag aagaaagcaa cagcagaaat gagtcagact   1620
gaggaagctt caactagcaa tcaagcaaag gaagcaagtc cagtcaatga ctatcaggcc   1680
cagaaagaaa gtcaaaaaga agttcgcaaa ctcatgcgac aaatcgaaag tctagaagct   1740
gaaattgaag agctagaaag tcaaagccaa gccatttctg aacaaatgtt ggaaacaaac   1800
gatgccgaca aactcatgga attacaggct gagctggaca aaatcagcca tcgtcaggaa   1860
gaagctatgc ttgagtggga agaattatca gagcaggtgt aa                      1902
```

<210> SEQ ID NO 118
<211> LENGTH: 633
<212> TYPE: PRT
<213> ORGANISM: Streptococcus pneumoniae

<400> SEQUENCE: 118

Met Ile Ile Leu Gln Ala Asn Lys Ile Glu Arg Ser Phe Ala Gly Glu
 1               5                   10                  15

Val Leu Phe Asp Asn Ile Asn Leu Gln Val Asp Glu Arg Asp Arg Ile
                20                  25                  30

Ala Leu Val Gly Lys Asn Gly Ala Gly Lys Ser Thr Leu Leu Lys Ile
            35                  40                  45

Leu Val Gly Glu Glu Pro Thr Ser Gly Glu Ile Asn Lys Lys Lys
        50                  55                  60

Asp Ile Ser Leu Ser Tyr Leu Ala Gln Asp Ser Arg Phe Glu Ser Glu
 65                  70                  75                  80

Asn Thr Ile Tyr Asp Glu Met Leu His Val Phe Asn Asp Leu Arg Arg
                 85                  90                  95

Thr Glu Arg Gln Leu Arg Gln Met Glu Leu Glu Met Gly Glu Lys Ser
            100                 105                 110

Gly Glu Asp Leu Asp Lys Leu Met Ser Asp Tyr Asp Arg Leu Ser Glu
        115                 120                 125

Asn Phe Arg Gln Ala Gly Gly Phe Thr Tyr Glu Ala Asp Ile Arg Ala
    130                 135                 140

Ile Leu Asn Gly Phe Lys Phe Asp Glu Ser Met Trp Gln Met Lys Ile
145                 150                 155                 160

-continued

```
Ala Glu Leu Ser Gly Gly Gln Asn Thr Arg Leu Ala Leu Ala Lys Met
            165                 170                 175
Leu Leu Glu Lys Pro Asn Leu Val Leu Asp Glu Pro Thr Asn His
        180                 185                 190
Leu Asp Ile Glu Thr Ile Ala Trp Leu Glu Asn Tyr Leu Val Asn Tyr
            195                 200                 205
Ser Gly Ala Leu Ile Ile Val Ser His Asp Arg Tyr Phe Leu Asp Lys
        210                 215                 220
Val Ala Thr Ile Thr Leu Asp Leu Thr Lys His Ser Leu Asp Arg Tyr
225                 230                 235                 240
Val Gly Asn Tyr Ser Arg Phe Val Glu Leu Lys Glu Gln Lys Leu Val
            245                 250                 255
Thr Glu Ala Lys Asn Tyr Glu Lys Gln Gln Lys Glu Ile Ala Ala Leu
        260                 265                 270
Glu Asp Phe Val Asn Arg Asn Leu Val Arg Ala Ser Thr Thr Lys Arg
            275                 280                 285
Ala Gln Ser Arg Arg Lys Gln Leu Glu Lys Met Glu Arg Leu Asp Lys
        290                 295                 300
Pro Glu Ala Gly Lys Lys Ala Ala Asn Met Thr Phe Gln Ser Glu Lys
305                 310                 315                 320
Thr Ser Gly Asn Val Val Leu Thr Val Glu Asn Ala Ala Val Gly Tyr
            325                 330                 335
Asp Gly Glu Val Leu Ser Gln Pro Ile Asn Leu Asp Leu Arg Lys Met
        340                 345                 350
Asn Ala Val Ala Ile Val Gly Pro Asn Gly Ile Gly Lys Ser Thr Phe
            355                 360                 365
Ile Lys Ser Ile Val Asp Gln Ile Pro Phe Ile Lys Gly Glu Lys Arg
        370                 375                 380
Phe Gly Ala Asn Val Glu Val Gly Tyr Tyr Asp Gln Thr Gln Ser Lys
385                 390                 395                 400
Leu Thr Pro Ser Asn Thr Val Leu Asp Glu Leu Trp Asn Asp Phe Lys
            405                 410                 415
Leu Thr Pro Glu Val Glu Ile Arg Asn Arg Leu Gly Ala Phe Leu Phe
        420                 425                 430
Ser Gly Asp Asp Val Lys Lys Ser Val Gly Met Leu Ser Gly Gly Glu
            435                 440                 445
Lys Ala Arg Leu Leu Leu Ala Lys Leu Ser Met Glu Asn Asn Asn Phe
        450                 455                 460
Leu Ile Leu Asp Glu Pro Thr Asn His Leu Asp Ile Asp Ser Lys Glu
465                 470                 475                 480
Val Leu Glu Asn Ala Leu Ile Asp Phe Asp Gly Thr Leu Leu Phe Val
            485                 490                 495
Ser His Asp Arg Tyr Phe Ile Asn Arg Val Ala Thr His Val Leu Glu
        500                 505                 510
Leu Ser Glu Asn Gly Ser Thr Leu Tyr Leu Gly Asp Tyr Asp Tyr Tyr
            515                 520                 525
Val Glu Lys Lys Ala Thr Ala Glu Met Ser Gln Thr Glu Glu Ala Ser
        530                 535                 540
Thr Ser Asn Gln Ala Lys Glu Ala Ser Pro Val Asn Asp Tyr Gln Ala
545                 550                 555                 560
Gln Lys Glu Ser Gln Lys Glu Val Arg Lys Leu Met Arg Gln Ile Glu
            565                 570                 575
Ser Leu Glu Ala Glu Ile Glu Glu Leu Glu Ser Gln Ser Gln Ala Ile
        580                 585                 590
```

Ser Glu Gln Met Leu Glu Thr Asn Asp Ala Asp Lys Leu Met Glu Leu
        595                 600                 605

Gln Ala Glu Leu Asp Lys Ile Ser His Arg Gln Glu Ala Met Leu
    610                 615                 620

Glu Trp Glu Glu Leu Ser Glu Gln Val
625                 630

<210> SEQ ID NO 119
<211> LENGTH: 1179
<212> TYPE: DNA
<213> ORGANISM: Streptococcus pneumoniae

<400> SEQUENCE: 119
atgaatcgct atgcagtgca gttgattagc cgtggggcta tcaataaaat gggaaatatg        60
ctctatgatt atggaaatag tgtctggttg gcttctatgg ggactatagg acagacagtt       120
ttaggaatgt atcagatttc tgagctcgtc acatctattc tcgtcaatcc ctttggcgga       180
gttatttcag accgtttttc tcgtcgtaag attttaatga cggcagatct tgtttgtggg       240
attctttgtc tggctatttc tttcataagg aatgatagct ggatgattgg cgctttgatt       300
gttgctaaca ttgtgcaggc tattgctttt gccttttctc gcacagccaa taaagctatc       360
ataactgaag tggtggagaa agatgagatt gtgatctata attctcgctt agagctggtt       420
ttgcaggttg taggtgttag ctctcctgtt ctttccttcc ttgttttaca gtttgcaagt       480
ctccatatga cgctactgct agactcgctg actttttca ttgcttttgt tctagtggct       540
ttccttccaa aagaggaagc aaaagttcaa gagaaaaagg cttttactgg agagatatt       600 tttgtagata tcaaggatgg gttacactat atctggcatc agcaagaaat tttcttcctt       660
ttgctggtag cttccagcgt taattctttt tttgcagctt ttgaatttct acttcccttt       720
tcgaatcagc tttacgggtc agaaggagcc tatgcaagta ttttaactat ggggctatt       780 ggttccatca ttggggctct tctagctagt aaaattaaag ctaatattta taatcttttg       840
attttactgg ctttgacagg tgtcggagtt tttatgatgg gattaccact tccaactttt       900
cttccttttt ctggaaattt agtttgtgaa ttgtttatga cgatttttaa tattcacttt       960
tttactcaag tacaaaccaa ggttgagagc gaatttcttg aagagtact gagtacaatt      1020 tttaccttag ctattctatt tatgcctatt gcaaaaggat ttatgacagt cttgccaagt      1080
gtccatcttt attctttctt gattattgga cttggagttg tagccttata tttcttagct      1140
ctcggatatg ttcgaactca ttttgaaaaa ttgatataa                             1179

<210> SEQ ID NO 120
<211> LENGTH: 392
<212> TYPE: PRT
<213> ORGANISM: Streptococcus pneumoniae

<400> SEQUENCE: 120

Met Asn Arg Tyr Ala Val Gln Leu Ile Ser Arg Gly Ala Ile Asn Lys
 1               5                  10                  15

Met Gly Asn Met Leu Tyr Asp Tyr Gly Asn Ser Val Trp Leu Ala Ser
            20                  25                  30

Met Gly Thr Ile Gly Gln Thr Val Leu Gly Met Tyr Gln Ile Ser Glu
        35                  40                  45

Leu Val Thr Ser Ile Leu Val Asn Pro Phe Gly Gly Val Ile Ser Asp
    50                  55                  60

Arg Phe Ser Arg Arg Lys Ile Leu Met Thr Ala Asp Leu Val Cys Gly
65                  70                  75                  80

```
Ile Leu Cys Leu Ala Ile Ser Phe Ile Arg Asn Asp Ser Trp Met Ile
                85                  90                  95

Gly Ala Leu Ile Val Ala Asn Ile Val Gln Ala Ile Ala Phe Ala Phe
            100                 105                 110

Ser Arg Thr Ala Asn Lys Ala Ile Ile Thr Glu Val Val Glu Lys Asp
        115                 120                 125

Glu Ile Val Ile Tyr Asn Ser Arg Leu Glu Leu Val Leu Gln Val Val
    130                 135                 140

Gly Val Ser Ser Pro Val Leu Ser Phe Leu Val Leu Gln Phe Ala Ser
145                 150                 155                 160

Leu His Met Thr Leu Leu Asp Ser Leu Thr Phe Phe Ile Ala Phe
                165                 170                 175

Val Leu Val Ala Phe Leu Pro Lys Glu Glu Ala Lys Val Gln Glu Lys
                180                 185                 190

Lys Ala Phe Thr Gly Arg Asp Ile Phe Val Asp Ile Lys Asp Gly Leu
            195                 200                 205

His Tyr Ile Trp His Gln Gln Glu Ile Phe Leu Leu Leu Val Ala
        210                 215                 220

Ser Ser Val Asn Phe Phe Ala Ala Phe Glu Phe Leu Leu Pro Phe
225                 230                 235                 240

Ser Asn Gln Leu Tyr Gly Ser Glu Gly Ala Tyr Ala Ser Ile Leu Thr
                245                 250                 255

Met Gly Ala Ile Gly Ser Ile Ile Gly Ala Leu Leu Ala Ser Lys Ile
            260                 265                 270

Lys Ala Asn Ile Tyr Asn Leu Leu Ile Leu Leu Ala Leu Thr Gly Val
        275                 280                 285

Gly Val Phe Met Met Gly Leu Pro Leu Pro Thr Phe Leu Ser Phe Ser
290                 295                 300

Gly Asn Leu Val Cys Glu Leu Phe Met Thr Ile Phe Asn Ile His Phe
305                 310                 315                 320

Phe Thr Gln Val Gln Thr Lys Val Glu Ser Glu Phe Leu Gly Arg Val
                325                 330                 335

Leu Ser Thr Ile Phe Thr Leu Ala Ile Leu Phe Met Pro Ile Ala Lys
            340                 345                 350

Gly Phe Met Thr Val Leu Pro Ser Val His Leu Tyr Ser Phe Leu Ile
        355                 360                 365

Ile Gly Leu Gly Val Val Ala Leu Tyr Phe Leu Ala Leu Gly Tyr Val
370                 375                 380

Arg Thr His Phe Glu Lys Leu Ile
385                 390

<210> SEQ ID NO 121
<211> LENGTH: 2466
<212> TYPE: DNA
<213> ORGANISM: Streptococcus pneumoniae

<400> SEQUENCE: 121
atgcaaaatc aattaaatga attaaaacga aaatgctgg aattttttcca gcaaaaacaa      60 aaaaataaaa aatcagctag acctggcaag aaaggttcaa gtaccaaaaa atctaaaacc     120
ttagataagt cagccatttt cccagctatt ttactgagta taaagccctt atttaactta     180
ctctttgtac tcggttttct aggaggaatg ttgggagctg ggattgcttt gggatacgga     240
gtggccttat ttgacaaggt tcgggtgcct cagacagaag aattggtgaa tcaggtcaag     300
gacatctctt ctatttcaga gattacctat tcggacggga cggtgattgc ttccatagag     360
```

```
agtgatttgt tgcgcacttc tatctcatct gagcaaattt cggaaaatct gaagaaggct    420
atcattgcga cagaagatga acactttaaa gaacataagg gtgtagtacc caaggcggtg    480
attcgtgcga ccttggggaa atttgtaggt ttgggttcct ctagtggggg ttcaaccttg    540
acccagcaac taattaaaca gcaggtggtt ggggatgcgc cgaccttggc tcgtaaggcg    600
gcagagattg tggatgctct tgccttggaa cgcgccatga ataaagatga gattttaacg    660
acctatctca atgtggctcc ctttggccga ataataagg gacagaatat tgcaggggct    720
cggcaagcag ctgagggaat tttcggtgta gatgccagtc agttgactgt tcctcaagca    780
gcattttag caggacttcc acagagtccc attacttact ctccttatga aaatactggg    840
gagttgaaga gtgatgaaga cctagaaatt ggcttaagac gggctaaggc agttctttac    900
agtatgtatc gtacaggtgc attaagcaaa gacgagtatt ctcagtacaa ggattatgac    960
cttaaacagg acttttacc atcgggcacg gttacaggaa tttcacgaga ctatttatac   1020
tttacaactt tggcagaagc tcaagaacgt atgtatgact atctagctca gagagacaat   1080
gtctccgcta aggagttgaa aaatgaggca actcagaagt tttatcgaga tttggcagcc   1140
aaggaaattg aaaatggtgg ttataagatt actactacca tagatcagaa aattcattct   1200
gccatgcaaa gtgcggttgc tgattatggc tatcttttag acgatggaac aggtcgtgta   1260
gaagtaggga atgtcttgat ggataaccaa acaggtgcta ttctaggctt tgtaggtggt   1320
cgtaattatc aagaaaatca aataatcat gcctttgata ccaaacgttc gccagcttct   1380
actaccaagc ccttgctggc ctacggtatt gctattgacc agggcttgat gggaagtgaa   1440
acgattctat ctaactatcc aacaaacttt gctaatggca atccgattat gtatgctaat   1500
agcaagggaa caggaatgat gaccttggga gaagctctga actattcatg gaatatccct   1560
gcttactgga cctatcgtat gctccgtgaa aagggtgttg atgtcaaggg ttatatggaa   1620
aagatgggtt acgagattcc tgagtacggt attgagagct tgccaatggg tggtggtatt   1680
gaagtcacag ttgcccagca taccaatggc tatcagacct tagctaataa tggagtttat   1740
catcagaagc atgtgatttc aaagattgaa gcagcagatg gtagagtggt gtatgagtat   1800
caggataaac cggttcaagt ctattcaaaa gctactgcga cgattatgca gggattgcta   1860
cgagaagttc tatcctctcg tgtgacaaca accttcaagt ctaacctgac ttctttaaat   1920
cctactctgg ctaatgcaga ttggattggg aagactggta caaccaacca agacgaaaat   1980
atgtggctca tgcttttcgac acctagatta accctaggtg gctggattgg gcatgatgat   2040
aatcattcat tgtcacgtag agcaggttat tctaataact ctaattacat ggctcatctg   2100
gtaaatgcga ttcagcaagc ttccccaagc atttggggga acgagcgctt tgctttagat   2160
cctagtgtag tgaaatcgga agtcttgaaa tcaacaggtc aaaaaccaga gaaggtttct   2220
gttgaaggaa aagaagtaga ggtcacaggt tcgactgtta ccagctattg ggctaataag   2280
tcaggagcgc cagcgacaag ttatcgcttt gctattggcg gaagtgatgc ggattatcag   2340
aatgcttggt ctagtattgt ggggagtcta ccaactccat ccagctccag cagttcaagt   2400
agtagttcta gcgatagcag taactcaagt actacacgac cttcttcttc aagggcgaga   2460
cgataa                                                              2466
```

<210> SEQ ID NO 122
<211> LENGTH: 821
<212> TYPE: PRT
<213> ORGANISM: Streptococcus pneumoniae

<400> SEQUENCE: 122

```
Met Gln Asn Gln Leu Asn Glu Leu Lys Arg Lys Met Leu Glu Phe Phe
  1               5                  10                  15

Gln Gln Lys Gln Lys Asn Lys Lys Ser Ala Arg Pro Gly Lys Lys Gly
             20                  25                  30

Ser Ser Thr Lys Lys Ser Lys Thr Leu Asp Lys Ser Ala Ile Phe Pro
         35                  40                  45

Ala Ile Leu Leu Ser Ile Lys Ala Leu Phe Asn Leu Leu Phe Val Leu
 50                  55                  60

Gly Phe Leu Gly Gly Met Leu Gly Ala Gly Ile Ala Leu Gly Tyr Gly
 65                  70                  75                  80

Val Ala Leu Phe Asp Lys Val Arg Val Pro Gln Thr Glu Glu Leu Val
                 85                  90                  95

Asn Gln Val Lys Asp Ile Ser Ser Ile Ser Glu Ile Thr Tyr Ser Asp
             100                 105                 110

Gly Thr Val Ile Ala Ser Ile Glu Ser Asp Leu Leu Arg Thr Ser Ile
         115                 120                 125

Ser Ser Glu Gln Ile Ser Glu Asn Leu Lys Lys Ala Ile Ala Thr
 130                 135                 140

Glu Asp Glu His Phe Lys Glu His Lys Gly Val Val Pro Lys Ala Val
145                 150                 155                 160

Ile Arg Ala Thr Leu Gly Lys Phe Val Gly Leu Gly Ser Ser Ser Gly
                 165                 170                 175

Gly Ser Thr Leu Thr Gln Gln Leu Ile Lys Gln Gln Val Val Gly Asp
         180                 185                 190

Ala Pro Thr Leu Ala Arg Lys Ala Ala Glu Ile Val Asp Ala Leu Ala
         195                 200                 205

Leu Glu Arg Ala Met Asn Lys Asp Glu Ile Leu Thr Thr Tyr Leu Asn
     210                 215                 220

Val Ala Pro Phe Gly Arg Asn Asn Lys Gly Gln Asn Ile Ala Gly Ala
225                 230                 235                 240

Arg Gln Ala Ala Glu Gly Ile Phe Gly Val Asp Ala Ser Gln Leu Thr
                 245                 250                 255

Val Pro Gln Ala Ala Phe Leu Ala Gly Leu Pro Gln Ser Pro Ile Thr
         260                 265                 270

Tyr Ser Pro Tyr Glu Asn Thr Gly Glu Leu Lys Ser Asp Glu Asp Leu
         275                 280                 285

Glu Ile Gly Leu Arg Arg Ala Lys Ala Val Leu Tyr Ser Met Tyr Arg
     290                 295                 300

Thr Gly Ala Leu Ser Lys Asp Glu Tyr Ser Gln Tyr Lys Asp Tyr Asp
305                 310                 315                 320

Leu Lys Gln Asp Phe Leu Pro Ser Gly Thr Val Thr Gly Ile Ser Arg
                 325                 330                 335

Asp Tyr Leu Tyr Phe Thr Thr Leu Ala Glu Ala Gln Glu Arg Met Tyr
         340                 345                 350

Asp Tyr Leu Ala Gln Arg Asp Asn Val Ser Ala Lys Glu Leu Lys Asn
         355                 360                 365

Glu Ala Thr Gln Lys Phe Tyr Arg Asp Leu Ala Ala Lys Glu Ile Glu
     370                 375                 380

Asn Gly Gly Tyr Lys Ile Thr Thr Thr Ile Asp Gln Lys Ile His Ser
385                 390                 395                 400

Ala Met Gln Ser Ala Val Ala Asp Tyr Gly Tyr Leu Leu Asp Asp Gly
                 405                 410                 415

Thr Gly Arg Val Glu Val Gly Asn Val Leu Met Asp Asn Gln Thr Gly
```

```
                420             425             430
Ala Ile Leu Gly Phe Val Gly Gly Arg Asn Tyr Gln Glu Asn Gln Asn
            435                 440                 445

Asn His Ala Phe Asp Thr Lys Arg Ser Pro Ala Ser Thr Thr Lys Pro
    450                 455                 460

Leu Leu Ala Tyr Gly Ile Ala Ile Asp Gln Gly Leu Met Gly Ser Glu
465                 470                 475                 480

Thr Ile Leu Ser Asn Tyr Pro Thr Asn Phe Ala Asn Gly Asn Pro Ile
                485                 490                 495

Met Tyr Ala Asn Ser Lys Gly Thr Gly Met Met Thr Leu Gly Glu Ala
            500                 505                 510

Leu Asn Tyr Ser Trp Asn Ile Pro Ala Tyr Trp Thr Tyr Arg Met Leu
        515                 520                 525

Arg Glu Lys Gly Val Asp Val Lys Gly Tyr Met Glu Lys Met Gly Tyr
    530                 535                 540

Glu Ile Pro Glu Tyr Gly Ile Glu Ser Leu Pro Met Gly Gly Gly Ile
545                 550                 555                 560

Glu Val Thr Val Ala Gln His Thr Asn Gly Tyr Gln Thr Leu Ala Asn
                565                 570                 575

Asn Gly Val Tyr His Gln Lys His Val Ile Ser Lys Ile Glu Ala Ala
            580                 585                 590

Asp Gly Arg Val Val Tyr Glu Tyr Gln Asp Lys Pro Val Gln Val Tyr
        595                 600                 605

Ser Lys Ala Thr Ala Thr Ile Met Gln Gly Leu Leu Arg Glu Val Leu
    610                 615                 620

Ser Ser Arg Val Thr Thr Thr Phe Lys Ser Asn Leu Thr Ser Leu Asn
625                 630                 635                 640

Pro Thr Leu Ala Asn Ala Asp Trp Ile Gly Lys Thr Gly Thr Thr Asn
                645                 650                 655

Gln Asp Glu Asn Met Trp Leu Met Leu Ser Thr Pro Arg Leu Thr Leu
            660                 665                 670

Gly Gly Trp Ile Gly His Asp Asp Asn His Ser Leu Ser Arg Arg Ala
        675                 680                 685

Gly Tyr Ser Asn Asn Ser Asn Tyr Met Ala His Leu Val Asn Ala Ile
    690                 695                 700

Gln Gln Ala Ser Pro Ser Ile Trp Gly Asn Glu Arg Phe Ala Leu Asp
705                 710                 715                 720

Pro Ser Val Val Lys Ser Glu Val Leu Lys Ser Thr Gly Gln Lys Pro
                725                 730                 735

Glu Lys Val Ser Val Glu Gly Lys Glu Val Glu Val Thr Gly Ser Thr
            740                 745                 750

Val Thr Ser Tyr Trp Ala Asn Lys Ser Gly Ala Pro Ala Thr Ser Tyr
        755                 760                 765

Arg Phe Ala Ile Gly Gly Ser Asp Ala Asp Tyr Gln Asn Ala Trp Ser
    770                 775                 780

Ser Ile Val Gly Ser Leu Pro Thr Pro Ser Ser Ser Ser Ser Ser Ser
785                 790                 795                 800

Ser Ser Ser Ser Asp Ser Ser Asn Ser Ser Thr Thr Arg Pro Ser Ser
                805                 810                 815

Ser Arg Ala Arg Arg
            820

<210> SEQ ID NO 123
<211> LENGTH: 1974
```

<212> TYPE: DNA
<213> ORGANISM: Streptococcus pneumoniae

<400> SEQUENCE: 123

```
atgaaaaaat tttatgtaag tccaattttt cctattctag taggattgat tgcgtttgga      60
gtcttatcca ctttcattat ttttgttaat aataatctgt tgacggtttt aattttgttt     120
cttttttgtag gaggctatgt ttttttattt aagaaactga gagtgcatta tacaaggagt    180
gatgtagaac agatacagta tgtaaaccac caagcggaag aaagtttgac agctctattg     240
gaacagatgc ctgtaggtgt tatgaaattg aatttatctt ctggagaggt tgagtggttt     300
aatccctatg ctgaattgat tttgaccaag gaagatggtg attttgattt agaagctgtt     360
caaacgatta tcaaggcttc agtaggaaat ccgtctactt atgccaagct tggtgagaag     420
cgttatgctg ttcatatgga tgcttcttcc ggtgttttgt attttgtaga tgtatccagg     480
gaacaagcca taacagatga attggtaaca agtagaccag tgattgggat tgtctctgtg     540
gataattatg atgatttgga ggatgaaact tctgagtcag atattagtca aatcaatagt     600
tttgtagcta attttatatc agagttttca gaaaaacaca tgatgttttc tcgtcgggta    660
agtatggatc gattttatct atttactgac tacacggtgc ttgagggctt gatgaatgat     720
aaattttctg ttattgatgc tttcagagaa gagtcgaaac agagacagtt gcccttgacc    780
ttaagtatgg gattttctta tggcgatgga atcatgatg atagggaa agttgctttg       840
ctcaatttga acttggctga agtacgtggt ggcgaccagg tggttgttaa ggaaaacgac    900
gaaacgaaaa atccagttta ttttggtggt gggtctgctg cttcaatcaa gcgtacacgg    960
actcgtacgc gcgctatgat gacagctatt tcagataaga ttcggagtgt agatcaggtt  1020
tttgtagtcg gtcacaaaaa tttagacatg atgctttgg gctctgctgt aggtatgcag   1080
ttgttcgcca gcaatgtgat tgaaaatagc tatgctcttt atgatgaaga acaaatgtct  1140
ccagatattg aacagctgt ttcattcata gaaaaagaag gagttacgaa gttgttgtct   1200
gttaaggatg caatggggat ggtgaccaat cgttctttgt tgattcttgt agaccattca  1260
aagacagcct taacattatc aaaagaattt tatgatttat ttacccaaac cattgttatt   1320
gaccaccata gaagggatca ggattttcca gataatgcgg ttattactta tatcgaaagt  1380
ggtgcaagta gtgccagtga gttggtaacg gaattgattc agttccagaa ttctaagaaa  1440
aatcgtttga gtcgtatgca agcaagtgtc ttgatggctg gtatgatgtt ggatactaaa  1500
aatttcacct cgcgagtaac tagtcggaca tttgatgttg ctagctatct cagaacgcgc  1560
ggaagtgata gtattgctat ccaggaaatc gctgcgacag attttgaaga atatcgtgag  1620
gtcaatgaac ttattttaca ggggcgtaaa ttaggttcag atgtactaat agcagaggct  1680
aaggacatga aatgctatga tacagttgtt attagtaagg cagcagatgc catgttagcc   1740
atgtcaggta ttgaagcgag ttttgttctt gcgaagaata cacaaggatt tatctctatc  1800
tcagctcgaa gtcgtagtaa actgaatgta caacggatta tggaagagtt aggcggtgga  1860
ggccacttta atttggcagc agctcaaatt aaagatgtaa ccttgtcaga agcaggtgaa   1920
aaactgacag aaattgtatt aaatgaaatg aaggaaaagg agaaagaaga atga          1974
```

<210> SEQ ID NO 124
<211> LENGTH: 657
<212> TYPE: PRT
<213> ORGANISM: Streptococcus pneumoniae

<400> SEQUENCE: 124

Met Lys Lys Phe Tyr Val Ser Pro Ile Phe Pro Ile Leu Val Gly Leu

```
              1               5                  10                 15
Ile Ala Phe Gly Val Leu Ser Thr Phe Ile Ile Phe Val Asn Asn Asn
                    20                 25                 30

Leu Leu Thr Val Leu Ile Leu Phe Leu Phe Val Gly Gly Tyr Val Phe
                35                 40                 45

Leu Phe Lys Lys Leu Arg Val His Tyr Thr Arg Ser Asp Val Glu Gln
            50                 55                 60

Ile Gln Tyr Val Asn His Gln Ala Glu Glu Ser Leu Thr Ala Leu Leu
65                      70                 75                 80

Glu Gln Met Pro Val Gly Val Met Lys Leu Asn Leu Ser Ser Gly Glu
                    85                 90                 95

Val Glu Trp Phe Asn Pro Tyr Ala Glu Leu Ile Leu Thr Lys Glu Asp
                    100                105                110

Gly Asp Phe Asp Leu Glu Ala Val Gln Thr Ile Ile Lys Ala Ser Val
                115                120                125

Gly Asn Pro Ser Thr Tyr Ala Lys Leu Gly Glu Lys Arg Tyr Ala Val
            130                135                140

His Met Asp Ala Ser Ser Gly Val Leu Tyr Phe Val Asp Val Ser Arg
145                 150                155                160

Glu Gln Ala Ile Thr Asp Glu Leu Val Thr Ser Arg Pro Val Ile Gly
                    165                170                175

Ile Val Ser Val Asp Asn Tyr Asp Asp Leu Glu Asp Glu Thr Ser Glu
                180                185                190

Ser Asp Ile Ser Gln Ile Asn Ser Phe Val Ala Asn Phe Ile Ser Glu
            195                200                205

Phe Ser Glu Lys His Met Met Phe Ser Arg Arg Val Ser Met Asp Arg
        210                215                220

Phe Tyr Leu Phe Thr Asp Tyr Thr Val Leu Glu Gly Leu Met Asn Asp
225                 230                235                240

Lys Phe Ser Val Ile Asp Ala Phe Arg Glu Ser Lys Gln Arg Gln
                    245                250                255

Leu Pro Leu Thr Leu Ser Met Gly Phe Ser Tyr Gly Asp Gly Asn His
                260                265                270

Asp Glu Ile Gly Lys Val Ala Leu Leu Asn Leu Asn Leu Ala Glu Val
            275                280                285

Arg Gly Gly Asp Gln Val Val Lys Glu Asn Asp Glu Thr Lys Asn
        290                295                300

Pro Val Tyr Phe Gly Gly Gly Ser Ala Ala Ser Ile Lys Arg Thr Arg
305                 310                315                320

Thr Arg Thr Arg Ala Met Met Thr Ala Ile Ser Asp Lys Ile Arg Ser
                325                330                335

Val Asp Gln Val Phe Val Val Gly His Lys Asn Leu Asp Met Asp Ala
                340                345                350

Leu Gly Ser Ala Val Gly Met Gln Leu Phe Ala Ser Asn Val Ile Glu
            355                360                365

Asn Ser Tyr Ala Leu Tyr Asp Glu Glu Gln Met Ser Pro Asp Ile Glu
    370                375                380

Arg Ala Val Ser Phe Ile Glu Lys Glu Gly Val Thr Lys Leu Leu Ser
385                 390                395                400

Val Lys Asp Ala Met Gly Met Val Thr Asn Arg Ser Leu Leu Ile Leu
                405                410                415

Val Asp His Ser Lys Thr Ala Leu Thr Leu Ser Lys Glu Phe Tyr Asp
                420                425                430
```

| | | | | | | | | | | | | |
|---|---|---|---|---|---|---|---|---|---|---|---|---|
|Leu|Phe|Thr|Gln|Thr|Ile|Val|Ile|Asp|His|His|Arg|Arg|Asp|Gln|Asp|
| | |435| | | |440| | | |445| | | | | |

Phe Pro Asp Asn Ala Val Ile Thr Tyr Ile Glu Ser Gly Ala Ser Ser
        450                 455                 460

Ala Ser Glu Leu Val Thr Glu Leu Ile Gln Phe Gln Asn Ser Lys Lys
465                 470                 475                 480

Asn Arg Leu Ser Arg Met Gln Ala Ser Val Leu Met Ala Gly Met Met
                485                 490                 495

Leu Asp Thr Lys Asn Phe Thr Ser Arg Val Thr Ser Arg Thr Phe Asp
            500                 505                 510

Val Ala Ser Tyr Leu Arg Thr Arg Gly Ser Asp Ser Ile Ala Ile Gln
        515                 520                 525

Glu Ile Ala Ala Thr Asp Phe Glu Glu Tyr Arg Glu Val Asn Glu Leu
    530                 535                 540

Ile Leu Gln Gly Arg Lys Leu Gly Ser Asp Val Leu Ile Ala Glu Ala
545                 550                 555                 560

Lys Asp Met Lys Cys Tyr Asp Thr Val Val Ile Ser Lys Ala Ala Asp
                565                 570                 575

Ala Met Leu Ala Met Ser Gly Ile Glu Ala Ser Phe Val Leu Ala Lys
            580                 585                 590

Asn Thr Gln Gly Phe Ile Ser Ile Ser Ala Arg Ser Arg Ser Lys Leu
        595                 600                 605

Asn Val Gln Arg Ile Met Glu Glu Leu Gly Gly Gly His Phe Asn
    610                 615                 620

Leu Ala Ala Ala Gln Ile Lys Asp Val Thr Leu Ser Glu Ala Gly Glu
625                 630                 635                 640

Lys Leu Thr Glu Ile Val Leu Asn Glu Met Lys Glu Lys Glu Lys Glu
                645                 650                 655

Glu

<210> SEQ ID NO 125
<211> LENGTH: 663
<212> TYPE: DNA
<213> ORGANISM: Streptococcus pneumoniae

<400> SEQUENCE: 125

```
atgaagtgct tgtatgtgg gcagactatg aagactgttt taactttag tagtctctta      60
cttctgagga atgatgactc ttgtctttgt tcagactgtg attctacttt tgaaagaatt    120
ggggaagaga actgtccaaa ttgtatgaaa acagagttgt caacaaagtg tcaagattgt    180
caactttggt gtaaagaggg agttgaagtc agtcatagag cgatttttac ttacaatcaa    240
gctatgaagg attttttcag tcggtataag tttgatggag acttcctgtt aagaaaagtt    300
ttcgcttcat ttttaagtga ggagttgaaa agtacaaag agtatcaatt tgttgtaatt    360
cccctaagtc ctgatagata tgctaataga ggatttaatc aggttgaggg cttggtagag    420
gcagcaggct ttgagtatct ggatttatta gagaaaagag aagagagagc cagttcttct    480
aaaaatcgtt cagagcgctt ggggacagaa cttcctttct ttattaaaag tggagtcact    540
attcctaaaa aaatcctact tatagatgat atctatacta caggagcaac tataaatcgt    600
gttaagaaac tgttggaaga agctggtgct aaggatgtaa aaacattttc ccttgtaaga    660
tga                                                                 663
```

<210> SEQ ID NO 126
<211> LENGTH: 220
<212> TYPE: PRT

<213> ORGANISM: Streptococcus pneumoniae

<400> SEQUENCE: 126

```
Met Lys Cys Leu Leu Cys Gly Gln Thr Met Lys Thr Val Leu Thr Phe
  1               5                  10                  15

Ser Ser Leu Leu Leu Leu Arg Asn Asp Asp Ser Cys Leu Cys Ser Asp
             20                  25                  30

Cys Asp Ser Thr Phe Glu Arg Ile Gly Glu Glu Asn Cys Pro Asn Cys
         35                  40                  45

Met Lys Thr Glu Leu Ser Thr Lys Cys Gln Asp Cys Gln Leu Trp Cys
     50                  55                  60

Lys Glu Gly Val Glu Val Ser His Arg Ala Ile Phe Thr Tyr Asn Gln
 65                  70                  75                  80

Ala Met Lys Asp Phe Phe Ser Arg Tyr Lys Asp Gly Asp Phe Leu
             85                  90                  95

Leu Arg Lys Val Phe Ala Ser Phe Leu Ser Glu Glu Leu Lys Lys Tyr
            100                 105                 110

Lys Glu Tyr Gln Phe Val Val Ile Pro Leu Ser Pro Asp Arg Tyr Ala
        115                 120                 125

Asn Arg Gly Phe Asn Gln Val Glu Gly Leu Val Glu Ala Ala Gly Phe
    130                 135                 140

Glu Tyr Leu Asp Leu Leu Glu Lys Arg Glu Arg Ala Ser Ser Ser
145                 150                 155                 160

Lys Asn Arg Ser Glu Arg Leu Gly Thr Glu Leu Pro Phe Phe Ile Lys
                165                 170                 175

Ser Gly Val Thr Ile Pro Lys Lys Ile Leu Leu Ile Asp Asp Ile Tyr
            180                 185                 190

Thr Thr Gly Ala Thr Ile Asn Arg Val Lys Lys Leu Leu Glu Glu Ala
        195                 200                 205

Gly Ala Lys Asp Val Lys Thr Phe Ser Leu Val Arg
    210                 215                 220
```

<210> SEQ ID NO 127
<211> LENGTH: 1299
<212> TYPE: DNA
<213> ORGANISM: Streptococcus pneumoniae

<400> SEQUENCE: 127

```
atgaaagtaa atttagatta tctcggtcgt ttatttactg agaatgaatt aacagaagaa      60
gaacgtcagt tggcggagaa acttccagca atgagaaagg agaagggaa acttttctgt     120 caacgctgta atagtactat tctagaagaa tggtatttgc ccatcggtgc ttactattgt     180
cgagagtgct tgctgatgaa gcgagtcaga agtgatcaaa ctttatacta ttttccgcag     240
gaggattttc caaagcaaga tgttctcaaa tggcgcggcc aattaactcc ttttcaagag     300
aaggtgtcag agggattgct tcaagtagta gacaagcaaa agccaacctt agttcatgcg     360
gtaacaggag ctggaaagac agaaatgatt tatcaagtag tggctaaagt gatcaatgcg     420
ggtggtgcag tgtgtttggc tagtcctcgc atagatgttt gtttggagct gtacaagcgc     480
ctgcaacagg attttcttg cgggatagct ttgctacatg agaatcgga accttatttt     540 cgaacaccac tagttgttgc aacaacccat cagttattga agttttatca agcttttgat     600
ttgctgatag tggatgaagt agatgctttt ccttatgttg ataatcccat gctttaccac     660
gctgtcaaga atagtgtaaa ggagaatgga ttgagaatct ttttaacagc gacttcgacc     720
aatgagttag ataaaaaggt ccgtttagga gaactaaaaa gactgaattt accgagacgg     780
```

```
tttcatggaa atccgttgat tattccaaaa ccaatttggt tatcggattt taatcgctac      840
ttagacaaga atcgtttgtc accaaagtta aagtcctata ttgagaagca gagaaagaca      900
gcttatccgt tactcatttt tgcttcagaa attaagaaag gggagcagtt agcagaaatc      960
ttacaggagc aatttccaaa tgagaaaatt ggctttgtat cttctgtaac agaggatcga     1020
ttagagcaag tacaagcttt tcgagatgga gaactgacaa tacttatcag tacgacaatc     1080
ttggagcgcg gagttacctt cccttgtgtg gatgttttcg tagtagaggc caatcatcgt     1140
ttgtttacca agtctagttt gattcagatt ggtggacgag ttggacgaag catggataga     1200
ccgacaggag atttgctttt cttccatgat gggttaaatg cttcaatcaa gaaggcgatt     1260
aaggaaattc agatgatgaa taaggaggct ggtctatga                            1299
```

<210> SEQ ID NO 128
<211> LENGTH: 432
<212> TYPE: PRT
<213> ORGANISM: Streptococcus pneumoniae

<400> SEQUENCE: 128

```
Met Lys Val Asn Leu Asp Tyr Leu Gly Arg Leu Phe Thr Glu Asn Glu
  1               5                  10                  15

Leu Thr Glu Glu Arg Gln Leu Ala Glu Lys Leu Pro Ala Met Arg
             20                  25                  30

Lys Glu Lys Gly Lys Leu Phe Cys Gln Arg Cys Asn Ser Thr Ile Leu
         35                  40                  45

Glu Glu Trp Tyr Leu Pro Ile Gly Ala Tyr Tyr Cys Arg Glu Cys Leu
     50                  55                  60

Leu Met Lys Arg Val Arg Ser Asp Gln Thr Leu Tyr Tyr Phe Pro Gln
 65                  70                  75                  80

Glu Asp Phe Pro Lys Gln Asp Val Leu Lys Trp Arg Gly Gln Leu Thr
                 85                  90                  95

Pro Phe Gln Glu Lys Val Ser Glu Gly Leu Leu Gln Val Val Asp Lys
            100                 105                 110

Gln Lys Pro Thr Leu Val His Ala Val Thr Gly Ala Gly Lys Thr Glu
        115                 120                 125

Met Ile Tyr Gln Val Val Ala Lys Val Ile Asn Ala Gly Gly Ala Val
    130                 135                 140

Cys Leu Ala Ser Pro Arg Ile Asp Val Cys Leu Glu Leu Tyr Lys Arg
145                 150                 155                 160

Leu Gln Gln Asp Phe Ser Cys Gly Ile Ala Leu Leu His Gly Glu Ser
                165                 170                 175

Glu Pro Tyr Phe Arg Thr Pro Leu Val Val Ala Thr Thr His Gln Leu
            180                 185                 190

Leu Lys Phe Tyr Gln Ala Phe Asp Leu Leu Ile Val Asp Glu Val Asp
        195                 200                 205

Ala Phe Pro Tyr Val Asp Asn Pro Met Leu Tyr His Ala Val Lys Asn
    210                 215                 220

Ser Val Lys Glu Asn Gly Leu Arg Ile Phe Leu Thr Ala Thr Ser Thr
225                 230                 235                 240

Asn Glu Leu Asp Lys Lys Val Arg Leu Gly Glu Leu Lys Arg Leu Asn
                245                 250                 255

Leu Pro Arg Arg Phe His Gly Asn Pro Leu Ile Ile Pro Lys Pro Ile
            260                 265                 270

Trp Leu Ser Asp Phe Asn Arg Tyr Leu Asp Lys Asn Arg Leu Ser Pro
        275                 280                 285
```

```
Lys Leu Lys Ser Tyr Ile Glu Lys Gln Arg Lys Thr Ala Tyr Pro Leu
        290                 295                 300

Leu Ile Phe Ala Ser Glu Ile Lys Lys Gly Glu Gln Leu Ala Glu Ile
305                 310                 315                 320

Leu Gln Glu Gln Phe Pro Asn Glu Lys Ile Gly Phe Val Ser Ser Val
                325                 330                 335

Thr Glu Asp Arg Leu Glu Gln Val Gln Ala Phe Arg Asp Gly Glu Leu
                340                 345                 350

Thr Ile Leu Ile Ser Thr Thr Ile Leu Glu Arg Gly Val Thr Phe Pro
            355                 360                 365

Cys Val Asp Val Phe Val Val Glu Ala Asn His Arg Leu Phe Thr Lys
        370                 375                 380

Ser Ser Leu Ile Gln Ile Gly Gly Arg Val Gly Arg Ser Met Asp Arg
385                 390                 395                 400

Pro Thr Gly Asp Leu Leu Phe Phe His Asp Gly Leu Asn Ala Ser Ile
                405                 410                 415

Lys Lys Ala Ile Lys Glu Ile Gln Met Met Asn Lys Glu Ala Gly Leu
                420                 425                 430

<210> SEQ ID NO 129
<211> LENGTH: 870
<212> TYPE: DNA
<213> ORGANISM: Streptococcus pneumoniae

<400> SEQUENCE: 129
atgcaaattc aaaaaagttt taagggggcag tctccctatg gcaagctgta tctagtggca      60
acgccgattg caatctaga tgatatgact tttcgtgcta tccagacctt gaaagaagtg      120
gactggattg ctgctgagga tacgcgcaat acagggcttt tgctcaagca ttttgacatt      180
tccaccaagc agatcagttt tcatgagcac aatgccaagg aaaaaattcc tgatttgatt      240
ggtttcttga aagcagggca agtattgct caggtctctg atgccggttt gcctagcatt      300
tcagaccctg gtcatgattt agttaaggca gctattgagg aagaaattgc agttgtgaca      360
gttccaggtg cctctgcagg aatttctgcc ttgattgcca gtggtttagc gccacagcca      420
catatctttt acggtttttt accgagaaaa tcaggtcagc agaagcaatt ttttggcttg      480
aaaaaagatt atcctgaaac acagattttt tatgaatcac ctcatcgtgt agcagacacg      540
ttggaaaata tgttagaagt ctacggtgac cgctccgttg tcttggtcag ggaattgacc      600
aaaatctatg aagaatacca acgaggtact atctctgagt tattagaaag cattgctgaa      660
acgccactca agggcgaatg tcttctcatt gttgagggtg ccagtcaggg tgtggaggaa      720
aaggacgagg aagacttgtt cgtagaaatt caaacccgca tccagcaagg tgtgaagaaa      780
aaccaagcta tcaaggaagt cgctaagatt taccagtgga ataaaagtca gctctacgct      840
gcctaccacg actgggaaga aaaacaataa                                        870

<210> SEQ ID NO 130
<211> LENGTH: 289
<212> TYPE: PRT
<213> ORGANISM: Streptococcus pneumoniae

<400> SEQUENCE: 130

Met Gln Ile Gln Lys Ser Phe Lys Gly Gln Ser Pro Tyr Gly Lys Leu
1               5                   10                  15

Tyr Leu Val Ala Thr Pro Ile Gly Asn Leu Asp Asp Met Thr Phe Arg
            20                  25                  30

Ala Ile Gln Thr Leu Lys Glu Val Asp Trp Ile Ala Ala Glu Asp Thr
```

```
                35                  40                  45
Arg Asn Thr Gly Leu Leu Lys His Phe Asp Ile Ser Thr Lys Gln
        50                  55                  60

Ile Ser Phe His Glu His Asn Ala Lys Glu Lys Ile Pro Asp Leu Ile
 65                  70                  75                  80

Gly Phe Leu Lys Ala Gly Gln Ser Ile Ala Gln Val Ser Asp Ala Gly
                85                  90                  95

Leu Pro Ser Ile Ser Asp Pro Gly His Asp Leu Val Lys Ala Ala Ile
            100                 105                 110

Glu Glu Glu Ile Ala Val Val Thr Val Pro Gly Ala Ser Ala Gly Ile
        115                 120                 125

Ser Ala Leu Ile Ala Ser Gly Leu Ala Pro Gln Pro His Ile Phe Tyr
    130                 135                 140

Gly Phe Leu Pro Arg Lys Ser Gly Gln Gln Lys Gln Phe Phe Gly Leu
145                 150                 155                 160

Lys Lys Asp Tyr Pro Glu Thr Gln Ile Phe Tyr Glu Ser Pro His Arg
                165                 170                 175

Val Ala Asp Thr Leu Glu Asn Met Leu Glu Val Tyr Gly Asp Arg Ser
            180                 185                 190

Val Val Leu Val Arg Glu Leu Thr Lys Ile Tyr Glu Tyr Gln Arg
        195                 200                 205

Gly Thr Ile Ser Glu Leu Leu Glu Ser Ile Ala Glu Thr Pro Leu Lys
    210                 215                 220

Gly Glu Cys Leu Leu Ile Val Glu Gly Ala Ser Gln Gly Val Glu Glu
225                 230                 235                 240

Lys Asp Glu Glu Asp Leu Phe Val Glu Ile Gln Thr Arg Ile Gln Gln
                245                 250                 255

Gly Val Lys Lys Asn Gln Ala Ile Lys Glu Val Ala Lys Ile Tyr Gln
            260                 265                 270

Trp Asn Lys Ser Gln Leu Tyr Ala Ala Tyr His Asp Trp Glu Glu Lys
        275                 280                 285

Gln

<210> SEQ ID NO 131
<211> LENGTH: 345
<212> TYPE: DNA
<213> ORGANISM: Streptococcus pneumoniae

<400> SEQUENCE: 131
atgataaaga aaggaaaggg ctgttttatg gacaaaaaag aattatttga cgcgctggat      60 gattttccc aacaattatt ggtaacctta gccgatgtgg aagccatcaa gaaaaatctc     120
aagagcctgg tagaggaaaa tacagctctt cgcttggaaa atagtaagtt gcgagaacgc    180
ttgggtgagg tggaagcaga tgctcctgtc aaggccaagc atgttcgcga aagtgtccgt    240
cgtatttacc gtgatggatt tcacgtatgt aatgattttt atggacaacg tcgagagcag    300
gacgaagaat gtatgttttg tgacgagttg ttatacaggg agtaa                    345

<210> SEQ ID NO 132
<211> LENGTH: 114
<212> TYPE: PRT
<213> ORGANISM: Streptococcus pneumoniae

<400> SEQUENCE: 132

Met Ile Lys Lys Gly Lys Gly Cys Phe Met Asp Lys Lys Glu Leu Phe
 1               5                  10                  15
```

Asp Ala Leu Asp Asp Phe Ser Gln Gln Leu Leu Val Thr Leu Ala Asp
            20                  25                  30

Val Glu Ala Ile Lys Lys Asn Leu Lys Ser Leu Val Glu Glu Asn Thr
        35                  40                  45

Ala Leu Arg Leu Glu Asn Ser Lys Leu Arg Glu Arg Leu Gly Glu Val
    50                  55                  60

Glu Ala Asp Ala Pro Val Lys Ala Lys His Val Arg Glu Ser Val Arg
65                  70                  75                  80

Arg Ile Tyr Arg Asp Gly Phe His Val Cys Asn Asp Phe Tyr Gly Gln
                85                  90                  95

Arg Arg Glu Gln Asp Glu Glu Cys Met Phe Cys Asp Glu Leu Leu Tyr
            100                 105                 110

Arg Glu

<210> SEQ ID NO 133
<211> LENGTH: 639
<212> TYPE: DNA
<213> ORGANISM: Streptococcus pneumoniae

<400> SEQUENCE: 133
atgtcaaaag gattttagt ctctcttgag ggaccagagg gagcaggcaa gaccagtgtt      60
ttagaggctc tgctaccaat tttagaggaa aaaggagtag aggtgttgac gacccgtgaa    120
cctggcggag tcttgattgg ggagaagatt cgggaagtga ttttggatcc aagtcatact    180
cagatggatg ctaaaacaga gctacttctc tatattgcca gtcgcagaca gcatttggtg    240
gaaaaagttc ttccagccct tgaagctggc aagttggtca tcatggatcg ttttatcgat    300
agttctgttg cctatcaggg atttggtcgt ggcttagata ttgaagccat tgactggctc    360
aatcagtttg cgacagatgg cctcaaaccc gatttgacac tctattttga catcgaggtg    420
gaagaagggc tggctcgtat tgctgctaat agtgaccgcg aggttaatcg tttggatttg    480
gaagggttgg acttgcataa aaaagttcgt caaggctacc tttctcttct ggataaagag    540
ggaaatcgca ttgtcaagat tgatgctagt ctcccttttgg agcaagttgt ggaaactacc    600
aaggctgtct tgtttgacgg aatgggcttg gccaaatga                            639

<210> SEQ ID NO 134
<211> LENGTH: 212
<212> TYPE: PRT
<213> ORGANISM: Streptococcus pneumoniae

<400> SEQUENCE: 134

Met Ser Lys Gly Phe Leu Val Ser Leu Glu Gly Pro Glu Gly Ala Gly
1               5                   10                  15

Lys Thr Ser Val Leu Glu Ala Leu Leu Pro Ile Leu Glu Glu Lys Gly
            20                  25                  30

Val Glu Val Leu Thr Thr Arg Glu Pro Gly Gly Val Leu Ile Gly Glu
        35                  40                  45

Lys Ile Arg Glu Val Ile Leu Asp Pro Ser His Thr Gln Met Asp Ala
    50                  55                  60

Lys Thr Glu Leu Leu Leu Tyr Ile Ala Ser Arg Gln His Leu Val
65                  70                  75                  80

Glu Lys Val Leu Pro Ala Leu Glu Ala Gly Lys Leu Val Ile Met Asp
                85                  90                  95

Arg Phe Ile Asp Ser Ser Val Ala Tyr Gln Gly Phe Gly Arg Gly Leu
            100                 105                 110

Asp Ile Glu Ala Ile Asp Trp Leu Asn Gln Phe Ala Thr Asp Gly Leu

```
                 115                 120                 125
Lys Pro Asp Leu Thr Leu Tyr Phe Asp Ile Glu Val Glu Glu Gly Leu
    130                 135                 140

Ala Arg Ile Ala Ala Asn Ser Asp Arg Glu Val Asn Arg Leu Asp Leu
145                 150                 155                 160

Glu Gly Leu Asp Leu His Lys Lys Val Arg Gln Gly Tyr Leu Ser Leu
                165                 170                 175

Leu Asp Lys Glu Gly Asn Arg Ile Val Lys Ile Asp Ala Ser Leu Pro
            180                 185                 190

Leu Glu Gln Val Val Glu Thr Thr Lys Ala Val Leu Phe Asp Gly Met
        195                 200                 205

Gly Leu Ala Lys
    210

<210> SEQ ID NO 135
<211> LENGTH: 474
<212> TYPE: DNA
<213> ORGANISM: Streptococcus pneumoniae

<400> SEQUENCE: 135
atggtagaac aaagaaaatc aattaccatg aaagatgttg ctttagaagc aggagttagt      60
gttggaactg tttcacgtgt aattaataaa gaaaaaggca ttaaagaagt aactttgaaa     120
aaagtggaac aagcgattaa actttgaat tacattccag attactacgc tagaggaatg      180
aaaaaaaatc gaacagaaac gattgcaatc attgtaccaa gtatctggca tcccttcttt     240
tcagaatttg ctatgcatgt ggaaaatgaa gtctataaga gaataacaa attactctta      300 tgttctatca atggtacaaa tagagagcaa gactatctgg agatgttgcg tcataataaa     360
gttgatggag tggttgccat tacctatagg ccaattgaac attacttgac gtcaggaatt     420
ccctttgtta gtattgaccg cacatactca gagattgcca ttccttgtgt ttca           474

<210> SEQ ID NO 136
<211> LENGTH: 158
<212> TYPE: PRT
<213> ORGANISM: Streptococcus pneumoniae

<400> SEQUENCE: 136

Met Val Glu Gln Arg Lys Ser Ile Thr Met Lys Asp Val Ala Leu Glu
1               5                   10                  15

Ala Gly Val Ser Val Gly Thr Val Ser Arg Val Ile Asn Lys Glu Lys
            20                  25                  30

Gly Ile Lys Glu Val Thr Leu Lys Lys Val Glu Gln Ala Ile Lys Thr
        35                  40                  45

Leu Asn Tyr Ile Pro Asp Tyr Tyr Ala Arg Gly Met Lys Lys Asn Arg
    50                  55                  60

Thr Glu Thr Ile Ala Ile Ile Val Pro Ser Ile Trp His Pro Phe Phe
65                  70                  75                  80

Ser Glu Phe Ala Met His Val Glu Asn Glu Val Tyr Lys Arg Asn Asn
                85                  90                  95

Lys Leu Leu Leu Cys Ser Ile Asn Gly Thr Asn Arg Glu Gln Asp Tyr
            100                 105                 110

Leu Glu Met Leu Arg His Asn Lys Val Asp Gly Val Val Ala Ile Thr
        115                 120                 125

Tyr Arg Pro Ile Glu His Tyr Leu Thr Ser Gly Ile Pro Phe Val Ser
    130                 135                 140

Ile Asp Arg Thr Tyr Ser Glu Ile Ala Ile Pro Cys Val Ser
```

```
                              145                 150                 155

<210> SEQ ID NO 137
<211> LENGTH: 374
<212> TYPE: DNA
<213> ORGANISM: Streptococcus pneumoniae

<400> SEQUENCE: 137
atgaatatat ttagaacaaa gaatgttagt ttagataaaa cagagatgca taggcatttg      60
aagttatggg atttgatttt gctgggtatc ggagccatgg tagggacagg cgtctttaca     120
atcacaggta ctgcagctgc aacacttgct ggcccagccc tagtgatttc aatcgttatt     180
tctgccttgt gtgtgggatt atcagccctc ttttttgcag aatttgcctc gcgagtaccc     240
gctacaggag gtgcctatag ttacctctat gctatcttag gagaattccc tgcctggttg     300
gctggttggt taaccatgat ggagttcatg acagccatat caggcgtagc ttcgggttgg     360
gcagcttatt ttaa                                                       374

<210> SEQ ID NO 138
<211> LENGTH: 124
<212> TYPE: PRT
<213> ORGANISM: Streptococcus pneumoniae

<400> SEQUENCE: 138

Met Asn Ile Phe Arg Thr Lys Asn Val Ser Leu Asp Lys Thr Glu Met
 1               5                  10                  15

His Arg His Leu Lys Leu Trp Asp Leu Ile Leu Leu Gly Ile Gly Ala
             20                  25                  30

Met Val Gly Thr Gly Val Phe Thr Ile Thr Gly Thr Ala Ala Ala Thr
         35                  40                  45

Leu Ala Gly Pro Ala Leu Val Ile Ser Ile Val Ile Ser Ala Leu Cys
     50                  55                  60

Val Gly Leu Ser Ala Leu Phe Phe Ala Glu Phe Ala Ser Arg Val Pro
 65                  70                  75                  80

Ala Thr Gly Gly Ala Tyr Ser Tyr Leu Tyr Ala Ile Leu Gly Glu Phe
                 85                  90                  95

Pro Ala Trp Leu Ala Gly Trp Leu Thr Met Met Glu Phe Met Thr Ala
            100                 105                 110

Ile Ser Gly Val Ala Ser Gly Trp Ala Ala Tyr Phe
        115                 120

<210> SEQ ID NO 139
<211> LENGTH: 1311
<212> TYPE: DNA
<213> ORGANISM: Streptococcus pneumoniae

<400> SEQUENCE: 139
atgaaatcaa gagtaaagga aacgagtatg gataaaattg tggttcaagg tggcgataat      60
cgtctggtag aagcgtgac gatcgaggga gcaaaaaatg cagtcttacc cttgttggca     120
gcgactattc tagcaagtga aggaaagacc gtcttgcaga atgttccgat tttgtcggat     180
gtctttatta tgaatcaggt agttggtggt ttgaatgcca aggttgactt tgatgaggaa     240
gctcatcttg tcaaggtgga tgctactggc gacatcactg aggaagcccc ttacaagtat     300
gtcagcaaga tgcgcgcctc catcgttgta ttagggccaa tccttgcccg tgtgggtcat     360
gccaaggtat ccatgccagg tggttgtacg attggtagcc gtcctattga tcttcatttg     420
aaaggtctgg aagctatggg ggttaagatt agtcagacag ctggttacat cgaagccaag     480
```

```
gcagaacgct tgcatggtgc tcatatctat atggactttc caagtgttgg tgcaacgcag    540
aacttgatga tggcagcgac tctggctgat ggggtgacag tgattgagaa tgctgcgcgt    600
gagcctgaga ttgttgactt agccattctc cttaatgaaa tgggagccaa ggtcaaaggt    660
gctggtacag agactataac cattactggt gttgagaaac ttcatggtac gactcacaat    720
gtagtccaag accgtatcga agcaggaacc tttatggtag ctgctgccat gactggtggt    780
gatgtcttga ttcgagacgc tgtctgggag cacaaccgtc ccttgattgc caagttactt    840
gaaatgggtg ttgaagtaat tgaagaagac gaaggaattc gtgttcgttc tcaactagaa    900
aatctaaaag ctgttcatgt gaaaaccttg ccccacccag gatttccaac agatatgcag    960
gctcaattta cagccttgat gacagttgca aaaggcgaat caaccatggt ggagacagtt   1020
ttcgaaaatc gtttccaaca cctagaagag atgcgccgca tgggcttgca ttctgagatt   1080
atccgtgata cagctcgtat tgttggtgga cagccttttgc agggagcaga agttctttca   1140
actgaccttc gtgccagtgc ggccttgatt ttgacaggtt tggtagcaca gggagaaact   1200
gtggtcggta aattggttca cttggataga ggttactacg gtttccatga aagttggcg    1260 cagctaggtg ctaagattca gcggattgag gcaagtgatg aagatgaata a           1311
```

<210> SEQ ID NO 140
<211> LENGTH: 436
<212> TYPE: PRT
<213> ORGANISM: Streptococcus pneumoniae

<400> SEQUENCE: 140

```
Met Lys Ser Arg Val Lys Glu Thr Ser Met Asp Lys Ile Val Val Gln
 1               5                   10                  15

Gly Gly Asp Asn Arg Leu Val Gly Ser Val Thr Ile Glu Gly Ala Lys
                20                  25                  30

Asn Ala Val Leu Pro Leu Leu Ala Ala Thr Ile Leu Ala Ser Glu Gly
            35                  40                  45

Lys Thr Val Leu Gln Asn Val Pro Ile Leu Ser Asp Val Phe Ile Met
        50                  55                  60

Asn Gln Val Val Gly Gly Leu Asn Ala Lys Val Asp Phe Asp Glu Glu
    65                  70                  75                  80

Ala His Leu Val Lys Val Asp Ala Thr Gly Asp Ile Thr Glu Glu Ala
                85                  90                  95

Pro Tyr Lys Tyr Val Ser Lys Met Arg Ala Ser Ile Val Val Leu Gly
                100                 105                 110

Pro Ile Leu Ala Arg Val Gly His Ala Lys Val Ser Met Pro Gly Gly
            115                 120                 125

Cys Thr Ile Gly Ser Arg Pro Ile Asp Leu His Leu Lys Gly Leu Glu
        130                 135                 140

Ala Met Gly Val Lys Ile Ser Gln Thr Ala Gly Tyr Ile Glu Ala Lys
    145                 150                 155                 160

Ala Glu Arg Leu His Gly Ala His Ile Tyr Met Asp Phe Pro Ser Val
                165                 170                 175

Gly Ala Thr Gln Asn Leu Met Met Ala Ala Thr Leu Ala Asp Gly Val
            180                 185                 190

Thr Val Ile Glu Asn Ala Ala Arg Glu Pro Glu Ile Val Asp Leu Ala
        195                 200                 205

Ile Leu Leu Asn Glu Met Gly Ala Lys Val Lys Gly Ala Gly Thr Glu
    210                 215                 220

Thr Ile Thr Ile Thr Gly Val Glu Lys Leu His Gly Thr Thr His Asn
    225                 230                 235                 240
```

```
Val Val Gln Asp Arg Ile Glu Ala Gly Thr Phe Met Val Ala Ala
            245                 250                 255

Met Thr Gly Gly Asp Val Leu Ile Arg Asp Ala Val Trp Glu His Asn
            260                 265                 270

Arg Pro Leu Ile Ala Lys Leu Leu Glu Met Gly Val Glu Val Ile Glu
            275                 280                 285

Glu Asp Glu Gly Ile Arg Val Arg Ser Gln Leu Glu Asn Leu Lys Ala
        290                 295                 300

Val His Val Lys Thr Leu Pro His Pro Gly Phe Pro Thr Asp Met Gln
305                 310                 315                 320

Ala Gln Phe Thr Ala Leu Met Thr Val Ala Lys Gly Glu Ser Thr Met
                325                 330                 335

Val Glu Thr Val Phe Glu Asn Arg Phe Gln His Leu Glu Glu Met Arg
            340                 345                 350

Arg Met Gly Leu His Ser Glu Ile Ile Arg Asp Thr Ala Arg Ile Val
            355                 360                 365

Gly Gly Gln Pro Leu Gln Gly Ala Glu Val Leu Ser Thr Asp Leu Arg
        370                 375                 380

Ala Ser Ala Ala Leu Ile Leu Thr Gly Leu Val Ala Gln Gly Glu Thr
385                 390                 395                 400

Val Val Gly Lys Leu Val His Leu Asp Arg Gly Tyr Tyr Gly Phe His
                405                 410                 415

Glu Lys Leu Ala Gln Leu Gly Ala Lys Ile Gln Arg Ile Glu Ala Ser
            420                 425                 430

Asp Glu Asp Glu
        435

<210> SEQ ID NO 141
<211> LENGTH: 1100
<212> TYPE: DNA
<213> ORGANISM: Streptococcus pneumoniae

<400> SEQUENCE: 141
atgttattag cgtcaacagt agccttgtca tttgccccag tattggcaac tcaagcagaa      60
gaagttcttt ggactgcacg tagtgttgag caaatccaaa acgatttgac taaaacggac     120
aacaaaacaa gttataccgt acagtatggt gatactttga gcaccattgc agaagccttg     180
ggtgtagatg tcacagtgct tgcgaatctg aacaaaatca ctaatatgga cttgattttc     240
ccagaaactg ttttgacaac gactgtcaat gaagcagaag aagtaacaga agttgaaatc     300
caaacacctc aagcagactc tagtgaagaa gtgacaactg cgacagcaga tttgaccact     360
aatcaagtga ccgttgatga tcaaactgtt caggttgcag accttctctca accaattgca     420 gaagttacaa agacagtgat tgcttctgaa gaagtggcac catctacggg cacttctgtc     480
ccagaggagc aaacgaccga aacaactcgc ccagttgcaa agaagctcc tcaggaaacg     540 actccagctg agaagcagga acacaaaca agccctcaag ctgcatcagc agtggaagca     600
actacaacaa gttcagaagc aaaagaagta gcatcatcaa atggagctac agcagcagtt     660
tctacttatc aaccagaaga aacgaaagta atttcaacaa cttacgaggc tccagctgcg     720
cccgattatg ctggacttgc agtagcaaaa tctgaaaatg caggtcttca accacaaaca     780
gctgccttta agaagaaatt gctaacttgt ttggcattac atcctttagt ggttatcgtc     840
caggagacag tggagatcac ggaaaaggtt tggctatcga cttatggta ccagaacgtt     900 cagaattagg ggataagatt gcggaatatg ctattcaaaa tatggccagc cgtggcatta     960
```

```
gttacatcat ctggaaacaa cgtttctatg ctccattcga tagcaaatat gggccagcta     1020
acacttggaa cccaatgcca gaccgtggta gtgtgacaga aaatcactat gatcacgttc     1080
acgtttcaat gaatggataa                                                 1100
```

<210> SEQ ID NO 142
<211> LENGTH: 302
<212> TYPE: PRT
<213> ORGANISM: Streptococcus pneumoniae

<400> SEQUENCE: 142

```
Met Leu Leu Ala Ser Thr Val Ala Leu Ser Phe Ala Pro Val Leu Ala
 1               5                  10                  15

Thr Gln Ala Glu Glu Val Leu Trp Thr Ala Arg Ser Val Glu Gln Ile
             20                  25                  30

Gln Asn Asp Leu Thr Lys Thr Asp Asn Lys Thr Ser Tyr Thr Val Gln
         35                  40                  45

Tyr Gly Asp Thr Leu Ser Thr Ile Ala Glu Ala Leu Gly Val Asp Val
     50                  55                  60

Thr Val Leu Ala Asn Leu Asn Lys Ile Thr Asn Met Asp Leu Ile Phe
 65                  70                  75                  80

Pro Glu Thr Val Leu Thr Thr Val Asn Glu Ala Glu Glu Val Thr
                 85                  90                  95

Glu Val Glu Ile Gln Thr Pro Gln Ala Asp Ser Ser Glu Val Thr
            100                 105                 110

Thr Ala Thr Ala Asp Leu Thr Thr Asn Gln Val Thr Val Asp Asp Gln
        115                 120                 125

Thr Val Gln Val Ala Asp Leu Ser Gln Pro Ile Ala Glu Val Thr Lys
    130                 135                 140

Thr Val Ile Ala Ser Glu Glu Val Ala Pro Ser Thr Gly Thr Ser Val
145                 150                 155                 160

Pro Glu Glu Gln Thr Thr Glu Thr Thr Arg Pro Val Ala Glu Glu Ala
                165                 170                 175

Pro Gln Glu Thr Thr Pro Ala Glu Lys Gln Glu Thr Gln Thr Ser Pro
            180                 185                 190

Gln Ala Ala Ser Ala Val Glu Ala Thr Thr Thr Ser Ser Glu Ala Lys
        195                 200                 205

Glu Val Ala Ser Ser Asn Gly Ala Thr Ala Ala Val Ser Thr Tyr Gln
    210                 215                 220

Pro Glu Glu Thr Lys Val Ile Ser Thr Thr Tyr Glu Ala Pro Ala Ala
225                 230                 235                 240

Pro Asp Tyr Ala Gly Leu Ala Val Ala Lys Ser Glu Asn Ala Gly Leu
                245                 250                 255

Gln Pro Gln Thr Ala Ala Phe Lys Lys Lys Leu Leu Thr Cys Leu Ala
            260                 265                 270

Leu His Pro Leu Val Val Ile Val Gln Glu Thr Val Glu Ile Thr Glu
        275                 280                 285

Lys Val Trp Leu Ser Thr Leu Trp Tyr Gln Asn Val Gln Asn
    290                 295                 300
```

<210> SEQ ID NO 143
<211> LENGTH: 1281
<212> TYPE: DNA
<213> ORGANISM: Streptococcus pneumoniae

<400> SEQUENCE: 143

```
ttgtttaaga aaaataaaga cattcttaat attgcattgc cagctatggg tgaaaacttt     60
```

-continued

```
ttgcagatgc taatgggaat ggtggacagt tatttggttg ctcatttagg attgatagct    120
atttcagggg tttcagtagc tggtaatatt atcaccattt atcaggcgat tttcatcgct    180
ctgggagctg ctatttccag tgttatttca aaaagcatag ggcagaaaga ccagtcgaag    240
ttggcctatc atgtgactga ggcgttgaag attaccttac tattaagttt cctttaggga    300
tttttgtcca tcttcgctgg gaaagagatg ataggacttt tggggacgga gagggatgta    360
gctgagagtg gtggactgta tctatctttg gtaggcggat cgattgttct cttaggttta    420
atgactagtc taggagcctt gattcgtgca acgcataatc cacgtctgcc tctctatgtt    480
agtttttat ccaatgcctt gaatattctt ttttcaagtc tagctatttt tgttctggat    540
atggggatag ctggtgttgc ttgggggaca attgtgtctc gtttggttgg tcttgtgatt    600
ttgtggtcac aattaaaact gccttatggg aagccaactt ttggtttaga taaggaactg    660
ttgaccttgg ctttaccagc agctggagag cgacttatga tgagggctgg agatgtagtg    720
atcattgcct tggtcgtttc ttttgggacg gaggcagttc tgggaatgc aatcggagaa     780
gtcttgaccc agtttaacta tatgcctgcc tttggcgtcg ctacggcaac ggtcatgctg    840
ttggcccgag cagttggaga ggatgattgg aaaagagttg ctagtttgag taaacaaacc    900
ttttggcttt ctctgttcct catgttgccc ctgtcctta gtatatatgt cttgggtgta     960
ccattaactc atctctatac gactgattct ctagcggtgg aggctagtgt tctagtgaca   1020
ctgtttttcac tacttgggac ccctatgacg acaggaacag tcatctatac ggcagtctgg  1080
cagggattag gaaatgcacg cctcccttt tatgcgacaa gtataggaat gtggtgtatc    1140
cgcattggga caggatatct gatggggatt gtgcttggtt ggggcttgcc tggtatttgg   1200
gcagggtctc tcttggataa tggttttcgc tggttatttc tacgctatcg ttaccagcgc   1260
tatatgagct tgaaaggata g                                             1281
```

<210> SEQ ID NO 144
<211> LENGTH: 426
<212> TYPE: PRT
<213> ORGANISM: Streptococcus pneumoniae

<400> SEQUENCE: 144

```
Leu Phe Lys Lys Asn Lys Asp Ile Leu Asn Ile Ala Leu Pro Ala Met
  1               5                  10                  15

Gly Glu Asn Phe Leu Gln Met Leu Met Gly Met Val Asp Ser Tyr Leu
                 20                  25                  30

Val Ala His Leu Gly Leu Ile Ala Ile Ser Gly Val Ser Val Ala Gly
             35                  40                  45

Asn Ile Ile Thr Ile Tyr Gln Ala Ile Phe Ile Ala Leu Gly Ala Ala
         50                  55                  60

Ile Ser Ser Val Ile Ser Lys Ser Ile Gly Gln Lys Asp Gln Ser Lys
     65                  70                  75                  80

Leu Ala Tyr His Val Thr Glu Ala Leu Lys Ile Thr Leu Leu Ser
                 85                  90                  95

Phe Leu Leu Gly Phe Leu Ser Ile Phe Ala Gly Lys Glu Met Ile Gly
                100                 105                 110

Leu Leu Gly Thr Glu Arg Asp Val Ala Glu Ser Gly Gly Leu Tyr Leu
            115                 120                 125

Ser Leu Val Gly Gly Ser Ile Val Leu Leu Gly Leu Met Thr Ser Leu
        130                 135                 140

Gly Ala Leu Ile Arg Ala Thr His Asn Pro Arg Leu Pro Leu Tyr Val
145                 150                 155                 160
```

```
Ser Phe Leu Ser Asn Ala Leu Asn Ile Leu Phe Ser Ser Leu Ala Ile
            165                 170                 175

Phe Val Leu Asp Met Gly Ile Ala Gly Val Ala Trp Gly Thr Ile Val
        180                 185                 190

Ser Arg Leu Val Gly Leu Val Ile Leu Trp Ser Gln Leu Lys Leu Pro
            195                 200                 205

Tyr Gly Lys Pro Thr Phe Gly Leu Asp Lys Glu Leu Leu Thr Leu Ala
        210                 215                 220

Leu Pro Ala Ala Gly Glu Arg Leu Met Met Arg Ala Gly Asp Val Val
225                 230                 235                 240

Ile Ile Ala Leu Val Val Ser Phe Gly Thr Glu Ala Val Ala Gly Asn
            245                 250                 255

Ala Ile Gly Glu Val Leu Thr Gln Phe Asn Tyr Met Pro Ala Phe Gly
        260                 265                 270

Val Ala Thr Ala Thr Val Met Leu Leu Ala Arg Ala Val Gly Glu Asp
            275                 280                 285

Asp Trp Lys Arg Val Ala Ser Leu Ser Lys Gln Thr Phe Trp Leu Ser
        290                 295                 300

Leu Phe Leu Met Leu Pro Leu Ser Phe Ser Ile Tyr Val Leu Gly Val
305                 310                 315                 320

Pro Leu Thr His Leu Tyr Thr Thr Asp Ser Leu Ala Val Glu Ala Ser
            325                 330                 335

Val Leu Val Thr Leu Phe Ser Leu Leu Gly Thr Pro Met Thr Thr Gly
        340                 345                 350

Thr Val Ile Tyr Thr Ala Val Trp Gln Gly Leu Gly Asn Ala Arg Leu
            355                 360                 365

Pro Phe Tyr Ala Thr Ser Ile Gly Met Trp Cys Ile Arg Ile Gly Thr
        370                 375                 380

Gly Tyr Leu Met Gly Ile Val Leu Gly Trp Gly Leu Pro Gly Ile Trp
385                 390                 395                 400

Ala Gly Ser Leu Leu Asp Asn Gly Phe Arg Trp Leu Phe Leu Arg Tyr
            405                 410                 415

Arg Tyr Gln Arg Tyr Met Ser Leu Lys Gly
        420                 425
```

<210> SEQ ID NO 145
<211> LENGTH: 894
<212> TYPE: DNA
<213> ORGANISM: Streptococcus pneumoniae

<400> SEQUENCE: 145

```
gtgggaagaa ttatcagagc aggtgtaaag atggaacatc ttggaaaagt atttcgtgaa    60
tttcgaacaa gtgaaattta ttcttttaaag gaagcagcag gcgaatcctg ctctacctct   120
cagttatctc gctttgagct tggggagtct gacctggcag tctcccgttt ctttgagatt   180
ttggataaca ttcatgtaac aatcgaaaat ttcatggata aggcaaggaa ttttcataat   240
catgaacatg tgtctatgat ggcacagatt atcccacttt actattcaaa cgatattgca   300
ggttttcaaa agcttcaaag agaacaactt gaaaagtcta gagttcgac gactccccctt   360
tattttgagc tgaactggat tttgctacaa ggtctgattt gtcaaagaga tgcgagttat   420
gatatgaagc aggatgattt gggtaaggta gcagattatc tcttcaaaac agaagaatgg   480
accatgtatg agttgattct tttcggtaac ctctatagtt tctacgatgt agactatgtc   540
actcggattg gtagagaagt tatggagagg gaggaatttt accaagagat tagtcgccat   600
```

```
aagagattag tgttgatttt ggccctcaat tgttaccagc attgtttaga gcattcttct    660 tttataatg ccaactattt tgaggcttat acagagaaga ttattgacaa aggtattaag     720
ctttatgagc gtaatgtttt ccattattta aaaggttttg ccttatatca aaaggacag     780 tgtaaagaag ctgtaagca gatgcaagag gccatgcata tttttgatgt gttaggtctt    840
ccagagcaag tagcctatta tcaggaacac tacgaaaaat ttgtcaaaag ttaa          894
```

<210> SEQ ID NO 146
<211> LENGTH: 297
<212> TYPE: PRT
<213> ORGANISM: Streptococcus pneumoniae

<400> SEQUENCE: 146

Val Gly Arg Ile Ile Arg Ala Gly Val Lys Met Glu His Leu Gly Lys
 1               5                  10                  15

Val Phe Arg Glu Phe Arg Thr Ser Gly Asn Tyr Ser Leu Lys Glu Ala
            20                  25                  30

Ala Gly Glu Ser Cys Ser Thr Ser Gln Leu Ser Arg Phe Glu Leu Gly
        35                  40                  45

Glu Ser Asp Leu Ala Val Ser Arg Phe Phe Glu Ile Leu Asp Asn Ile
    50                  55                  60

His Val Thr Ile Glu Asn Phe Met Asp Lys Ala Arg Asn Phe His Asn
65                  70                  75                  80

His Glu His Val Ser Met Met Ala Gln Ile Ile Pro Leu Tyr Tyr Ser
                85                  90                  95

Asn Asp Ile Ala Gly Phe Gln Lys Leu Gln Arg Glu Gln Leu Glu Lys
            100                 105                 110

Ser Lys Ser Ser Thr Thr Pro Leu Tyr Phe Glu Leu Asn Trp Ile Leu
        115                 120                 125

Leu Gln Gly Leu Ile Cys Gln Arg Asp Ala Ser Tyr Asp Met Lys Gln
    130                 135                 140

Asp Asp Leu Gly Lys Val Ala Asp Tyr Leu Phe Lys Thr Glu Glu Trp
145                 150                 155                 160

Thr Met Tyr Glu Leu Ile Leu Phe Gly Asn Leu Tyr Ser Phe Tyr Asp
                165                 170                 175

Val Asp Tyr Val Thr Arg Ile Gly Arg Glu Val Met Glu Arg Glu Glu
            180                 185                 190

Phe Tyr Gln Glu Ile Ser Arg His Lys Arg Leu Val Leu Ile Leu Ala
        195                 200                 205

Leu Asn Cys Tyr Gln His Cys Leu Glu His Ser Ser Phe Tyr Asn Ala
    210                 215                 220

Asn Tyr Phe Glu Ala Tyr Thr Glu Lys Ile Ile Asp Lys Gly Ile Lys
225                 230                 235                 240

Leu Tyr Glu Arg Asn Val Phe His Tyr Leu Lys Gly Phe Ala Leu Tyr
                245                 250                 255

Gln Lys Gly Gln Cys Lys Glu Gly Cys Lys Gln Met Gln Glu Ala Met
            260                 265                 270

His Ile Phe Asp Val Leu Gly Leu Pro Glu Gln Val Ala Tyr Tyr Gln
        275                 280                 285

Glu His Tyr Glu Lys Phe Val Lys Ser
    290                 295

<210> SEQ ID NO 147
<211> LENGTH: 1068
<212> TYPE: DNA
<213> ORGANISM: Streptococcus pneumoniae

<400> SEQUENCE: 147

```
atgtctaaca ttcaaaacat gtccctggag gacatcatgg gagagcgctt tggtcgctac        60
tccaagtaca ttattcaaga ccgggctttg ccagatattc gtgatgggtt gaagccggtt       120
cagcgccgta ttctttattc tatgaataag gatagcaata cttttgacaa gagctaccgt       180
aagtcggcca agtcagtcgg gaacatcatg gggaatttcc acccacacgg ggattcttct       240
atctatgatg ccatggttcg tatgtcacag aactggaaaa atcgtgagat tctagttgaa       300
atgcacggta taacggttc tatggacgga gatcctcctg cggctatgcg ttatactgag        360
gcacgtttgt ctgaaattgc aggctacctt cttcaggata tcgagaaaaa gacagttcct       420
tttgcatgga ctttgacga tacggagaaa gaaccaacgg tcttgccagc agccttttca        480
aacctcttgg tcaatggttc gactgggatt tcggctggtt atgccacaga cattcctccc       540
cataatttag ctgaggtcat agatgctgca gtttacatga ttgaccaccc aactgcaaag       600
attgataaac tcatggaatt cttgcctgga ccagacttcc ctacaggggc tattattcag       660
ggtcgtgatg aaatcaagaa agcttatgag actgggaaag gcgcgtggt tgttcgttcc        720
aagactgaaa ttgaaaagct aaaggtggt aaggaacaaa tcgttattat tgagattcct       780
tatgaaatca ataaggccaa tctagtcaag aaaatcgatg atgttcgtgt taataacaag       840
gtagctggga ttgctgaggt tcgtgatgag tctgaccgtg atggtcttcg tatcgctatc       900
gaacttaaga agacgctaa tactgagctt gttctcaact acttatttaa gtacaccgac       960
ctacaaatca actacaactt taatatggtg gcgattgaca atttcacacc tcgtcaggtt      1020
ggattgttcc aatcctgtct agctatatcg ctcaccgtcg agaagtga                    1068
```

<210> SEQ ID NO 148
<211> LENGTH: 355
<212> TYPE: PRT
<213> ORGANISM: Streptococcus pneumoniae

<400> SEQUENCE: 148

```
Met Ser Asn Ile Gln Asn Met Ser Leu Glu Asp Ile Met Gly Glu Arg
  1               5                  10                  15

Phe Gly Arg Tyr Ser Lys Tyr Ile Ile Gln Asp Arg Ala Leu Pro Asp
                 20                  25                  30

Ile Arg Asp Gly Leu Lys Pro Val Gln Arg Arg Ile Leu Tyr Ser Met
             35                  40                  45

Asn Lys Asp Ser Asn Thr Phe Asp Lys Ser Tyr Arg Lys Ser Ala Lys
         50                  55                  60

Ser Val Gly Asn Ile Met Gly Asn Phe His Pro His Gly Asp Ser Ser
     65                  70                  75                  80

Ile Tyr Asp Ala Met Val Arg Met Ser Gln Asn Trp Lys Asn Arg Glu
                 85                  90                  95

Ile Leu Val Glu Met His Gly Asn Asn Gly Ser Met Asp Gly Asp Pro
            100                 105                 110

Pro Ala Ala Met Arg Tyr Thr Glu Ala Arg Leu Ser Glu Ile Ala Gly
        115                 120                 125

Tyr Leu Leu Gln Asp Ile Glu Lys Lys Thr Val Pro Phe Ala Trp Asn
    130                 135                 140

Phe Asp Asp Thr Glu Lys Glu Pro Thr Val Leu Pro Ala Ala Phe Pro
145                 150                 155                 160

Asn Leu Leu Val Asn Gly Ser Thr Gly Ile Ser Ala Gly Tyr Ala Thr
                165                 170                 175
```

```
Asp Ile Pro Pro His Asn Leu Ala Glu Val Ile Asp Ala Ala Val Tyr
            180                 185                 190
Met Ile Asp His Pro Thr Ala Lys Ile Asp Lys Leu Met Glu Phe Leu
            195                 200                 205
Pro Gly Pro Asp Phe Pro Thr Gly Ala Ile Ile Gln Gly Arg Asp Glu
            210                 215                 220
Ile Lys Lys Ala Tyr Glu Thr Gly Lys Gly Arg Val Val Arg Ser
225                 230                 235                 240
Lys Thr Glu Ile Glu Lys Leu Lys Gly Gly Lys Gln Ile Val Ile
                245                 250                 255
Ile Glu Ile Pro Tyr Glu Ile Asn Lys Ala Asn Leu Val Lys Lys Ile
            260                 265                 270
Asp Asp Val Arg Val Asn Asn Lys Val Ala Gly Ile Ala Glu Val Arg
            275                 280                 285
Asp Glu Ser Asp Arg Asp Gly Leu Arg Ile Ala Ile Glu Leu Lys Lys
            290                 295                 300
Asp Ala Asn Thr Glu Leu Val Leu Asn Tyr Leu Phe Lys Tyr Thr Asp
305                 310                 315                 320
Leu Gln Ile Asn Tyr Asn Phe Asn Met Val Ala Ile Asp Asn Phe Thr
                325                 330                 335
Pro Arg Gln Val Gly Leu Phe Gln Ser Cys Leu Ala Ile Ser Leu Thr
            340                 345                 350
Val Glu Lys
        355

<210> SEQ ID NO 149
<211> LENGTH: 684
<212> TYPE: DNA
<213> ORGANISM: Streptococcus pneumoniae

<400> SEQUENCE: 149
atgccgacat tagaaatagc acaaaaaaaa ctggagttca ttaagaaggc agaagaatat      60
tacaatgcct tgtgtacaaa tatacagttg agcggagata aactaaaagt aatttccgtt    120
acttctgtta accctgggga aggaaaaaca actacttcca taaatatagc atggtcgttt    180
gcgcgtgcag gctataaaac tcttttgatc gatggcgata ctcgaaattc agttatgtta    240
ggagttttta aatctcgtga aaaaattaca gggctaacag aattttatc tgggacagct    300 gatttatctc acggtttatg tgatacaaat attgaaaatt tatttgtagt tcaatcggga    360
tctgtatcac caaaccctac agccttgtta caaagtaaaa attttaatga tatgattgaa    420
acattgcgta atatttttga ttatatcatt attgatacac cgcctattgg aattgttatt    480
gatgcggcaa ttatcactca aaagtgtgat gcgtccatct tggtaacagc aacaggtgag    540
gcgaataaac gtgatatcca aaagcgaaa caacaattaa acaaacagg gaaactgttc    600 ctaggagttg ttttaaataa attggatatc tcggttaata gtatggagt ttacggttcc    660 tatggaaatt atggtaaaaa ataa                                          684

<210> SEQ ID NO 150
<211> LENGTH: 227
<212> TYPE: PRT
<213> ORGANISM: Streptococcus pneumoniae

<400> SEQUENCE: 150

Met Pro Thr Leu Glu Ile Ala Gln Lys Lys Leu Glu Phe Ile Lys Lys
  1               5                  10                  15

Ala Glu Glu Tyr Tyr Asn Ala Leu Cys Thr Asn Ile Gln Leu Ser Gly
```

```
                     20                  25                  30
Asp Lys Leu Lys Val Ile Ser Val Thr Ser Val Asn Pro Gly Glu Gly
                 35                  40                  45

Lys Thr Thr Thr Ser Ile Asn Ile Ala Trp Ser Phe Ala Arg Ala Gly
             50                  55                  60

Tyr Lys Thr Leu Leu Ile Asp Gly Asp Thr Arg Asn Ser Val Met Leu
 65                  70                  75                  80

Gly Val Phe Lys Ser Arg Glu Lys Ile Thr Gly Leu Thr Glu Phe Leu
                 85                  90                  95

Ser Gly Thr Ala Asp Leu Ser His Gly Leu Cys Asp Thr Asn Ile Glu
            100                 105                 110

Asn Leu Phe Val Val Gln Ser Gly Ser Val Ser Pro Asn Pro Thr Ala
            115                 120                 125

Leu Leu Gln Ser Lys Asn Phe Asn Asp Met Ile Glu Thr Leu Arg Lys
        130                 135                 140

Tyr Phe Asp Tyr Ile Ile Ile Asp Thr Pro Pro Ile Gly Ile Val Ile
145                 150                 155                 160

Asp Ala Ala Ile Ile Thr Gln Lys Cys Asp Ala Ser Ile Leu Val Thr
                165                 170                 175

Ala Thr Gly Glu Ala Asn Lys Arg Asp Ile Gln Lys Ala Lys Gln Gln
            180                 185                 190

Leu Lys Gln Thr Gly Lys Leu Phe Leu Gly Val Val Leu Asn Lys Leu
        195                 200                 205

Asp Ile Ser Val Asn Lys Tyr Gly Val Tyr Ser Tyr Gly Asn Tyr
    210                 215                 220

Gly Lys Lys
225

<210> SEQ ID NO 151
<211> LENGTH: 1194
<212> TYPE: DNA
<213> ORGANISM: Streptococcus pneumoniae

<400> SEQUENCE: 151
atggaggcaa atatgaaaca tctaaaaaca ttttacaaaa aatggtttca attattagtc     60
gttatcgtca ttagctttt tagtggagcc ttgggtagtt tttcaataac tcaactaact    120
caaaaaagta gtgtaaacaa ctctaacaac aatagtacta ttacacaaac tgcctataag    180
aacgaaaatt caacaacaca ggctgttaac aaagtaaaag atgctgttgt ttctgttatt    240
acttattcgg caaacagaca aaatagcgta tttggcaatg atgatactga cacagattct    300
cagcgaatct ctagtgaagg atctggagtt atttataaaa agaatgataa agaagcttac    360
atcgtcacca caatcacgt tattaatggc gccagcaaag tagatattcg attgtcagat    420
gggactaaag tacctggaga aattgtcgga gctgacactt tctctgatat tgctgtcgtc    480
aaaatctctt cagaaaaagt gacaacagta gctgagtttg tgattctag taagttaact    540 gtaggagaaa ctgctattgc catcggtagc ccgttaggtt ctgaatatgc aaatactgtc    600
actcaaggta tcgtatccag tctcaataga aatgtatcct aaaatcgga agatggacaa    660 gctatttcta caaaagccat ccaaactgat actgctatta acccaggtaa ctctggcggc    720
ccactgatca atattcaagg gcaggttatc ggaattacct caagtaaaat tgctacaaat    780
ggaggaacat ctgtagaagg tcttggtttc gcaattcctg caaatgatgc tatcaatatt    840
attgaacagt tagaaaaaaa cggaaaagtg acgcgtccag ctttgggaat ccagatggtt    900
aatttatcta atgtgagtac aagcgacatc agaagactca atattccaag taatgttaca    960
```

```
tctggtgtaa ttgttcgttc ggtacaaagt aatatgcctg ccaatggtca ccttgaaaaa    1020
tacgatgtaa ttacaaaagt agatgacaaa gagattgctt catcaacaga cttacaaagt    1080
gctctttaca accattctat cggagacacc attaagataa cctactatcg taacgggaaa    1140
gaagaaacta cctctatcaa acttaacaag agttcaggtg atttagaatc ttaa          1194
```

<210> SEQ ID NO 152
<211> LENGTH: 397
<212> TYPE: PRT
<213> ORGANISM: Streptococcus pneumoniae

<400> SEQUENCE: 152

```
Met Glu Ala Asn Met Lys His Leu Lys Thr Phe Tyr Lys Lys Trp Phe
 1               5                  10                  15

Gln Leu Leu Val Val Ile Val Ile Ser Phe Phe Ser Gly Ala Leu Gly
                20                  25                  30

Ser Phe Ser Ile Thr Gln Leu Thr Gln Lys Ser Ser Val Asn Asn Ser
            35                  40                  45

Asn Asn Asn Ser Thr Ile Thr Gln Thr Ala Tyr Lys Asn Glu Asn Ser
        50                  55                  60

Thr Thr Gln Ala Val Asn Lys Val Lys Asp Ala Val Val Ser Val Ile
65                  70                  75                  80

Thr Tyr Ser Ala Asn Arg Gln Asn Ser Val Phe Gly Asn Asp Asp Thr
                85                  90                  95

Asp Thr Asp Ser Gln Arg Ile Ser Ser Glu Gly Ser Gly Val Ile Tyr
            100                 105                 110

Lys Lys Asn Asp Lys Glu Ala Tyr Ile Val Thr Asn Asn His Val Ile
        115                 120                 125

Asn Gly Ala Ser Lys Val Asp Ile Arg Leu Ser Asp Gly Thr Lys Val
    130                 135                 140

Pro Gly Glu Ile Val Gly Ala Asp Thr Phe Ser Asp Ile Ala Val Val
145                 150                 155                 160

Lys Ile Ser Ser Glu Lys Val Thr Thr Val Ala Glu Phe Gly Asp Ser
                165                 170                 175

Ser Lys Leu Thr Val Gly Glu Thr Ala Ile Ala Ile Gly Ser Pro Leu
            180                 185                 190

Gly Ser Glu Tyr Ala Asn Thr Val Thr Gln Gly Ile Val Ser Ser Leu
        195                 200                 205

Asn Arg Asn Val Ser Leu Lys Ser Glu Asp Gly Gln Ala Ile Ser Thr
    210                 215                 220

Lys Ala Ile Gln Thr Asp Thr Ala Ile Asn Pro Gly Asn Ser Gly Gly
225                 230                 235                 240

Pro Leu Ile Asn Ile Gln Gly Gln Val Ile Gly Ile Thr Ser Ser Lys
                245                 250                 255

Ile Ala Thr Asn Gly Gly Thr Ser Val Glu Gly Leu Gly Phe Ala Ile
            260                 265                 270

Pro Ala Asn Asp Ala Ile Asn Ile Ile Glu Gln Leu Glu Lys Asn Gly
        275                 280                 285

Lys Val Thr Arg Pro Ala Leu Gly Ile Gln Met Val Asn Leu Ser Asn
    290                 295                 300

Val Ser Thr Ser Asp Ile Arg Arg Leu Asn Ile Pro Ser Asn Val Thr
305                 310                 315                 320

Ser Gly Val Ile Val Arg Ser Val Gln Ser Asn Met Pro Ala Asn Gly
                325                 330                 335
```

His Leu Glu Lys Tyr Asp Val Ile Thr Lys Val Asp Lys Glu Ile
             340                 345                 350

Ala Ser Ser Thr Asp Leu Gln Ser Ala Leu Tyr Asn His Ser Ile Gly
         355                 360                 365

Asp Thr Ile Lys Ile Thr Tyr Tyr Arg Asn Gly Lys Glu Glu Thr Thr
     370                 375                 380

Ser Ile Lys Leu Asn Lys Ser Ser Gly Asp Leu Glu Ser
385                 390                 395

<210> SEQ ID NO 153
<211> LENGTH: 939
<212> TYPE: DNA
<213> ORGANISM: Streptococcus pneumoniae

<400> SEQUENCE: 153
atggcagaaa tttatctagc aggtggttgt ttttggggcc tagaggaata tttttcacgc      60
atttctggag tgctagaaac cagtgttggc tacgctaatg gtcaagtcga acgaccaat     120 taccagttgc tcaaggaaac agaccatgca gaaacggtcc aagtgattta cgatgagaag     180
gaagtgtcac tcagagagat tttacttat tatttccgag ttatcgatcc tctatctatc     240
aatcaacaag ggaatgaccg tggtcgccaa tatcgaactg ggatttatta tcaggatgaa     300
gcagatttgc cagctatcta cacagtggtg caggagcagg aacgcatgct gggtcgaaag     360
attgcagtag aagtggagca attacgccac tacattctgg ctgaagacta ccaccaagac     420
tatctcagga agaatccttc aggttactgt catatcgatg tgaccgatgc tgataagcca     480
ttgattgatg cagcaaacta tgaaaagcct agtcaagagg tgttgaaggc cagtctatct     540
gaagagtctt atcgtgtcac acaagaagct gctacagagg ctccatttac caatgcctat     600 gaccaaaacct ttgaagaggg gatttatgta gatattacga caggtgagcc actctttttt     660
gccaaggata gtttgcttc aggttgtggt tggccaagtt ttagccgtcc gatttccaaa     720
gagttgattc attattacaa ggatctgagc catggaatgg agcgaattga agttcgttct     780
cgttcaggca gtgctcactt gggtcatgtt ttcacagatg gaccgcggga gttaggcggc     840
ctccgttact gtatcaattc tgcttcttta cgctttgtgg ccaaggatga gatggaaaaa     900
gcaggatatg gctatctatt gccttactta aacaaataa                           939

<210> SEQ ID NO 154
<211> LENGTH: 312
<212> TYPE: PRT
<213> ORGANISM: Streptococcus pneumoniae

<400> SEQUENCE: 154

Met Ala Glu Ile Tyr Leu Ala Gly Gly Cys Phe Trp Gly Leu Glu Glu
  1               5                  10                  15

Tyr Phe Ser Arg Ile Ser Gly Val Leu Glu Thr Ser Val Gly Tyr Ala
             20                  25                  30

Asn Gly Gln Val Glu Thr Thr Asn Tyr Gln Leu Leu Lys Glu Thr Asp
         35                  40                  45

His Ala Glu Thr Val Gln Val Ile Tyr Asp Glu Lys Glu Val Ser Leu
     50                  55                  60

Arg Glu Ile Leu Leu Tyr Tyr Phe Arg Val Ile Asp Pro Leu Ser Ile
 65                  70                  75                  80

Asn Gln Gln Gly Asn Asp Arg Gly Arg Gln Tyr Arg Thr Gly Ile Tyr
                 85                  90                  95

Tyr Gln Asp Glu Ala Asp Leu Pro Ala Ile Tyr Thr Val Val Gln Glu
            100                 105                 110

```
Gln Glu Arg Met Leu Gly Arg Lys Ile Ala Val Glu Val Glu Gln Leu
        115                 120                 125

Arg His Tyr Ile Leu Ala Glu Asp Tyr His Gln Asp Tyr Leu Arg Lys
    130                 135                 140

Asn Pro Ser Gly Tyr Cys His Ile Asp Val Thr Asp Ala Asp Lys Pro
145                 150                 155                 160

Leu Ile Asp Ala Ala Asn Tyr Glu Lys Pro Ser Gln Glu Val Leu Lys
                165                 170                 175

Ala Ser Leu Ser Glu Glu Ser Tyr Arg Val Thr Gln Glu Ala Ala Thr
            180                 185                 190

Glu Ala Pro Phe Thr Asn Ala Tyr Asp Gln Thr Phe Glu Glu Gly Ile
        195                 200                 205

Tyr Val Asp Ile Thr Thr Gly Glu Pro Leu Phe Phe Ala Lys Asp Lys
    210                 215                 220

Phe Ala Ser Gly Cys Gly Trp Pro Ser Phe Ser Arg Pro Ile Ser Lys
225                 230                 235                 240

Glu Leu Ile His Tyr Tyr Lys Asp Leu Ser His Gly Met Glu Arg Ile
                245                 250                 255

Glu Val Arg Ser Arg Ser Gly Ser Ala His Leu Gly His Val Phe Thr
            260                 265                 270

Asp Gly Pro Arg Glu Leu Gly Gly Leu Arg Tyr Cys Ile Asn Ser Ala
        275                 280                 285

Ser Leu Arg Phe Val Ala Lys Asp Glu Met Glu Lys Ala Gly Tyr Gly
    290                 295                 300

Tyr Leu Leu Pro Tyr Leu Asn Lys
305                 310

<210> SEQ ID NO 155
<211> LENGTH: 870
<212> TYPE: DNA
<213> ORGANISM: Streptococcus pneumoniae

<400> SEQUENCE: 155
atgaagatta ttgtacctgc aaccagtgcc aatatcgggc caggttttga ctcggtcggt    60
gtagctgtaa ccaagtatct tcaaattgag gtctgcgaag aacgagatga gtggctgatt   120
gaacaccaga ttggcaaatg gattccacat gacgagcgta atctcttgct caaaatcgct   180
ttgcaaattg taccagactt gcaaccaaga cgcttgaaaa tgaccagtga tgtcccttg    240 gcgcgcggtt tgggttcttc cagctcggtt atcgttgctg ggattgaact agccaaccaa   300
ctgggtcaac tcaacttatc agaccatgaa aaattgcagt tagcgaccaa gattgaaggg   360
catcctgaca tgtggctcc agccatttat ggtaatctcg ttattgcaag ttctgttgaa    420
gggcaagtct ctgctatcgt agcagacttt ccagagtgtg attttctagc ttacattcca   480
aactatgaat tacgtactcg cgacagccgt agtgtcttgc ctaaaaaatt gtcttataag   540
gaagctgttg ctgcaagttc tatcgccaat gtagcggttg ctgccttgtt ggcaggagac   600
atggtgaccg ctgggcaagc aatcgaggga gacctcttcc atgagcgcta tcgtcaggac   660
ttggtaagag aatttgcgat gattaagcaa gtgaccaaag aaaatggggc ctatgcaacc   720
tacctttctg gtgctgggcc gacagttatg gttctggctt ctcatgacaa gatgccaaca   780
attaaggcag aattggaaaa gcaaccttcc aaaggaaaac tgcatgactt gagagttgat   840
acccaaggtg tccgtgtaga agcaaaataa                                    870

<210> SEQ ID NO 156
```

<211> LENGTH: 289
<212> TYPE: PRT
<213> ORGANISM: Streptococcus pneumoniae

<400> SEQUENCE: 156

```
Met Lys Ile Ile Val Pro Ala Thr Ser Ala Asn Ile Gly Pro Gly Phe
 1               5                  10                  15

Asp Ser Val Gly Val Ala Val Thr Lys Tyr Leu Gln Ile Glu Val Cys
             20                  25                  30

Glu Glu Arg Asp Glu Trp Leu Ile Glu His Gln Ile Gly Lys Trp Ile
         35                  40                  45

Pro His Asp Glu Arg Asn Leu Leu Lys Ile Ala Leu Gln Ile Val
 50                  55                  60

Pro Asp Leu Gln Pro Arg Arg Leu Lys Met Thr Ser Asp Val Pro Leu
 65                  70                  75                  80

Ala Arg Gly Leu Gly Ser Ser Ser Val Ile Val Ala Gly Ile Glu
                 85                  90                  95

Leu Ala Asn Gln Leu Gly Gln Leu Asn Leu Ser Asp His Glu Lys Leu
                100                 105                 110

Gln Leu Ala Thr Lys Ile Glu Gly His Pro Asp Asn Val Ala Pro Ala
                115                 120                 125

Ile Tyr Gly Asn Leu Val Ile Ala Ser Val Glu Gly Gln Val Ser
130                 135                 140

Ala Ile Val Ala Asp Phe Pro Glu Cys Asp Phe Leu Ala Tyr Ile Pro
145                 150                 155                 160

Asn Tyr Glu Leu Arg Thr Arg Asp Ser Arg Ser Val Leu Pro Lys Lys
                165                 170                 175

Leu Ser Tyr Lys Glu Ala Val Ala Ala Ser Ser Ile Ala Asn Val Ala
                180                 185                 190

Val Ala Ala Leu Leu Ala Gly Asp Met Val Thr Ala Gly Gln Ala Ile
                195                 200                 205

Glu Gly Asp Leu Phe His Glu Arg Tyr Arg Gln Asp Leu Val Arg Glu
                210                 215                 220

Phe Ala Met Ile Lys Gln Val Thr Lys Glu Asn Gly Ala Tyr Ala Thr
225                 230                 235                 240

Tyr Leu Ser Gly Ala Gly Pro Thr Val Met Val Leu Ala Ser His Asp
                245                 250                 255

Lys Met Pro Thr Ile Lys Ala Glu Leu Glu Lys Gln Pro Phe Lys Gly
                260                 265                 270

Lys Leu His Asp Leu Arg Val Asp Thr Gln Gly Val Arg Val Glu Ala
                275                 280                 285

Lys
```

<210> SEQ ID NO 157
<211> LENGTH: 564
<212> TYPE: DNA
<213> ORGANISM: Streptococcus pneumoniae

<400> SEQUENCE: 157

```
atgaaatatc acgattacat ctgggattta ggtggaactt tactggataa ttatgaaact    60
tcaacagctg catttgttga acattggca ctgtatggta tcacacaaga ccatgacagt   120
gtctatcaag ctttaaaggt ttctactcct tttgcgattg agacattcgc tcccaattta   180
gagaattttt tagaaaagta caaggaaaat gaagccagag agcttgaaca cccgattta   240 tttgaaggag tttctgacct attggaagac atttcaaatc aaggtggccg tcattttttg   300
```

```
gtctctcatc gaaatgatca ggttttggaa attttagaaa aaacctctat agcagcttat        360
tttacagaag tggtgacttc tagctcaggc tttaagagaa agccaaatcc cgaatccatg        420
ctttatttaa gagaaaagta tcagattagc tctggtcttg tcattggtga tcggccgatt        480
gatatcgaag caggtcaagc tgcaggactt gatacccact tgtttaccag tatcgtgaat        540
ttaagacaag tattagacat ataa                                              564
```

<210> SEQ ID NO 158
<211> LENGTH: 187
<212> TYPE: PRT
<213> ORGANISM: Streptococcus pneumoniae

<400> SEQUENCE: 158

```
Met Lys Tyr His Asp Tyr Ile Trp Asp Leu Gly Gly Thr Leu Leu Asp
  1               5                  10                  15

Asn Tyr Glu Thr Ser Thr Ala Ala Phe Val Glu Thr Leu Ala Leu Tyr
             20                  25                  30

Gly Ile Thr Gln Asp His Asp Ser Val Tyr Gln Ala Leu Lys Val Ser
         35                  40                  45

Thr Pro Phe Ala Ile Glu Thr Phe Ala Pro Asn Leu Glu Asn Phe Leu
     50                  55                  60

Glu Lys Tyr Lys Glu Asn Glu Ala Arg Glu Leu Glu His Pro Ile Leu
 65                  70                  75                  80

Phe Glu Gly Val Ser Asp Leu Leu Glu Asp Ile Ser Asn Gln Gly Gly
                 85                  90                  95

Arg His Phe Leu Val Ser His Arg Asn Asp Gln Val Leu Glu Ile Leu
            100                 105                 110

Glu Lys Thr Ser Ile Ala Ala Tyr Phe Thr Glu Val Val Thr Ser Ser
        115                 120                 125

Ser Gly Phe Lys Arg Lys Pro Asn Pro Glu Ser Met Leu Tyr Leu Arg
    130                 135                 140

Glu Lys Tyr Gln Ile Ser Ser Gly Leu Val Ile Gly Asp Arg Pro Ile
145                 150                 155                 160

Asp Ile Glu Ala Gly Gln Ala Ala Gly Leu Asp Thr His Leu Phe Thr
                165                 170                 175

Ser Ile Val Asn Leu Arg Gln Val Leu Asp Ile
            180                 185
```

<210> SEQ ID NO 159
<211> LENGTH: 1875
<212> TYPE: DNA
<213> ORGANISM: Streptococcus pneumoniae

<400> SEQUENCE: 159

```
atgacagaag aaatcaaaaa tctgcaggca caggattatg atgccagtca aattcaagtt         60 ttagggctt tagaggctgt tcgtatgcgt ccagggatgt acattggatc aacctcaaaa        120
gaaggtcttc accatctagt ctgggaaatt gttgataact caattgacga ggccttggca        180
ggatttgcca gccatattca agttttttatt gagccagatg attcgattac tgttgtggat        240
gatgggcgtg gtatcccagt cgatattcag gaaaaaacag gccgtcctgc tgttgagacc        300
gtctttacag tccttcacgc tggaggaaag ttcggcggtg gtggtacaa ggtttcaggt        360 ggtcttcacg gggtggggtc gtcagtagtt aatgcccttt ccactcaatt agacgttcat        420
gttcacaaaa atggtaagat tcattaccaa gaataccgtc gtggtcatgt tgtcgcagat        480
cttgaaatag ttggagatac ggataaaaca ggaacaactg ttcacttcac accggaccca        540
```

-continued

```
aaaatcttca ctgaaacaac aatctttgat tttgataaat taaataaacg gattcaagag    600
ttggcctttc taaatcgcgg tcttcaaatt tcaattacag ataagcgcca aggtttggaa    660
caaaccaagc attatcatta tgaaggtggg attgctagtt acgttaata  tatcaacgag    720
aacaaggatg taatctttga tacaccaatc tatacagacg gtgagatgga tgatatcaca    780
gttgaggtag ccatgcagta cacaactggt taccatgaaa atgtcatgag tttcgccaat    840
aatattcata cccatgaagg tggaaacacat gaacaaggtt tccgtacagc cttgacacgt    900
gttatcaacg attatgctcg taaaaataag ttactgaaag acaatgaaga taatttaaca    960
ggggaagatg ttcgcgaagg cttaactgca gttatctcag ttaaacaccc aaatccacag   1020
tttgaaggac aaaccaagac caaattggga aatagcgaag tggtcaagat taccaatcgc   1080
ctcttcagtg aagctttctc cgatttcctc atggaaaatc cacagattgc caaacgtatc   1140
gtagaaaaag gaattttggc tgccaaggct cgtgtggctg ccaagcgtgc gcgtgaagtc   1200
acacgtaaaa aatctggttt ggaaatttcc aaccttccag ggaaactagc agactgttct   1260
tctaataacc ctgctgaaac agaactcttc atcgtcgaag gagactcagc tggtggatca   1320
gccaaatctg gtcgtaaccg tgagtttcag gctatcctt  caattcgcgg taagattttg   1380
aacgttgaaa aagcaagtat ggataagatt ctagccaacg aagaaattcg tagtctttc   1440
acagccatgg aacaggatt  tggcgcagaa tttgatgttt cgaaagcccg ttaccaaaaa   1500
ctcgttttga tgaccgatgc cgatgtcgat ggagcccaca ttcgtaccct tcttttaacc   1560
ttgatttatc gttatatgaa accaatccta gaagctggtt atgtttatat tgcccaacca   1620
ccaatctatg gtgtcaaggt tggaagcgag attaaagaat atatccagcc gggtgcagat   1680
caagaaatca aactccaaga agctttagcc cgttatagtg aaggtcgtac caaaccgact   1740
attcagcgtt ataagggct  aggtgaaatg gacgatcatc agctgtggga aacaaccatg   1800
gatcccgaac atcgcttgat ggctagagtt tctgtagatg atgtgcagaa gcagataaaa   1860
tctttgatat gttga                                                   1875
```

<210> SEQ ID NO 160
<211> LENGTH: 624
<212> TYPE: PRT
<213> ORGANISM: Streptococcus pneumoniae

<400> SEQUENCE: 160

```
Met Thr Glu Glu Ile Lys Asn Leu Gln Ala Gln Asp Tyr Asp Ala Ser
  1               5                  10                  15

Gln Ile Gln Val Leu Glu Gly Leu Glu Ala Val Arg Met Arg Pro Gly
             20                  25                  30

Met Tyr Ile Gly Ser Thr Ser Lys Glu Gly Leu His His Leu Val Trp
         35                  40                  45

Glu Ile Val Asp Asn Ser Ile Asp Glu Ala Leu Ala Gly Phe Ala Ser
     50                  55                  60

His Ile Gln Val Phe Ile Glu Pro Asp Asp Ser Ile Thr Val Val Asp
 65                  70                  75                  80

Asp Gly Arg Gly Ile Pro Val Asp Ile Gln Glu Lys Thr Gly Arg Pro
                 85                  90                  95

Ala Val Glu Thr Val Phe Thr Val Leu His Ala Gly Gly Lys Phe Gly
            100                 105                 110

Gly Gly Gly Tyr Lys Val Ser Gly Gly Leu His Gly Val Gly Ser Ser
        115                 120                 125

Val Val Asn Ala Leu Ser Thr Gln Leu Asp Val His Val His Lys Asn
    130                 135                 140
```

-continued

```
Gly Lys Ile His Tyr Gln Glu Tyr Arg Arg Gly His Val Val Ala Asp
145                 150                 155                 160

Leu Glu Ile Val Gly Asp Thr Asp Lys Thr Gly Thr Val His Phe
                165                 170                 175

Thr Pro Asp Pro Lys Ile Phe Thr Glu Thr Thr Ile Phe Asp Phe Asp
                180                 185                 190

Lys Leu Asn Lys Arg Ile Gln Glu Leu Ala Phe Leu Asn Arg Gly Leu
            195                 200                 205

Gln Ile Ser Ile Thr Asp Lys Arg Gln Gly Leu Glu Gln Thr Lys His
        210                 215                 220

Tyr His Tyr Glu Gly Gly Ile Ala Ser Tyr Val Glu Tyr Ile Asn Glu
225                 230                 235                 240

Asn Lys Asp Val Ile Phe Asp Thr Pro Ile Tyr Thr Asp Gly Glu Met
                245                 250                 255

Asp Asp Ile Thr Val Glu Val Ala Met Gln Tyr Thr Thr Gly Tyr His
                260                 265                 270

Glu Asn Val Met Ser Phe Ala Asn Asn Ile His Thr His Glu Gly Gly
            275                 280                 285

Thr His Glu Gln Gly Phe Arg Thr Ala Leu Thr Arg Val Ile Asn Asp
        290                 295                 300

Tyr Ala Arg Lys Asn Lys Leu Leu Lys Asp Asn Glu Asp Asn Leu Thr
305                 310                 315                 320

Gly Glu Asp Val Arg Glu Gly Leu Thr Ala Val Ile Ser Val Lys His
                325                 330                 335

Pro Asn Pro Gln Phe Glu Gly Gln Thr Lys Thr Lys Leu Gly Asn Ser
                340                 345                 350

Glu Val Val Lys Ile Thr Asn Arg Leu Phe Ser Glu Ala Phe Ser Asp
            355                 360                 365

Phe Leu Met Glu Asn Pro Gln Ile Ala Lys Arg Ile Val Glu Lys Gly
        370                 375                 380

Ile Leu Ala Ala Lys Ala Arg Val Ala Ala Lys Arg Ala Arg Glu Val
385                 390                 395                 400

Thr Arg Lys Lys Ser Gly Leu Glu Ile Ser Asn Leu Pro Gly Lys Leu
                405                 410                 415

Ala Asp Cys Ser Ser Asn Asn Pro Ala Glu Thr Glu Leu Phe Ile Val
                420                 425                 430

Glu Gly Asp Ser Ala Gly Gly Ser Ala Lys Ser Gly Arg Asn Arg Glu
            435                 440                 445

Phe Gln Ala Ile Leu Pro Ile Arg Gly Lys Ile Leu Asn Val Glu Lys
        450                 455                 460

Ala Ser Met Asp Lys Ile Leu Ala Asn Glu Glu Ile Arg Ser Leu Phe
465                 470                 475                 480

Thr Ala Met Gly Thr Gly Phe Gly Ala Glu Phe Asp Val Ser Lys Ala
                485                 490                 495

Arg Tyr Gln Lys Leu Val Leu Met Thr Asp Ala Asp Val Asp Gly Ala
            500                 505                 510

His Ile Arg Thr Leu Leu Leu Thr Leu Ile Tyr Arg Tyr Met Lys Pro
        515                 520                 525

Ile Leu Glu Ala Gly Tyr Val Tyr Ile Ala Gln Pro Pro Ile Tyr Gly
530                 535                 540

Val Lys Val Gly Ser Glu Ile Lys Glu Tyr Ile Gln Pro Gly Ala Asp
545                 550                 555                 560

Gln Glu Ile Lys Leu Gln Glu Ala Leu Ala Arg Tyr Ser Glu Gly Arg
```

```
                    565                 570                 575
Thr Lys Pro Thr Ile Gln Arg Tyr Lys Gly Leu Gly Glu Met Asp Asp
                580                 585                 590

His Gln Leu Trp Glu Thr Thr Met Asp Pro Glu His Arg Leu Met Ala
            595                 600                 605

Arg Val Ser Val Asp Asp Val Gln Lys Gln Ile Lys Ser Leu Ile Cys
        610                 615                 620

<210> SEQ ID NO 161
<211> LENGTH: 1446
<212> TYPE: DNA
<213> ORGANISM: Streptococcus pneumoniae

<400> SEQUENCE: 161
atgagtagac gttttaaaaa atcacgttca cagaaagtga agcgaagtgt taatatagtt      60
ttgctgacta tttatttatt gttagtttgt tttttattgt tcttaatctt taagtacaat     120
atccttgctt ttagatatct taatctagtg gtaactgcgt tagtcctact agttgccttg     180
gtagggctac tcttgattat ctataaaaaa gctgaaaagt ttactatttt tctgttggtg     240
ttctctatcc ttgtcagctc tgtgtcgctc tttgcagtac agcagtttgt tggactgacc     300
aatcgtttaa atgcgacttc taattactca gaatattcaa tcagtgtcgc tgttttagca     360
gatagtgaga tcgaaaatgt tacgcaactg acgagtgtga cagcaccgac tgggactaat     420
aatgaaaata ttcagaaatt actagctgat atcaagtcaa gtcagaatac cgatttgacg     480
gtcaaccaga gttcgtctta cttggcagct tacaagagtt tgattgcagg ggagactaag     540
gccattgtcc taaatagtgt ctttgaaaac atcatcgagt cagagtatcc agactacgca     600
tcgaagataa aaaagattta tactaaggga ttcactaaaa aagtagaagc tcctaagacg     660
tctaagagtc agtcttttcaa tatctatgtt agtggaattg acacctatgg tcctattagt     720
tcggtgtcgc gatcagatgt caacatcctg atgactgtca atcgagatac caagaaaatc     780
ctcttgacca aacgccacg tgatgcctat gtaccaatcg cagatggtgg aaataatcaa     840
aaagataaat tgactcatgc gggcatttat ggagttgatt cgtccattca caccttagaa     900
aatctctatg gagtggatat caattactat gtgcgattga acttcacttc gttttttgaaa     960 ttgattgatt tgtgggtgg aattgatgtt tataatgatc aagaatttac tgcccatacg    1020
aatggaaagt attaccctgc aggcaatgtt catcttgatt cagaacaggc tctcggtttt    1080
gttcgtgagc gctactccct agcagatggc gatcgtgacc gcgggcgcca tcaacaaaag    1140
gtgattgtgg ctatccttca aaaattaacg tcaaccgaag tgctgaaaaa ttatagtacg    1200
atcattaata gcttgcaaga ttctatccaa acaaatatgc cacttgagac catgataaat    1260
ttggtcaatg ctcagttaga aagtggaggg aattataaag taaattctca agatttaaaa    1320
gggacaggtc ggatggatct tccttcttat gcaatgccag acagtaacct ctatgtgatg    1380
gaaatagatg atagtagttt agctgtagtt aaagcagcta acaggatgt gatggagggt    1440 agatga                                                               1446

<210> SEQ ID NO 162
<211> LENGTH: 481
<212> TYPE: PRT
<213> ORGANISM: Streptococcus pneumoniae

<400> SEQUENCE: 162

Met Ser Arg Arg Phe Lys Lys Ser Arg Ser Gln Lys Val Lys Arg Ser
  1               5                  10                  15
```

-continued

```
Val Asn Ile Val Leu Leu Thr Ile Tyr Leu Leu Val Cys Phe Leu
            20                  25                  30

Leu Phe Leu Ile Phe Lys Tyr Asn Ile Leu Ala Phe Arg Tyr Leu Asn
        35                  40                  45

Leu Val Val Thr Ala Leu Val Leu Leu Val Ala Leu Val Gly Leu Leu
    50                  55                  60

Leu Ile Ile Tyr Lys Lys Ala Glu Lys Phe Thr Ile Phe Leu Leu Val
65                  70                  75                  80

Phe Ser Ile Leu Val Ser Ser Val Ser Leu Phe Ala Val Gln Gln Phe
                85                  90                  95

Val Gly Leu Thr Asn Arg Leu Asn Ala Thr Ser Asn Tyr Ser Glu Tyr
            100                 105                 110

Ser Ile Ser Val Ala Val Leu Ala Asp Ser Glu Ile Glu Asn Val Thr
        115                 120                 125

Gln Leu Thr Ser Val Thr Ala Pro Thr Gly Thr Asn Asn Glu Asn Ile
    130                 135                 140

Gln Lys Leu Leu Ala Asp Ile Lys Ser Ser Gln Asn Thr Asp Leu Thr
145                 150                 155                 160

Val Asn Gln Ser Ser Ser Tyr Leu Ala Ala Tyr Lys Ser Leu Ile Ala
                165                 170                 175

Gly Glu Thr Lys Ala Ile Val Leu Asn Ser Val Phe Glu Asn Ile Ile
            180                 185                 190

Glu Ser Glu Tyr Pro Asp Tyr Ala Ser Lys Ile Lys Lys Ile Tyr Thr
        195                 200                 205

Lys Gly Phe Thr Lys Lys Val Glu Ala Pro Lys Thr Ser Lys Ser Gln
    210                 215                 220

Ser Phe Asn Ile Tyr Val Ser Gly Ile Asp Thr Tyr Gly Pro Ile Ser
225                 230                 235                 240

Ser Val Ser Arg Ser Asp Val Asn Ile Leu Met Thr Val Asn Arg Asp
                245                 250                 255

Thr Lys Lys Ile Leu Leu Thr Thr Thr Pro Arg Asp Ala Tyr Val Pro
            260                 265                 270

Ile Ala Asp Gly Gly Asn Asn Gln Lys Asp Lys Leu Thr His Ala Gly
        275                 280                 285

Ile Tyr Gly Val Asp Ser Ser Ile His Thr Leu Glu Asn Leu Tyr Gly
    290                 295                 300

Val Asp Ile Asn Tyr Tyr Val Arg Leu Asn Phe Thr Ser Phe Leu Lys
305                 310                 315                 320

Leu Ile Asp Leu Leu Gly Gly Ile Asp Val Tyr Asn Asp Gln Glu Phe
                325                 330                 335

Thr Ala His Thr Asn Gly Lys Tyr Tyr Pro Ala Gly Asn Val His Leu
            340                 345                 350

Asp Ser Glu Gln Ala Leu Gly Phe Val Arg Glu Arg Tyr Ser Leu Ala
        355                 360                 365

Asp Gly Asp Arg Asp Arg Gly Arg His Gln Gln Lys Val Ile Val Ala
    370                 375                 380

Ile Leu Gln Lys Leu Thr Ser Thr Glu Val Leu Lys Asn Tyr Ser Thr
385                 390                 395                 400

Ile Ile Asn Ser Leu Gln Asp Ser Ile Gln Thr Asn Met Pro Leu Glu
                405                 410                 415

Thr Met Ile Asn Leu Val Asn Ala Gln Leu Glu Ser Gly Gly Asn Tyr
            420                 425                 430

Lys Val Asn Ser Gln Asp Leu Lys Gly Thr Gly Arg Met Asp Leu Pro
        435                 440                 445
```

```
Ser Tyr Ala Met Pro Asp Ser Asn Leu Tyr Val Met Glu Ile Asp Asp
    450                 455                 460

Ser Ser Leu Ala Val Val Lys Ala Ala Ile Gln Asp Val Met Glu Gly
465                 470                 475                 480

Arg

<210> SEQ ID NO 163
<211> LENGTH: 732
<212> TYPE: DNA
<213> ORGANISM: Streptococcus pneumoniae

<400> SEQUENCE: 163
atgatagaca tccattcgca tatcgttttt gatgtagatg acggtcccaa gtcaagagag     60
gaaagcaagg ctctcttggc agaatcctac agacagggg tgcgaaccat tgtttctacc    120
tctcaccgtc gcaagggcat gtttgaaact ccggaagaga agatagcaga aactttctt    180 caggttcggg aaatagctaa ggaagtggcg agtgacttgg tcattgctta cggggctgaa    240
atttattaca caccagatgt tctggataag ctggaaaaaa agcggattcc gaccctcaat    300
gatagtcgtt atgccttgat agagtttagt atgaacactc cttatcgcga tattcatagc    360
gccttgagca agatcttgat gttgggaatt actccagtca ttgcccacat tgagcgctat    420
gatgctcttg aaaataatga aaaacgcgtt cgagaactga tcgatatggg ctgttacacg    480
caagtaaata gttcacatgt cctcaaaccc aaacttttg gcgaacgtta taaattcatg    540
aaaaaaagag ctcagtattt tttagagcag gatttggttc atgtcattgc aagtgatatg    600
cacaatctag acggtagacc tcctcatatg gcagaagcat atgaccttgt acccaaaaa    660 tacggagaag cgaaggctca ggaacttttt atagacaatc ctcgaaaaat tgtaatggat    720
caactaattt ag                                                       732

<210> SEQ ID NO 164
<211> LENGTH: 243
<212> TYPE: PRT
<213> ORGANISM: Streptococcus pneumoniae

<400> SEQUENCE: 164

Met Ile Asp Ile His Ser His Ile Val Phe Asp Val Asp Asp Gly Pro
  1               5                  10                  15

Lys Ser Arg Glu Glu Ser Lys Ala Leu Leu Ala Glu Ser Tyr Arg Gln
            20                  25                  30

Gly Val Arg Thr Ile Val Ser Thr Ser His Arg Arg Lys Gly Met Phe
        35                  40                  45

Glu Thr Pro Glu Glu Lys Ile Ala Glu Asn Phe Leu Gln Val Arg Glu
    50                  55                  60

Ile Ala Lys Glu Val Ala Ser Asp Leu Val Ile Ala Tyr Gly Ala Glu
 65                  70                  75                  80

Ile Tyr Tyr Thr Pro Asp Val Leu Asp Lys Leu Glu Lys Lys Arg Ile
                85                  90                  95

Pro Thr Leu Asn Asp Ser Arg Tyr Ala Leu Ile Glu Phe Ser Met Asn
           100                 105                 110

Thr Pro Tyr Arg Asp Ile His Ser Ala Leu Ser Lys Ile Leu Met Leu
       115                 120                 125

Gly Ile Thr Pro Val Ile Ala His Ile Glu Arg Tyr Asp Ala Leu Glu
   130                 135                 140

Asn Asn Glu Lys Arg Val Arg Glu Leu Ile Asp Met Gly Cys Tyr Thr
145                 150                 155                 160
```

```
Gln Val Asn Ser Ser His Val Leu Lys Pro Lys Leu Phe Gly Glu Arg
            165                 170                 175

Tyr Lys Phe Met Lys Lys Arg Ala Gln Tyr Phe Leu Glu Gln Asp Leu
        180                 185                 190

Val His Val Ile Ala Ser Asp Met His Asn Leu Asp Gly Arg Pro Pro
            195                 200                 205

His Met Ala Glu Ala Tyr Asp Leu Val Thr Gln Lys Tyr Gly Glu Ala
    210                 215                 220

Lys Ala Gln Glu Leu Phe Ile Asp Asn Pro Arg Lys Ile Val Met Asp
225                 230                 235                 240

Gln Leu Ile

<210> SEQ ID NO 165
<211> LENGTH: 3990
<212> TYPE: DNA
<213> ORGANISM: Streptococcus pneumoniae

<400> SEQUENCE: 165
```

| | | | | | |
|---|---|---|---|---|---|
| ttgatttata | taatcgctat | caatataaca | atgcaatcag | gaggttttgc | aatgaaacat | 60 |
| gaaaaacaac | agcgttttc | tattcgtaaa | tacgctgtag | gagcagcttc | tgttctaatt | 120 |
| ggatttgcct | tccaagcaca | gactgttgca | gccgatggag | ttactcctac | tactacagaa | 180 |
| aaccaaccga | ccatccatac | ggtttctgat | tcccctcaat | catccgaaaa | tcggactgag | 240 |
| gaaacaccta | agcagtgct | tcaaccagaa | gctccaaaaa | ctgtagaaac | agaaactcca | 300 |
| gctactgata | aggtagctag | tcttccaaaa | acagaagaaa | aaccacaaga | ggaagttagt | 360 |
| tcaactccta | gtgataaagc | agaagtggta | actccaactt | ctgctgaaaa | agaaactgct | 420 |
| aataaaaagg | cagaagaagc | tagccctaaa | aaggaagaag | cgaaagaggt | tgattctaaa | 480 |
| gagtcaaata | cagacaagac | tgacaaggat | aaaccagcta | aaaagatga | agcgaaagca | 540 |
| gaggctgaca | aaccggcaac | agaggcagga | aaggaacgtg | ctgcaactgt | aaatgaaaaa | 600 |
| ctagcgaaaa | agaaaattgt | ttctattgat | gctggacgta | aatatttctc | accagaacag | 660 |
| ctcaaggaaa | tcatcgataa | agcgaaacat | tatggctaca | ctgatttaca | cctattagtc | 720 |
| ggaaatgatg | gactccgttt | catgttggac | gatatgagca | tcacagctaa | cggcaagacc | 780 |
| tatgccagtg | acgatgtcaa | acgcgccatt | gaaaaaggta | caaatgatta | ttacaacgat | 840 |
| ccaaacggca | atcacttaac | agaaagtcaa | atgacagatc | tgattaacta | tgccaaagat | 900 |
| aaaggtatcg | gtctcattcc | gacagtaaat | agtcctggac | acatggatgc | gattctcaat | 960 |
| gccatgaaag | aatttgggaat | ccaaaaccct | aactttagct | attttgggaa | gaaatcagcc | 1020 |
| cgtactgtcg | atcttgacaa | cgaacaagct | gtcgcttta | caaaagccct | tatcgacaag | 1080 |
| tatgctgctt | atttcgcgaa | aaagactgaa | atcttcaaca | tcggacttga | tgaatatgcc | 1140 |
| aatgatgcga | cagatgctaa | aggttggagt | gtgcttcaag | ctgataaata | ctatccaaac | 1200 |
| gaaggctacc | ctgtaaaagg | ctatgaaaaa | tttattgcct | acgccaatga | cctcgctcgt | 1260 |
| attgtaaaat | cgcacggtct | caaaccaatg | gcttttaacg | acggtatcta | ctacaatagc | 1320 |
| gacacaagct | ttggtagttt | tgacaaagac | atcatcgttt | ctatgtggac | tggtggttgg | 1380 |
| ggaggctacg | atgtcgcttc | ttctaaacta | ctagctgaaa | aaggtcacca | aatccttaat | 1440 |
| accaatgatg | cttggtacta | cgttcttgga | cgaaacgctg | atggccaagg | ctggtacaat | 1500 |
| ctcgatcagg | ggctcaatgg | tattaaaaac | acaccaatca | cttctgtacc | aaaaacagaa | 1560 |
| ggagctgata | tcccaatcat | cggtggtatg | gtagctgctt | gggctgacac | tccatctgca | 1620 |

```
cgttattcac catcacgcct cttcaaactc atgcgtcatt ttgcaaatgc caacgctgaa    1680
tacttcgcag ctgattatga atctgcagag caagcactta acgaggtacc aaaagacctg    1740
aaccgttata ctgcagaaag cgtcacggcc gtaaagaag ctgaaaaagc tattcgctct    1800
ctcgatagca accttagccg tgcccaacaa gatacgattg atcaagccat tgctaaactt    1860
caagaaactg tcaacaactt gaccctcacg cctgaagctc aaaaagaaga agaagctaaa    1920
cgtgaggttg aaaaacttgc caaaaacaag gtaatctcaa tcgatgctgg acgcaaatac    1980
tttactctga accagctcaa acgcatcgta gacaaggcca gtgagctcgg atattctgat    2040
gtccatctcc ttctaggaaa tgacggactt cgctttctac tcgatgatat gaccattact    2100
gccaacggaa aaacctatgc tagtgatgac gttaaaaaag ctattatcga aggaactaaa    2160
gcttactacg acgatccaaa cggtactgca ctaacacagg cagaagtaac agagctaatt    2220
gaatacgcta atctaaggca tcggtctc atcccagcta ttaacagtcc aggtcacatg    2280
gatgctatgc tggttgccat ggaaaaatta ggtattaaaa atcctcaagc ccactttgat    2340
aaagtttcaa aaacaactat ggacttgaaa aacgaagaag cgatgaactt tgtaaaagcc    2400
ctcatcggta aatacatgga cttctttgca ggtaaaacaa gattttcaa ctttggtact    2460 gacgaatacg ccaacgatgc gactagtgcc caaggctggt actacctcaa gtggtatcaa    2520
ctctatggca aatttgccga atatgccaac accctcgcag ctatggccaa agaaagaggg    2580
cttcaaccaa tggccttcaa cgatggcttc tactatgaag acaaggacga tgttcagttt    2640
gacaaagatg tcttgatttc ttactggtct aaaggctggt ggggatataa cctcgcatca    2700
cctcaatacc tagcaagcaa aggctataaa ttcttgaata ccaacggtga ctggtactac    2760
attcttggtc aaaaaccaga agatggtggt ggtttcctca agaaagctat tgagaatact    2820
ggaaaaacac cattcaatca actagcttct accaaatatc ctgaagtaga tcttccaaca    2880
gtcggaagta tgcttttcaat ctgggcagat agaccaagcg ctgaatacaa ggaagaggaa    2940
atctttgaac tcatgactgc ctttgcagac cacaacaaag actactttcg tgctaattat    3000
aatgctctcc gcgaagaatt agctaaaatt cctacaaact tagaaggata tagtaaagaa    3060
agtcttgagg cccttgacgc agctaaaaca gctctaaatt acaacctcaa ccgtaataaa    3120
caagctgagc ttgacacgct tgtagccaac ctaaaagccg ctcttcaagg cctcaaacca    3180
gctgtaactc attcaggaag cctagatgaa aatgaagtgg ctgccaatgt tgaaaccaga    3240
ccagaactca tcacaagaac tgaagaaatt ccatttgaag ttatcaagaa agaaaatcct    3300 aacctccccag ccgtcagga aaatattatc acagcaggag tcaaaggtga acgaactcat    3360
tacatctctg tactcactga aaatggaaaa acaacagaaa cagtccttga tagccaggta    3420
accaaagaag ttataaaacca agtggttgaa gttggcgctc ctgtaactca aagggtgat    3480 gaaagtggtc ttgcaccaac tactgaggta aaacctagac tggatatcca agaagaagaa    3540 attccatttta ccacagtgac ttgtgaaaat ccactcttac tcaaaggaaa acacaagtc    3600 attactaagg gcgtcaatgg acatcgtagc aacttctact ctgtgagcac ttctgccgat    3660
ggtaaggaag tgaaaacact tgtaaatagt gtcgtagcac aggaagccgt tactcaaata    3720
gtcgaagtcg gaactatggt aacacatgta ggcgatgaaa acggacaagc cgctattgct    3780
gaagaaaaac caaaactaga atcccaagcc caaccagctc catcaactgc tcctgctgag    3840
gaaagcaaag ttcttcctca agatccagct cctgtggtaa cagagaaaaa acttcctgaa    3900
acaggaactc acgattctgc aggactagta gtcgcaggac tcatgtccac actagcagcc    3960
tatggactca ctaaaagaaa agaagactaa                                     3990
```

-continued

```
<210> SEQ ID NO 166
<211> LENGTH: 1329
<212> TYPE: PRT
<213> ORGANISM: Streptococcus pneumoniae

<400> SEQUENCE: 166

Met Ile Tyr Ile Ile Ala Ile Asn Ile Thr Met Gln Ser Gly Gly Phe
1               5                   10                  15

Ala Met Lys His Glu Lys Gln Gln Arg Phe Ser Ile Arg Lys Tyr Ala
            20                  25                  30

Val Gly Ala Ala Ser Val Leu Ile Gly Phe Ala Phe Gln Ala Gln Thr
        35                  40                  45

Val Ala Ala Asp Gly Val Thr Pro Thr Thr Glu Asn Gln Pro Thr
    50                  55                  60

Ile His Thr Val Ser Asp Ser Pro Gln Ser Ser Glu Asn Arg Thr Glu
65                  70                  75                  80

Glu Thr Pro Lys Ala Val Leu Gln Pro Glu Ala Pro Lys Thr Val Glu
                85                  90                  95

Thr Glu Thr Pro Ala Thr Asp Lys Val Ala Ser Leu Pro Lys Thr Glu
            100                 105                 110

Glu Lys Pro Gln Glu Glu Val Ser Ser Thr Pro Ser Asp Lys Ala Glu
        115                 120                 125

Val Val Thr Pro Thr Ser Ala Glu Lys Glu Thr Ala Asn Lys Lys Ala
    130                 135                 140

Glu Glu Ala Ser Pro Lys Lys Glu Gly Ala Lys Glu Val Asp Ser Lys
145                 150                 155                 160

Glu Ser Asn Thr Asp Lys Thr Asp Lys Asp Lys Pro Ala Lys Lys Asp
                165                 170                 175

Glu Ala Lys Ala Glu Ala Asp Lys Pro Ala Thr Glu Ala Gly Lys Glu
            180                 185                 190

Arg Ala Ala Thr Val Asn Glu Lys Leu Ala Lys Lys Ile Val Ser
        195                 200                 205

Ile Asp Ala Gly Arg Lys Tyr Phe Ser Pro Glu Gln Leu Lys Glu Ile
    210                 215                 220

Ile Asp Lys Ala Lys His Tyr Gly Tyr Thr Asp Leu His Leu Leu Val
225                 230                 235                 240

Gly Asn Asp Gly Leu Arg Phe Met Leu Asp Asp Met Ser Ile Thr Ala
                245                 250                 255

Asn Gly Lys Thr Tyr Ala Ser Asp Asp Val Lys Arg Ala Ile Glu Lys
            260                 265                 270

Gly Thr Asn Asp Tyr Tyr Asn Asp Pro Asn Gly Asn His Leu Thr Glu
        275                 280                 285

Ser Gln Met Thr Asp Leu Ile Asn Tyr Ala Lys Asp Lys Gly Ile Gly
    290                 295                 300

Leu Ile Pro Thr Val Asn Ser Pro Gly His Met Asp Ala Ile Leu Asn
305                 310                 315                 320

Ala Met Lys Glu Leu Gly Ile Gln Asn Pro Asn Phe Ser Tyr Phe Gly
                325                 330                 335

Lys Lys Ser Ala Arg Thr Val Asp Leu Asp Asn Glu Gln Ala Val Ala
            340                 345                 350

Phe Thr Lys Ala Leu Ile Asp Lys Tyr Ala Ala Tyr Phe Ala Lys Lys
        355                 360                 365

Thr Glu Ile Phe Asn Ile Gly Leu Asp Glu Tyr Ala Asn Asp Ala Thr
    370                 375                 380
```

-continued

```
Asp Ala Lys Gly Trp Ser Val Leu Gln Ala Asp Lys Tyr Tyr Pro Asn
385                 390                 395                 400
Glu Gly Tyr Pro Val Lys Gly Tyr Glu Lys Phe Ile Ala Tyr Ala Asn
            405                 410                 415
Asp Leu Ala Arg Ile Val Lys Ser His Gly Leu Lys Pro Met Ala Phe
                420                 425                 430
Asn Asp Gly Ile Tyr Tyr Asn Ser Asp Thr Ser Phe Gly Ser Phe Asp
        435                 440                 445
Lys Asp Ile Ile Val Ser Met Trp Thr Gly Trp Gly Tyr Asp
450                 455                 460
Val Ala Ser Ser Lys Leu Leu Ala Glu Lys Gly His Gln Ile Leu Asn
465                 470                 475                 480
Thr Asn Asp Ala Trp Tyr Tyr Val Leu Gly Arg Asn Ala Asp Gly Gln
                485                 490                 495
Gly Trp Tyr Asn Leu Asp Gln Gly Leu Asn Gly Ile Lys Asn Thr Pro
            500                 505                 510
Ile Thr Ser Val Pro Lys Thr Glu Gly Ala Asp Ile Pro Ile Ile Gly
        515                 520                 525
Gly Met Val Ala Ala Trp Ala Asp Thr Pro Ser Ala Arg Tyr Ser Pro
530                 535                 540
Ser Arg Leu Phe Lys Leu Met Arg His Phe Ala Asn Ala Asn Ala Glu
545                 550                 555                 560
Tyr Phe Ala Ala Asp Tyr Glu Ser Ala Glu Gln Ala Leu Asn Glu Val
                565                 570                 575
Pro Lys Asp Leu Asn Arg Tyr Thr Ala Glu Ser Val Thr Ala Val Lys
            580                 585                 590
Glu Ala Glu Lys Ala Ile Arg Ser Leu Asp Ser Asn Leu Ser Arg Ala
        595                 600                 605
Gln Gln Asp Thr Ile Asp Gln Ala Ile Ala Lys Leu Gln Glu Thr Val
610                 615                 620
Asn Asn Leu Thr Leu Thr Pro Glu Ala Gln Lys Glu Glu Ala Lys
625                 630                 635                 640
Arg Glu Val Glu Lys Leu Ala Lys Asn Lys Val Ile Ser Ile Asp Ala
                645                 650                 655
Gly Arg Lys Tyr Phe Thr Leu Asn Gln Leu Lys Arg Ile Val Asp Lys
            660                 665                 670
Ala Ser Glu Leu Gly Tyr Ser Asp Val His Leu Leu Leu Gly Asn Asp
        675                 680                 685
Gly Leu Arg Phe Leu Leu Asp Asp Met Thr Ile Thr Ala Asn Gly Lys
690                 695                 700
Thr Tyr Ala Ser Asp Asp Val Lys Lys Ala Ile Ile Glu Gly Thr Lys
705                 710                 715                 720
Ala Tyr Tyr Asp Asp Pro Asn Gly Thr Ala Leu Thr Gln Ala Glu Val
                725                 730                 735
Thr Glu Leu Ile Glu Tyr Ala Lys Ser Lys Asp Ile Gly Leu Ile Pro
            740                 745                 750
Ala Ile Asn Ser Pro Gly His Met Asp Ala Met Leu Val Ala Met Glu
        755                 760                 765
Lys Leu Gly Ile Lys Asn Pro Gln Ala His Phe Asp Lys Val Ser Lys
770                 775                 780
Thr Thr Met Asp Leu Lys Asn Glu Glu Ala Met Asn Phe Val Lys Ala
785                 790                 795                 800
Leu Ile Gly Lys Tyr Met Asp Phe Phe Ala Gly Lys Thr Lys Ile Phe
                805                 810                 815
```

```
Asn Phe Gly Thr Asp Glu Tyr Ala Asn Asp Ala Thr Ser Ala Gln Gly
                820                 825                 830

Trp Tyr Tyr Leu Lys Trp Tyr Gln Leu Tyr Gly Lys Phe Ala Glu Tyr
        835                 840                 845

Ala Asn Thr Leu Ala Ala Met Ala Lys Glu Arg Gly Leu Gln Pro Met
850                 855                 860

Ala Phe Asn Asp Gly Phe Tyr Tyr Glu Asp Lys Asp Val Gln Phe
865                 870                 875                 880

Asp Lys Asp Val Leu Ile Ser Tyr Trp Ser Lys Gly Trp Gly Tyr
                885                 890                 895

Asn Leu Ala Ser Pro Gln Tyr Leu Ala Ser Lys Gly Tyr Lys Phe Leu
                900                 905                 910

Asn Thr Asn Gly Asp Trp Tyr Tyr Ile Leu Gly Gln Lys Pro Glu Asp
                915                 920                 925

Gly Gly Gly Phe Leu Lys Lys Ala Ile Glu Asn Thr Gly Lys Thr Pro
            930                 935                 940

Phe Asn Gln Leu Ala Ser Thr Lys Tyr Pro Glu Val Asp Leu Pro Thr
945                 950                 955                 960

Val Gly Ser Met Leu Ser Ile Trp Ala Asp Arg Pro Ser Ala Glu Tyr
                965                 970                 975

Lys Glu Glu Ile Phe Glu Leu Met Thr Ala Phe Ala Asp His Asn
                980                 985                 990

Lys Asp Tyr Phe Arg Ala Asn Tyr Asn Ala Leu Arg Glu Glu Leu Ala
                995                 1000                1005

Lys Ile Pro Thr Asn Leu Glu Gly Tyr Ser Lys Glu Ser Leu Glu Ala
    1010                1015                1020

Leu Asp Ala Ala Lys Thr Ala Leu Asn Tyr Asn Leu Asn Arg Asn Lys
1025                1030                1035                1040

Gln Ala Glu Leu Asp Thr Leu Val Ala Asn Leu Lys Ala Ala Leu Gln
                1045                1050                1055

Gly Leu Lys Pro Ala Val Thr His Ser Gly Ser Leu Asp Glu Asn Glu
                1060                1065                1070

Val Ala Ala Asn Val Glu Thr Arg Pro Glu Leu Ile Thr Arg Thr Glu
                1075                1080                1085

Glu Ile Pro Phe Glu Val Ile Lys Lys Glu Asn Pro Asn Leu Pro Ala
    1090                1095                1100

Gly Gln Glu Asn Ile Ile Thr Ala Gly Val Lys Gly Glu Arg Thr His
1105                1110                1115                1120

Tyr Ile Ser Val Leu Thr Glu Asn Gly Lys Thr Thr Glu Thr Val Leu
                1125                1130                1135

Asp Ser Gln Val Thr Lys Glu Val Ile Asn Gln Val Val Glu Val Gly
            1140                1145                1150

Ala Pro Val Thr His Lys Gly Asp Glu Ser Gly Leu Ala Pro Thr Thr
            1155                1160                1165

Glu Val Lys Pro Arg Leu Asp Ile Gln Glu Glu Ile Pro Phe Thr
    1170                1175                1180

Thr Val Thr Cys Glu Asn Pro Leu Leu Leu Lys Gly Lys Thr Gln Val
1185                1190                1195                1200

Ile Thr Lys Gly Val Asn Gly His Arg Ser Asn Phe Tyr Ser Val Ser
                1205                1210                1215

Thr Ser Ala Asp Gly Lys Glu Val Lys Thr Leu Val Asn Ser Val Val
            1220                1225                1230

Ala Gln Glu Ala Val Thr Gln Ile Val Glu Val Gly Thr Met Val Thr
```

```
                    1235                1240                1245
His Val Gly Asp Glu Asn Gly Gln Ala Ala Ile Ala Glu Glu Lys Pro
         1250                1255                1260
Lys Leu Glu Ile Pro Ser Gln Pro Ala Pro Ser Thr Ala Pro Ala Glu
     1265                1270                1275                1280
Glu Ser Lys Val Leu Pro Gln Asp Pro Ala Pro Val Val Thr Glu Lys
             1285                1290                1295
Lys Leu Pro Glu Thr Gly Thr His Asp Ser Ala Gly Leu Val Val Ala
         1300                1305                1310
Gly Leu Met Ser Thr Leu Ala Ala Tyr Gly Leu Thr Lys Arg Lys Glu
         1315                1320                1325
Asp

<210> SEQ ID NO 167
<211> LENGTH: 825
<212> TYPE: DNA
<213> ORGANISM: Streptococcus pneumoniae

<400> SEQUENCE: 167
atgaacaaaa aaacaagaca gacactaatc ggactgctag tgttattgct tttgtctaca      60
gggagctatt atatcaagca gatgccgtcg gcacctaata gtcccaaaac caatcttagt     120
cagaaaaaac aagcgtctga agctcctagt caagcattgg cagagagtgt cttaacagac     180
gcagtcaaga gtcaaataaa ggggagtctg gagtggaatg gctcaggtgc ttttatcgtc     240
aatggtaata aacaaatctc agatgccaag gtttcaagta agccctacgc tgacaataaa     300
acaaagacag tgggcaagga actgttccaa ccgtagcta atgccctctt gtctaaggcc     360
actcgtcagt acaagaatcg taagaaact gggaatggtt caacttcttg gactcctcca      420
ggttggcatc aggtcaagaa tctaaagggc tcttataccc atgcagtcga tagaggtcat     480
ttgttaggct atgccttaat cggtggtttg atggttttg atgcctcaac aagcaatcct      540
aaaaacattg ctgttcagac agcctgggca atcaggcac aagccgagta ttcgactggt      600
caaaactact atgaaagcaa ggtgcgtaaa gccttggacc aaaacaagcg tgtccgttac     660
cgtgtaaccc tttactacgc ttcaaacgag gatttagttc cctcagcttc acagattgaa     720
gccaagtctt cggatggaga attggaattc aatgttctag ttcccaatgt tcaaagggga     780
cttcaactgg attaccgaac tggagaagta actgtaactc agtaa                    825

<210> SEQ ID NO 168
<211> LENGTH: 274
<212> TYPE: PRT
<213> ORGANISM: Streptococcus pneumoniae

<400> SEQUENCE: 168

Met Asn Lys Lys Thr Arg Gln Thr Leu Ile Gly Leu Leu Val Leu Leu
 1               5                  10                  15
Leu Leu Ser Thr Gly Ser Tyr Tyr Ile Lys Gln Met Pro Ser Ala Pro
             20                  25                  30
Asn Ser Pro Lys Thr Asn Leu Ser Gln Lys Lys Gln Ala Ser Glu Ala
         35                  40                  45
Pro Ser Gln Ala Leu Ala Glu Ser Val Leu Thr Asp Ala Val Lys Ser
     50                  55                  60
Gln Ile Lys Gly Ser Leu Glu Trp Asn Gly Ser Gly Ala Phe Ile Val
 65                  70                  75                  80
Asn Gly Asn Lys Thr Asn Leu Asp Ala Lys Val Ser Ser Lys Pro Tyr
                 85                  90                  95
```

Ala Asp Asn Lys Thr Lys Thr Val Gly Lys Glu Thr Val Pro Thr Val
                100                 105                 110

Ala Asn Ala Leu Leu Ser Lys Ala Thr Arg Gln Tyr Lys Asn Arg Lys
            115                 120                 125

Glu Thr Gly Asn Gly Ser Thr Ser Trp Thr Pro Pro Gly Trp His Gln
        130                 135                 140

Val Lys Asn Leu Lys Gly Ser Tyr Thr His Ala Val Asp Arg Gly His
145                 150                 155                 160

Leu Leu Gly Tyr Ala Leu Ile Gly Gly Leu Asp Gly Phe Asp Ala Ser
                165                 170                 175

Thr Ser Asn Pro Lys Asn Ile Ala Val Gln Thr Ala Trp Ala Asn Gln
            180                 185                 190

Ala Gln Ala Glu Tyr Ser Thr Gly Gln Asn Tyr Glu Ser Lys Val
        195                 200                 205

Arg Lys Ala Leu Asp Gln Asn Lys Arg Val Arg Tyr Arg Val Thr Leu
        210                 215                 220

Tyr Tyr Ala Ser Asn Glu Asp Leu Val Pro Ser Ala Ser Gln Ile Glu
225                 230                 235                 240

Ala Lys Ser Ser Asp Gly Glu Leu Glu Phe Asn Val Leu Val Pro Asn
                245                 250                 255

Val Gln Lys Gly Leu Gln Leu Asp Tyr Arg Thr Gly Val Thr Val
            260                 265                 270

Thr Gln

<210> SEQ ID NO 169
<211> LENGTH: 225
<212> TYPE: DNA
<213> ORGANISM: Streptococcus pneumoniae

<400> SEQUENCE: 169
gtgctaagat tcagcggatt gaggcaagtg atgaagatga ataagaaatc aagctacgta      60
gtcaagcgtt tactttttagt catcatagta ctgattttag gtactctggc tctaggaatc    120
ggtttaatgg taggttatgg aatcttgggc aagggtcaag atccatgggc tatcctgtct    180
ccagcaaaat ggcaggaatt gattcataaa tttacaggaa attag                    225

<210> SEQ ID NO 170
<211> LENGTH: 74
<212> TYPE: PRT
<213> ORGANISM: Streptococcus pneumoniae

<400> SEQUENCE: 170

Val Leu Arg Phe Ser Gly Leu Arg Gln Val Met Lys Met Asn Lys Lys
1               5                  10                  15

Ser Ser Tyr Val Val Lys Arg Leu Leu Leu Val Ile Ile Val Leu Ile
                20                  25                  30

Leu Gly Thr Leu Ala Leu Gly Ile Gly Leu Met Val Gly Tyr Gly Ile
            35                  40                  45

Leu Gly Lys Gly Gln Asp Pro Trp Ala Ile Leu Ser Pro Ala Lys Trp
        50                  55                  60

Gln Glu Leu Ile His Lys Phe Thr Gly Asn
65                  70

<210> SEQ ID NO 171
<211> LENGTH: 40
<212> TYPE: DNA
<213> ORGANISM: Artificial Sequence

```
<220> FEATURE:
<223> OTHER INFORMATION: Description of Artificial Sequence: Primer

<400> SEQUENCE: 171
cgagatctga tatctcacaa acagataacg gcgtaaatag                              40

<210> SEQ ID NO 172
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 172
gaagatcttc cccgggatca caaacagata acggcgtaaa tag                         43

<210> SEQ ID NO 173
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 173
cgagatctga tatccatcac aaacagataa cggcgtaaat ag                          42

<210> SEQ ID NO 174
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 174
cgggatcctt atggacctga atcagcgttg tc                                     32

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 175
ggatgctttg tttcaggtgt atc                                               23

<210> SEQ ID NO 176
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 176
catgatatcg gtacctcaag ctcatatcat tgtccggcaa tggtgtgggc ttttttgtt        60 ttagcggata acaatttcac ac                                                82

<210> SEQ ID NO 177
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 177
gcggatcccc cgggcttaat taatgtttaa acactagtcg aagatctcgc gaattctcct       60
```

```
gtgtgaaatt gttatccgct a                                              81

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 178
cgccagggtt ttcccagtca cgac                                           24

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 179 tcagggggc ggagcctatg                                                 20

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 180
tcgtatgttg tgtggaattg tg                                             22

<210> SEQ ID NO 181
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 181
tccggctcgt atgttgtgtg gaattg                                         26

<210> SEQ ID NO 182
<211> LENGTH: 5
<212> TYPE: PRT
<213> ORGANISM: Artificial Sequence
<220> FEATURE:
<221> NAME/KEY: SITE
<222> LOCATION: (3)
<223> OTHER INFORMATION: Xaa=Any amino acid
<220> FEATURE:
<223> OTHER INFORMATION: Description of Artificial Sequence: Cell wall
      anchoring motif

<400> SEQUENCE: 182

Leu Pro Xaa Thr Gly
  1               5

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 183
gcgggatccg ccaccatg                                                  18
```

<210> SEQ ID NO 184
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 184
ttgcggccgc                                                                  10

<210> SEQ ID NO 185
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 185
cggatccgcc accatgggtc taattgaaga cttaaaaaat caa                             43

<210> SEQ ID NO 186
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 186
ttgcggccgc caatgctaga ctaaacacaa gactca                                     36

<210> SEQ ID NO 187
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 187
cgcggatcca tgaaaaaaat ctattcattt ttagca                                     36

<210> SEQ ID NO 188
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 188
ccctcgaggg ctacttccga tacattttaa actgtagg                                   38

<210> SEQ ID NO 189
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 189
cggatccgcc accatgagtc atgtcgctgc aaatg                                      35

<210> SEQ ID NO 190
<211> LENGTH: 32
<212> TYPE: DNA
<213> ORGANISM: Artificial Sequence
<220> FEATURE:
<223> OTHER INFORMATION: Description of Artificial Sequence: Primer

```
<400> SEQUENCE: 190
ttgcggccgc ataccaaacg ctgacatcta cg                              32

<210> SEQ ID NO 191
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 191
cggatccgcc accatgcaaa aagagcggta tggttatg                        38

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 192
ttgcggccgc accccattc ttaatccctt                                  30

<210> SEQ ID NO 193
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 193
cggatccgcc accatggagg tatgtgaaat gtcacgtaaa                      40

<210> SEQ ID NO 194
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 194
ttgcggccgc ttttacaaag tcaagcaaag cc                              32

<210> SEQ ID NO 195
<211> LENGTH: 48
<212> TYPE: PRT
<213> ORGANISM: Streptococcus pneumoniae

<400> SEQUENCE: 195

Gly Ile Arg Leu Arg Asn Met Leu Phe Lys Ile Trp Pro Ala Val Ala
 1               5                  10                  15

Leu Val Thr Ser Ser Gly Asn Asn Val Ser Met Leu His Ser Ile Ala
                20                  25                  30

Asn Met Gly Gln Leu Thr Leu Gly Thr Gln Cys Gln Thr Val Val Val
            35                  40                  45

<210> SEQ ID NO 196
<211> LENGTH: 11
```

```
<212> TYPE: PRT
<213> ORGANISM: Streptococcus pneumoniae

<400> SEQUENCE: 196

Gln Lys Ile Thr Met Ile Thr Phe Thr Phe Gln
 1               5                   10
```

NUCLEIC ACIDS AND PROTEINS FROM STREPTOCOCCUS PNEUMONIAE

This application is a continuation of U.S. patent application Ser. No. 09/769,744, filed Jan. 26, 2001, now abandoned, which is a continuation of International Patent Application No. PCT/GB99/02452 filed Jul. 27, 1999, which claims benefit of U.S. Provisional Application No. 60/125,329 filed Mar. 19, 1999, and claims benefit of United Kingdom 9816336.3 filed Jul. 27, 1998, all of the following of which are hereby incorporated by reference.

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

*Streptococcus pneumoniae*, commonly referred to as the pneumococcus, is an important pathogenic organism. The continuing significance of *Streptoccocus pneumoniae* infections in relation to human disease in developing and developed countries has been authoritatively reviewed (Siber, G. R., *Science*, 265: 1385-1387 (1994)). That indicates that on a global scale this organism is believed to be the most common bacterial cause of acute respiratory infections, and is estimated to result in 1 million childhood deaths each year, mostly in developing countries (Stansfield, S. K., *Pediatr. Infect. Dis.*, 6: 622 (1987)). In the USA it has been suggested (Breiman et al, *Arch. Intern. Med.*, 150: 1401 (1990)) that the pneumococcus is still the most common cause of bacterial pneumonia, and that disease rates are particularly high in young children, in the elderly, and in patients with predisposing conditions such as asplenia, heart, lung and kidney disease, diabetes, alcoholism, or with immunosupressive disorders, especially AIDS. These groups are at higher risk of pneumococcal septicaemia and hence meningitis and therefore have a greater risk of dying from pneumococcal infection. The pneumococcus is also the leading cause of otitis media and sinusitis, which remain prevalent infections in children in developed countries, and which incur substantial costs.

The need for effective preventative strategies against pneumococcal infection is highlighted by the recent emergence of penicillin-resistant pneumococci. It has been reported that 6.6% of pneumoccal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics*, 214:1 (1992)). The rates of penicillin resistance can be higher (up to 20%) in some hospitals (Breiman et al, J. Am. Med. Assoc., 271: 1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent character. This approach has been used in the development of a vaccine against *Haemophilus influenzae*, for instance. There are, however, issues of cost concerning both the multi-polysaccharide vaccines and those based on conjugates.

A third approach is to look for other antigenic components which offer the potential to be vaccine candidates. This is the basis of the present invention. Using a specially developed bacterial expression system, we have been able to identify a group of protein antigens from pneomococcus which are associated with the bacterial envelope or which are secreted.

Thus, in a first aspect the present invention provides a *Streptococcus pneumoniae* protein or polypeptide having a sequence selected from those shown in table 1.

In a second aspect, the present invention provides a *Streptococcus pneumoniae* protein or polypeptide having a sequence selected from those shown in table 2. A protein or polypeptide of the present invention may be provided in substantially pure form.

For example, it may be provided in a form which is substantially free of other proteins. As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject. Thus, in the latter case, the protein or polypeptide may be capable of not only generating an antibody response but, in addition, a non-antibody based immune response.

The skilled person will appreciate that homologues or derivatives of the proteins or polypeptides of the invention will also find use in the context of the present invention, ie as antigenic/immunogenic material. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In the case of homologues and derivatives, the degree of identity with a protein or polypeptide as described herein is less important than that the homologue or derivative should retain the antigenicity or immunogenicity of the original protein or polypeptide. However, suitably, homologues or derivatives having at least 60% similarity (as discussed above) with the proteins or polypeptides described herein are provided. Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic/immunogenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, ie those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form. These techniques are disclosed, for example, in J. Sambrook et al *Molecular Cloning* 2nd Edition, Cold Spring Harbor Laboratory Press (1989). Thus, in a third aspect, the present invention provides a nucleic acid molecule comprising or consisting of a sequence which is:

(i) any of the DNA sequences set out in Table 1 or their RNA equivalents;
(ii) a sequence which is complementary to any of the sequences of (i);
(iii) a sequence which codes for the same protein or polypeptide, as those sequences of (i) or (ii);
(iv) a sequence which has substantial identity with any of those of (i), (ii) and (iii);
(v) a sequence which codes for a homologue, derivative or fragment of a protein as defined in Table 1.

In a fourth aspect the present invention provides a nucleic acid molecule comprising or consisting of a sequence which is:

(i) any of the DNA sequences set out in Table 2 or their RNA equivalents;
(ii) a sequence which is complementary to any of the sequences of (i);
(iii) a sequence which codes for the same protein or polypeptide, as those sequences of (i) or (ii);
(iv) a sequence which has substantial identity with any of those of (i), (ii) and (iii); or
(v) a sequence which codes for a homologue, derivative or fragment of a protein as defined in Table 2.

The nucleic acid molecules of the invention may include a plurality of such sequences, and/or fragments. The skilled person will appreciate that the present invention can include novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S. pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree.

Typically primers will be at least 15-25 nucleotides long.

As a further alternative chemical synthesis may be used. This may be automated. Relatively short sequences may be chemically synthesised and ligated together to provide a longer sequence.

There is another group of proteins from S. pneumoniae which have been identified using the bacterial expression system described herein. These are known proteins from S. pneumoniae, which have not previously been identified as antigenic proteins. The amino acid sequences of this group of proteins, together with DNA sequences coding for them are shown in Table 3. These proteins, or homologues, derivatives and/or fragments thereof also find use as antigens/immunogens. Thus, in another aspect the present invention provides the use of a protein or polypeptide having a sequence selected from those shown in Tables 1-3, or homologues, derivatives and/or fragments thereof, as an immunogen/antigen.

In yet a further aspect the present invention provides an immunogenic/antigenic composition comprising one or more proteins or polypeptides selected from those whose sequences are shown in Tables 1-3, or homologues or derivatives thereof, and/or fragments of any of these. In preferred embodiments, the immunogenic/antigenic composition is a vaccine or is for use in a diagnostic assay.

In the case of vaccines suitable additional excipients, diluents, adjuvants or the like may be included. Numerous examples of these are well known in the art.

It is also possible to utilise the nucleic acid sequences shown in Tables 1-3 in the preparation of so-called DNA vaccines. Thus, the invention also provides a vaccine composition comprising one or more nucleic acid sequences as defined herein. DNA vaccines are described in the art (see for instance, Donnelly et al, *Ann. Rev. Immunol.*, 15:617-648 (1997)) and the skilled person can use such art described techniques to produce and use DNA vaccines according to the present invention.

As already discussed herein the proteins or polypeptides described herein, their homologues or derivatives, and/or fragments of any of these, can be used in methods of detecting/diagnosing S. pneumoniae. Such methods can be based on the detection of antibodies against such proteins which may be present in a subject. Therefore the present invention provides a method for the detection/diagnosis of S. pneumoniae which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence S. pneumoniae. Such antibodies form another aspect of the invention. Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, $F(ab')_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in PNAS, 81, 6851-6855 (1984) and by Takeda et al in Nature. 314, 452-454 (1985).

Synthetic constructs also include molecules comprising an additional moiety that provides the molecule with some desirable property in addition to antigen binding. For example the moiety may be a label (e.g. a fluorescent or radioactive label). Alternatively, it may be a pharmaceutically active agent.

Antibodies, or derivatives thereof, find use in detection/diagnosis of S. pneumoniae. Thus, in another aspect the present invention provides a method for the detection/diagnosis of S. pneumoniae which comprises the step of bringing into contact a sample to be tested and antibodies capable of binding to one or more proteins described herein, or to homologues, derivatives and/or fragments thereof.

In addition, so-called "Affibodies" may be utilised. These are binding proteins selected from combinatorial libraries of an alpha-helical bacterial receptor domain (Nord et al,) Thus, Small protein domains, capable of specific binding to different target proteins can be selected using combinatorial approaches.

It will also be clear that the nucleic acid sequences described herein may be used to detect/diagnose S. pneumoniae. Thus, in yet a further aspect, the present invention provides a method for the detection/diagnosis of S. pneumoniae which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (ie usually fragments of such sequences) may be used to detect nucleic acid from *S. pneumoniae*.

In additional aspects, the present invention provides:

(a) a method of vaccinating a subject against *S. pneumoniae* which comprises the step of administering to a subject a protein or polypeptide of the invention, or a derivative, homologue or fragment thereof, or an immunogenic composition of the invention;

(b) a method of vaccinating a subject against *S. pneumoniae* which comprises the step of administering to a subject a nucleic acid molecule as defined herein;

(c) a method for the prophylaxis or treatment of *S. pneumoniae* infection which comprises the step of administering to a subject a protein or polypeptide of the invention, or a derivative, homologue or fragment thereof, or an immunogenic composition of the invention;

(d) a method for the prophylaxis or treatment of *S. pneumoniae* infection which comprises the step of administering to a subject a nucleic acid molecule as defined herein;

(e) a kit for use in detecting/diagnosing *S. pneumoniae* infection comprising one or more proteins or polypeptides of the invention, or homologues, derivatives or fragments thereof, or an antigenic composition of the invention; and (f) a kit for use in detecting/diagnosing *S. pneumoniae* infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises antagonising, inhibiting or otherwise interfering with the function or expression of said protein and determining whether *S. pneumoniae* is still viable.

A suitable method for inactivating the protein is to effect selected gene knockouts, ie prevent expression of the protein and determine whether this results in a lethal change. Suitable methods for carrying out such gene knockouts are described in Li et al, *P.N.A.S.*, 94:13251-13256 (1997) and Kolkman et al, 178:3736-3741 (1996).

In a final aspect the present invention provides the use of an agent capable of antagonising, inhibiting or otherwise interfering with the function or expression of a protein or polypeptide of the invention in the manufacture of a medicament for use in the treatment or prophylaxis of *S. pneumoniae* infection.

As mentioned above, we have used a bacterial expression system as a means of identifying those proteins which are surface associated, secreted or exported and thus, would find use as antigens.

The information necessary for the secretion/export of proteins has been extensively studied in bacteria. In the majority of cases, protein export requires a signal peptide to be present at the N-terminus of the precursor protein so that it becomes directed to the translocation machinery on the cytoplasmic membrane. During or after translocation, the signal peptide is removed by a membrane associated signal peptidase. Ultimately the localization of the protein (i.e. whether it be secreted, an integral membrane protein or attached to the cell wall) is determined by sequences other than the leader peptide itself.

We are specifically interested in surface located or exported proteins as these are likely to be antigens for use in vaccines, as diagnostic reagents or as targets for therapy with novel chemical entities. We have therefore developed a screening vector-system in *Lactococcus lactis* that permits genes encoding exported proteins to be identified and isolated. We provide below a representative example showing how given novel surface associated proteins from *Streptococcus pneumoniae* have been identified and characterized. The screening vector incorporates the staphylococcal nuclease gene nuc lacking its own export signal as a secretion reporter. Staphylococcal nuclease is a naturally secreted heat-stable, monomeric enzyme which has been efficiently expressed and secreted in a range of Gram positive bacteria (Shortle, *Gene*, 22:181-189 (1983); Kovacevic et al., *J. Bacteriol.*, 162:521-528 (1985); Miller et al., *J. Bacteriol.*, 169:3508-3514 (1987); Liebl et al., *J. Bacteriol.*, 174:1854-1861 (1992); Le Loir et al., *J. Bacteriol.*, 176:5135-5139 (1994); Poquet et al., *J. Bacteriol.*, 180:1904-1912 (1998)).

Recently, Poquet et al. ((1998), supra) have described a screening vector incorporating the nuc gene lacking its own signal leader as a reporter to identify exported proteins in Gram positive bacteria, and have applied it to *L. lactis*. This vector (pFUN) contains the pAMβ1 replicon which functions in a broad host range of Gram-positive bacteria in addition to the ColE1 replicon that promotes replication in *Escherichia coli* and certain other Gram negative bacteria. Unique cloning sites present in the vector can be used to generate transcriptional and translational fusions between cloned genomic DNA fragments and the open reading frame of the truncated nuc gene devoid of its own signal secretion leader. The nuc gene makes an ideal reporter gene because the secretion of nuclease can readily be detected using a simple and sensitive plate test: Recombinant colonies secreting the nuclease develop a pink halo whereas control colonies remain white (Shortle, (1983), supra; Le Loir et al., (1994), supra).

Thus, the invention will now be described with reference to the following representative example, which provides details of how the proteins, polypeptides and nucleic acid sequences described herein identified as antigenic targets.

We describe herein the construction of three reporter vectors and their use in *L. lactis* to identify and isolate genomic DNA fragments from *Streptococcus pneumoniae* encoding secreted or surface associated proteins.

The invention will now be described with reference to the examples, which should not be construed as in any way limiting the invention. The examples refer to the figures in which:

FIG. 1: shows the results of a number of DNA vaccine trials; and

FIG. 2: shows the results of further DNA vaccine trials.

EXAMPLE 1

(i) Construction of the pTREP1-nuc Series of Reporter Vectors (a) Construction of Expression Plasmid pTREP1

The pTREP1 plasmid is a high-copy number (40-80 per cell) theta-replicating gram positive plasmid, which is a derivative of the pTREX plasmid which is itself a derivative of the previously published pIL253 plasmid. pIL253 incorporates the broad Gram-positive host range replicon of pAMβ1 (Simon and Chopin, *Biochimie*, 70:559-567 (1988)) and is non-mobilisable by the *L lactis* sex-factor. pIL253 also lacks the tra function which is necessary for transfer or efficient mobilisation by conjugative parent plasmids exemplified by pIL501. The Enterococcal pAMβ1 replicon has previously been transferred to various species including *Streptococcus, Lactobacillus* and *Bacillus* species as well as *Clostridium acetobutylicum*, (Oultram and Klaenhammer, *FEMS Microbiological Letters*, 27:129-134 (1985); Gibson et al., (1979); LeBlanc et al., *Proceedings of the National*

*Academy of Science USA,* 75:3484-3487 (1978)) indicating the potential broad host range utility. The pTREP1 plasmid represents a constitutive transcription vector.

The pTREX vector was constructed as follows. An artificial DNA fragment containing a putative RNA stabilising sequence, a translation initiation region (TIR), a multiple cloning site for insertion of the target genes and a transcription terminator was created by annealing 2 complementary oligonucleotides and extending with Tfl DNA polymerase. The sense and anti-sense oligonucleotides contained the recognition sites for NheI and BamHI at their 5' ends respectively to facilitate cloning. This fragment was cloned between the XbaI and BamHI sites in pUC19NT7, a derivative of pUC19 which contains the T7 expression cassette from pLET1 (Wells et al, *J. Appl. Bacteriol.,* 74:629-636 (1993)) cloned between the EcoRI and HindIII sites. The resulting construct was designated pUCLEX. The complete expression cassette of pUCLEX was then removed by cutting with HindIII and blunting followed by cutting with EcoRI before cloning into EcoRI and SacI (blunted) sites of pIL253 to generate the vector pTREX (Wells and Schofield, *In Current advances in metabolism, genetics and applications-NATO ASI Series,* H 98:37-62 (1996)). The putative RNA stabilising sequence and TIR are derived from the *Escherichia coli* T7 bacteriophage sequence and modified at one nucleotide position to enhance the complementarity of the Shine Dalgarno (SD) motif to the ribosomal 16s RNA of *Lactococcus lactis* (Schofield et al. pers. coms. University of Cambridge Dept. Pathology.).

A *Lactococcus lactis* MG1363 chromosomal DNA fragment exhibiting promoter activity which was subsequently designated P7 was cloned between the EcoRI and BglII sites present in the expression cassette, creating pTREX7. This active promoter region had been previously isolated using the promoter probe vector pSB292 (Waterfield et al, *Gene,* 165: 9-15 (1995)). The promoter fragment was amplified by PCR using the Vent DNA polymerase according to the manufacturer.

The pTREP1 vector was then constructed as follows. An artificial DNA fragment which included a transcription terminator, the forward pUC sequencing primer, a promoter multiple-cloning site region and a universal translation stop sequence was created by annealing two overlapping partially complementary synthetic oligonucleotides together and extending with sequenase according to manufacturers instructions. The sense and anti-sense (pTREP$_F$ and pTREP$_R$) oligonucleotides contained the recognition sites for EcoRV and BamHI at their 5' ends respectively to facilitate cloning into pTREX7. The transcription terminator was that of the *Bacillus penicillinase* gene, which has been shown to be effective in *Lactococcus* (Jos et al., *Applied and Environmental Microbiology,* 50:540-542 (1985)). This was considered necessary as expression of target genes in the pTREX vectors was observed to be leaky and is thought to be the result of cryptic promoter activity in the origin region (Schofield et al. pers. coms. University of Cambridge Dept. Pathology.). The forward pUC primer sequencing was included to enable direct sequencing of cloned DNA fragments. The translation stop sequence which encodes a stop codon in 3 different frames was included to prevent translational fusions between vector genes and cloned DNA fragments. The pTREX7 vector was first digested with EcoRI and blunted using the 5'-3' polymerase activity of T4 DNA polymerase (NEB) according to manufacturer's instructions. The EcoRI digested and blunt ended pTREX7 vector was then digested with Bgl II thus removing the P7 promoter. The artificial DNA fragment derived from the annealed synthetic oligonucleotides was then digested with EcoRV and Bam HI and cloned into the EcoRI(blunted)-Bgl II digested pTREX7 vector to generate pTREP. A *Lactococcus lactis* MG1363 chromosomal promoter designated P1 was then cloned between the EcoRI and BglII sites present in the pTREP expression cassette forming pTREP1. This promoter was also isolated using the promoter probe vector pSB292 and characterised by Waterfield et al., (1995), supra. The P1 promoter fragment was originally amplified by PCR using vent DNA polymerase according to manufacturers instructions and cloned into the pTREX as an EcoRI-BglII DNA fragment. The EcoRI-BglII P1 promoter containing fragment was removed from pTREX1 by restriction enzyme digestion and used for cloning into pTREP (Schofield et al. pers. coms. University of Cambridge, Dept. Pathology.).

(b) PCR Amplification of the *S. aureus* nuc Gene.

The nucleotide sequence of the *S. aureus* nuc gene (EMBL database accession number V01281) was used to design synthetic oligonucleotide primers for PCR amplification. The primers were designed to amplify the mature form of the nuc gene designated nucA which is generated by proteolytic cleavage of the N-terminal 19 to 21 amino acids of the secreted propeptide designated Snase B (Shortle, (1983), supra). Three sense primers (nucS1, nucS2 and nucS3, Appendix 1) were designed, each one having a blunt-ended restriction endonuclease cleavage site for EcoRV or SmaI in a different reading frame with respect to the nuc gene. Additionally BglII and BamHI were incorporated at the 5' ends of the sense and anti-sense primers respectively to facilitate cloning into BamHI and BglII cut pTREP1. The sequences of all the primers are given in Appendix 1. Three nuc gene DNA fragments encoding the mature form of the nuclease gene (NucA) were amplified by PCR using each of the sense primers combined with the anti-sense primer described above. The nuc gene fragments were amplified by PCR using *S. aureus* genomic DNA template, Vent DNA Polymerase (NEB) and the conditions recommended by the manufacturer. An initial denaturation step at 93° C. for 2 min was followed by 30 cycles of denaturation at 93° C. for 45 sec, annealing at 50° C. for 45 seconds, and extension at 73° C. for 1 minute and then a final 5 min extension step at 73° C. The PCR amplified products were purified using a Wizard clean up column (Promega) to remove unincorporated nucleotides and primers.

(c) Construction of the pTREP1-nuc Vectors

The purified nuc gene fragments described in section b were digested with Bgl II and BamHI using standard conditions and ligated to BamHI and BglII cut and dephosphorylated pTREP1 to generate the pTREP1-nuc1, pTREP1-nuc2 and pTREP1-nuc3 series of reporter vectors. General molecular biology techniques were carried out using the reagents and buffer supplied by the manufacture or using standard conditions (Sambrook and Maniatis, (1989), supra). In each of the pTREP1-nuc vectors the expression cassette comprises a transcription terminator, lactococcal promoter P1, unique cloning sites (BglII, EcoRV or SmaI) followed by the mature form of the nuc gene and a second transcription terminator. Note that the sequences required for translation and secretion of the nuc gene were deliberately excluded in this construction. Such elements can only be provided by appropriately digested foreign DNA fragments (representing the target bacterium) which can be cloned into the unique restriction sites present immediately upstream of the nuc gene.

In possessing a promoter, the pTREP1-nuc vectors differ from the pFUN vector described by Poquet et al. (1998), supra, which was used to identify *L. lactis* exported proteins by screening directly for Nuc activity directly in *L. lactis*. As the pFUN vector does not contain a promoter upstream of the nuc open reading frame the cloned genomic DNA fragment must also provide the signals for transcription in addition to those elements required for translation initiation and secretion of Nuc. This limitation may prevent the isolation of genes that are distant from a promoter for example genes which are within polycistronic operons. Additionally there can be no guarantee that promoters derived from other species of bacteria will be recognised and functional in *L. lactis*. Certain promoters may be under stringent regulation in the natural host but not in *L. lactis*. In contrast, the presence of the P1 promoter in the pTREP1-nuc series of vectors ensures that promoterless DNA fragments (or DNA fragments containing promoter sequences not active in *L. lactis*) will still be transcribed.

(d) Screening for Secreted Proteins in *S. pneumoniae*

Genomic DNA isolated from *S. pneumoniae* was digested with the restriction enzyme Tru9I. This enzyme which recognises the sequence 5'-TTAA-3' was used because it cuts A/T rich genomes efficiently and can generate random genomic DNA fragments within the preferred size range (usually averaging 0.5-1.0 kb). This size range was preferred because there is an increased probability that the P1 promoter can be utilised to transcribe a novel gene sequence. However, the P1 promoter may not be necessary in all cases as it is possible that many Streptococcal promoters are recognised in *L. lactis*. DNA fragments of different size ranges were purified from partial Tru9I digests of *S. pneumoniae* genomic DNA. As the Tru 9I restriction enzyme generates staggered ends the DNA fragments had to be made blunt ended before ligation to the EcoRV or SmaI cut pTREP1-nuc vectors. This was achieved by the partial fill-in enzyme reaction using the 5'-3' polymerase activity of KLENOW enzyme. Briefly Tru9I digested DNA was dissolved in a solution (usually between 10-20 µl in total) supplemented with T4 DNA ligase buffer (New England Biolabs; NEB) (1×) and 33 µM of each of the required dNTPs, in this case dATP and dTTP. KLENOW enzyme was added (1 unit KLENOW enzyme (NEB) per µg of DNA) and the reaction incubated at 25° C. for 15 minutes. The reaction was stopped by incubating the mix at 75° C. for 20 minutes. EcoRV or SmaI digested pTREP-nuc plasmid DNA was then added (usually between 200-400 ng). The mix was then supplemented with 400 units of T4 DNA ligase (NEB) and T4 DNA ligase buffer (1×) and incubated overnight at 16° C. The ligation mix was precipitated directly in 100% Ethanol and 1/10 volume of 3M sodium acetate (pH 5.2) and used to transform *L. lactis* MG1363 (Gasson, 1983). Alternatively, the gene cloning site of the pTREP-nuc vectors also contains a BglII site which can be used to clone for example Sau3AI digested genomic DNA fragments.

*L. lactis* transformant colonies were grown on brain heart infusion agar and nuclease secreting (Nuc$^+$) clones were detected by a toluidine blue-DNA-agar overlay (0.05 M Tris pH 9.0, 10 g of agar per liter, 10 g of NaCl per liter, 0.1 mM CaCl2, 0.03% wt/vol. salmon sperm DNA and 90 mg of Toluidine blue O dye) essentially as described by Shortle, 1983, supra and Le Loir et al., 1994, supra). The plates were then incubated at 37° C. for up to 2 hours. Nuclease secreting clones develop an easily identifiable pink halo. Plasmid DNA was isolated from Nuc$^+$ recombinant *L. lactis* clones and DNA inserts were sequenced on one strand using the NUC-SEQ sequencing primer described in Appendix 1, which sequences directly through the DNA insert.

Isolation of Genes Encoding Exported Proteins from *S. pneumoniae*

A large number of gene sequences putatively encoding exported proteins in *S. pneumoniae* have been identified using the nuclease screening system. These have now been further analysed to remove artefacts. The sequences identified using the screening system have been analysed using a number of parameters.

1. All putative surface proteins were analysed for leader/signal peptide sequences using the software programs Sequencher (Gene Codes Corporation) and DNA Strider (Marck, *Nucleic Acids Res.*, 16:1829-1836 (1988)). Bacterial signal peptide sequences share a common design. They are characterised by a short positively charged N-terminus (N region) immediately preceding a stretch of hydrophobic residues (central portion-h region) followed by a more polar C-terminal portion which contains the cleavage site (c-region). Computer software is available which allows hydropathy profiling of putative proteins and which can readily identify the very distinctive hydrophobic portion (h-region) typical of leader peptide sequences. In addition, the sequences were checked for the presence of or absence of a potential ribosomal binding site (Shine-Dalgarno motif) required for translation initiation of the putative nuc reporter fusion protein.

2. All putative surface protein sequences were also matched with all of the protein/DNA sequences using the publicly databases [OWL-proteins inclusive of SwissProt and GenBank translations]. This allows us to identify sequences similar to known genes or homologues of genes for which some function has been ascribed. Hence it has been possible to predict a function for some of the genes identified using the LEEP system and to unequivocally establish that the system can be used to identify and isolate gene sequences of surface associated proteins. We should also be able to confirm that these proteins are indeed surface related and not artifacts. The LEEP system has been used to identify novel gene targets for vaccine and therapy.

3. Some of the genes identified proteins did not possess a typical leader peptide sequence and did not show homology with any DNA/protein sequences in the database. Indeed these proteins may indicate the primary advantage of our screening method, i.e. the isolation of atypical surface-related proteins, which may have been missed in all previously described screening protocols or approaches based on sequence homology searches.

In all cases, only partial gene sequences were initially obtained. Full length genes were obtained in all cases by reference to the TIGR *S. pneumoniae* database. Thus, by matching the originally obtained partial sequences with the database, we were able to identify the full length gene sequences. In this way, as described herein, three groups of genes were clearly identified, ie a group of genes encoding previously unidentified *S. pneumoniae* proteins, a second group exhibiting some homology with known proteins from a variety of sources and a third group which encoded known *S. pneumoniae* proteins, which were, however, not known as antigens.

EXAMPLE 2

Vaccine Trials pcDNA3.1+ as a DNA Vaccine Vector
pcDNA3.1+

The vector chosen for use as a DNA vaccine vector was pcDNA3.1 (Invitrogen) (actually pcDNA3.1+, the forward orientation was used in all cases but may be referred to as pcDNA3.1 here on). This vector has been widely and successfully employed as a host vector to test vaccine candidate genes to give protection against pathogens in the literature (Zhang, et al., Kurar and Splitter, Anderson et al.). The vector was designed for high-level stable and non-replicative transient expression in mammalian cells. pcDNA3.1 contains the ColE1 origin of replication which allows convenient high-copy number replication and growth in *E. coli*. This in turn allows rapid and efficient cloning and testing of many genes. The pcDNA3.1 vector has a large number of cloning sites and also contains the gene encoding ampicillin resistance to aid in cloning selection and the human cytomegalovirus (CMV) immediate-early promoter/enhancer which permits efficient, high-level expression of the recombinant protein. The CMV promoter is a strong viral promoter in a wide range of cell types including both muscle and immune (antigen presenting) cells. This is important for optimal immune response as it remains unknown as to which cells types are most important in generating a protective response in vivo. A T7 promoter upstream of the multiple cloning site affords efficient expression of the modified insert of interest and which allows in vitro transcription of a cloned gene in the sense orientation.

Zhang, D., Yang, X., Berry, J. Shen, C., McClarty, G. and Brunham, R. C. (1997) "DNA vaccination with the major outer-membrane protein genes induces acquired immunity to *Chlamydia trachomatis* (mouse pneumonitis) infection". *Infection and Immunity,* 176, 1035-40.

Kurar, E. and Splitter, G. A. (1997) "Nucleic acid vaccination of *Brucella abortus* ribosomal L7/L12 gene elicits immune response". *Vaccine,* 15, 1851-57.

Anderson, R., Gao, X.-M., Papakonstantinopoulou, A., Roberts, M. and Dougan, G. (1996) "Immune response in mice following immunisation with DNA encoding fragment C of tetanus toxin". *Infection and Immunity,* 64, 3168-3173.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the gene protein. It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the surface of the bacteria surface or secreted. Where an N-terminal leader peptide sequence was not immediately obvious, primers were designed to target the whole of the gene sequence for cloning and ultimately, expression in pcDNA3.1.

Having said that, however, other additional features of proteins may also affect the expression and presentation of a soluble protein. DNA sequences encoding such features in the genes encoding the proteins of interest were excluded during the design of oligonucleotides. These features included:

1. LPXTG (SEQ ID NO: 182) cell wall anchoring motifs.
2. LXXC (SEQ ID NO: 197) ipoprotein attachment sites.
3. Hydrophobic C-terminal domain.
4. Where no N-terminal signal peptide or LXXC (SEQ ID NO: 197) was present the start codon was excluded.
5. Where no hydrophobic C-terminal domain or LPXTG (SEQ ID NO: 182) motif was present the stop codon was removed.

Appropriate PCR primers were designed for each gene of interest and any and all of the regions encoding the above features was removed from the gene when designing these primers. The primers were designed with the appropriate enzyme restriction site followed by a conserved Kozak nucleotide sequence (in most cases (NB except in occasional instances for example ID59) GCCACC was used. The Kozak sequence facilitates the recognition of initiator sequences by eukaryotic ribosomes) and an ATG start codon upstream of the insert of the gene of interest. For example the forward primer using a BamH1 site the primer would begin GCGG-GATCCGCCACCATG (SEQ ID NO: 183) followed by a small section of the 5' end of the gene of interest. The reverse primer was designed to be compatible with the forward primer and with a Not1 restriction site at the 5' end in most cases (this site is TTGCGGCCGC) (SEQ ID NO: 184) (NB except in occasional instances for example ID59 where a Xho1 site was used instead of Not1).

PCR Primers

The following PCR primers were designed and used to amplify the truncated genes of interest.

```
ID5
Forward Primer
                                      (SEQ ID NO: 185)
5' CGGATCCGCCACCATGGGTCTAATTGAAGACTTAAAAAATCAA 3'

Reverse Primer
                                      (SEQ ID NO: 186)
5' TTGCGGCCGCCAATGCTAGACTAAACACAAGACTCA 3'

ID59
Forward Primer
                                      (SEQ ID NO: 187)
5' CGCGGATCCATGAAAAAAATCTATTCATTTTTAGCA 3'

Reverse Primer
                                      (SEQ ID NO: 188)
5' CCCTCGAGGGCTACTTCCGATACATTTTAAACTGTAGG 3'

ID51
Forward Primer
                                      (SEQ ID NO: 189)
5' CGGATCCGCCACCATGAGTCATGTCGCTGCAAATG 3'

Reverse Primer
                                      (SEQ ID NO: 190)
5' TTGCGGCCGCATACCAAACGCTGACATCTACG 3'

ID29
Forward Primer
                                      (SEQ ID NO: 191)
5' CGGATCCGCCACCATGCAAAAAGAGCGGTATGGTTATG 3'

Reverse Primer
                                      (SEQ ID NO: 192)
5' TTGCGGCCGCACCCCCATTCTTAATCCCTT 3'

ID50
Forward Primer
                                      (SEQ ID NO: 193)
5' CGGATCCGCCACCATGGAGGTATGTGAAATGTCACGTAAA 3'

Reverse Primer
                                      (SEQ ID NO: 194)
5' TTGCGGCCGCTTTTACAAAGTCAAGCAAAGCC 3'
```

Cloning

The insert along with the flanking features described above was amplified using PCR against a template of genomic DNA isolated from type 4 *S. pneumoniae* strain 11886 obtained from the National Collection of Type Cultures. The PCR product was cut with the appropriate restriction enzymes and cloned in to the multiple cloning site of pcDNA3.1 using conventional molecular biological techniques. Suitably mapped clones of the genes of interested were cultured and the plasmids isolated on a large scale (>1.5 mg) using Plasmid Mega Kits (Qiagen). Successful cloning and maintenance of genes was confirmed by restriction mapping and sequencing ~700 base pairs through the 5' cloning junction of each large scale preparation of each construct.

Strain Validation

A strain of type 4 was used in cloning and challenge methods which is the strain from which the S. pneumoniae genome was sequenced. A freeze dried ampoule of a homogeneous laboratory strain of type 4 S. pneumoniae strain NCTC 11886 was obtained from the National Collection of Type Strains. The ampoule was opened and the cultured re suspended with 0.5 ml of tryptic soy broth (0.5% glucose, 5% blood). The suspension was subcultured into 10 ml tryptic soy broth (0.5% glucose, 5% blood) and incubated statically overnight at 37° C. This culture was streaked on to 5% blood agar plates to check for contaminants and confirm viability and on to blood agar slopes and the rest of the culture was used to make 20% glycerol stocks. The slopes were sent to the Public Health Laboratory Service where the type 4 serotype was confirmed.

A glycerol stock of NCTC 11886 was streaked on a 5% blood agar plate and incubated overnight in a CO2 gas jar at 37° C. Fresh streaks were made and optochin sensitivity was confirmed.

Pneumococcal Challenge

A standard inoculum of type 4 S. pneumoniae was prepared and frozen down by passaging a culture of pneumococcus 1× through mice, harvesting from the blood of infected animals, and grown up to a predetermined viable count of around $10^9$ cfu/ml in broth before freezing down. The preparation is set out below as per the flow chart.

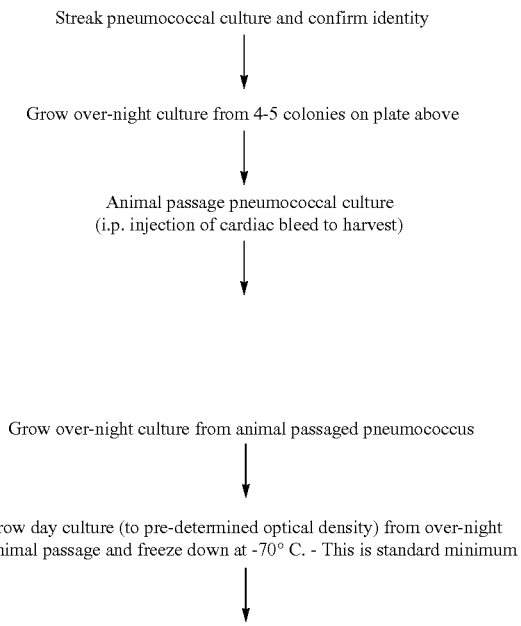

An aliquot of standard inoculum was diluted 500× in PBS and used to inoculate the mice.

Mice were lightly anaesthetised using halothane and then a dose of $1.4 \times 10^5$ cfu of pneumococcus was applied to the nose of each mouse. The uptake was facilitated by the normal breathing of the mouse, which was left to recover on its back.

S. pneumoniae Vaccine Trials

Vaccine trials in mice were carried out by the administration of DNA to 6 week old CBA/ca mice (Harlan, UK). Mice to be vaccinated were divided into groups of six and each group was immunised with recombinant pcDNA3.1+ plasmid DNA containing a specific target-gene sequence of interest. A total of 100 µg of DNA in Dulbecco's PBS (Sigma) was injected intramuscularly into the tibialis anterior muscle of both legs (50 µl in each leg). A boost was carried using the same procedure 4 weeks later. For comparison, control groups were included in all vaccine trials. These control groups were either unvaccinated animals or those administered with non-recombinant pcDNA3.1+ DNA (sham vaccinated) only, using the same time course described above. 3 weeks after the second immunisation, all mice groups were challenged intra-nasally with a lethal dose of S. pneumoniae serotype 4 (strain NCTC 11886). The number of bacteria administered was monitored by plating serial dilutions of the inoculum on 5% blood agar plates. A problem with intranasal immunisations is that in some mice the inoculum bubbles out of the nostrils, this has been noted in results table and taken account of in calculations. A less obvious problem is that a certain amount of the inoculum for each mouse may be swallowed. It is assumed that this amount will be the same for each mouse and will average out over the course of inoculations.

However, the sample sizes that have been used are small and this problem may have significant effects in some experiments. All mice remaining after the challenge were killed 3 or 4 days after infection. During the infection process, challenged mice were monitored for the development of symptoms associated with the onset of S. pneumoniae induced-disease. Typical symptoms in an appropriate order included piloerection, an increasingly hunched posture, discharge from eyes, increased lethargy and reluctance to move. The latter symptoms usually coincided with the development of a moribund state at which stage the mice were culled to prevent further suffering. These mice were deemed to be very close to death, and the time of culling was used to determine a survival time for statistical analysis. Where mice were found dead, the survival time was taken as the last time point when the mouse was monitored alive.

Interpretation of Results

A positive result was taken as any DNA sequence that was cloned and used in challenge experiments as described above which gave protection against that challenge. Protection was taken as those DNA sequences that gave statistically significant protection (to a 95% confidence level (p<0.05)) and also those which were marginal or close to significant using Mann-Whitney or which show some protective features for example there were one or more outlying mice or because the time to the first death was prolonged. It is acceptable to allow marginal or non-significant results to be considered as potential positives when it is considered that the clarity of some of the results may be clouded by the problems associated with the administration of intranasal infections.

| | Mean survival times (hours) | | | | | | | | |
|---|---|---|---|---|---|---|---|---|---|
| Mouse number | Unvacc control (1) | pcDNA 3.1+ (1) | ID5 (1) | Unvacc control (2) | ID59 (2) | Unvacc control (5) | ID59 (5) | Unvacc control (6) | ID51 (6) |
| 1 | 47.5 | 61.0 | 61.0 | 49.0 | 55.0 | 58.0 | 55.3 | 71.6* | 50.0 |
| 2 | 57.0 | 47.5 | 61.0 | 51.0 | 55.0 | 75.0 | 98.0 | 60.7 | 99.9T |
| 3 | 47.5 | 50.5 | 57.0 | 49.0 | 55.0 | 48.0 | 58.5 | 98.5 | 53.6 |
| 4 | 47.5 | 50.5 | 72.0 | 55.0 | 69.5 | 46.7 | 55.3 | (101.2)*T | 99.9 |
| 5 | 77.0 | 72.0 | 47.5 | 49.0 | 74.0 | 58.0 | 53.5 | 60.7 | 59.4 |
| 6 | 57.0 | 50.5 | mouse died | 49.0 | mouse died | 75.0 | 98.0 | 50.8 | 50.0* |
| Mean | 55.6 | 55.3 | 59.7 | 50.3 | 61.7 | 60.1 | 69.8 | 68.4 | 68.8 |
| sd | 11.5 | 9.4 | 8.8 | 2.4 | 9.3 | 12.5 | 21.9 | 18.3 | 24.4 |
| p value 1 | — | — | 0.1722 | — | 0.0064 | — | 0.2862 | — | <36.0 |
| p value 2 | — | — | 0.2565 | — | — | — | — | — | — |

*bubbled when dosed so may not have received full inoculum.
T - terminated at end of experiment having no symptoms of infection.
Numbers in brackets - survival times disregarded assuming incomplete dosing
p value 1 refers to significance tests compared to unvaccinated controls
p value 2 refers to significance tests compared to pcDNA3.1+ vaccinated controls Statistical Analyses.

Trial 1—None of the other groups had significantly longer survival times than the controls. The survival times of the unvaccinated and pcDNA3.1 control groups were not significantly different. One of the mice from ID5 was an outlying result and the mean survival times for ID5 were extended but not significantly so.

Trial 2—The group vaccinated with ID59 had significantly longer survival times than the unvaccinated control group.

Trial 5—The group vaccinated with ID59 again survived for an average of almost 10 hours longer than the controls but the results were not quite statistically significant.

Trial 6—The group vaccinated with ID51 did not have survival times significantly higher than unvaccinated controls (p=<36.0), however, there were 2 outlying mice in the vaccinated group.

Vaccine Trials 7 and 8 (See FIG. 2)

| | Mean survival times (hours) | | | |
|---|---|---|---|---|
| Mouse number | Unvacc control (7) | ID29 (7) | Unvacc control (8) | ID50 (8) |
| 1 | 59.6 | 73.1 | 45.1 | 60.6 |
| 2 | 47.2 | 54.8 | 50.8 | 60.6 |
| 3 | 59.6 | 59.3 | 60.4 | 51.1 |
| 4 | 70.9 | 54.8* | 55.2 | 60.6 |
| 5 | 68.6* | 59.3 | 45.1 | 60.6 |
| 6 | 76.0 | 54.8 | 45.1 | 60.6 |
| Mean | 63.6 | 59.35 | 50.2 | 59.1 |
| sd | 10.3 | 7.1 | 6.4 | 3.9 |
| p value 1 | — | <39.0 | — | 0.0048 |

*bubbled when dosed so may not have received full inoculum.
T - terminated at end of experiment having no symptoms of infection.
Numbers in brackets - survival times disregarded assuming incomplete dosing
p value 1 refers to significance tests compared to unvaccinated controls Statistical Analyses.

Trial 7—The ID29 vaccinated group showed prolonged times to the first death. T

Trial 8—The group vaccinated with ID50 survived significantly longer than unvaccinated controls.

Appendix I—Oligonucleotide Primers

```
nucS1
     Bgl II Eco RV
5'- cgagatctgatatctcacaaacagataacggcgtaaatag -3'     (SEQ ID NO: 171)

nucS2
     Bgl II      Sma I
5'- gaagatcttccccgggatcacaaacagataacggcgtaaatag -3'  (SEQ ID NO: 172)

nucS3
     Bgl II   Eco RV
5'- cgagatctgatatccatcacaaacagataacggcgtaaatag -3'   (SEQ ID NO: 173)

nucR
        Bam HI
5'- cgggatccttatggacctgaatcagcgttgtc -3'             (SEQ ID NO: 174)

NUCSEQ
5'- ggatgctttgtttcaggtgtatc -3'                      (SEQ ID NO: 175)

pTREP_F
```

-continued pTREP_R
5'- gcggatcccccgggcttaattaatgtttaaacactagtcgaagatct cgcgaattctcctgtgtgaaattgttatccgcta -3' (SEQ ID NO: 177)

pUC_F
5'- cgccagggttttcccagtcacgac -3' (SEQ ID NO: 178)

V_R
5'- tcaggggggcggagcctatg -3' (SEQ ID NO: 179)

V_1
5'- tcgtatgttgtgtggaattgtg -3' (SEQ ID NO: 180)

V2
5'- tccggctcgtatgttgtgtggaattg -3' (SEQ ID NO: 181)

5'- catgatatcggtacctcaagctcatatcattgtccggcaatggtgtg ggctttttttgttttagcggataacaatttcacac -3' (SEQ ID NO: 176)

TABLE 1

ID4 1200 bp (SEQ ID NO: 1)
ATGAGAAATATGTGGGTTGTAATCAAGGAAACCTATCTTCGACATGTCGA
GTCATGGAGTTTCTTCTTTATGGTGATTTCGCCGTTCCTCTTTTTAGGAA
TCTCTGTAGGAATTGGGCATCTCCAAGGTTCTTCTATGGCTAAAAATAAT
AAAGTGGCAGTAGTGACAACAGTGCCATCTGTAGCAGAAGGACTGAAGAA
TGTAAATGGTGTTAACTTCGACTATAAAGACGAAGCAAGTGCCAAAGAAG
CAATTAAAGAAGAAAAATTAAAAGGTTATTTGACCATTGATCAAGAAGAT
AGTGTTCTAAAGGCAGTTTATCATGGCGAAACATCGCTTGAAAATGGAAT
TAAATTTGAGGTTACAGGTACACTCAATGAACTGCAAAATCAGCTTAATC
GTTCAACTGCTTCCTTGTCTCAAGAGCAGGAAAAACGCTTAGCGCAGACA
ATTCAATTCACAGAAAAGATTGATGAAGCCAAGGAAAATAAAAAGTTTAT
TCAAACAATTGCAGCAGGTGCCTTAGGATTCTTTCTTTATATGATTCTGA
TTACCTATGCGGGTGTAACAGCTCAGGAAGTTGCCAGTGAAAAAGGCACC
AAAATTATGGAAGTCGTTTTTTCTAGCATAAGGGCAAGTCACTATTTCTA
TGCGCGGATGATGGCTTGTTTCTAGTGATTTTAACGCATATTGGGATCT
ATGTTGTAGGTGGTCTGGCTGCCGTTTTGCTCTTTAAAGATTTGCCATTC
TTGGCTCAGTCTGGTATTTTGGATCACTTGGGAGATGCTATCTCACTGAA
TACCTTGCTCTTTATTTTGATCAGTCTTTTCATGTACGTAGTCTTGGACG
CCTTCCTAGGATCTATGTTTCTCGTCCTGAGGACTCAGGGAAAGCCTGT
CGCCTTTGATGATTTTGATTAGGGGTGGTTTTTTGGAGTGACAGCTCTA
GGTGCAGCTGGTGACAATCTCCTCTTGAAGATTGTTCTTATATTCCCTT
TATTTCGACCTTCTTTATGCCGTTTCGAACGATTAATGACTATGCGGGGG
GAGCAGAAGCATGGATTTCACTTGCTATTACAGTGATTTTTGCGGTGGTA
GCAACAGGATTTATCGGACGCATGTATGCTAGTCTCGTTCTTCAAACGGA
TGATTTAGGGATTTGGAAAACCTTAAACGTGCCTTATCTTATAAATAG (SEQ ID NO: 2)
MRNMWVVIKETYLRHVESWSFFFMVISPFLFLGISVVGIHLQGSSMAKNN
KVAVVTTVPSVAEGLKNVNGVNFDYKDEASAKEAIKEEKLKGYLTIDQED
SVLKAVYHGETSLENGIKFEVTGTLNELQNQLNRSTASLSQEQEKRLAQT
IQFTEKIDEAKENKKFIQTIAAGALGFFLYMILITYAGVTAQEVASEKGT
KIMEVVFSSIRASHYFYARMMALFLVILTHIGIYVVGGLAAVLLFKDLPF
LAQSGILDHLGDAISLNTLLFILISLFMYVVLAAFLGSMVSRPEDSGKAL
SPLMILIMGGFFGVTALGAAGDNLLLKIGSYIPFISTFFMPFRTINDYAG
GAEAWISLAITVIFAVVATGFIGRMYASLVLQTDDLGIWKTFKRALSYK

ID5 1125 bp (SEQ ID NO: 3)
CCTGGGAAAGTCTTGAAAATTATGATAGAATGGTGGAAGGAAAAATTCAG
GAGAGTAGTAGTGACTCAAAATGTTGAAAGTCTTCTCGTATCCATTGTAA
TCAGTGCATACAATGAAGAAAAATATCTGCCTGGTCTAATTGAAGACTTA
AAAAATCAAACCTATCCTAAAGAGGATATTGAAATTCTATTTATAAATGC
TATGTCCACAGATGGGACCACAGCTATCATTCAGCAATTTATAAAGGAAG
ATACAGAGTTTAACTCAATTAGATTGTATAACAATCCTAAGAAAAATCAA
GCTAGTGGTTTTAACCTGGGAGTTAAACATTCGTAGGGGACCTTATTTT
AAAAAATTGATGCTCATTCAAAAGTTACTGAGACTTTTGTAATGAACAATG
TGGCTATTATTCAACAAGGTGAATTTGTCTGTGGGGGCCTAGACCGACG
ATTGTCGAAGGAAAGGAAATGGGCAGAGACCTTGCATCTTGTTAGGAA
AATATGTTTGGCAGTAGCATTGCCAATTATCGAAATAGTTCTGAGGATAG
ATATGTTTCTTCTATTTTTCATGGAATGTATAAACGAGAGGTTTTCCAGA
AGGTTGGTTTAGTAAATGAGCAACTTGGCCGAACTGAAGATAATGATATT
CATTATAGAATTCGAGAATATGGTTATAAAATCCGCTATAGCCCAAGTAT
TCTATCTTATCAGTATATTCGACCAACATTCAAGAAAATGCTGCATCAAA
AGTATTCAAATGGTTTGTGGATTGGCTTGACAAGTCATGTTCAGTTTAAG
TGTTTATCATTATTTCACTATGTTCCTGTTTATTGTTTTGAGTCTTGT
GTTTAGTCTAGCATTGTTACCGATCACATTCGTATTCATAACTTTACTAT
TAGGTGCCTATTTTCTACTTTTGTCATTACTCACTTTGCTTGACTTTATT
AAAACATAAAAATGGATTTCTAATTGTGATGCCCTTATTTATTTTCCA
TTCACTTTGCTTATGGCCTTGGGACGATTGTAGGTTTAATTAGAGGATTT
AATGGAAGAAGGAGTACAAGAGAACAATAATTTATTTGGATAAAATAAG
CCAAATAAATCAAAATATGCTATAA (SEQ ID NO: 4)
PGKVLKIMIEWWKEKFRRVVVTQNVESLLVSIVISAYNEEKYLPGLIEDL
KNQTYPKEDIEILFINAMSTDGTTAIIQQFIKEDTEFNSIRLYNNPKKNQ
ASGFNLGVKHSVGDLILKIDAHSKVTETFVMNNVAIIQQGEFVCGGPRPT
IVEGKGKWAETLHLVEENMFGSSIANYRNSSEDRYVSSIFHGMYKREVFQ
KVGLVNEQLGRTEDNDIHYRIREYGYKIRYSPSILSYQYIRPTFKKMLHQ
KYSNGLWIGLTSHVQFKCLSLFHYVPCLFVLSLVFSLALLPITFVFITLL
LGAYFLLLSLLTLLTLLKHKNGFLIVMPILFSIHFAYGLGTIVGLIRGF
KWKKEYKRTIIYLDKISQINQNML

ID11 696 bp (SEQ ID NO: 5)
ATGATGAAAGAACAAAATACGATAGAAATCGATGTATTTCAATTAGTTAA
AAGCTTGTGGAAACGCAAGCTAATGATTTTAATAGTGGCACTTGTGACAG
GTGCGGGGGCTTTTGCATATAGCACTTTTATTGTTAAGCCAGAATATACG
AGTACCACGCGAATTTACGTAGTGAATCGCAATCAAGGAGACAAGCCGGG
GTTGACAAATCAGGATTTGCAGGCAGGAACTTATCTGGTAAAAGACTACC
GTGAGATTATCCTTTCGCAGGATGTTTTGGAGGAAGTTGTTTCTGATTTG
AAACTAGATTTGACGCCAAAAGGTTTGGCTAATAAAATTAAAGTGACAGT
ACCAGTTGATACCCGTATTGTCTCTATTTCAGTTAATGATCGAGTTCCTG
AAGAGGCAAGCCGTATCGCTAACTCTTTGAGAGAAGTAGCTGCTCAAAAA
ATTATCAGTATTACTCGTGTCTTTGACGTGACAACACTGGAGGAGGCAAG
GCCGGCATCCCTCTTCGCCAAATATTAAACGCAATACACTAATTG
GTTTTTTGGCAGGGGTGATTGGAACTAGTGTTATAGTTCTTCATCTTGAA
CTTTTGGATACTCGTGTGAAACGTCCGGAAGATATCGAAATACATTGCA
GATGACACTTTTGGGAGTTGTGCCAAACTTGGGTAAGTTGAAATAG (SEQ ID NO: 6)
MMKEQNTIEIDVFQLVKSLWKRKLMILIVALVTGAGAFAYSTFIVKPEYT
STTRIYVVNRNQGDKPGLTNQDLQAGTYLVKDYREIILSQDVLEEVVSDL
KLDLTPKGLANKIKVTVPVDTRIVSISVNDRVPEEASRIANSLREVAAQK
IISITRVSDVTTLEEARPAISPSSPNIKRNTLIGFLAGVIGTSVIVLHLE
LLDTRVKRPEDIENTLQMTLLGVVPNLGKLK

ID19 555 bp (SEQ ID NO: 7)
ATGGTAAAAGTAGCAGTTATATTAGCTCAGGGCTTTGAAGAAATTGAAGC
CTTGACAGTTGTAGATGTCTTGCGTCGAGCCAATATCACATGTGATATGG
TTGGTTTTGAAGAGCAAGTAACGGGTTCGCATGCAATCCAAGTAAGAGCA
GATCATGTCTTTGATGGAGATTTATCGACTATGATATGATTGTTCTTCC
TGGAGGTATGCCTGGTTCTGCACATTTACGTGATAATCAGACCTTGATTC
AAGAATTGCAAGCTTCGACAAGAAGGGGAAGAAACTAGCAGCCATTTGT
GCGGCACCAATTGCCCTCAATCAAGCAGAGATATTGAAAAATAAGCGATA
CACTTGTTATGACGGCGTTCAAGAGCAAATCCTTGATGGTCACTACGTCA
AGGAACAGTAGTGGTAGATGTCAGTTGACAACCAGTCGGGTCCTTCA
ACAGCCCTTGCCTTTGCCTACGAGTTGGTGGAGCAACTAGGAGGGGACGC
AGAGAGTTTACGAACAGGAATGCTCTATCGAGATGTCTTTGGTAAAAATC
AGTAA

TABLE 1-continued (SEQ ID NO: 8)
MVKVAVILAQGFEEIEALTVVDVLRRANITCDMVGFEEQVTGSHAIQVRA
DHVFDGDLSDYDMIVLPGGMPGSAHLRDNQTLIQELQSFEQEGKKLAAIC
AAPIALNQAEILKNKRYTCYDGVQEQILDGHYVKETVVVDGQLTTSRGPS
TALAFAYELVEQLGGDAESLRTGMLYRDVFGKNQ ID27 306 bp (SEQ ID NO: 9)
GTGGTAGGGATGGTAGAACCAAACCTAGAAAGCCTTATAAAAGATCTTTA
CAATCATGCTCGACATGATTTGAGTGAAGATTTAGTTGCTGCTCTCCTAG
AGACTACTAAAAAACTGCCTACTACAAATGAGCAATTGCAGGCAGTTCGT
CTCTCAGGCCTGGTCAATCGTGAATTGCTCCTAAATCCCAAACATCCAGC
ACCTGAGTTGCTCAACTTGGCTCGCTTTGTCAAAAGAGAAGAAGCCAAGT
ACAGAGGAACTGCGACTTCTGCGCTTATGTATGAGGAACTCTTTAAAATG
CTTTGA (SEQ ID NO: 10)
MVGMVEPNLESLIKDLYNHARDLSEDLVAALLETTKKLPTTNEQLQAVRL
SGLVNRELLLNPKHPAPELLNLARFVKREEAKYRGTATSALMYEELFKML ID29 945 bp (SEQ ID NO: 11)
TTGTTCTTAAAAAAGGAAAGAGAGGTAATCAGCATGCGTAAATGGACAAA
AGGATTTCTCATCTTTGGTGTGGTGACTACCGTTATCGGCTTTATCCTGC
TTTTTGTAGGTATCCAATCTGACGGGAtTAAGAGCCTACTTTCCATGTCC
AAAGAACCTGTCTATGATAGCCGTACGGAAAAGCTAACCTTTGGCAAGGA
AGTCGAAAACCTAGAAATTACTCTCCACCAACACACGCTCACCATCACAG
ACTCTTTCGATGATCAAATCCACATTTCTTACCATCCATCTCTTTCTGCT
CACCATGATCTTATCACCAATCAGAACGATAGAACTCTGAGTCTCACTGA
TAAGAAACTGTCTGAAACTCCGTTTCTCTTCTGGAATTGGTGGGATT
CTTCATATCGCAAGTAGCTACTCTAGTCGTTTTGAAGAAGTTATTCTCCG
ACTACCAAAAGGGAGAACTCTAAAAGGGATCAACATCTCAGCCAATCGCG
GACAAACCACCATCATAAATGCTAGCCTTGAAAATGCGACCCTCAATACA
AACAGCTATATCCTCCGAATTGAAGGAAGTCGTATCAAAAACAGTAAACT
CACAACGCCCAATATCGTTAATACTTTGATACAGTTCTTACAGATAGTC
AGCTAGAGTCAACAGAGAATCACTTCCACGCTGAAAATATCCAAGTCCAT
GGCAAGTTGAACTGACTGCCAAAGATTATCTCAGAATCATCCTAGACCAG
AAAGAAAGCCAACGAATTAACTGGGACATCTCAAGCAACTATGGTTCTAT
CTTCCAATTCACAAGAGAAAAGCCTGAATCAAGAGGTACGGAATTAAGCA
ACCCTTACAAAACTGAAAAAACCGATGTCAAGGATCAACTCATTGCGAGA
TCTGATGATAATATTGATCTAATATCCACACCAAGCAGACGTTGA (SEQ ID NO: 12)
MFLKKEREVISMRKWTKGFLIFGVVTTVIGFILLFVGIQSDGIKSLLSMS
KEPVYDSRTEKLTFGKEVENLEITLHQHTLTITDSFDDQIHISYHPSLSA
HHDLITNQNDRTLSLTDKKLSETPFLSSGIGGILHIASSYSSRFEEVILR
LPKGRTLKGINISANRGQTTIINASLENATLNTNSYILRIEGSRIKNSKL
TTPNIVNIFDTVLTDSQLESTENHFHAENIQVHGKVELTAKDYLRIILDQ
KESQRINWDISSNYGSIFQFTREKPESRGTELSNPYKTEKTDVKDQLIAR
SDDNIDLISTPSRR ID30 879 bp (SEQ ID NO: 13)
ATGAAACAAGAATGGTTTGAAAGTAATGATTTTGTAAAAACAACAAGCAA
GAACAAGCCTGAAGAGCAAGCTCAAGAGGTTGCAGCAAGGCTGAAGAAAC
GATAGCCGATCTCGATACACCAATTGAAAAAAATACTCAGTTAGAGGAGG
AAGTCCCTCAAGCTGAAGTCGAATTGGAAAGCCAGCAAGAAGAGAAAATT
GAAGCTCCTGAAGACAGTGAAGCGAGAACAGAAATAGAAGAAAAGAAGGC
ATCTAATTCTACTGAAGAAGAGCCAGACTTTCTAAAGAAACAAGAGAA
TCACTATAGCTGAAGAGAGCCAAGAAGCTCTTCCTCAGCAAAAAGCAACC
ACGAAAGAGCCACTTCTTATCAGTAAATCTTTAGAAAGTCCTTATATCCC
CGACCAAGCTCCAAAATCTAGGGATAAATGGAAAGAGCAAGTGCTTGATT
TTTGGTCTTGGCTAGTGGAAGCAATCAAATCTCCTACAAGTAAGTTGGAA
ACAAGTATCACACACAGTTACACAGCCTTTCTCTTGCTCATTCTGTTTTC
TGCATCTTCCTTTTTCTTTAGTATCTATCACATCAAACATGCTTACTATG
GACATATAGCAAGCATTAACAGTCGCTTCCCTGAGCAGCTAGCTCCTTTA
ACTCTTTTTTCTATCATCTCTATCCTAGTAGCGACAACTCACTTCTTT
TTCATTCCTCTTGGGTAGTTTCGTTGTGAGACGATTTATCCACCAGGAAA
AGGACTGGACGCTAGACAAGGTTCTCCAACAATATAGTCAACTCTTGGCA
ATTCCAATCTCCTCACTGCTATTGTAGTTTCTTGCTTTCTTTGATAGC
CTACGATTTACAGCCCTCTTGTGTGTGA (SEQ ID NO: 14)
MKQEWFESNKFVKTTSKNKPEEQAQEVADKAEETIADLDTPIEKNTQLEE
EVPQAEVELESQQEEKIEAPEDSEARTEIEEKKASNSTEEEPDLSKETEK
VTIAEESQEALPQQKATTKEPLLISKSLESPYIPDQAPKSRDKWKEQVLD FWSWLVEAIKSPTSKLETSITHSYTAFLLLILFSASSFFFSIYHIKHAYY
GHIASINSRFPEQLAPLTLFSIISILVATTLFFFSFLLGSFVVRRFIHQE
KDWTLDKVLQQYSQLLAIPISSLLLLVSLLSLIAYDLQPSCV ID105 990 bp (SEQ ID NO: 15)
ATGCAACTCGCTTCTTCCGGTCTACTCATTGTTCGTCTGGTACAATTTGTT
CTTAAAAAAGGAAAGAGAGGTAATCAGCATGCGTAAATGGACAAAAGGAT
TTCTCATCTTTGGTGTGGTGACTACCGTTATCGGCTTTATCCTGCTTTTT
GTAGGTATCCAATCTGACGGGATTAAGAGCCTACTTTCCATGTCCAAAGA
ACCTGTCTATGATAGCCGTACGGAAAAGCTAACCTTTGGCAAGGAAGTCG
AAAACCTAGAAATTACTCTCCACCAACACACGCTCACCATCACAGACTCTT
TCGATGATCAAATCCACATTTCTTACCATCCATCTCTTTCTGCTCACCAT
GATCTTATCACCAATCAGAACGATAGAACTCTGAGTCTCACTGATAAGAA
ACTGTCTGAAACTCCGTTTCTCTCTTCTGGAATTGGTGGGATTCTTCATA
TCGCAAGTAGCTACTCTAGTCGTTTTGAAGAAGTTATTCTCCGACTACCA
AAAGGGAGAACTCTAAAAGGGATCAACATCTCAGCCAATCGCGGACAAAC
CACCATCATAAATGCTAGCCTTGAAAATGCGACCCTCAATACAAACAGCT
ATATCCTCCGAATTGAAGGAAGTCGTATCAAAAACAGTAAACTCACAACG
CCCAATATCGTTAATACTTTTGATACAGTTCTTACAGATAGTCAGCTAGA
GTCAACAGAGAATCACTTCCACGCTGAAAATATCCAAGTCCATGGCAAGG
TTGAACTGACTGCCAAAGATTATCTCAGAATCATCCTAGACCAGAAAGAA
AGCCAACGAATTAACTGGGACATCTCAAGCAACTATGGTTCTATCTTCCA
ATTCACAAGAGAAAAGCCTGAATCAAGAGGTACGGAATTAAGCAACCCTT
ACAAAACTGAAAAAACCGATGTCAAGGATCAACTCATTGCGAGATCTGAT
GATAATATTGATCTAATATCCACACCAAGCAGACGTTGA (SEQ ID NO: 16)
MQLASSVYSLFVWYNLFLKKEREVISMRKWTKGFLIFGVVTTVIGFILLF
VGIQSDGIKSLLSMSKEPVYDSRTEKLTFGKEVENLEITLHQHTLTITDS
FDDQIHISYHPSLSAHHDLITNQNDRTLSLTDKKLSETPFLSSGIGGILH
ISSYSSRFEEVILRLPKGRTLKGINISANRGQTTIINASLENATLNTNSY
ILRIEGSRIKNSKLTTPNIVNIFDTVLTDSQLESTENHFHAENIQVHGKV
ELTAKDYLRIILDQKEPQRINWDISSNYGSIFQFTREKPESRGTELSNPY
KTEKTDVKDQLIARSDDNIDLISTPSRR ID107 -78 bp (SEQ ID NO: 17)
ATGGATATGTAAAATGAAGCAGGGAGGGAGCAGGGCGTGCTGGGGATGGAG
AGTGGGGAGGGACGCTGCTATTTTAATC (SEQ ID NO: 18)
MICKMKQGGSRACWGWRVGEGRCYFN ID109 714 bp (SEQ ID NO: 19)
CGATAAAGAGGCCTTGAGTAATCTCAATTTGCAGATTGAAAATGGAGAGA
TTATGGGCTTGATTGGTCATAATGGGGCTGGAAAATCGACCACTATAAAA
TCCCTAGTCAGTATCATTTCACCCAGCAGTGGTCGTATTTTGGTAGACGG
TCAGGAGTTATCGGAAAATCGCTTGGCTATTAAACGAAAGATTGGCTACG
TAGCAGACTCGCCTGACTTTTTTCGCTTAACGGCCAATGAATTTTGGG
AATTGATCGCCTCATCCTATGATCTGAGTAGATCTGACTTGGAGGCTAGT
CTAGCTAGGCTATTGAACGTTTTTGATTTTGCTGAAAATCGCTATCAGGT
TATTGAAACTCTTTCTCACGGAATGCGTCAGAAAGTCTTTGTCATCGGAG
CACTCTTGTCTGATCCCGATATTTGGGTTTTGGACGAACCCTTGACTGGT
TTGGATCCCCAGGCTGCCTTTGATTTGAAACAGATGATGAAGGAACATGC
ACAAAAAGGGAAGACAGTCTTGTTTTCAACTCATGTCCTAGAGGTGGCAG
AGCAAGTCTGTGATCGGATTGCCATTTTGAAAAAGGGGCATTTGATTTAT
TGTGGTAAGGTAGAGGACTTGAGGAAAGACCACCCAGACCAGTCTTTGGA
AAGTATCTACCTTAGTCTTGCTGGTAGAAAAGAGGAGGTTGCGGATGCGT
CTCAAGGTCATTAA (SEQ ID NO: 20)
DKEALSNLNLQIENGEIMGLIGHNGAGKSTTIKSLVSIISPSSGRILVDG
QELSENRLAIKRKIGYVADSPDLFLRLTANEFWELIASSYDLSRSDLEAS
LARLLNVFDFAENRYQVIETLSHGMRQKVFVIGALLSDPDIWVLDEPLTG
LDPQAAFDLKQMMKEHAQKGKTVLFSTHVLEAEQVCDRIAILKKGHLIY
CGKVEDLRKDHPDQSLESIYLSLAGRKEEVADASQGH ID112 360 bp (SEQ ID NO: 21)
ATGGCTTTGTTTCAGAGAGAGGAGCAGTACGGAAGACACCAATGGCAAG
TCCAATAATGAGACCTATGATGGTTCCGACGATAGAGATTAAAAGAGTGA
TACCAGCACCACGCAAGAGTTGTTGCCAGTTTTCAGAAAGAATTTTAGCA
ACTTGGCTAAAGAAACTACTGCTAGTCTCTTCAGTTGTTGTAGCTTCGGC
AGGTTGTTCCTGATCATACGATCCATCAAGGCAACTTGGTCATCTTTTG TABLE 1-continued AAATGGTTTCAATGCTGGCATTGATTTGGCTAATACGATTGTCATTTTTA
CGAAGCCCGATAGCGATAGCTGTATCTTCTTCCCCAGTTTTGAAACCAGG
TTCTACTTGA (SEQ ID NO: 22)
MALFSERGAVRKTPMASPIMRPMMVPTIEIKRVIPAPRKSCCQFSERILA
TWLKKLLLVSSVVVASAGCSLIIRSIKATWSSFEMVSMLALIWLIRLSFL
RSPIAIAVSSSPVLKPGST

ID 128 - 3.43

(SEQ ID NO: 23)
ATGAAATTTAGTAAAAAATATATAGCAGCTGGATCAGCTGTTATCGTATC
CTTGAGTCTATGTGCCTATGCACTAAACCAGCATCGTTCGCAGGAAAATA
AGGACAATAATCGTGTCTCTTATGTGGATGGCAGCCAGTCAAGTCAGAAA
AGTGAAAACTTGACACCAGACCAGGTTAGCCAGAAAGAAGGAATTCAGGC
TGAGCAAATTGTAATCAAAATCAGATCAGGGCTATGTAACGTCACACGG
TGACCACTATCATTACTATAATGGGAAAGTTCCTTATGATGCCCTCTTTA
GTGAAGAACTCTTGATGAAGGATCCAAACTATCAACTTAAAGACGCTGAT
ATTGTCAATGAAGTCAAGGGTGGTTATATCATCAAGGTCGATGGAAAATA
TTATGTCTACCTGAAAGATGCAGCTCATGCTGATAATGTTCGAACTAAA
ATGAAATCAATCGTCAAAAACAAGAACATGTCAAAGATAATGAGAAGGTT
AACTCTAATGTTGCTGTAGCAAGGTCTCAGGGACGATATACGACAAATGA
TGGTTATGTCTTTAATCCAGCTGATATTATCGAAGATACGGGTAATGCTT
ATATCGTTCCTCATGGAGGTCACTATCACTACATTCCCAAAAGCGATTTA
TCTGCTAGTGAATTAGCAGCAGCTAAAGCACATCTGGCTGGAAAAAATAT
GCAACCGAGTCAGTTAAGCTATTCTTCAACAGCTAGTGACAATAACACGC
AATCTGTAGCAAAAGGATCAACTAGCAAGCCAGCAAATAAATCTGAAAAT
CTCCAGAGTCTTTTGAAGGAACTCTATGATTCACCTAGCGCCCAACGTTA
CAGTGAATCAGATGGCCTGGTCTTTGACCCTGCTAAGATTATCAGTCGTA
CACCAAATGGAGTTGCGATTCCGCATGGCGACCATTACCACTTTATTCCT
TACAGCAAGCTTTCTGCCTTAGAAGAAAAGATTGCCAGAATGGTGCCTAT
CAGTGGAACTGGTTCTACAGTTTCTACAAATGCAAAACCTAATGAAGTAG
TGTCTAGTCTAGGCAGTCTTTCAAGCAATCCTTCTTCTTTAACGACAAGT
AAGGAGCTCTCTTCAGCATCTGATGGTTATATTTTTAATCCAAAAGATAT
CGTTGAAGAAACGGCTACAGCTTATATTGTAAGACATGGTGATCATTTCC
ATTACATTCCAAATCAAATCAATTTGGGCAACCGACTCTTCCAAACAAT
AGTCTAGCAACACCTTCTCCATCTCTTCCAATCAATCCAGGAACTTCACA
TGAGAAACATGAAGAAGATGGATACGGATTTGATGCTAATCGTATTATCG
CTGAAGATGAATCAGGTTTTGTCATGAGTCACGGAGACCACAATCATTAT
TTCTTCAAGAAGGACTTGACAGAAGAGCAAATTAAGGTGCGCAAAAACAT
TTAG (SEQ ID NO: 24)
MKFSKKYIAAGSAVIVSLSLCAYALNQHRSQENKDNNRVSYVDGSQSSQK
SENLTPDQVSQKEGIQAEQIVIKITDQGYVTSHGDHYHYYNGKVPAYDAL
FSEELLMKDPNYQLKDADIVNEVKGGYIIKVDGKYYVYLKDAAHADNVRT
KDEINRQKQEHVKDNEKVNSNVAVARSQGRYTTNDGYVFNPADIIEDTGN
AYIVPHGGHYHYIPKSDLSASELAAAKAHLAGKNMQPSQLSYSSTASDNN
TQSVAKGSTSKPANKSENLQSLLKELYDSPSAQRYSESDGLVFDPAKIIS
RTPNGVAIPHGDHYHFIPYSKLSALEEKIARMVPISGTGSTVSTNAKPNE
VVSSLGSLSSNPSSLTTSKELSSASDGYIFNPKDIVEETATAYIVRHGDH
FHYIPKSNQIGQPTLPNNSLATPSPSLPINPGTSHEKHEEDGYGFDANRI
IAEDESGFVMSHGDHNHYFFKKDLTEEQIKVRKNI*

TABLE 2

ID2 840 bp (SEQ ID NO: 25)
ATGGGAATTGCTCTAGAAAATGTGAATTTTACATATCAAGAAGGTACTCC
CTTAGCTTCAGCAGCTTTGTCGGATGTTTCTTTGACGATTGAAGATGGCT
CTTATACAGCTTTAATTGGGCACACAGGTAGTGGTAAATCAACTATTTTA
CAACTCTTAAATGGTTTATTGGTGCCAAGTCAAGGGAGTGTGAGGGTTTT
TGATACCTTAATCACCTCGACTTCTAAAAATAAAGATATTCGTCAAATTA
GAAAACAGGTTGGCTTGGTATTTCAGTTTGCTGAAAATCAGATTTTTGAA
GAAACGGTTTTGAAGGACGTTGCTTTTGGACCGCAAAATTTTGGAGTTTC
TGAAGAAGATGCTGTGAAGACTGCGCGTGAGAAACTGGCTCTGGTTGGGA
ATTGATGAACACTTTTTGATCGTAGTCCGTTTGAGCTGTCAGGGGGGAC
AAATGAGACGTGTTGCCATTGCAGGCATACTTGCCATGGAGCCAGCTATA
TTAGTCTTAGATGAGCCAACAGCTGGTCTAGATCCTCTAGGGAGAAAAGA
GTTGATGACCCTGTTCAAAAAATCCACCAGTCAGATCAGGGATGACCATCGTCT
TGGTAACGCATTTGATGGATGATGTTGCTGAATATGCGAATCAAGTCTAT
GTAATGAAAAGGGACGTTTAGTAAAGGGGGGCAAACCAAGTGATGTCTTT
CAAGACGTTGTTTTTATGGAAGAAGTTCAGTTGGGAGTACCTAAAATTA
CGGCCTTTTGTAAACGATTGGCTGATAGACGCGTGTCATTTAAACGATTAC
CGATTAAGATAGAGGAGTTCAAGGAGTCGCTAAATGGATAG

TABLE 2-continued (SEQ ID NO: 26)
MGIALENVNFTYQEGTPLASAALSDVSLTIEDGSYTALIGHTGSGKSTIL
QLLNGLLVPSQGSVRVFDTLITSTSKNKDIRQIRKQVGLVFQFAENQIFE
ETVLKDVAFGPQNFGVSEEDAVKTAREKLALVGIDESLFDRSPFELSGGQ
MRRVAIAGILAMEPAILVLDEPTAGLDPLGRKELMTLFKKLHQSGMTIVL
VTHLMDDVAEYANQVYVMEKGRLVKGGKPSDVFQDVVFMEEVQLGVPKIT
AFCKRLADRGVSFKRLPIKIEEFKESLNG ID 3 6360 bp (SEQ ID NO: 27)
TACCCGGTAGTCTTAGCAGACACATCTAGCTCTGAAGATGCTTTAAACAT
CTCTGATAAAGAAAAAGTAGCAGAAAATAAAGAGAAACATGAAAATATCC
ATAGTGCTATGGAAACTTCACAGGATTTTAAAGAGAAGAAAACAGCAGTC
ATTAAGGAAAAGAAGTTGTTAGTAAAAATCCTGTGATAGACAATAACAC
TAGCAATGAAGCAACAAAATGAAAGAAGAAATTCCAATAAATCCCAAG
GAGATTATACGGACTCATTTGTGAATAAAAACACAGAAAATCCCAAAAA
GAAGATAAAGTTGTCTATATTGCTGAATTTAAAGATAAGAATCTGGAGA
AAAAGCAATCAAGGAACTATCCAGTCTTAAGAATACAAAAGTTTTATATA
CTTATGATAGAATTTTTAACGGTAGTGCCATAGAAACAACTCCAGATAAC
TTGGACAAAATTAAACAAATAGAAGGTATTTCATCGGTTGAAAGGGCACA
AAAAGTCCAACCCATGATGAATCAATGCCAGAAAGGAAATTGGAGTTGAG
GAAGCTATTGATTACCTAAAGTCTATCAATGCTCCGTTTGGGAAAAATTT
TGATGGTAGAGGTATGGTCATTTCAAATATCGATACTGGAACAGATTTA
GACATAAGGCTATGGAATCGATGATGATGCCAAAGCCTCAATGAGATTT
AAAAAAGAAGACTTAAAAGGCACTGATAAAAATTATTGGTTGAGTGATAA
AATCCCTCATGCGTTCAATTATTATAATGGTGGCAAAATCACTGTAGAAA
AATATGATGATGGAAGGATTATTTTGACCCACATGGATGCATATTGCA
GGGATTCTTGCTGGAAATGATACTGAACAAGACATCAAAACATTTAACGG
CATAGATGGAATTGCACCTAATGCACAAATTTTCTCTTACAAAATGTATT
CTGACGCAGGATCTGGGTTTGCGGGTGATGAAACAATGTTTCATGCTATT
GAAGATTCTATCAAACACAACGTTGATGTTGTTTCGGTATCATCTGGTTT
TACAGGAACAGGTCTTGTAGGTGAGAAATATTGGCAAGCTATTCGGGCAT
TAAGAAAGCAGGCATTCCAATGGTTGTCGCTACGGGTAACTATGCGACT
TCTGCTTCAAGTTCTCATGGGATTAGTAGCAAATAATCATCTGAAAATG
ACCGACACTGGAAATGTAACACGAACTGCAGCACATGAAGATGCGATAGC
GGTCGCTTCTGCTAAAATCAAACAGTTGAGTTTGATAAAGTTAACATAG
GTGGAGAAAGTTTTAAATACAGAAATATAGGGGCCTTTTCGATAAGAGT
AAAATCACAACAAATGAAGATGGAACAAAAGCTCCTAGTAAATTAAAATT
TGTATATATAGGCAAGGGGCAAGACCAAGATTTGATAGGTTTGGATCTTA
GGGGCAAAATTGCAGTAATGGATAGAATTTATACAAAGGATTTAAAAAAT
GCTTTTAAAAAAGCTATGGATAAGGGTGCACGCGCCATTATGGTGTAAAT
ACTGTAAATTACTACAATAGAGATAATTGGACAGAGCTTCCAGCTATGGG
ATATGAAGCGGATGAAGGTACTAAAAGTCAAGTGTTTTCAATTTCAGGAG
ATGATGTGTAAAAGCTATGGAACATGATTAATCCTGATAAAAAAACTGAA
GTCAAAAGAAATAAATAAAGAAGATTTTAAAGATAAATTGGAGCAATACTA
TCCAATTGATATGGAAAGTTTTAATTCCAACAAACCGAATGTAGGTGACG
AAAAAGAGATTGACTTTAAGTTTGCACCTGACACAGACAAAGAACTCTAT
AAAGAAGATATCATCGTTCCAGCAGGATCTACATCTTGGGGGCCAAGAT
AGATTTACTTTTAAAACCCGATGTTTCAGCACCTGGTAAAAATATTAAAT
CCACGCTTAATGTTATTAATGGCAAATCAACTTATGGCTATATGTCAGGA
ACTAGTATGGCGACTCCAATCGTGGCAGCTTCTACTGTTTTGATTAGACC
GAAATTAAAGGAAATGCTTGAAAGACCTGTATTGAAAAATCTAATGAAGA
ATGACAAAATAGATCTTACAAGTCTTACAAAAATTGCCCTACAAAATACT
GCGCGACCTATGATGGATGCAACTCTTGGAAAGAAAAAAGTCAATACTT
TGCATCACCTAGACAACAGGGAGCAGGCCTAATTAATGTGGCCAATGCTT
TGAGAATGAAGTTGTAGCAACTTTCAAAAACACTGATTCTAAAGGTTTG
GTAAACTCATATGGTTCCATTTCTCTTAAAGAAATAAAAGGTGATAAAAA
ATACTTTACAATCAAGCTTCACAATACATCAAACAGACCTTTGACTTTTA
AAGTTTCAGCATCAGCGATAACTACAGATTCTCTAACTGACAGATTAAAA
CTTGATGAACATATAAAGATGAAAAATCTCCAGATGGTAAGCAAATTGT
TCCAGAAATTCACCCAGAAAAAGTCAAAGGAGCAAATATCACATTTGAGC
ATGATACTTTCACTATAGGCGCAAATTCTAGCTTTGATTTGAATGCGTTA
TAAATGTTGGAGAGGCCAAAACAAAATAAATTTGTAGAATCATTTATT
CATTTTGAGTCAGTGGAAGCGATGGAAGCTCTAAACTCCAGCGGGAAGAA
AATAAACTTCCAACCTTCTTTGTCGATGCCTCTAATGGGATTTGCTGGGA
ATTGGAACCACGAACCAATCCTTGATAAATGGGCTTGGGAAGGGTCA
AGATCAAAAACACTGGGAGGTTATGATGATGATGGTAAACCGAAATTCC
AGGAACCTTAAATAAGGGAATTGGTGGAGAACATGGTATAGATAAATTA
ATCCAGCAGGAGTTTATCAAAATAGAAAAGATAAAAATACAACATCCTGA
ATCAAAATCCAGAATTATTTGCTTTCAATAACGAAGGGATCAACAAATCTCCA
TCATCAAGTGGTTCTAAGATTGCTAACATTTATCCTTTAGATTCAAATGG
AAATCCTCAAGATGCTCAACTTGAAAGAGGATTAACACCTTCTCCACTTG
TATTAAGAATGCAGAAGAGGATTTCATTCATAATGTAATAACAAATAA
GAGGGAGAAAATCAAAGAGACTTAAAGTCATTCTGAGAGAACACTTTAT
TAGAGGAATTTTAAATTCTAAAAGCAATGATGCAAAGGGAATCAAATCAT
CTAAACTAAAAGTTTGGGGTGACTTGAAGTGGGATGGACTCATCTATAAT
CCTAGAGGTAGAGAAGAAAATGCACCAGAAAGTAAGGATAATCAAGATCC
TGCTACTAAGATAAGAGGTCAATTTGAACCGATTGCGGAAGGTCAATATT

TABLE 2-continued

```
TCTATAAATTTAAATATAGATTCTAAAGATTACCCATGGCAGGTTTCCTA
TATTCCTGTAAAAATTGATAACACCGCCCCTAAGATTGTTTCGGTTGATT
TTTCAAATCCTGAAAAAATTAAGTTGATTACAAAGGATACTTAATCATAA
GGTAAAAGATCAGTATAAGAATGAAACGCTATTTGCGAGAGATCAAAAAG
AACATCCTGAAAAATTTGACGAGATTGCCAACGAAGTTTGGTATGCTGGC
GCCGCTCTTGTTAATGAAGATGGGAGAGGTTGAAAAAAATCTTGAAGTAAC
TTACGCAGGTGAGGGTCAAGGAAGAAATAGAAAACTTGATAAAGACGGAA
ATACCATTTATGAAATTAAAGGTGCGGGAGATTTAAGGGGAAAAATCATT
GAAGTCATTGCATTAGATGGTTCTAGCAATTTCACAAAGATTCATAGAAT
TAAATTTGCTAATCAGGCTGATGAAAAGGGGATGATTTCCTATTATCTAG
TAGATCCTGATCAAGATTCATCTAAATATCAAAAGCTTGGCGAGATTGCA
GAATCTAAATTTAAAAAATTTAGGAAATGAAAAGAGGGGTAGTCTAAAA
AAGATACAACTGGGGTAGAACATCATCATCAAGAAAATGAAGAGTCTAT
TAAAGAAAAAATCTAGTTTTACTATTGATAGAAATATTTCAACAATTAGA
GACTTTGAAAATAAAGACTTAAAGAAACTCATTAAAAAGAAATTTAGAGA
AGTTGATGATTTACAAGTGAAACTGGTAAGAGAATGGAGGAATACGATT
ATAAATACGATGATAAAGGAAATATAGCCTACGATGATGGGACTGAT
CTAGAATATGAAACTGAGAAACTTGACGAAATCAAATCAAAAATTTATGG
TGTTCTAAGTCCGTCTAAAGATGGACACTTTGAAATTCTTGGAAAGATAA
GTAATGTTTCTAAAAATGCCAAGGTATATTATGGGAATAACTATAAATCT
ATAGAAATCAAAGCGACCAAGTATGATTTCCACTCAAAAACGATGACAT
TGATCTATACGCTAATATTAATGATATTGGATGGATTAGCTTTTGCAG
GAGATATGAGATTATTTGTTAAAGATAATGATCAGAAAAAAGCTGAAATT
AAAATTAGAATGCCTGAAAAAATTAAGGAAACTAAATCAGAATATCCCTA
TGTATCAAGTTATGGGAATGTCATAGAATTAGGGGAAGGAGATCTTTCAA
AAAACAAACCAGACAATTTAACTAAAATGGAATCTGGTAAAATCTATTCT
GATTCAGAAAACAACAATATCTGTTAAAGGATAATATCATTCTAAGAAAA
AGGCTATGCACTAAAAGTGACTACCTATAATCCTGGAAAAACGGATATGT
TAGAAGGAAATGGAGTCTATAGCAAGGAAGATATAGCAAAAATACAAAAG
GCCAATCCTAATCTAAGAGCCCCTTTCAGAAACAACAATTTATGCTGATAG
TAGAAATGTTGAAGATGGAAGAAGTACCCAATCTGTATTAATGTCGGCTT
TGGACGGCTTTAACATTATAAGGTATCAAGTGTTTACATTTAAAATGAAC
GATAAAGGGAACTATCGATAAAGACGGAATCTTGTGACGAGATTCTTC
TAAACTTGTATTATTTGGTAAGGATGATAAAGAATACACTGGAGGAGTA
AGTTCAATGTAGAAGCTATAAAGAAGATGGCTCCATGTTATTTATTGAT
ACCAAACCAGTAAACCTTTCAATGGATAAGAACTACTTTAATCCATCTAA
ATCTAATAAAATTTATGTACGAAATCCAGAATTTTATTTAAGAGGTAAGA
TTTCTGATAAGGTGGTTTTAACTGGGAATTGAGAGTTAATGAATCGGTT
GTAGATAATTATTTAATCTACGGAGATTTACACATTGATAACACTAGAGA
TTTTAATATTAAGCTGAATGTTAAAGACGGTGACATCATGGACTGGGAA
TGAAAGACTATAAAGCAAACGGATTTCCAGATAAGGTAACAGATATGGAT
GGAAATGTTTATCTTCAAACTGGCTATAGCGATTTGAATGCTAAAGCAGT
TGGAGTCCACTATCAGTTTTTATATGATAATGTTAAACCCGAAGTAAACA
TTGATCCTAAGGGAAATACTAGTATCGAATATGCTGATGGAAATCTGTA
GTCTTTAACATCAATGATAAAAGAAATAATGGATTCGATGGTGAGATTCA
AGAACAACATATTTATAATGGAAAAGAATATACATCATTTAATGATA
TTAAACAAATAATAGACAAGCAACACTAAACATTAAGATTGTTGTAAAAGAT
TTTGCAAGAAATACAACCGTAAAGAATTCATTTTAAATAAAGATACGGG
AGAGGTAAGTGAATTAAAACCTCATAGGGTAACTGTGACCATTCAAATG
GAAAAGAAATGAGTTCAACGATAGTGTCGGAAGAGATTGTTTATTTTACT
GTTTATAAGGGTGAATTAGAAAAGGATACCAATTTGATGGTTGGGAAATT
TCTGGTTTCGAAGGTAAAAAAGACGCTGGCTATGTTATTAATCTATCAAA
AGATACCTTTATAAAACCTGTATTCAAGAAAATAGAGGAGAAAAAGGAGG
AAGAAAATAAACCTACTTTTGATGTCTGAAAAAAGAAAGATAACCCACAA
GTAAACCATAGTCAATTAAATGAAAGTCACAGAAAAGAGGATTTACAAAG
AGAAGAGCATTCACAAAATCTGATTCAACTAAGGATGTTACAGCTACAG
TTCTTGATAAAAACAATATCAGTAGTAAATCAACTACTAACAATCCTAAT
AAGTTGCCAAAAACTGGAACAGCAAGCGGAGCCCAGACACTATTAGCTGC
CGGAATAATGTTTATAGTAGGAATTTTTCTTGGATTGAAGAAAAAAATC
AAGATTAA
```

(SEQ ID NO: 28)
YPVVLADTSSSEDALNISDKEKVAENKEKHENIHSAMETSQDFKEKTAVI
KEKEVVSKNPVIDNNTSNEEAKIKEENSNKSQGDYTDSFVNKNTENPKKE
DKVVYIAEFKDKESGEKAIKELSSLKNTKVLYTYDRIFNGSAIETTPDNL
DKIKQIEGISSVERAQKVQPMMNHARKEIGVEEAIDYLKSINAPFGKNFD
GRGMVISNIDTGTDYRHKAMRIDDDAKASMRFKKEDLKGRDKNYWLSDKI
PHAFNYYNGGKITVEKYDDGRDYFDPHGMHIAGILAGNDTEQDIKNFNGI
DGIAPNAQIFSYKMYSDAGSFPAGDETMFHAIEDSIKHNVDVVSVSSGFT
GTGLVGEKYWQAIRALRKAGIPMVVATGNYATSASSSSWDLVANNHLKMT
DTGNVTRTAAHEDAIAVASAKNQTVEFDKVNIGGESPKYRNIGAFFDKSK
ITTNEDGTKAPSKLKFVYIGKGQDQDLIGLDLRGKIAVMDRIYTKDLKNA
FKKKAMDKGARAIMVVNTVNYYNRDNWTELPAMGYEADEGTKSQVFSISGD
DGVKLWNMINPDKKTEVKRNNKEDFKDKLEQYYPIDMESFNSNKPNVGDE
KEIDFKFAPDTDKELYKEDIIVPAGSTSWGPRIDLLLKPDVSAPGKNIKS
TLNYINGKSTYGYMSGTSMATPIVAASTVLIRPKLKEMLERPVLKNLKGD
DKIDLTSLTKIALQNTARPMMDATSWKEKSQYFASPRQQGAGLINVANAL
RNEVVATFKNTDSKGLVNSYGSISLKEIKGDKKYFTIKLHNTSNRPLTFK
VSASAIITTDSLTDRLKLDETYKDEKSPDGKQIVPEIHPEKVKGANITFEH
DTFTIGANSSFDLNAVINVGEAKNKNKFVESFIHFESVEAEALNSSGKKI
NFQPSLSMPLMGFAGNWNHEPILDKWAWEEGSRSKTLGGYDDDGKPKIPG
TLNKGIGGEHGIDKFNPAGVIQNRKDKNTTSLDQNPELFAFNNEGINAPS
SSGSKIANIYPLDSNGNPQDAQLERGLTPSPLVLRSAEEGLISIVNTNKE
GENQRDLKVISREHGIRGILNSKSNDAKGIKSSKLKVWGDLKWDGLIYNP
RGREENAPESKDNQDPATKIRGQFEPIAEGQYFYKFKYRLTKDYPWQVSY
IPVKIDNTAPKIVSVDFSNPEKIKLITKDTYHKVKDQYKNETLFARDQKE
HPEKFDEIANEVWYAGAALVNEDGEVEKNLEVTYAGEGQGRNTKLDKDGN
TIYEIKGAGDLRGKIIEVIALDGSSNFTKIHRIKFANQADEKGMISYYLV
DPDQDSSKYQKLGEIAESKFKNLGNGKEGSLKKDTTGVEHHHQENEESIK
EKSSFTIDRNISTIIRDFENKDLKKLIKKKFREVDDFTSETGKRMEEYDY
KYDDKGNIIAYDDGTDLEYETEKLDEIKSKIYGVLSPSKDGHFEILGKIS
NVSKNAKVYYGNNYKSIEIKATKYDFHSKTMTFDLYANINDIVDGLAFAG
DMRLFVKDNDQKKAEIKIRMPEKIKETKSEYPYVSSYGNVIELGEGDLSK
NKPDNLTKMESGKIYSDSEKQQYLLKDNIILRKGYALKVTTYNPGKTDML
EGNGVYSKEDIAKIQKANPNLRALSETTIYADSRNVEDGRSTQSVLMSAL
DGFNIIRYQVFTFKMNDKGEAIDKDGNLVTDSSKLVLFGKDDKEYTGEDK
FNVEAIKEDGSMLFIDTKPVNLSMDKNYFNPSKSNKIYVRNPEFYLRGKI
SDKGGFNWELRVNESVVDNYLIYGDLHIDNTRDFNIKLNVKDGDIMDWGM
KDYKANGFPDKVTDMDGNVYLQTGYSDLNAKAVGVHYQFLYDNVKPEVNI
DPKGNTSIEYADGKSVVFNINDKRNNGFDGEIQEQHIYINGKEYTSFNDI
KQIIDKTLNIKIVVKDFARNTTVKEFILNKDTGEVSELKPHRVTVTIQNG
KEMSSTIVSEEDFILPVYKGELEKGYQFDGWEISGFEGKKDAGYVINLSK
DTFIKPVFKKIEEKKEEENKPTFDVSKKKDNPQVNHSQLNESHRKEDLQR
EEHSQKSDSTKDVTATVLDKNNISSKSTTNNPNKLPKTGTASGAQTLLAA
GIMFIVGIFLGLKKKNQD

ID6 597 bp (SEQ ID NO: 29)
```
CTTGAATTAAATAAAAAACGTCATGCGACTAAGCATTTTACTGATAAGCT
TGTTGATCCCAAAGATGTGCGTACGGCTATCGAAATTGCAACCTTAGCGC
CAAGCGCCCACAACAGCCAGCCTTGGAAATTTGTGGTGGTACGTGAGAAA
AATGCTGAACTGGCAAAGTTAGCTTATGGTTCCAATTTTGAACAGGTATC
ATCAGCGCCTGTAACCATTGCCTTGTTTACAGATACGGACTTAGCCAAAC
GTGCTCGTAAGATTGCCCGTGTTGGTGGTGCTAATAACTTTTCTTGAAGA
GCAACTTCAATATTTTATGAAAAATCTGCCAGCTGAGTTTGCCCGTTACA
GTGAGCAACAAGTCAGCGACTACCTAGCTCTCAATGCAGGTTTGGTTGCC
ATGAACTTGGTTCTTGCATTGACAGACCAAGGAATTGGTTCTAACATTAT
TCTTGGTTTTTGACAATCAAAAGTTAATGAAGTTGGAAATCGAAGACC
GTTTCCGCCCAGAACTCTTGATCACAGTGGGTTATACAGACGAAAAATTG
GAACCAAGCTACCGCTTGCCAGTAGATGAAATCATCGAGAAAAGATAG
```

(SEQ ID NO: 30)
LELNKKRHATKHFTDKLVDPKDVRTAIEIATLAPSAHNSQPWKFVVVREK
NAELAKLAYGSNFEQVSSAPVTIALFTDTDLAKRARKIARVGGANFSEEQ
LQYFMKNLPAEFARYSEQQVSDYLALNAGLVAMNLVLALTDQGIGSNIIL
GFDKSKVNEVLEIEDRFRPELLITVGYTDEKLEPSYRLPVDEIIEKR

ID7 1401 bp (SEQ ID NO: 31)
```
ATGACAGCAATTGATTTTACAGCAGAAGTAGAAAAACGCAAAGAAGACCT
CTTGGCTGACTTGTTTAGCCTTTTGGAAATCAATTCAGAACGTGATGACA
GCAAGGCTGATGCCCAGCATCCATTGGGCCTGGTCCAGTAAAAGCCTTG
GAGAAATTCCTTGAAATCGCAGACCGCATGGCTACCCAACTAAGAATGT
TGATAACTATGCAGGACATTTTGAGTTTGGTGATGGAGAAGAAGTTCTCG
GAATCTTTGCCCATATGGATGTGGTGCCTGCTGGTAGCGGTTGGGACACA
GACCCTTACACACCAACTATCAAAGATGGTCGCCTTTATGCGCGCGGGC
TTCGGACGATAAGGGTCCTACAACAGCTTGTTACTATGGTTTGAAAATCA
TCAAAGAATTGGGTCTTCCAACTTCTAAGAAAGTTCGCTTCATCGTTGGA
ACAGACGAAGAATCAGGCTGGGCAGACATGGACTACTACTTTGAGCACGT
AGGACTTGCCAAACCAGATTTCGGTTTCTCACCAGATGCTGAATTTCCAA
TCATCAATTGGTGAAAAAGGAAATATCACGGAATACCTCCACTTTGCAGGA
GAAAATACAGGTGTTGCCCGTCTTCACACGTTTACAGGTGGTTTACGTGA
AAATATGGTACCAGATATCAGCAACAGCAGTCGTTTCAGGTGACTTGGCTG
ACTTTCAAGCTAACTAGATGCCTTTGTTGCAGAACACAAACTTAGAGGAG
AACTCCAAGAAGAAGCTGGCAAATACAAGGTGACGATCATTGGTAAATCA
GCCCACGGTGCTATGCCTGCTTCAGGTGTCAATGGCGCAACTTACCTTGC
CCTCTTCCTCAGCCAGTTTGGCTTTGCTGGTCCAGCCAAAGACTACCTTG
ACATCGCAGGTAAAATTCCTTGAACGATCATGAGGGTGAAAATCTTAAG
ATTGCTCATGTGGATGAAAAGATGGGTGCCTTTCTATGAATGCCGGCGT
CTTCCACTTCGATGAAACAAGTGCTGATAATACCATTGCCCTCAACATCC
GCTATCCAAAAGGACAAGTCCAGAACAAATCAAGTCAATCCTTGAAAAC
TTGCCAGTTGTTTCTGTTAGCCTGTCTGAACACGGTTCACACGCCTCACTA
TGTGCCAATGGAAGAAATCCACTTGTGCAAACCTTGTTGAATATCTATGAAA
AACAAACTGGCTTTAAGGTCATGAACAAGTCATCGGTGGTGGAACCTTT
GGTCGCTTGCTAGAACGCGGAGTTGCCTACGGTGCTATGTTCCCAGACTC
GATTGATACCATGCACCAAGCCAATGAATTTATCGCCTTGGATGATCTTT
TCCGAGCAGCAGCAATTTATGCCGAAGCTATTTACGAATTGATCAAATAA
```

TABLE 2-continued (SEQ ID NO: 32)
MTAIDFTAEVEKRKEDLLADLFSLLEINSERDDSKADAQHPFGPGPVKAL
EKFLEIADRDGYPTKNVDNYAGHFEFGDGEEVLGIFAHMDVVPAGSGWDT
DPYTPTIKDGRLYARGASDDKGPTTACYYGLKIIKELGLPTSKKVRFIVG
TDEESGWADMDYYFEHVGLAKDFGFSPDAEFPIINGEKGNITEYLHFAGE
NTGVARLHSFTGGLRENMVPESATAVVSGDLADLQAKLDAFVAEHKLRGE
LQEEAGKYKVTIIGKSAHGAMPASGVNGATYLALFLSQFGFAGPAKDYLD
IAGKILLNDHEGENLKIAHVDEKMGALSMNAGVFHFDETSADNTIALNIR
YPKGTSPEQIKSILENLPVVSVSLSEHGHTPHYVPMEDPLVQTLLNIYEK
QTGFKGHEQVIGGGTFGRLLERGVAYGAMFPDSIDTMHQANEFIALDDLF
RAAAIYAEAIYELIK ID8 1617 bp (SEQ ID NO: 33)
GTGTATACTATTATAAAATCAAATATAAAAAAATTTAGTTTATTAACGAT
ATTTATTGTTGCTGGTCAATTATTGCTAATTTATGCAGCAACTATTAATG
CTCTGGTGTTGAATGAATTAATTGCGATGAATTTAGAGCGGTTTTTGAAA
TTGTCAATCTACCAAATGATTGTCTGGTGTGGATAATATTCCTTGACTG
GGTAGTGAAAAATTATCAGATGTTGAAGTGATCCAAGAGTTTAATCTAGAGA
TTCGAAATAGAGTTGCCACAGACATCTCTAACTCTACCTATCAAGAATTT
CATAGTAAATCATCAGGAACATATCTTTCGTGGCTAAATAATGATGTTCA
GACTTTAAATGATCAGGCGTTTAAACAACTTTTTTAGTAATAAAAGGAA
TTTCTGGTACTATATTTGCAGTTGTGACTCTTAATCACTATCATTGGTCA
TTGACTGTAGCCACCTTGTTTTCATTAATGATTATGCTACTTGTACCAAA
AATCTTTGCATCGAAAATGCCGAGAAGTTAGTCTAAATTTAACTAACCAA
AATGAAGCTTTTTTAAAATCTAGTGAGACTATATTGAATGGATTTGATGT
GTTAGCGTCCTTGAATCTTTATATGTATTGCCTAAGAAAATTAAAGAAG
CAGGAATTTTATTAAAGATGGTTATACAAAGAAAGACAACTGTAGAAACG
TTAGCAGGCGCTATTAGCTTCTTTCTCAATATTTTTTTTCAGATATCTC
TCGTTTTTTAACAGGCTATCTTGCAATAAAAGGAATAGTGAAAATTGGT
ACTATTGAAGCAATAGGAGCACTAACAGGTGTTATTTTTACAGCGCTAGG
TGAATTAGGAGGTCAATTATCCTCTATTATGGTACGAAGCCTATTTTTT
AAAATTGTATTCAATTAATCCAATTGAGTCAAATAAAATGAATGATATCG
AACCAAATGAGGTGAATAGAGATTTTCCGTTATATGAAGCAAAAAATATT
TGCTATAAGTATGGAGATAAAGAAATATTAAAAACTTAAATTTTTGTTT
TCAACGTAATGAAAAGTATTAATTTTAGGTGAAAGTGGAACGGGAATC
TACATTATTAAAATTATTGAATGGCTTTTTGAGAGATTATAGTGGAGAAT
TGCGATTCTGCGGGGATATATAAAAAAAACCTCCTATTTAAATATGGTT
TCGAATGTTCTATATGTAGATCAAAAAGCTTATTTGTTTGAAGGTACGAT
TAGAGATAATATTTTATTGGAAGAAAATTATACTGATGAAGAACTTACAC
AGTCTTTAGAGCAAGTTGGTTTGAGTGTAAAAGATTTTCCTAATAACATT
TTAGATTATTATGTTGGTGATGATGGGAGATTACTGTCAGGAGGGCAGAA
ACAAAAAATTACTTTAGCTAGAGGGCTAATTAGAAATAAGAAAATAGTAT
TAATTGACGAGGGAACTTCTGCTATCGATAGGAGAACTTCGTTAGCGATT
GAACGTAAGATATTAGATAGAGAGGATTTGACTGTCATTATTGTTACCCA
TGCTCCGCATCCGGAACTTAAACAATATTTTACTAAGATATATCAATTTC
CAAAGGATTTTATTTAA (SEQ ID NO: 34)
MYTIIKSNIKKFSLLTIFIVAGQLLLIYAATINALVLNELIAMNLERFLK
LSIYQMIVWCGIIFLDWVVKNYQVEVIQEFNLEIRNRVATDISNSTYQEF
HSKSSGTYLSWLNNDVQTLNDQAFKQLFLVIKGISGTIFAVVTLNHYHWS
LTVATLFSLMIMLLVPKIFASKMREVSLNLTNQNEAFLKSSETILNGFDV
LASLNLLYVLPKKIKEAGILLKMVIQRKTTVETLAGAISFFLNIFFQISL
VFLTGYLAIKGIVKIGTIEGALTGVIFTALGELGGQLSSIIGTKPIFLKL
YSINPIESNKMNDIEPNEVNRDFPLYEAKNICYKYGDKILKNLNFCQR
NEKYLILGESGSGKSTLLKLLNGFLRDYSGELRFCGDDIKKTSYLNMVSN
VLYVDQKAYLFEGTIRDNILLEENYTDEEILQSLEQVGLSVKDFPNNILD
YYVGDDGRLLSGGQKQKITLARGLIRNKKIVLIDEGTSAIDRRTSLAIER
KILDREDLTVIIVTHAPHPELKQYFTKIYQFPKDFI ID9 705 bp (SEQ ID NO: 35)
ATAACAGTTAAACAGATTATGGACGAAATAGCCGTTTCAGATATGACTGC
AAGGCGCTATTTACAGGAATTAGCTGATAAAGATTTGCTGATTCGTGTGC
ATGGTGGAGCTGAAAAACTTCGAACCAACTCCCCTTTTGACTAATGAGCGA
TCAAATATTGAAAACAAGCCCTCCAAACGGCAGAAAAACAAGAAATAGC
CCATTTTGCAGGCAGTCTAGTAGAAGAAAGAGAAACTATTTTCATTGGAC
CAGGAACAACATTAGAGTTTTTGCGCGTGAGTTGCCTATTGACAATATC
CGCGTCGTAACCAATGTCTCTGTTTTTCTGATTTTAAGCGAACAAGAA
ATTAACAGATTTGATTTTAATAGGTGGAAATTATCGCGATATTACAGGTG
CTTTTGTTGGTACATTGACCCTACAAAATCTCTCTAATCTCCAATTTTCT
AAAGCTTTCGTTAGCTGTAATGGTATTCAAACGGAGCTCTAGCTACTTT
TAGCGAGGAAGAGGGAGAGGCTCAACGCATCGCTTTAATAATTCTAATA
AAAATATTTACTCGCAGATCATAGCAAGTTCAATAAGTTTGATTTTTAT
ACTTTTTATAATGTATCAAATCTTGATACTATTGTTTCAGATTCTAAACT

AAGTGATTCAATCCTTTTTAAGCTATCTAAACACATTAAAGTCATCAAGC
CTTAA (SEQ ID NO: 36)
ITVKQIMDEIAVSDMTARRYLQELADKDLLIRVHGGAEKLRTNSLLTNER
SNIEKQALQTAEKQEIAHFAGSLVEERETIFIGPGTTLEFFARELPIDNI
RVVTNSLPVFLILSERKLTDLILIGGNYRDITGAFVGTLTLQNLSNLQFS
KAFVSCNGIQNGALATFSEEEGEAQRIALNNSNKKYLLADHSKFNKFDFY
TFYNVSNLDTIVSDSKLSDSILFKLSKHIKVIKP

ID10 483 bp (SEQ ID NO: 37)
ATGACTGAGTTTTCGTTAGATCTTCTTCTAGAAGCCATTAAACTAGCTCG
TTGGACCTACTACTATCACTTGAAACAGCTAGACAAAACAGATAAAGACC
AAGAGCTTAAAACTGAAATTCAATCCATCTTTATCGAACACAAGGGAAAT
TATGCTTATCGCCGGGTTCATTTAGAACTAAGAAATCGTGGTTATCTGGT
AAATCATAAAAGAGTTCAAGGCTTGaTGAAAGTACTCAATTTACAAGCTA
AAATGCAAAGAAACGAAAATATTCTTCTCATAAAGGAGACGTTGGTAAG
AAGGCAGAGAATCTCATTCAAGCCCAATTTGAAGGCTCTAAAACAATGGA
AAAGTGCTACACAGATGTGACTGAATTTGCCATTCCAGCAAGTACTCAAA
AGCTTTACTTATCACCAGTTTTAGATGGCTTTAACAGCGAAATTATTGCT
TTTAATCTTTCTTGTTCGCCTAATTTAGAATAA (SEQ ID NO: 38)
MTEFSLDLLLEAIKLARWTYYYHLKQLDKTDKDQELKTEIQSIFIEHKGNY
AYRRVHLELRNRGYLVNHKRVQGLMKVLNLQAKMRKKRKYSSHKGDVGKK
AENLIQAQFEGSKTMEKCYTDVTEFAIPASTQKLYLSPVLDGFNSEIIAF
NLSCSPNLE

ID14 1266 bp (SEQ ID NO: 39)
CCAGGATTGGTACCGTTGCAAGTGGTGTGCCTTTCCTCCTAAAGGAAAA
TGGAGGAAAAATCAATCAATCAGCACATTCAGATATCAAAGTTGCTAAGG
TATTGGTCAAGGATGAAGATGAAAAAAATCGCTTGCTTGCAGCAGGGAAT
GACTTTAACTTTGTAACCAATGTGGATGATATTTTATCAGACCAGGATAT
TACTATCGTAGTGGAATTGATGGGCGTATTGAGCCTGCTAAAACCTTTA
TCACTCGTGCCTTGGAAGCTGGAAAACACGTTGTTACTGCTAACAAGGAC
CTTTTAGCTGTCCATGGCGCAGAATTGCTAGAAATCGCTCAAGCTAACAA
GGTAGCACTTTACTACGAAGCAGCAGTTGCTGGTGGGATTCCAATTCTTC
GTACTTTAGCAAATTCCTTGGCTTCTGATAAAATTACGCGCGTGCGTTGGA
GTAGTCAACGGAACTTCCAACTTCATGGTGACCAAGATGGTGGAAGAAGG
CTGGTCTTACGATGATGCTCTTGCGGAAGCACAACGTCTAGGATTTGCAG
AAAGCGATCCGACGAATGACGTAGATGGGATTGATGCAGCCTACAAGATG
GTTATTTGAGCCAATTTGCCTTGGCATGAAGATTGCCTTTGATGAGT
AGCCCACAAGGGAATCCGCAATATCACACCAGAAGACGTAGCGTAGCTC
AAGAGCTTGGTTACGTAGTGAAATTGGTTGGTTCTATTGAGGAACTTCT
TCAGGTATTGCTGCAGAAGTGACTCCAACCTTCCTACCTAAAGCGCACCC
ACTTGCTGGTGTGAATGGCGTAATGAACGCTGTCTTTGTAGAAATCTACG
GTATTGGTGAGTCTATGTACTACGACCAGGTGCGGGTCAAAAACCAACT
GCAACAAGTGTTGTAGCTGATATTGTCCGTATCGTTCGTCGTTGAATGA
TGGTACTATTGGCAAAGACTTCAACGAATATGCCGTGACTTGGTCTTGGC
AAATCGTGAAGATGTCAAAGCAAACTACTATTTCTCAATCTTGGCTCTAG
ACTCAAAAGGTCAGGTCTTGAAGTTGGCTGAAATCTTCAATGCTCAAGAT
ATTTCCTTTAAGCAAATCCTTCAAGATGGCAAAGAGGGTGACAAGGCGCG
TGTCGTTATCATCACACAAGATTAATAAAGCCCAGCTTGAAAATGTCT
CAGCTGAATTGAAGAAGGTTTCAGAATTCGACCTCTTGAATACCTTCAAG
GTGCTAGGAGAATAA (SEQ ID NO: 40)
PGFGTVASGVPFLLKENGGKINQSAHSDIKVAKVLVKDEDEKNRLLAAGN
DFNFVTNVDDILSDQDITIVVELMGRIEPAKTFITRALEAGKHVVTANKD
LLAVHGAELLEIAQANKVALYYEAAVAGGIPILRTLANSLASDKITRVLG
VVNGTSNFMVTKMVEEGWSYDDALAEAQRLGFAESDPTNDVDGIDAAYKM
VILSQFAFGMKIAFDDVAHKGIRNITPEDVAVAQELGYVVKLVGSIEETS
SGIAAEVTPTFLPKAHPLASVNGVMNAVFVESIGIGESMYYGPGAGQKPT
ATSVVADIVRIVRRLNDGTIGKDFNEYSRDLVLANPEDVKANYYFSILAL
DSKGQVLKLAEIFNAQDISFKQILQDGKEGDKARVVIITHKINKAQLENV
SAELKKVSEFDLLNTFKVLGE

ID16 1725 bp (SEQ ID NO: 41)
ATGAAACACCTATTATCTTACTTCAAACCCTACATCAAGGAATCAATTTT
AGCCCCCTGTTCAAGCTGTTAGAAGCTGTTTTTGAGCTCTTGGTTCCCA
TGGTGATTGCTGGGATTGTTGACCAATCTTTACCTCAGGGAGATCAAGGT
CATCTCTGGATGCAGATTGGCCTGCTCCTTATCTTTGCAGTAATTGGCGT
TTTAGTGGCCTTGATAGCTCAATTTTACTCAGCAAAGGCAGCAGTAGGTT
CTGCTAAGGAATTGACAACGATCTTTATCGTCATATCTTTCCTTGCCC
AAGGACAGCAGAGACCGTCTGACAACTTCTAGTTTGGTCACTCGCTTGAC

TABLE 2-continued

TTCGGATACCTACCAGATTCAGACTGGTATCAATCAATTCCTGCGTCTCT
TTTTTACGAGCGCCCATTATCGTTTTTGGTGCCATTTTTATGGCTTATCGA
ATCTCAGCTGAGTTGACTTTCTGGTTCTTAGTCTTGGTTGCCATTTTGAC
CATTGTCATTGTAGGGTTATCTCGATTGGTCAATCCTTTCTACAGTAGTT
TCAGAAAGAAAACGGACCAACTGGTTCAGGAAACGCGCCAGCAATTGCAA
GGGATGCGGGTTATTCGTGCTTTTGGTCAAGAAAACGAGAGTTACAGAT
TTTTCAAACCCTTAACCAAGTTTATGCTAGATTACAAGAAAAGACAGGTT
TCTGGTCTAGTTTATTAACACCTCTGACCTATCTGATTGTCAATGGAACT
CTTCTCGTTATTATCTGGCAAGGCTATATTTCAATTCAAGGAGGAGTGCT
CAGTCAAGGTGCTCTCATTGCTCTTATCAATTACCTCTTACAGATTTTGG
TGGAATTGGTCAAGCTAGCCATGTTGATCAATTCCCTCAACCAGTCCTAT
ATCTCAGTCAAGCGAATCGAGGAAGTCTTTGTTGAGGCTCCAGAGGATA
CCATTCAGAGTTAGAACAAAAGCAAGCTACCAGAGATAAGGTTTTACAAG
TCCAAGAATTGACCTTTACCTATCCTGATGCGGCCCAGCCTTCTCTGAGA
TACATTTCCTTTGATATGACTCAAGGACAAATTCTAGGTATCATCGGGGG
AACTGGTTCTGGTAAATCAAGCTTGGTGCAACTCTTACTTGGACTTTATC
CAGTAGACAAGGGGAACTTGCCTTTATCAAAATGGACGTAGCTCCTCTT
AATTTGGAGCAGTGGCGGTCTTGGATTGCCTATGTACCTCAAAAGGTCGA
ACTCTTTAAAGGAACCATTCGTTCCAACTTGACTCTAGGTTTCAATCAAG
AAGTATCTGACCAGGAACTCTGGCAGGCCTTGGAGATTGCGCAAGCTAAG
GATTTTGTCAGTGAAAAGGAAGGACTCTTGGATGCTCTAGTTGAGGCGG
GGGGCGAAATTTCTCAGGTGGACAAAACAAAAGATTGCTCTATCGCCCGAG
CAGTCTTGCGCCAGGCTCCGTTTCTCATCCTAGATGATGCAACCTCGGCA
CTGGATACCATTACAGAGTCCAAGCTCTTGAAAGCTATTAGAGAAATTT
TCCAAACACGAGCTTAATTTTGATCTCTCAACGAACCTCAACTTTACAGG
TGGCGGACCAGATTCTCCTCTTGAAAAAGGTGAGTTGCTAGCTGTTGGC
AAGCACGATGACTTGATGAAATCCAGCCAAGTCTATTGTGAAATCAATGC
ATCCCAACATGGAAGGAGGACTAG (SEQ ID NO: 42)
MKHLLSYFKPYIKESILAPLFKLLEAVFELLVPMVIAGIVDQSLPQGDQG
HLWMQIGLLIFAVIGVLVALIAQFYSAKAAVGSAKELTNDLYRHILSLPK
DSRDRLTTSSLVTRLTSDTYQIQTGINQFLRLFLRAPIIVFGAIFMAYRI
SAELTFWFLVLVAILTIVIVGLSRLVNPFYSSLRKKTDQLVQETRQQLQG
MRVIRAFGQEKRELQIFQTLNQVYARLQEKTGFWSSLLTPLTYLIVNGTL
LVIIWQGYISIQGGVSLQGALIALINYLLQILVELVKLAMLINSLNQSYI
SVKRIEEVFVEAPEDIHSELEQKQATRDKVLQVQELTFTYPDAAQPSLRY
ISFDMTQGQILGIIGGTGSGKSSLVQLLLGLYPVDKGNIDLYQNGRSPLN
LEQWRSWIAYVPQKVELFKGTIRSNLTLGFNQEVSDQELWQALEIAQAKD
FVSEKEGLLDALVEAGGRNFSGGQKQRLSIARAVLRQAPFLILDDATSAL
DTITESKLLKAIRENFPNTSLILISQRTSTLQMADQILLLEKGELLAVGK
HDDLMKSSQVYCEINASQHGKED

ID18 1224 bp (SEQ ID NO: 43)
ATGAAACGTTCTCTCGACTCAAGAGTCGATTACAGTTTGCTCTTGCCAGT
ATTTTTTTCTACTGGTCATCGGTGTGGTGGCTATCTATATAGCCGTTAGTC
ATGATTATCCCAATAATATTCTGCCCATTTTAGGGCAGCAGGTCGCCTGG
ATTGCCTTGGGGCTTGTGATTGGTTTTGTGGTCATGCTCTTTAATACAGA
AATTTCTTTGGAAGGTGACCCCCTTCTATATATTTAGGCTTGGGACTTA
TGATCTTGCCGATTGTATTTTATAATCCAAGCTTAGTTGCATCAACGGGT
GCCAAAAACTGGGTATCAATAAATGGAATTACCCTATTCCAACCGTCAGA
ATTTATGAAGATATCCTATATCCTCATGTTGGCTCGTGTCATTGTCAT
TTACAAAGAAACATAAGGAATGGAGACGCACGGTTCCGCTGGACTTTTG
TTAATTTTCTGGATGATTCTCTTTACCATTCCAGTCCTAGTTCTTTTAGC
ACTTCAAAGTGACTTGGGGACGGCTTTGGTTTTGTAGCCATTTTCTCAG
GAATCGTTTTATTATCAGGGGTTTCTTGGAAAATTATTATCCAGTATTT
GTGACTGCTGTAACAGGAGTTGCTGGTTTCTTAGCTATCTTTATTAGCAA
GGACGGACGAGCTTTTCTTCACCAGATTGGAATGCCGACCTACCAATTA
ATCGGATTTTGGCTTGGCTCAATCCCTTTGAGTTTGCCCAAACAACGACT
TACCAGCAGGCTCAAGGGCAGAATGCCATTGGGAGTGGTGGCTTATTTGG
TCAGGGATTTAATGCTTCGAATCTGCTTATCCCAGTTCGAGAGTCAGATA
TGATTTTTACGGTTATTGCAGAAGATTTTGGCTTTATTGGCTCTGTCCTG
GTTATTGCCCTCTATCTCATGTTGATTTACCGTATGTTGAAGATTACTCT
TAAATCAAATAACCAGTTCTACACTTATATTTCCACAGGTTTGATTATGA
TGTTGCTCTTCCACATCTTTGAGAATATCGGTGCTGGTACTGGACTACTTT
CCTTTGACTGGGGATTCCCTTGCCTTTCATTTCGCAAGGGGGATCAGCTAT
TATCAGTAATCTGATTGGTGTTGGTTTGCTTTTATCGATGAGTTACCAGA
CTAATCTAGCTGAAGAAAAGAGCGGAAAAGTCCCATTCAAACGGAAAAG
GTTGTATTAAAACAAATTAAATAA (SEQ ID NO: 44)
MKRSLDSRVDYSLLLPVFFLLVIGVVAIYIAVSHDYPNNILPILGQQVAW
IALGLVIGFVVMLFNTEFLWKVTPFLYILGLGLMILPIVFYNPSLVASTG
AKNWVSINGITLFQPSEFMKISYILMLARVIVQFTKKHKEWRRTVPLDFL
LIFWMILFTIPVLLLALQSDLGTALVFVAIFSGIVLLSGVSWKIIIPVF
VTAVTGVAGFLAIFISKDGRAFLHQIGMPTYQINRILAWLNPFEFAQTTT
YQQAQGQIAIGSGGLFGQGFNASNLLIPVRESDMIFTVIAEDFGIFGSVL
VIALYLMLIYRMLKITLKSNNQFYTYISTGLIMMLLFHIFENIGAVTGLL

PLTGIPLPFISQGGSAIISNLIGVGLLLSMSYQTNLAEEKSGKVPFKRKK
VVLKQIK

ID22 987 bp (SEQ ID NO: 45)
ATGGTGGCTAAGAAAAAAATCTTATTTTTTATGTGGTCTTTTTCTCTTGG
AGGTGGTGCAGAGAAGATTCTATCAACCATTGTTTCAAATCTGGATCCAG
AAAAGTATGATATTGATATTCTTGAAATGGAGCACTTTGACAAGGGATAT
GAATCGTTCCAAAGCATGTACGCATTTTAAATCCCTTCAAGATTATCG
CCAAACCAGATGGTTACGAGCTTTTTTGTGGAGAATGAGAATTTATTTC
CAAGACTGACTCGTCGTTTGCTTGTAAAAGATGATTATGATGTTGAAGTT
TCTTTTACCATTATGAATCCACCCACTGTTGTTCTCTAAAAGAAGAGAAGT
CAAGAAGATACTTGGATTCATGGAAGTATTGAAGAACTTCTTAAGGATA
GCTCTAAAGAGATACATAGAAGCCAGTTGGATGCTGCGAATACAATTG
TAGGGATTTCAAAAAGGACCAGCAATTCTATCAAGGAAGTTTATCCAGAT
TATACTTCTAAATTACAGACAATCTACAATGGATATGATTTTCAGACTAT
TCTAGAAAAATCTCAAGAGAAGATCGATATCGAGATTGCTCCTCAAAGTA
TCTGTACTATCGGACGGATTGAGGAAATAAGGGTTCTGACCGTGAGTGG
AAGTGATACGATTATTACACCAAGAGGGAAAAAACTATCATCTATTT
ATCGGGCTGATGAAGAGGAACTGAAAAAACGAGTCAAAGAGTA
TGGGATTGAGGACTATGTACATTTCCTTGGTTATCAAAAAAATCCTTATC
AGTACTATCTCAGACGAAAGTTCTTTTGTCTATGTCTAAACAAGAAGGT
TTTCCTGGAGTGTATGTGGAGGCCTTGAGTCTGGGACTCCCTTTTATCTC
TACGGACGTTGGAGGGGCTGAGGAATTATCCCAAGAAGGGACGATTTGGAC
AAATCATTGAGAGCAATCAAGAGGCAGCTCAGGCGATTACTAATTACATG
ACTTCTGCCTCAAACTTGATGTCGATGAGGCTAGCCAATTCATTCAACAA
TTTACAATTACAAAACAAATCGAACAAGTAGAAAAACTATTAGAGGAGTA
G (SEQ ID NO: 46)
MVAKKKILFFMWSFSLGGGAEKILSTIVSNLDPEKYDIDILEMEHFDKGY
ESVPKHVRILKSLQDYRQTRWLRAFLWRMRIYFPRLTRRLLVKDDYDVEV
SFTIMNPPLLFSKRREVKKISWIHGSIEELLKDSSKRESHRSQLDAANTI
VGISKKTSNSIKEVYPDYTSKLQTIYNGYDFQTILEKSQEKIDIEIAPQS
ICTIGRIEENKGSDRVVEVIRLLHQEGKNYHLYFIGAGDMEEELKKRVKE
YGIEDYVHFLGYQKNPYQYLSQTKVLLSMSKQEGFPGVYVEALSLGLPFI
STDVGGAEELSQEGRFGQIIESNQEAAQAITNYMTSASNFDVDEASQFIQ
QFTITKQIEQVEKLLEE

ID23 1434 bp (SEQ ID NO: 47)
ATGGAAACTGCATTAATTAGTGTGATTGTGCCAGTCTATAATGTGGCGCA
GTACCTAGAAAAATCGATAGCTTCCATTCAGAAGCAGACCTATCAAAATC
TGGAAATTATTCTTGTTGATGATGGTGCAACAGATGAAAGTGGTCGCTTG
TGTGATTCAATCGCTGAACAAGATGACAGGGTGTCAGTGCTTCATAAAAA
GAACGAAGGATTGTCGCAAGCACGAAATGATGGGATGAAGCAGGCTCACG
GGGATTATCTGATTTTTATTGACTCAGATGATTATATCCATCCAGAAATG
ATTCAGACGTTATATGAGCAATTAGTTCAAGAAGATGCGGATGTTTCGAG
CTGTGGTGTCATGAATGCTATGCTAATGATGAAGCCCACAGTCAGCCAA
TCAGGATGACTATTTGTCTGTGATTCTCAAACATTTCTAAAGGAATACC
TCATAGGTGAAAAATACCTGGGACGATTTGCAATAAGCTAATCAAGAGA
GACAGATTGCAACTGCCCCTATCCTTTCCTCAAGGGGTTGATTTACGAAGAT
GCCTATTACCATTTTGATTTAATCAAGTTGGCCAAGAAGTATGTGGTTAA
TACTAAACCCTATTATTACTATTTCCATAGAGGGGATAGTATTACGACCA
AACCCTATGCAGAGAAGGATTTAGCCTATATTGATATCTACCAAAAGTTT
TATAATGAAGTTGTGAAAAACTAGCCTGACTTGAAAGAGGTCGCTTTTT
CAGATTGGCTATGCCCACTTCTTTATTCTGGATAAGATGTTGCTAGATG
ATCAGTATAAACAGTTTGAAGCCTATTCTCAGATTCATCGTTTTTAAAAG
GCCATGCCTTTGCTATTTCTAGGAATCCAATTTTCCGTAAGGGGAGAAGA
ATTAGTGCTTTGGCCCTATTCATAAATATTTCCTTATATCGATTCTTATT
ACTGAAAAATATTGAAAAATCTAAAAAATTACATTAG (SEQ ID NO: 48)
METALISVIVPVYNVAQYLEKSIASIQKQTYQNLEIILVDDGATDESGRL
CDSIAEQDDRVSVLHKKNEGLSQARNDGMKQAHGDYLIFIDSDDYIHPEM
IQSLYEQLVQEDADVSSCGVMNVYANDESPQSANQGGYFVCDSQTFLKEY
LIGEKIPGTICNKLIKRQIATALSPPKGLIYEDAYYHFDLIKLAKKYVVN
TKPYYYYFHRGDSITTKPYAEKDLAYIDIYQKFYNEVVKNYPDLKEVAFF
RLAYAHFFILDKMLLDDQYKQFEAYSQIHRFLKGHAFAISRNPIFRKGRR
ISALALFINISLYRFLLLKNIEKSKKLH

ID24 735 bp (SEQ ID NO: 49)
ATGAGAATCAAAGAGAAACCAATAATATTAATGGAGGAATAAAAAATGT
AAGTAAGCATTATGGTCATTCAATCATTCTCAAAGATATAAATTTTGCAC
TTAACAAGGGTGAAATTGTTGGTCTAGCAGGGAGAAATGGAGTTGGTAAG
AGTACGTTGATGAAAATTCTTGTTCAGAATAATCAACCGACTTGCAGGTAA

TABLE 2-continued

```
TATTATAAGCAGTGATAATGTTGGGTATTTAATCGAAGAACCAAATTATT
TTTATCTAAAACAGGTTTAGAGAATTTAAAATATTTGTCAAATTTATATG
GTGTTGACTACAATCAAGAAAGATTTAGATGTTTGATCCAAGAGTTAGAT
TTGACTCAGTCTATTAATAAAAAAGTAAAGACCTATTCTTTGGGTACAAA
ACAAAAATTAGCTTTGCTTCTAACTCTCGTTACGGAACCTGATATATTGA
TTTTAGATGAACCGACTAATGTTTAGATATTGAATCATCACAAATAGTT
TTAGCGGTTCTAAAAAAATTAGCTTTACATGAAAATGTGGGAATTTTAAT
ATCGAGTCATAAATTAGAAGACATTGAAGAAATTTGTGAGAGAGTTCTTT
TCTTGGAGAACGGGCTTTTGACATTTCAAAAAGTAGGAAAAGATAGTCAT
AATTTCTTGTTTGAGATAGCTTTTTCATCAGCTACAGATAGAGACATTTT
CATTACCAAACAAGAATTTTGGGATATTGTTTAG
```

(SEQ ID NO: 50)
MRIKEKTNNINGGIKNVSKHYGHSIILKDINFALNKGEIVGLAGRNGVGK
STLMKILVQNNQPTSGNIISSDNVGYLIEEPKLFLSKTGLENLKYLSNLY
GVDYNQERFRCLIQELDLTQSINKKVKTYSLGTKQKLALLLLTLVTEPDIL
ILDEPTNGLDIESSQIVLAVLKKLALHENVGILISSHKLEDIEEICERVL
FLENGLLTFQKVGKDSHNFLFEIAFSSATDRDIFITKQEFWDIV

ID25 1704 bp (SEQ ID NO: 51)
```
ATGACTGAATTAGATAAACGTCACCGCAGTAGCATTTATGACAGCATGGT
TAAATCACCTAACCGTGCTATGCTTCGTGCGACTGGTATGACAGATAAGG
ACTTTGAAACATCGATTGTGGGAGTGATTTCGACTTGGGCGGAAAATACA
CCATGTAACATTCACTTGCATGATTTCGGGAACTGGCTAAAGAAGGTGT
CAAATCTGCAGGCGCTTGGCCTGTACAGTTTGGAACCATTACCGTAGCGG
ACGGGATCGCTATGGGAACGCCTGGTATGCGTTTCTCTCTAACATCTCGT
GACATCATCGCGGACTCCATCGAGGCGGCTATGAGTGGTCACAACGTGGA
TGCCTTCGTCGCTATCGGTGGCTGTGACAAGAACATGCCTGGATCTATGA
TTGCTATTGCTAATATGGATATCCCAGCTATTTTCGCCTATGGTGGAACT
ATTGCACCGGGAAATCTTGATGGTAAAGATATCGACTTGGTTTCTGTCTT
TGAAGGTATCGGAAAATGGAACCACGGTGACATGACAGCTGAAGACGTGA
AACGTCTTGAATGTAATGCCTGCCCTGGCCCTGGTGGTTGTGGTGGTATG
TATACTGCTAATACCATGGCAACTGCTATCGAAGTTCTAGGGATGAGTTT
GCCAGGGTCATCCTCTCACCCAGCTGAATCAGCTGATAAGAAAGAAGATA
TCGAAGCAGCAGGACGTGCTGTTGTTAAGATGTTGGAACTTGGTCTCAAA
CCATCAGATATCTTGACTCGTGAAGCCTTTGAAGATGCTATCGTTGTAAC
GATGGCTCTCGGTGGTTCTACAAACGCCACTCTTCACTTGCTCGCCATTG
CCCATGCCGCAAATGTTGACTTGTCACTTGAGGACTTCAATACGATTCAA
GAACGTGTGCCTCACTTGGCCGACTTGAAACCATCTGGTCAGTATGTCTT
CCAAGACCTCTACGAAGTCGGTGGTGTCCCTGCGGTTATGAAGTATTTGT
TGGCAAATGGTTTCCTTCACGGAGATCGCATCACATGTACTGGTAAGACT
GTAGCTGAAAACTTTGCTGACTTTGCAGACTTGACTCCAGGCCAAAAG
TTATCATGCCACTTGAAAATCCAAACGTGCGGATGGTCCGCTTATCATC
TTGAACGGGAACCTTGCTCCTCGACGGTGCAGTTGCCAAGGTATCAGGTGT
TAAAGTGCGTCGTCACGTTGGGCCAGCTAAGGTCTTTGACTCAGAAGAAG
ATGCCGATTCAGGCCGTTCTGACAGATGAAATCGTTGATGGCGATGTAGTC
GTTGTTCGTTTTGTTGGACCTAAAGGTGGTCCTGGTATGCCTGAGATGCT
ATCACTTCTTCAATGATTGTTGGTAAAGGTCAAGGAGATAAGGTGGCCGT
CTTGACGGACGGACGTTTCTCTGGTGGTACTTATGGTCTGGTTGTTGGAC
ATATCGCTCCTGAAGCTCAGGATGGTGGACCAATTGCCTATCTCCGTACC
GGCGATATCGTTACGGTTGACCAAGATACCAAAGAAATTTCTATGGCCGT
ATCCGAAGAAGAACTTGAAAAACGCAAGGCAGAAACAACCTTGCCACCAC
TTTACAGCCGTGGTGTCCTCGGTAAATATGCCCACATCGTATCATCTGCT
TCACGCGGAGCCGTGACAGACTTCTGGAATATGGACAAGTCAGGTAAAAA
ATAA
```

(SEQ ID NO: 52)
MTELDKRHRSSIYDSMVKSMVKSPNRAMLRATGMTDKDFETSIVGVISTW
AENTPCNIHLHDFGKLAKEGVKSAGAWPVQFGTITVADGIAMGTPGMRFS
LTSRDIIADSIEAAMSGHNVDAFVAIGGCDKNMPGSMIAIANMDIPAIFA
YGGTIAPGNLDGKDIDLVSVFEGIGKWNHGDMTAEDVKRLECNACPGPGG
CGGMYTANTMTAIEVLGMSLPGSSSHPAESADKKEDIEAAGRAVVKMLE
LGLKPSDILTREAFEDAITVTMALGGSTNATLHLLAIAHAANVDLSLEDF
NTIQERVPHLADLKPSGQYVFQDLYEVGGVPAVMKYLLANGFLHGDRITC
TGKTVAENLADFADLTPGQKVIMPLENPKRADGPLIILNGNLAPDGAVAK
VSGVKVRRHVGPAKVFDSEEDAIQAVLTDEIVDGDVVVVRFVGPKGGPGM
PEMLSLSSSMIVGKGQGDKVALLTDGRFSGGTYGLVVGHLAPEAQDGGPIA
YLRTGDIVTVDQDTKEISMAVSEEELEKRKAETTLPPLYSRGVLGKYAHI
VSSASRGAVTDFWNMDKSGKK

ID26 274 bp (SEQ ID NO: 53)
```
ATGTTATAATAAAAATAAAGAATTTAAGGAGAAATACAATATGTCAATTT
TTATTGGAGGAGCATGGCCATATGCAAACGGTTCGTTACATATTGGTCAC
GCGGCAGCGCTTTTACCGGGGGATATTCTTGCAAGATACTATCGTCAGAA
GGGAGAGGAAGTTTTATATGTTTCTGGAAGTGATTGTAATGGAACCCCTA
```

TABLE 2-continued

```
TTTCTATCAGAGCTAAAAAAGAAAATAAGTCTGTGAAAGAAATTGCTGAT
TTTTATCATAAGGAATTTAATCCA
```

(SEQ ID NO: 54)
CYNKNKEFKEKYNMSIFIGGAWPYANGSLHIGHAAALLPGDILARYYRQK
GEEVLYVSGSDCNGTPISIRAKKENKSVKEIADFYHKEFNP

ID28 1065 bp (SEQ ID NO: 55)
```
ATGACAACATTATTTTCAAAAATTAAAGAAGTAACAGAACTTGCTGCAGT
CTCAGGTCATGGAGCCCTGTCCGTGCTTATCTTCGTGAAAAGTTGACAC
CGCATGTGGATGAAGTGGTGACAGATGGCTTGGGTGGTATTTTTGGTATC
AAACATTCAGAAGCTGTGGATGCACCGCGCGTCTTGGTCGCTTCTCATAT
GGACGAAGTTGGTTTTATGGTCAGCGAAATCAAGCCAGATGGTACCTTCC
GTGTCGTAGAAATCGGTGGCTGGAACCCCATGGTGGTTAGCAGCCAACGT
TTCAAACTCTTGACTCGTGATGGTCATGAAATTCCTGTGATTTCAGGTTC
TGTTCCTCCGCATTTGACTCGTGGAAAGGGGGACCAACCATGCCAGCCA
TTGCCGATATCGTTTTTGATGGTGGTTTTGCGGACAAGGCTGAGGCAGAA
AGTTTTGGCATCCGTCCTGGTGATACCATTGTACCAGATAGTTCTGCAAT
TTTGACAGCCAATGAAAAAAATATCATCTCAAAAGCTTGGGATAACCGCT
ACGGTGTCCTCATGGTAAGCGAGCTAGCTGAAGCTTTATCGGGTCAAAAA
CTCGGCAATGAACTCTATCTGGGTTCTAACGTCAAGAAGAAGTTGGTCT
GCGTGGCGCTCATACCTCTACAACCAAGTTTGACCCAGAAGTCTTCCTCG
CAGTTGATTGCTCACCAGCAGGTGATGTCTACGGTGGTCAAGGCAAGATT
GGAGATGGAACGTTGATTCGTTTCTATGATCCAGGTCACTTGCTTCTCCC
AGGGATGAAGGATTTCCTTTTGACAACGGCTGAAGAAGCTGGTATCAAGT
ACCAATACTACTGTGGAAAGGCGGAACAGATGCAGGTGCAGCTCATCTG
AAAAATGGTGGTGTCCCATCAACAACTATCGGTGTCTGCGCTCGTTATAT
CCATTCTCACCAAACCCTCTATGCAATGGATGACTTCCTAGAAGCGCAAG
CTTTCCTTACAAGCCTTGGTGAAGAAATTGGATCGTTCAACGGTTGATTTG
ATTAAACATTATTAA (SEQ ID NO: 56)
MTTLFSKIKEVTELAAVSGHEAPVRAYLREKLTPHVDEVVTDGLGGIFGI
KHSEAVDAPRVLVASHMDEVGFMVSEIKPDGTFRVVEIGGWNPMVVSSQR
FKLLTRDGHEIPVISGSVPPHLTRGKGGPTMPAIADIVFDGGFADKAEAE
SFGIRPGDTIVPDSSAILTANEKNIISKAWDNRYGVLMVSELAEALSGQK
LGNELYLGSNVQEEVGLRGAHTSTTKFDPEVFLAVDCSPAGDVYGGQGKI
GDGTLIRFYDPGHLLLPGMKDFLLTTAEEAGIKYQYYCGKGGTDAGAAHL
KNGGVPSTTIGVCARYIHSHQTLYAMDDFLEAQAFLQALVKKLDRSTVDL
IKHY

ID31 1182 bp (SEQ ID NO: 57)
```
ATGGAATTTTCTATGAAATCAGTCAAAGGACTACTCTTTATCATAGCTAG
TTTTATCTTGACTCTTTTGACTTGGATGAACACTTCTCCCCAATTCATGA
TTCCAGGACTAGCTTTAACAAGCCTATCTCTGACTTTTATCCTAGCCACT
CGTCTCCACTACTAGAAAGCTTCTTCAACAGTTTGGAGAAGGCTTACACC
GTCCACAAATTCACAGCCTTTCTCTCAATCATCCTACTAATCTTTCATAA
CTTTAGTATGGGCGGTTTGTGGGGCTCTCGCTTAGCTGCTCAGTTTGGCA
ATCTTGCCATCTATATCTTTGCCAGCATCATCCTTGTCGCCTATTTAGGC
AAATACATCCAATACGAAGCTTGGCGATGGATTCACCGCCTGGTTTACCT
AGCCTATATTTTAGGACTCTTTCACATCTACATGATAATGGGCAATCGTC
TCCTTACATTTAATCTTCTAAGTTTTCTTGTTGGTAGCTATGCCCTTTTA
GGCTTACTAGCTGGTTTTTATATCATTTTTCTATATCAAAAGATTTCCTT
CCCCTATCTAGGGAAAATTACCCATCTCAAACGCTTAAATCACGATACTA
GAGAAATTCAAATCCATCTTAGCAGACCCTTTCAACTATCAATCAGGACAA
TTTGCCTTTCTAAAGATTTTCCAAGAAGGCTTTGAAAGTGCTCCCGCATCC
CTTTTCTATCTCAGGAGGTCATGGTCAAACTCTTTACTTTACTGTTAAAA
CTTCAGGCGACCATACCAAGAATATCTATGATAATCTTCAAGCCGGCAGC
AAAGTAACCCTAGACAGAGCTTACGGACACATGATCATAGAAGAAGGACG
AGAAAATCAGGTTTGGATTGCTAGGGATATTGGGATCACCCCCTTCATC
CTTACATCCGTGAACATCCTATTTTAGATAAACAGGTTCACTTCTACTAT
AGCTTCCGTGGAGATGAAAATGCAGTCTACCTAGATTTACTCCGTAACTA
TGCTCAGAAAAATCCTAATTTTGAACTCCATCTAATCGACAGTACAAAG
ACGGCTATCTTAATTTTGAACAAAAAGAAGTGCCCGAACATGCAACCGTC
TATATGTGTGGTCCTATTTCTATGATGAAGGCACTTGCCAAACAGATTAA
GAAACAAAATCCAAAAACAGAGCATATTTAC
```

(SEQ ID NO: 58)
MEFSMKSVKGLLFIIASFILTLLTWMNTSPQFMIPGLALTSLSLTFILAT
RLPLLESWFHSLEKVYTVHKFTAFLSIILLIFSMGGLWGSRLAAQFGNLA
IYIFASIILVAYLGKYIQYEAWRWIHRLVYLAYILGLFHIYMIMGNRLLT
FNLLSFLVGSYALLGLLAGFYIIFLYQKISFPYLGKITHLKRLNHDTREI
QIHLSRPFNYQSGQFAFLKIFQEGFESAPHPFSISGGHQTLYFVKTSG
DHTKNIYDNLQAGSKVTLDRAYGHMIIEEGRENQVWIAGGIGITPFISYI
REHPILDKQVHFYYSFRGDENAVYLDLLRNYAQKNPNFELHLIDSTKDGY
LNFEQKEVPEHATVYMCGPISMMKALAKQIKKQNPKTEHIY

TABLE 2-continued

ID32 900 bp (SEQ ID NO: 59)
ATGACTTTTAAATCAGGCTTTGTAGCCATTTTAGGACGTCCCAATGTTGG
GAAGTCAACCTTTTTAAATCACGTTATGGGGCAAAAGATTGCCATCATGA
GTGACAAGGCGCAGACAACGCGCAATAAAATCATGGGAATTTACACGACT
GATAAGGAGCAAATTGTCTTTATCGACACACCAGGGATTCACAAGCCTAA
AACAGCTCTCGGAGATTTCATGGTTGAGTCTGCCTACAGTACCCTTCGCG
AAGTGGACACTGTTCTTTTCATGGTGCCTGCTGATGAAGCGCGTGGTAAG
GGGGACGATATGATTATCGAGCGTCTCAAGGCTGCCAAGGTTCCTGTGAT
TTTGGTGGTGAATAAAATCGATAAGGTCCATCCAGACCAGCTCTTGTCTC
AGATTGATGACTTCCGTAATCAAATGGACTTTAAGGAAATTGTTCCAATC
TCAGCCCTTCAGGGAAATAACGTGTCTCGTCAGTGGATATTTTGAGTGA
AATCTGGATGAAGGTTTCCAATATTTCCCGTCTGATCAAATCACAGACC
ATCCAGAACGTTTCTTGGTTTCAGAATGGTTCGCGAGAAAGTCTGCACCT
AACTCGTGAAGAGATTCCGCATTCTGTAGCAGTAGTTGTTGACTCTATGA
AACGAGACGAAGAGACAACAAGGTTCACATCCGTGCAACCATCATGGTC
GAGCGCGATAGCCAAAAGGGATTATCATCGGTAAAGGTGGCGCTATGCT
TAAGAAAATCGGTAGCATGGCCCGTCGTGATATCGAACTCATGCTAGGAG
ACAAGGTCTTCCTAGAAACCTGGGTCAAGGTCAAGAAAAACTGGCGCGAT
AAAAAGCTAGATTTGGCTGACTTTGGCTATAATGAAAGAGAATACTAA (SEQ ID NO: 60)
MTFKSGFVAILGRPNVGKSTFLNGVMGQKIAIMSKDAQTTRNKIMGIYTT
DKEQIVFIDTPGIHKPKTALGDFMVESAYSTLREVDTVLFMVPADEARGK
GDDMIIERLKAAKVPVILVVNKIDKVHPDQLLSQIDDFRNQMDFKEIVPI
SALQGNNVSRLVDILSENLDEGFQYFPSDQITDHPERFLVSEMVREKVLH
LTREEIPHSVAVVVDSMKRDEETDKVHIRATIMVERDSQKGIIIGKGGAM
LKKIGSMARRDIELMLGDKVFLETWVKVKKNWRDKKLDLADFGYNEREY

ID33 855 bp (SEQ ID NO: 61)
CTGCTTCTTGTTTTTACAGAAGGAGGACTTATGCCTGAATTACCTGAGGT
TGAAACCGTTTGTCGTGGCTTAGAAAAATTGATTATAGGAAAGAAGATTT
CGAGTATAGAAATTCGCTACCCCAAGATGATTAAGACGGATTTGGAAGAG
TTTCAAAGGGAATTGCCTAGTCAGATTATCGAGTCAATGGGACGTCGTGG
AAAATATTTGCTTTTTTATCTGACAGACAAGGTCTTGATTTCCCATTTGC
GGATGGAGGGCAAGTATTTTTACTATCCAGACCAAGGACCTGAACGCAAG
CATGCCCATGTTTTCTTTCATTTTGAAGATGGTGGCACGCTTGTTTATGA
GGATGTTCGCAAGTTTGGAACCATGGAACTCTTGGTGCCTGACCTTTTAG
ACGTCTACTTTATTTCTAAAAAATTAGGTCCTGAACCAAAAAGCCTATCA
AATCCCATCTCCTAGACCAGACCTGCCCTTGCCAAGTCCAAAAAGCCTAT
CAAATCCCATCTCCTAGACCAGACCTTGGTAGCTGGACTTGGCAATATCT
ATGTGGATGAGGTTCTCTGGCGAGCTCAGGTTCATCCAGCTAGACCTTCC
CAGACTTTGACAGCAGAAGAAGCGACTGCCATTCATGACCAGACCATTGC
TGTTTTGGGCCAGGCTGTTGAAAAAGGTGGCTCCACCATTCGGACTTATA
CCAATGCCTTTGGGGAAGATGGAAGCATGCAGGACTTTCATCAGGTCTAT
GATAAGACTGGTCAAGAATGTGTACGCTGTGGTACCATCATTGAGAAAAT
TCAACTAGGCGGACGTGGAACCCACTTTTGTCCAAACTGTCAAAGGAGGG
ACTGA (SEQ ID NO: 62)
MLLVFTEGGLMPELPEVETVCRGLEKLIIGKKISSIEIRYPKMIKTDLEE
FQRELPSQIIESMGRRGKYLLFYLTDKVLISHLRMEGTLVYEDVRKFGTMELLVPDLLDVYFISKKLGPEPSEQD
FDLQVFQSALAKSKKPIKSHLLDQTLVAGLGNIYVDEVLWRAQVHPARPS
QTLTAEEATAIHDQTIAVLGQAVEKGGSTIRTYTNAFGEDGSMQDFHQVY
DKTGQECVRCGTIIEKIQLGGRGTHFCPNCQRRD

ID34 633 bp (SEQ ID NO: 63)
TTGTCCAAACTGTCAAAGGAGGGACTGATGGGAAAAATCATCGGAATCAC
TGGGGGAATTGCCTCTGGTAAGTCAACTGTGACAAATTTTCTAAGACAGC
AAGGCTTTCAAGTAGTGGATGCCGACGCAGTCGTCCACCAACTACAGAAA
CCTGGTGGTCGTCGTTTGAGGCTCTAGTACAGCACTTTGGGCAAGAAAT
CATTCTTGAAAACGGAGAACTCAATGCCCTCTCCTAGCTAGTCTCATCT
TTTCAAATCCTGATGAACGAGAATGGTCTAAGCAAATTCAAGGGGAGATT
ATCCGTGAGGAACTGGCTCATTTGGAGAGACAGTTGGCTCAGACAGAAGA
GATTTTCTTCATGGATATTCCCCTACTTTTTGAGCAGGACTACAGCGATT
GGTTTGCTGAGACTTGGTTGGTCTATGTGGACCGAGATGCCCAAGTGGAA
CGCTTAATGAAAAGGGACCAGTTGTCCAAAGATGAAGCTGAGTCTCGTCT
GGCAGCCCAGTGGCCTTTAGAAAAAAAAGAAAGATTTGGCCAGCCAGGTTC
TTGATAATAATGGCAATCAGAACCAGCTTCTTAATCAAGTGCATATCCTT
CTTGAGGGAGGTAGGCAAGATGACAGAGATTAA (SEQ ID NO: 64)
MSKLSKEGLMGKIIGITGGIASGKSTVTNFLRQQGFQVVDADAVVHQLQK
PGGRLFEALVQHFGQEIILENGELNRPLLASLIFSNPDEREWSKQIQGEI
IREELATLREQLAQTEEIFFMDIPLLFEQDYSDWFAETWLVYVDRDAQVE
RLMKRDQLSKDEAESRLAAQWPLEKKKDLASQVLDNNGNQNQLLNQVHIL
LEGGRQDDRD

ID35 1269 bp (SEQ ID NO: 65)
TTGATAATAATGGCAATCAGAACCAGCTTCTTAATCAAGTGCATATCCTT
CTTGAGGGAGGTAGGCAAGATGACAGAGATTAACTGGAAGGATAATCTGC
GCATTGCCTGGTTTGGTAATTTTCTGACAGGAGCCAGTATTTCTTTGGTT
GTACCTTTTATGCCCATCTTCGTGGAAAATCTAGGTGTAGGGAGTCAGCA
AGTCGCTTTTTATGCAGGCTTAGCAATTTCTGTCTCTGCTATTTCCGCGG
CGCTCTTTTCTCCTATTTGGGGTATTCTTGCTGACAAATACGGCCGAAA
CCCATGATGATTCGCGCAGGTCTTGCTATGACTATCACTATGGGAGGCTT
GGCCTTTGTCCCAAATATCTATTGGTTAATCTTTCTTCGTTTACCTAAAC
GGTGTATTTGCAGGTTTTGTTTCCTAATGCAACGGCACTGATAGCCAGTC
AGGTTCCAAAGGAGAAAATCAGGCTCTGCCTTAGGTACTTTGTCTACAGG
CGTAGTTGCAGGTACTCTAACTGGTCCCTTTATTGGTGGCTTTATCGCAG
AATTATTTGGCATTCGTACAGTTTTCTTTACTGGTTGGTAGTTTTCTATT
TTTAGCTGCTATTTTGACTATTTGCTTTATCAAGGAAGATTTTCAACCAG
TAGCCAAGGAAAAGGCTATTCCAACAAAGGAATTATTTACCTCGGTTAAA
ATCCCTATCTTTTGCTCAATCTCTTTTTAACCAGTTTTGTCATCCAATTT
TCAGCTCAATCGATTGGCCCTATTTTGGCTCTTTATGTACGCGACTTAGG
GCAGACAGAGAATCTTCTTTTTGTCTCTGGTTTGATTGTGTCCAGTATGG
GCTTTTCCAGCATGATGAGTGCAGGAGTCATGGGCAAGCTAGGTGACAAG
GTGGGCAATCATCGTCTCTTGGTTGTCGCCCAGTTTTATTCAGTCATCAT
CTATCCTCTGTGCCAATGCCTCTAGCCCCCTTCAACTAGGACTCTATC
GTTTCCTCTTTGGATTGGGAACCGGTGCCTTGATTCCCGGGGTTAATGCC
CTACTCAGCAAAATGACTCCCAAAGCCGGCATTTCGAGGGTCTTTGCCTT
CAATCAGGTATTCTTTTATCTGGGAGGTGTTGTTGGTCCCATGGCAGGTT
CTGCAGTAGCAGGTCAATTTGGCTACCCATGCTGTCTTTATGCGACAAG
CCTTTGTGTTGCCTTTAGTTGTCTCTTTAACCTGATTCAATTTCGAACAT
TATTAAAAGTAAAGGAAATCTAG (SEQ ID NO: 66)
MIIMAIRTSPFLIKCISFLREVGKMTEINWKDNLRIAWFGNFLTGASISLV
VPFMPIFVENLGVGSQQVAFYAGLAISVSAISAALFSPIWGILADKYGRK
PMMIRAGLAMTITMGGLAFVPNIYWLIFLRLLNGVFAGFVPNATALIASQ
VPKEKSGSALGTLSTGVVAGTLTGPFIGGFIAELFGIRTVFELLVGSFLF
LAAILTICFIKEDFQPVAKEKAIPTKELFTSVKYPYLLLNLFLTSFVIQF
SAQSIGPILALYVRDLGQTENLLFVSGLIVSSMGFSSMMSAGVMGKLGDK
VGNHRLLVVAQFYSVIIYLLCANASSPLQLGLYRFLFGLGTGALIPGVNA
LLSKMTPKAGISRVFAFNQVFFYLGGVVGPMAGSAVAGQFGYHAVFYATS
LCVAFSCLFNLIQFRTLLKVKEI

ID36 1311 bp (SEQ ID NO: 67)
ATGGCCCTACCAACTATTGCCATTGTAGGACGTCCCAATGTTGGGAAATC
AACCCTATTTAATCGGATCGCTGGTGAGCGAATCTCCATTGTAGAAGATG
TCGAAGGAGTGACACGTGACCGTATTTATGCAACGGGTGAGTGGCTCAAT
CGTTCTTTTAGCATGATTGATACAGGAGGAATTGATGATGTCGATGCTCC
TTTCATGGAACAAATCAAGCACCAGGCAGAAATTGCCATGGAAGAAGCAG
ATGTTATCGTTTTGTCGTGTCTGATAGGAAGGAATTACTGATGCAGAC
GAATACGTAGCTCGTAAGCTTTATAAGACCCACAAACCAGTTATCCTCGC
AGTCAACAAGGTGGACAACCCTGAGATGAGAATGATGATATATATGATTT
CTATGCTCTCGGTTTGGGTGAACCATTGCCTATCTCATCTGTCCATGGAA
TCGGTACAGGGGATGTGCTAGATGCGATCGTAGAAAATCTTCCAAATGAA
TATGAGGAAGAAATCCAGATGTCATTAAGTTTAGCTTGATTGGTCGTCC
TAACGTTGGAAATCAAGCTTGATCAATGCTATCTTGGGAGAAGACCGTGT
TATGCTAGTCCTGTTCTGAACAACTCGTGATGCCATTGATACCCACTTT
ACAGATACAGATGGTCAAGAGTTTACCATGATTGATACGGCTGGATATGCG
TAAGTCTGGTAAGGTTTATGAAAATACTGAGAAATACTCTGTTATGCCGT
GCCATGCCTGCTATTGACCGTTCAGATGTGGTCTTGATGGTCATCAATGC
GGAAGAAGGCATTCGTGGATACGACAAGCGTATCGCAGGATTTGCCCATG
AAGCTGGTAAAGGGATGATTATCGTGGTCAACAAGTGGGATACGCTTGAA
AAAGATAACCACACTATGAAAAACTGGGAAGAAGATATCCGTGAGCAGTT
CCAATACCTGCCTTACGCACCGATTATCTTTGTATCAGCTTTAACCAAGC
AACGTCTCCACAAACTTCCTGAGATGATTAAGCAAAATCAGCGAAAGTCAA
AATACACGTATTCCATCAGCTGTCTTGAACGATGTCATCATGGATGCCCA
TTGCCATCAACCCAACACCGACGACAAAGGAAAACGTCTCAAGATTTTC
TATGCGACCCAAGTGGCAACCAAACCACCAACCTTTGTCATCTTTGTCAA
TGAAGAAGAACTCATGCACTTTTCTTACCTGCGTTTCTTGGAAAATCAAA
TCGGCAAGGCCTTTGTTTTTGAGGGAACACCGATTCATCTCATCGCAAGA
AAACGCAAATAA

TABLE 2-continued (SEQ ID NO: 68)
MALPTIAIVGRPNVGKSTLFNRIAGERISIVEDVEGVTRDRIYATGEWLN
RSFSMIDTGGIDDVDAPFMEQIKHQAEIAMEEADVIVFVVSGKEGITDAD
EYVARKLYKTHKPVILAVNKVDNPEMRNDIYDFYALGLGEPLPISSVHGI
GTGDVLDAIVENLPNEYEEENPDVIKFSLIGRPNVGKSSLINAILGEDRV
IASPVAGTTRDAIDTHFTDTDGQEFTMIDTAGMRKSGKVYENTEKYSVMR
AMRAIDRSDVVLMVINAEEGIREYDKRIAGFAHEAGKMIIVVNKWDTLEK
DNHTMKNWEEDIREQFQYLPYAPIIFVSALTKQRLHKLPEMIKQISESQN
TRIPSAVLNDVIMDAIAINPTPTKDGKRLKIFYATQVATKPPTFVIFNEE
ELMHFSYLRFLENQIRKAFVFEGTPIHLIARKRK ID37 714 bp (SEQ ID NO: 69)
ATGACAGAAACCATTAAATTGATGAAGGCTCATACTTCAGTGCGCAGGTT
TAAAGAGCAAGAAATTCCCCAAGTAGACTTAAATGAAGATTTTGACAGAG
CCCAGATGGCATCATCTTGGAAGAATTTCCAATCCTACTCTGTGATTGTG
GTACGAAGTCAAGAGAAGAAAGATGCCTTGTATGAATTGGTACCTCAAGA
AGCCATTCGCCAGTCTGCTGTTTTCCTTCTCTTTGTCGGAGATTTGAACC
GAGCAGAAAAGGGAGCCCGACTTCATACCGACACCTTCCAACCCCAAGGT
GTGGAAGGTCTCTTGATTAGTTCGGTCGATGCAGCTCTTGCTGGACAAAA
CGCCTTGTTGGCAGCTTGAAAGCTTGGGCTATGGTGGTGTGATTATCGGT
TTGGTTCGATACAAGTCTGAAGAAGTGGCAGAGCTCTTTAACCTACCTGA
CTACACCTATTCTGTCTTTGGGATGGCACTGGGTGTGCCAAATCAACATG
ATGATATGAAACCGAGACTGCCACTAGAGAATGTTGTCTTTGAGGAAGAA
TACCAAGAACAGTCAACTGAGGCAATCCAAGCTTATGACCGTGTTCAGGC
TGACTATGCTGGGGCGTGCGACCACAAGCTGGAGTCAGCGCCTAGCAG
AACAGTTTGGTCAAGCTGAACCAAGCTCAACTAGAAAAAATCTTGAACAG
AAGAAATTATTGTAG (SEQ ID NO: 70)
MTETIKLMKAHTSVRRFKEQEIPQVDLNEILTAAQMASSWKNFQSYSVIV
VRSQEKKDALYELVPQEAIRQSAVFLLFVGDLNRAEKGARLHTDTFQPQG
VEGLLISSVDAALAGQNALLAAESLGYGGVIIGLVRYKSEEVAELFNLPD
YTYSVFGMALGVPNQHHDMKPRLPLENVVFEEEYQEQSTEAIQAYDRVQA
DYAGARATTSWSQRLAEQFGQAEPSSTRKNLEQKKLL ID38 729 bp (SEQ ID NO: 71)
ATGACAGAAATTAGACTAGAGCACGTCAGTTATGCCTATGGTCAGGAGAG
GATTTTAGAGGATATCAACCTACAGGTGACTTCAGGCGAAGTGGTTTCCA
TCCTAGGCCCAAGTGGTGTTGGAAAGACCACCCTCTTTAATCTAATCGCT
GGGATTTTAGAAGTTCAGTCAGGGAGAATTGTCCTTGATGGTGAAGAAAA
TCCCAAGGGGCGCGTGAGTTATATGTTGCAAAAGGATCTGCTCTTGACAG
ACAAGACGGTCTTGGAAATATCATTCTGCCCCTCTTGATTCAAAAGGTG
GATAAGGCAGAAGCTATTTCCCGACGGATAAAATTCTTGCGACCTTCCAG
CTGACAGCTGTAGCCTTACTCCGGACCTACCTTTTTGGGCACAAGCTCTT
TCTTAGATGAGGCCTTTAGCGCCTTGAGTGAGATGACAAAGATGGAACTC
CACGCTTGGTATCTTGAGATTCACAAGCAGTTGCAGCTAACAACCCTGAT
CATCACGCATAGTATTGAGGAGGCCCTCAATCTCAGCGACCGTATCTATA
TCTTGAAAAATCGCCCTGGGCAGATTGTTTCAGAAATTAAACTAGATTGG
TCTGAAGATGAGGACAAGGAAGTCCAAAAGATTGCCTACAAACGTCAAAT
TTTGGCGGAATTAGGACTAGATAAGTAG (SEQ ID NO: 72)
MTEIRLEHVSYAYGQERILEDINLQVTSGEVVSILGPSGVGKTTLFNLIA
GILEVQSGRIVLDGEENPKGRVSYMLQKDLLLEHKTVLGNIILPLLIQKV
DKAEAISRADKILATFQLTAVRDKYPHELSGGMRQRVALLRTYLFGHKLF
LLDEAFSALDEMTKMELHAWYLEIHKQLQLTTLIITHSIEEALNLSDRIY
ILKNRPGQIVSEIKLDWSEDEDKEVQKIAYKRQILAELGLDK ID39 2433 bp (SEQ ID NO: 73)
ATGAACTATTCAAAAGCATTGAATGAATGTATCGAAAGTGCCTACATGGT
TGCTGGACATTTTGGAGCTCGTTATCTAGAGTCGTGGCACTTGTTGATTG
CCATGTCTAATCACAGTTATAGTGTAGCAGGGCAACTTTAAATGATTAT
CCGTATGAGATGGACGTTTAGAAGAGGTGGCTTTGGAACTTGCCGTTCTA
GGACTATAGCAGGATGAAACCTTTACGGAGTTGCCGTTCTCCCGTCGTT
TGCAGGTTCTTTTTGATGAAGCAGAGTATGTAGCGTCAGTGGTCCATGCT
AAGGTACTAGGGACAGAGCACGTCCTCTATGCGATTTTGCATGATAGCAA
TGCCTTGGCGACTCGTATCTTGGAGAGGGCTGGTTTTTCATAGAAGACA
AGAAAGATCAGGTCAAGATTGCTGCTCTTCGTCGAAATTTAGAAGAACGG
GCAGGCTGGACTCGTGAAGATCTCAAGGCTTTACGCCAACGCCATCGTAC
AGTAGCTGACAAGCAAAATTCTATGGCCAATATGATGGGCATGCCGCAGA
CTCCTAGTGGTGGTCTCGAGGATTATACGCATGATTTGACAGAGCAAGCG
CGTTCTGGCAAGTTAGAACCAGTCATCGGTCGGGACAAGGAAATCTCACG TATGATTCAAATCTTGAGCCGGAAGACTAAGAACAACCCTGTCTTGGTTG
GGGATGCTGGTGTCGGGAAAACAGCTCTGGCGCTTGGTCTTGCCCAGCGT
ATTGCTAGTGGTGACGTGCCTGCGAAATGGCTAAGATGCGCGTGTTAGAA
CTTGATTGATGAATGTCGTTGCAGGGACACGCTTCCGTGGTGACTTTGA
AGAACGCATGAATAATATCATCAAGGATATTGAAGAAGATGGCCAAGTCA
TCCTCTTTATCGATGAACTCCACACCATCATGGGTTCTGGTAGCGGGATT
GATTCGACTCTGGATGCGGCCAATATCTTGAAACCAGCCTTGGCGCGTGG
AACTTTGGAGAACGGTTGGTGCCACTACTCAGGAAGAATATCAAAAACATA
TCGAAAAAGATGCGGCACTTTCTCGTCGTTTCGCTAAAGTGACGATTGAA
GAACCAAGTGTGGCAGATAGTATGACTATTTTACAAGGTTTGAAGGCGAC
TTATGAGAAACATCACCGTGTACAAATCACAGATGAAGCGGTTGAAACAG
CGGTTAAGATGGCTCATCGTTATTTAACCAGTCGTCACTTGCCAGACTCT
GCTATCGATCTCTTGGATGAGGCGGCAGCAACAGTGCAAAATAAGGCAAA
GCATGTAAAAGCAGACGATTCAGATTTGAGTCCAGCTGACAAGGCCTGAT
GGATGGCAAGTGGAAACAGGCAGCCCAGCTAATCGCAAAGAAGAGGAAG
TACCTGTCTACAAAGACTTGGTGACAGAGTCTGATATTTTGACCACCTTG
AGTCGCTTGTCAGGAATCCGCATTCAAAAACTGACTCAAACGGATGCTAA
GAAGTATTTAAATCTTGAAGCAGAACTCCATAAACGGGTTATCGGTCAAG
ATCAAGTCGTTTCAAGCATTAGCCGTGCCATTCGCCGCAACCAGTCAGGG
ATTCGCAGTCATAAGCGTCCGATTGGTTCCTTTATGTTCCTAGGGCCTAC
AGGTGTCGGGAAACTCGAGCTAAGCCAAGGCTCTGGCAGGATCTCTTTTG
ACGACGAATCAGCCCTTAATCCGCTTTGATATGATGGAGTATATGGAGAA
TTTGCAGCTAGTCGTCTCAACGGAGCTCCTCCAGGCTATGTAGGGATATGA
AGAAGGTGGGGAGTTGACAGAGAAGGTTCGCAATAAACCCTATTCCGTTC
TCCTCTTTGATGAGGTAGGAGAAGGCCCACCCAGATATCTTTGAATTGTTC
TTGCAGGTTCTGGATGACGGTGTCTTGACAGATAGCAAGGGACGCAAGGT
CGATTTTTCAAATACCATTATCATTATGACATCGAATCTAGGTGCGACTG
CCCTTCGTGATGATAAGACTGTTGGTTTTGGGGCTAAGGATATTCGTTTT
GACCAGGAAATATGGAAAAACGCATGTTTGAAGAACTGAAAAAAGCTTA
TAGACCGGAATTCATCAACCGTATTGATGAGAAGGTGGTCTTCCATAGCC
TATCTAGTGATCATATGCAGGAAGTGGTGAAGATTATGTCAAGCCTTTA
GTGGCAAGTTTGACTGAAAAAGGCATTGACTTGAAATTACAAGCTTCAGC
TCTGAAATTGTTAGCAAATCAAGGATATGACCCAGAGATGGGAGCTCGG
CACTTCGCAGAACCCTGCAAACAGAAGTGGAGGACAAGTTGGCAGAACTT
CTTCTCAAGGGAGATTTAGTGGCAGGCAGCACACTTAAGATTGGTGTCAA
AGCAGGCCAGTTAAAATTTGATATTGCATAA (SEQ ID NO: 74)
MNYSKALNECIESAYMVAGHFGARYLESWHLLIAMSNHSYSVAGATLNDY
PYEMDRLEEVALELTETDYSQDETFTELPFSRRLQVLFDEAEYVASVVHA
KVLGTEHVLYAILHDSNALATRILERAGFSYEDKKDQVKIAALRRNLEER
AGWTREDLKALRQRHRTVADKQNSMANMMGMPQTPSGGLEDYTHDLTEQA
RSGKLEPVIGRDKEISRMIQILSRKTKNNPVLVGDAGVGKTALALGLAQR
IASGDVPAEMAKMRVLELKLMNVVAGTRFRGDFEERMNNIIKDIEEDGQV
ILFIDELHTIMGSGSGIDSTLDAANILKPALARGTLRTVGATTQEEYQKH
IEKDAALSRRFAKVTIEEPSVADSMTILQGLKATYEKHHRVQITDEAVET
AVKMAHRYLTSRHLPDSAIDLLDEAAATVQNKAKHVKADDSDLSPADKAL
MDGKWKQAAQLIAKEEEVPVYKDLVTESDILTTLSRLSGIPVQKLTQTDA
KKYLNLEAELHKRVIGQDQAVSSISRAIRRNQSGIRSHKRPIGSFMFLGP
TGVGKTELAKALAEVLLFDEVKEAHPDIFNVLLQVLDDGVLTDSGRKVD
FSNTIIIMTSNLGARALRDDKTVGFGAKDIRFDQENMEKRMFEELKKAYR
PEFINRIDEKVVFHSLSSDHMQEVVKIMVKPLVASLTEKGIDLKLQASAL
KLLANQGYDPEMGARPLRRTLQTEVEDKLAELLLKGDLVAGSTLKIGVKA
GQLKFDIA ID40 1008 bp (SEQ ID NO: 75)
ATGAAGAAAACATGGAAAGTGTTTTAACGCTTGTAACAGCTCTTGTAGC
TGTTGTGCTTGTGGCCTGTGGTCAAGGAACTGCTTCTAAAGACAACAAAG
AGGCAGAACTTAAGAAGGTTGACTTTATCCTAGACTGGACACCAAATACC
AACCCACACAGGGCTTTATGTTGCCAAGGAAAAAGGTTATTTCAAAGAAGC
TGGGAGTGGATGTTGATTTGAAATTGCCACCAGAAGAAGAAGTTCTTCTGACT
TGGTTATCAACGGAAAGGCACCATTTTGCAGTGTATTTCCAAGACTACATG
GCTAAGAAATTGGAAAAGGAGCAGGAATCACTGCCGTTGCAGCTATTGT
TGAACACAATACATCAGGAATCATCTCTCGTAAATCTGATAATGTAAGCA
GTCCAAAGACTTGGTTGGTAAGAAATATGGGACATGGAATGACCCAACT
GAACTTGCTATGTTGAAAACCTTGGTAGAATCTCAAGGTGGAGACTTTGA
GAAGGTTGAAAAGTACCAAATAACGACTCAAACTCAATCACACCGATTG
CCAATGGCGTCTTTGATACTGCTTGGATTACTACGGTTGGGATGGTATC
CTTGCTAAATCTCAAGGTGTAGATCTAACTTCATGTACTTGAAAGACTA
TGTCAAGGAGTTTGACTACTATTCACCAGTTATCATCGCAAACAACGACT
ATCTGAAAGATAACAAAGAAGAAGCTCGCAAAGTCATCCAAGCCATCAAA
AAAGGCTACCAATATGCCATGCATGAACATGCAAGAAGAAGCTCAGATATTCT
CATCAAGAATGCACCTGAACTCAAGGAAAAACGTGACTTTGTCATCGAAT
CTCAAAATACTTGTCAAAAGAATACGCAAGCGACAAGGAAAATGGGGT
CAATTTGACGCAGCTCGCTGGAATGCTTTCTACAATGGGATAAAGAAAT
GGTATCCTTAAAGAAGACTTGACAGACAAAGGCTTCACCAACGAATTTGT
GAAATAA TABLE 2-continued (SEQ ID NO: 76)
MKKTWKVFLTLVTALVAVVLVACGQGTASKDNKEAELKKVDFILDWTPNT
NHTGLYVAKKEKGYFKEAGVDVDLKLPPEESSSDLVINGKAPFAVYFQDY
MAKKLEKGAGITAVAAIVEHNTSGIISRKSDNVSSPKDLVGKKYGTWNDP
TELAMLKTLVESQGGDFEKVEKVPNNDSNSITPIANGVFDTAWIYYGWDG
ILAKSQGVDANFMYLKDYVKEFDYYSPVIIANNDYLKDNKEEARKVIQAI
KKGYQYAMEHPEEAAKILIKNAPELKEKRDFVIESQKYLSKEYASDKEKW
GQFDAARWNAFYKWDKENGILKEDLTDKGFTNEFVK ID41 762 bp (SEQ ID NO: 77)
TTGATGAGAAACTTGAGAAGTATACTGAGACGACACATTAGTCTATTGGG
CTTTTCTCCGAGTATTGTCAATCTGGCAGTTAGCAGGTTTTCTTAAACTTC
TCCCCAAGTTTATCCTGCCGACACCTCTTGAAATTCTCCAGCCCTTTGTT
CGTGACAGAGAATTTCTCTGGCACCATAGCTGGGCGACCTTGAGAGTGGC
TTTACTGGGGCTGATTTTGGGAGTTTTGATTGCCTGTCTTATGGCTGTGC
TCATGGATAGTTTGACTTGGCTCAATGACCTGATTTACCCTATGATGGTG
GTCATTCAGACCATTCCGACCATTGCCATAGCTCCTATCCTGGTCTTGTG
GCTAGGTTATGGGATTTTGCCCAAGATTGTCTTGATTATCTTAACGACAA
CCTTTCCCATCATCGTTAGTATTTTGGACGGTTTTAGGCATTGCGACAAG
GATATGCTGACCTTGTTAGTCTGATGCGGGCCAAGCCTTGGCAAATCCT
GTGGCATTTTAAATCCCAGTTAGCCTGCCTTACTTTTATGCAGGTCTGA
GGGTCAGTGCTCCTACGCCTTTATCACACTGTGGTATCTGAGTGGTTGG
GAGGTTTTGAAGGTCTTGGTGTTTATATGATTCAGTCTAAAAAACTGTTT
CAGTATGATACCATGTTTGCCATTATTATTCTGGTGTCGATTATCAGTCT
TTTGGGTATGAAGCTGGTCGATATCAGTGAAAAATATGTCGATTAAATGGA
AACGTTCGTAG (SEQ ID NO: 78)
MMRNLRSILRRHISLLGFLGVLSIWQLAGFLKLLPKFILPTPLEILQPFV
RDEFLWHHSWATLRVALLGLILGVLIACLMAVLMDSLTWLNDLIYPMMVV
IQTIPTIAIAPILVLWLGYGILPKIVLIILTTTFPIIVSILDGFRHCDKD
MLTLFSLMRAKPWQILWHFKIPVSLPYFYAGLRVSVSYAFITTVVSEWLG
GFEGLGVYMIQSKKLFQYDTMFAIIILVSIISLLGMKLVDISEKYVIKWK
RS ID42 372 bp (SEQ ID NO: 79)
TTGATTTTTAATCCTATTTGCTGTATGATAAGGGAAAAGAAAGGGGACAG
AGATATGGCTTTTACCAATACCCACATGCGATCTGCTAGTTTTGGTATTG
TTACCAGCTTGCCTGATGACATCATTGACTCTTTTTGGTATATCATCGAC
CATTTCTTAAAAAATGTCTTTGAATTGGAAGAAGAACTCGAGTTTCAATT
GCTTAATAACCAAGGAAAGATTACCTTCCACTTTTCAGTCAACACCTCC
CTACAGCCATTGATTTTGACTTTAACCATCCTTTCGACCTCGTTATCCCC
CAAGAGTACTGGTTTTAGACATGGACGGTAGAAAACTATCCTCCTCCCA
GAAGAAAATGACCTATTTTAA (SEQ ID NO: 80)
MIFNPICCMIREKKGDRDMAFTNTHMRSASFGIVTSLPDDIIDSFWYIID
HFLKNVFELEEELEFQLLNNQGKITFHFSSQHLPTAIDFDFNHPFDPRYP
PRVLVLDMDGRETILLPEENDLF ID43 1569 bp (SEQ ID NO: 81)
ACAGCGGTGTCATTCTATCTATTTTAAGAAAAGTAATAATCAATTGTTAA
AAATAGTAAAAAATTGGAGGTTCTGATGAAATATTTTGTTCCTAATGAG
GTATTCAGTATTCGTAAATTAAAGGTGGGGACTTGCTCGGTACTATTGGC
AATTTCAATTTTGGGAAGCCAAGGTATTTATCCGGATGAAGTTGTTACTA
GTTCTTCACCGATGGCTACAAAAGAGTCTTCTAATGCAATTACTAATGAT
TTAGATAATTCACCCAACTGTTAATCAGAATCGTTCTGCTGAAATGATTGC
CTCTAATTCAACCACTAATGGTTTAGAATTCGTTAAGTGTTAATAGCA
TCAGCTCTAATGGTACTATTCGTTCCAATTCACAATTAGACAACAGAACA
GTTGAATCTACAGTAACATCTACTAATGAAAATAAGAGTTATAAGGAAGA
TGTTATAAGTGACAGAATTCATCAAAAAGAATTGAAGATACTGCTTTAAG
TGTAAAAGATTATGGTCAGTAGGTGATGGGATTCATGATGATCGACAAG
CAATTCAAGATGCAATAGATGCTGCAGCTCAAGGGCTAGGTGGAGGGAAT
GTATATTTTCCCTGAAGGAACCTTATTTAGTAAAAGAAATTGTTTTTAA
AAAGTCATACACACTTAGAATTGAATGATAAGGCTACAATTCTAAATGT
ATAAATATTAAGAATCACCCTTCCATTGTTTTTATGACAGGTTTATTTAC
GGATGATGGTGCGCAAGTAGAATGGGGCCCAACAGAAGATATTAGTTATT
CTGGTGGTACGATATGAACGGTGCTTTGAATGAAGAAGGAACTAAA
GCAAAAAATCTACCACTTATAAATTCTTCAGGTGCATTTGCTATTGGGAA
TTCAAATAACGTAACTATAAAAGTGAACATTCAAGATAGTTATCAAG
GGCATGCTATTCAAATTGCAGGTTCGAAAATGTATTAGTTGATAATTCT
CGTTTTCTTGGGCAAGCCTTACCCAAAACGATGAAGGATGGGCAAATCAT
AAGTAAGGAGAGCATTCAGATTGAACCATTAACTAGAAAAGGTTTTCCTT
ATGCCTTGAATGATGATGGGAAAAAATCTGAAAATGTGACTATTCAAAAT
TCCTATTTTGGCAAAGTGATAATCTGGGGAATTAGTAACAGCAATTGGC
ACACACTATCAAACATTGTCGACACAGAACCCCTCTAATATTAAAATTCA
AAATAATCATTTTGATAACATGATGTATGCAGGTGTACGTTTTACAGGAT
TCACTGATGTATTAATCAAAGGAAATCGCTTTGATAAGAAAGTTAAAGGA
GAGAGTGTACATTATCGAGAAAGCGGAGCAGCTTTAGTAAATGCTTATAG
CTATAAAAACACTAAAGACCTATTAGATTTAAATAAACAGGTGGTTATCG
CCAAAATATATTAATATTGCCGATCCTAAAACAAAAGCGATACAGGTTG
CAAAAGATAGTGCAGAATGTTTAGGAAAAGTATCAGATATTACTGTAACA
AAAAATGTAATTAATAATAATTCTAAGGAAACAGAACAACCAAATATTGA
ATTATTACGAGTTAGTGATAATTTAGTAGTCTCAGAGAATAGT (SEQ ID NO: 82)
QRCHSIYFKKSNNQLLKIVKKLEVLMKYFVPNEVFSIRKLKVGTCSVLLA
ISILGSQGILSDEVVTSSSPMATKESSNAITNDLDNSPTVNQNRSAEMIA
SNSTTNGLDNSLSVNSISSNGTIRSNSQLDNRTVESTVTSTNENKSYKED
VISDRIIKKEFEDTALSVKDYGAVGDGIHDDRQAIQDAIDAAAQGLGGGN
VYFPEGTYLVKEIVFLKSHTHLELNEKATILNGINIKNGPSIVFMTGLFT
DDGAQVEWGPTEDISYSGGTIDMNGALNEEGTKAKNLPLINSSGAFAIGN
SNNVTIKNVTFKDSYQGHAIQIAGSKNVLVDNSRFLGQALPKTMKDGQII
SKESIQIEPLTRKGFPYALNDDGKKSENVTIQNSYFGKSDKSGELVTAIG
THYQTLSTQNPSNIKIQNNHFDNMMYAGVRFTGFTDVLIKGNRFDKKVKG
ESVHYRESGAALVNAYSYKNTKDLLDLNKQVVIAENIFNIADPKTKAIRV
AKDSAECLGKVSDITVTKNVINNNSKETEQPNIELLRVSDNLVVSENS ID44 324 bp (SEQ ID NO: 83)
GTGATGAAAGAAACTCAGCTATTAAAAGGTGTTCTTGAAGGTTGTGTCTT
GGATATGATTGGTCAAAAAGAGCGGTATGGTTATGAGTTGGTTCAGACTT
TGCGAGAGGCTGGATTTGATACTATCGTTCCAGGAACTATTTATCCTTTG
TTGCAAAAGTTAGAAAAAAATCAATGGATAAGAGGCGACATGCGCCCGTC
GCCAGATGGTCCAGATCGGAAGTATTTTTCATTAATGAAAGAAGGAGAAG
AGCGTGTCTCAGTCTTTTGGCAACAATGGGACGATTTGAGTCAAAAAGTA
GAAGGGATTAAGAATGGGGGTTAA (SEQ ID NO: 84)
MMKETQLLKGVLEGCVLDMIGQKERYGYELVQTLREAGFDTIVPGTIYPL
LQKLEKNQWIRGDMRPSPDGPDRKYFSLMKEGEERVSVFWQQWDDLSQKV
EGIKNGG ID45 816 bp (SEQ ID NO: 85)
ATGAAGAAAATGAAGTATTACGAAGAAACAAGCGCTTTGCTACATGAGTT
TTCTGAGGAGGAATCAAATCAGAAGTATTTTGAGGAGTTGTGGGAGTTTTA
TCTTGCTGGATTTCTCTATGATGAAGACTATCTCAGAGAGCAGATCTATT
TGATGATGCTAGATTTCTCAGAAGCAGAACAGAGATGGCATGAGTGCAGAG
GATTATCTAGGTAAGAATCCTAAAAAAATAATGAAAGAGATTCTCAAGGG
AGCACCTCGCAGTTCTATCAAAGAGTCCCTTTTGACGCGCAATTCTTGTCC
TGGCGGTATTACGTTATTATCAACTACTAAGTGATTTTTCTAAAGGTCCT
CTCCTTAACAGTCAATTTGCTCACATTTTTAGGGCAACTTCTTATTTTTCT
GATTGGATTTGGACTTGTGGCCACAATTTTACGAAGAAGTTTAGTCCAAG
ATTCTCCTAAAATGAAAATTGGCACTTACATTGTTGTTGGGACTATAGTT
CTTGTCATTGGTATTTGGAATTGGAAAGAAGCGGTCTTTCGTCCATTT
GTCAGTATGATTATTGCCCATCTTGTGGTGGGTTCTCTGCTCCGTTATTA
TGAGTGGATGGGAATTTCAAATGTTTTCCTTACAAAATTTATTCCTTTAG
CTGTCCTCTTTATTGGAATCTTTGTCTTGTTCCGTGGGTTTAAGAAGATA
AAATGGAGTGAAGTATAG (SEQ ID NO: 86)
MKKMKYYEETSALLHEFSEENQKYFEELWESFNLAGFLYDEDYLREQIYL
MMLDFSEAERDGMSAEDYLGKNPKKIMKEILKGAPRSSIKESLLTPILVL
AVLRYYQLLSDFSKGPLLTVNLLTFLGQLLIFLIGFGLVATILRRSLVQD
SPKMKIGTYIVVGTIVLLVVLGYVGMASPIQEGAFYIPAPWDSLSVFTIS
LVIGIWNWKEAVFRPFVSMIIAHLVVGSLLRYYEWMGISNVFLTKVIPLA
VLFIGIFVLFRGFKKIKWSEV ID46 348 bp (SEQ ID NO: 87)
CTGTTTTTTATTTATACTCAATGAAAATCAAAGAGCAAACTAGGAAGCT
AGCCGCAGGTTGCTCAAAACACTGTTTTGAGGTTGTAGACGAAACTGACG
AAGTCAGCTCAAAACATGTTTTGAGGTTGTAGATGAAACTGACGAAGTC
AGCTCAAAACACTGTTTTGAGGTTGTAGATGAAACTGACGAAGTCAGCTC
AAAACACTGTTTTGAGGTTGTAGATGAAACTGACGAAGTCAGCTCAAAAC
ATGTTTTTGAGGTTGTAGATGAAACTGACGAAGTCAGTAACCATACATAC
GGTAGGGCGACGCTGACGTGGTTTGAAGAGATTTCGAAGAGTATTAA TABLE 2-continued (SEQ ID NO: 88)
MFFYLYSMKIKEQTRKLAAGCSKHCFEVVDETDEVSSKHVFEVVDETDEV
SSKHCFEVVDETDEVSSKHCFEVVDETDEVSSKHVFEVVDETDEVSNHTY
GRATLTWFEEIFEEY ID47 1260 bp (SEQ ID NO: 89)
ATGCAGAATCTGAAATTTGCCTTTTCATCTATCATGGCTCACAAGATGCG
TTCTTTTGCTTACTATGATTGGGATTATTATCGGTGTTTCATCAGTTGTTG
TGATTATGGCTTTGGGTGATTCCCTATCTCGTCAAGTCAATAAAGATATG
ACTAAATCTCAGAAAAATATTAGCGTCTTTTTCTCTCCTAAAAAAAGTAA
AGACGGGTCTTTTACTCAGAAACAATCAGCTTTTACGGTTTCTGGAAAGG
AAGAGGAAGTTCCTGTTGAACGCGCAAACCGCAAGAATCCTGGGTCCAAG
AGGCAGCTAAACTGAAGGGAGTGGATAGTTACTATGTAACCAATTCAACG
AATGCCATCTTGACCTATCAAGATAAAAAGGTTGAGAATGCTAATTTGAC
AGGTGGAACAGAACTTACATGGACGCTGTTAAGAATGAAATTATTGCAGG
TCGTAGTCTGAGAGAGCAAGATTTCAAAGAGTTTGCAAGTGTCATTTTGC
TAGATGAGGAATTGTCCATTAGTTTATTTGAATCCTCAAGAGGCTATT
AACAAGGTTGTAGAAGTCAATGGATTTAGTTACCGGGTCATTGGGGTTTA
TACTAGTCCGGAGGCTAAAAGATCAAAATATATGGGTTTGGTGGCTTGC
CTATTACTACCAATATCTCCCTTGCTGCAATTTTAATGTAGATGAAATA
GCTAATATTGTCTTTCGAGTGAATGATACCAGTTTAACCCCAACTCTGGG
TCCAGAACTGGCACGAAAAATGACAGAACTTGCAGGCTTACAACAGGGAG
AATACCAGGTGGCAGATGAGTCCGTTGTATTTGCAGAAATTCAACAATCG
TTTAGTTTTATGACGACGATTATTAGTTCCATCGCAGGGATTTCTCTCTT
TGTTGGAGGAACTGGTGTCATGAACATCATGCTGGTTTCGGTGACAGAGC
GCACTCGTGAGATTGGTCTTCGTAAGGCTTTGGGTGCAACACGTGCCAAT
ATTTTAATTCAGTTTTTGATTGAATCCATGATTTTGACCTTGTTAGGTGG
CTTAATTGGCTTGACAATTGCAAGTGGTTTAACTGCCTTAGCAGGTTTGT
TACTGCAAGGTTTAATAGAAGGTATAGAAGTTGGAGTATCAATCCCAGTC
GCCCTATTTAGTCTTGCAGTTTCGGCTAGTGTTGGTATGATTTTTGGAGT
CTTGCCAGCCAACAAGGCATCGAAACTTGATCCAATTGAAGCCCTTCGTT
ATGAATGA (SEQ ID NO: 90)
MQNLKFAFSSIMAIHKMRSLLTMIGIIIGVSSVVVIMALGDSLSRQVNKD
MTKSQKNISVFFSPKKSKDGSFTQKQSAFTVSGKEEEVPVEPPKPQESWV
QEAAKLKGVDSYYVTNSTNAILTYQDKKVENANLTGGNRTYMDAVKNEII
AGRSLREQDFKEFASVILLDEELSISLFESPQEAINKVVEVNGFSYRVIG
VYTSPEAKRSKIYGFGGLPITTNISLAANFNVDEIANIVFRVNDTSLTPT
LGPELARKMTELAGLQQGEYQVADESVVFAEIQQSFSFMTTIISSIAGIS
LFVGGTGVMNIMLVSVTERTREIGLRKALGATRANILIQFLIESMILTLL
GGLIGLTIASGLTALAGLLLQGLIEGIEVGVSIPVALFSLAVSASVGMIF
GVLPANKASKLDPIEALRYE ID48 705 bp (SEQ ID NO: 91)
CTGATGAAGCAACTAATTAGTCTAAAAATATCTTCAGAAGTTACCGTAA
TGGTGACCAAGAACTGCAGGTTCTCAAAAATATCAATCTAGAAGTGAATG
AGGGTGAATTTGTAGCCATCATGGGACCATCTGGGTCTGGTAAGTCCACT
CTGATGAATACGATACCTAGTGGATACACCAACCAGTGGAGAATATTA
TCTTGAAGGTCAAGAAGTGGCTGGGCTTGGTGAAAAGCAACTAGCTAAGG
TCCGTAACCAACAAATCGGTTTTGTCTTTCAGCAGTTCTTTCTTCTATCG
AAGCTCAATGCTCTGCAAAATGTAGAATTGCCCTTGATTTACGCAGGAGT
TTCGTCTTCAAAAACGTCGCAAGTTGGCTGAGGAATATTTAGACAAGGTT
GAATTGACAGAACGTAGTCACCATTTACCTTCAGAATTATCTGGTGGTCA
AAAGCAACGTGTAGCCATTGCGCGTGCCTTGGTAAACAATCCTTCTATTA
TCCTAGCGGATGAACCGACAGGAGCCTTGGATACCAAAACAGGTAACCAA
ATTATGCAATTATTGGTTGATTTGAATAAAGAAGGAAAAACCATTATCAT
GGTAACGCATGAGCCTGAGATTGCTGCCTATGCCAAACGTCAGATTGTCA
TTCGGGATGGGTCATTTCGTCTGACAGTGCTCAGTTAGGAAAGGAGGAA
AACTAA (SEQ ID NO: 92)
MMKQLISLKNIFRSYRNGDQELQVLKNINLEVNEGEFVAIMGPSGSGKST
LMNITGMLDTPTSGEYYLEGQEVAGLGEKQLAKVRNQQIGFVFQQFFLLS
KLNALQNVELPLIYAGVSSSKRRKLAEEYLDKVELTERSHHLPSELSGGQ
KQRVAIARALVNNPSIILADEPTGALDTKTGNQIMQLLVDLNKEGKTIIM
VTHEPEIAAYAKRQIVIRDGVISSDSAQLGKEEN ID49 1200 bp (SEQ ID NO: 93)
ATGAAGAAAAGAATGGTAAAGCTAAAAAGTGGCAACTGTATGCAGCAAT
CGGTGCTGCGAGTGTAGTTGTATTGGGTGCTGGGGGGATTACTCTTTAG
ACAACCTTCTCAGACTGCTCTAAAAGATGAGCCTACTCATCTTGTTGTTG
CCAAGGAAGGAAGCGTGGCCTCCTCTGTTTTATTGTCAGGGACAGTAACA GCAAAAAATGAACAATATGTTTATTTTGATGCTAGTAAGGGTGATTTAGA
TGAAATCCTTGTTTCTGTGGGCGATAAGGTCAGCGAAGGGCAGGCTTTAG
TCAAGTACAGTAGTTCAGAAGCGCAGGCGGCCTATGATTCAGCTAGTCGA
GCAGTAGCTAGGGCAGATCGTCATATCAATGAACTCAATCAAGCACGAAA
TGAAGCCGCTTCAGCTCCGGCTCCACAGTTACCAGCGCCAGTAGGAGGAG
AAGATGCAACGGTGCAAAGCCCAACTCCAGTGGCTGGAAATTCTGTTGCT
TCTATTGACGCTCAATTGGGTGATGCCCGTGATGCGCGTGCAGATGCTGC
GGCGCAATTAAGCAAGGCTCAAAGTCAATTGGATGCAACAACTGTTCTCA
GTACCCTAGAGGGAACTGTGGTCGAAGTCAATAGCAATGTTTCTAAATCT
CCAACAGGGGCGAGTCAAGTTATGGTTCATATTGTCAGCAATGAAAATTT
ACAAGTCAAGGGAGAATTGTCTGAGTACAATCTAGCCAACCTTTCTGTAG
GTCAAGAAGTAAGCTTTACTTCTAAAGTGTATCCTGATAAAAAATGGACT
GGGAAATTAAGCTATATTTCTGACTATCCTAAAAACAATGGTGAAGCAGC
TAGTCCAGCAGCCGGGAATAATACAGGTTCTAAATACCCTTATACTATTG
ATGTGACAGGCGAGGTTGGTGATTTGAAACAAGGTTTTTCTGTCAACATT
GAGGTTAAAAGCAAAACTAAGGCTATTCTTGTTCCTGTTAGCAGTCTAGT
AATGGATGATAGTAAAAATTATGTCTGGATTGTGGATGAACAACAAAAGG
CTAAAAAAGTTGAGGTTTCATTGGGAAATGCTGACGGAGCAAATGCTAAT
GAACAAAATCAAGAAATCACTTCTGGTTTAACGAACGGTGCTAAGGTCAT
CAGTAATCCAACATCTTCCTTGGAAGAAGGAAAAGAGGTGAAGGCTGATG
AAGCAACTAATTAG (SEQ ID NO: 94)
MKKKNGKAKKWQLYAAIGAASVVVLGAGGILLFRQPSQTALKDEPTHLVV
AKEGSVASSVLLSGTGTAKNEQYBYFDASKGDLDEILVSVGDKVSEGQAL
VKYSSSEAQAAYDSASRAVARADRHINELNQARNEAASAPAPQLPAPVGG
EDATVQSPTPVAGNSVASIDAQLGDARDARADAAAQLSKAQSQLDATTVL
STLEGTVVEVNSNVSKSPTGASQVMVHIVSNENLQVKGELSEYNLANLSV
GQEVSFTSKVYPDKKWTGKLSYISDYPKNNGEAASPAAGNNTGSKYPYTI
DVTGEVGDLKQGFSVNIEVKSKTKAILVPVSSLVMDDSKNYVWIVDEQQK
AKKVEVSLGNADAENQEITSGLTNGAKVISNPTSSLEEGKEVKADEATN ID50 759 bp (SEQ ID NO: 95)
ATGTCACGTAAACCATTTATCGCTGGTAACTGGAAAATGAACAAAAATCC
AGAAGAAGCTAAAGCATTCGTTGAAGCAGTTGCATCAAAACTTCCTTCAT
CAGATCTTGTTGAAGCAGGTATCGCTGCTCCAGCTCTTGATTTGACAACT
GTTCTTGCTGTTGCAAAAGGCTCAAACCTTAAAGTTGCTGCTCAAAACTG
CTACTTTGAAAATGCAGGTGCTTTCACTGGTGAAAATAGCCCACAAGTTT
TGAAAGAAATCGGTACTGACTACGTTGTTATCGGTCACTCAGAACGCCGT
GACTACTTCCATGAAACTGATGAAGATATCAACAAAAAAGCAAAAGCAAT
CTTTGCGAACGGTATGCTTCCAATCATCTGTTGTGGTGAATCACTTGAAA
CTTACGAAGCTGGTAAAGCTGCTGAATTCGTAGGTGCTCAAGTATCTGCT
GCATTGGCTGGATTGACTGCTGAACAAGTTGCTGCCTCAGTTATCGCTTA
TGAGCCAATCTGGGCTATCGGTACTGGTAAATCAGCTTCACAAGACGATG
CACAAAAAATGTGTAAAGTTGTTCGTGACGTTGTAGCTGCTGACTTTGGT
CAAGAAGTCGCAGACAAAGTTCGTGTTCAATACGGTGGTTCTGTTAAACC
TGAAAATGTTGCTTCATACATGGCTTGCCCAGACGTTGACGGTGCCCTTG
TAGGTGGTGCGTCACTTGAAGCTGAAAGCTTCTTGGCTTTGCTTGACTTT
GTAAAATAA (SEQ ID NO: 96)
MSRKPFIAGNWKMNKNPEEAKAFVEAVASKLPSSDLVEAGIAAPALDLTT
VLAVAKGSNLKVAAQNCYFENAGAFTGETSPQVLKEIGTDYVVIGHSERR
DYFHETDEDINKKAKAIFANGMLPIICCGESLETYEAGKAAEFVGAQVSA
ALAGLTAEQVAASVIAYEPIWAIGTGKSASQDDAQKMCKVVRDVVAADFG
QEVADKVRVQYGGSVKPENVASYMACPDVDGALVGGASLEAESFLALLDF
VK ID51 1473 bp (SEQ ID NO: 97)
TTGAAAACAAAAATTGGATTAGCAAGTATCTGTTTACTAGGCTTGGCAAC
TAGTCATGTCGCTGCAAATGAAACTGAAGTAGCAAAAACTTCGCAGGATA
CAACGCACAGCTTCAAGTAGTTCAGAGCAAAATCAGTCTTCTAATAAAACG
CAAACGAGCGCAGAAGTACAGACTAATGCTGCTGCCCACTGGGATGGGGA
TTATTATGTAAAGGATGATGGTTCTAAAGCTCAAAGTGAATGGATTTTTG
ACAACTACTATAAGGCTTGGTTTTATATTAATTCAGATGGTCGTTACTCG
CAGAATGAATGGCATGGAAATTACTACCTGAAATCAGGTGGATATATGGC
CCAAAACGAGTGGATCTATGACAGTAATTACAAGAGTTGGTTTTATCTCA
AGTCAGATGGGCTTATGTCATCAAGAATGGCAATTGATTGGAAATAA
TGGTACTACTTCAAGAAGTGGGGTTACATGGCTAAAAGCCAATGGCAAGG
AAGTTATTCTTGAATGGTCAAGGAGCTATGATGCAAAATGAATGGCTCT
ATGATCCAGCCTATTCTGCTTATTTTATCTAAAATCCGATGGAACTTAT
GCTAACCAAGAGTGGCAAAAAGTGGCCCAAATGGTAACTTGTAAGAA
GTGGGGCTATATGGCTCGGAATGAGTGGCAAGGCAACTACTATTTGACTG
GAAGTGGTGCCATGGCGACTGACGAAGTGATTATGGATGGTACTCGCTAT
ATCTTTGCGGCCTCTGGTGAGCTCAAAGAAAAAAAAGATTTGAATGTCGG
CTGGGTTCACAGAGATGGTAAGCGCTATTTCTTTAATAATAGAGAAGAAC
AAGTGGGAACCGAACATGCTAAGAAAGTCATTGATATTAGTGAGCACAAT

TABLE 2-continued

```
GGTCGTATCAATGATTGGAAAAAGGTTATTGATGAGAACGAAGTGGATGG
TGTCATTGTTCGTCTAGGTTATAGCGGTAAAGAAGACAAGGAATTGGCGC
ATAACATTAAGGAGTTAAACCGTCTGGGAATTCCTTATGGTGTCTATCTC
TATACCTATGCTGAAAATGAGACCGTGCTGAGAGTGACGCTAAACAGACC
ATTGAACTTATAAAGAAATACAATATGAACCTGTCTTACCCTATCTATTA
TGATGTTGAGAATTGGAATATGTAAATAAGAGCAAGAGAGCTCCAGTGA
TACAGGCACTTGGGTTAAAATCATCAACAAGTACATGGACACGATGAAGC
AGGCGGGTTATCAAAATGTGTATGTCTATAGCTATCGTAGTTTTATTACAG
ACGCGTTTAAAACACCCAGATATTTTAAAACATGTAACTGGGTAGCGGCC
TATACGAATGCTTTAGAATGGGAAAACCCTCATTATTCAGGAAAAAAGG
TTGGCAATATACCTCTTCTGAATACATGAAAGGAATCCAAGGGCGCGTAG
ATGTCAGCGTTTGGTATTAA (SEQ ID NO: 98)
MKTKIGLASICLLGLATSHVAANETEVAKTSQDTTTASSSSEQNQSSNKT
QTSAEVQTNAAAHWDGDYYVKDDGSKAQSEWIFDNYYAKAWPYINSDGRY
SQNEWHGNYYLKSGGYMAQNEWIYDSNYKSWFYLKSDGAYAHQEWQLIGN
KWYYFKKWGYMAKSQWQGSYFLNGQGAMMQNEWLYDPAYSAYFYLKSDGT
YANQEWQKVGGKWYYFKKWGYMARNEWQGNYYLTGSGAMATDEVIMDGTR
YIFAASGELKEKKDLNVGWVHRDGKRYFFNNREEQVGTEHAKKVIDISEH
NGRINDWKKVIDENEVDGVIVRLGYSGKEDKELAHNIKELNRLGIPYGVY
LYTYAENETDAESDAKQTIELIKKYNMNLSYPIYYDVENWEYVNKSKRAP
SDTGTWVKIINKYMDTMKQAGYQNVVYSYRSLLQTRLKHPDILKHVNWV
AAYTNALEWENPHYSGKKGWQYTSSEYMKGIQGRVDVSVWY

ID52 774 bp (SEQ ID NO: 99)
ATGAAAAAATTTGCCAACCTTTATCTGGGACTGGTCTTTCTGGTCCTCTA
CCTGCCTATCTTTTACTTGATTGGCTATGCCTTTAATGCTGGTGATGATA
TGAATAGCTTTACAGGTTTTAGCTGGACTCACTTTGAAACCATGTTTGGA
GATGGGAGACTCATGCTGATTTTGGCTCAGACATTTTTCTTGGCCTTCCT
ATCAGCCTTGATAGCGACCATTATCGGGACTTTTGGTGCCATTTACATCT
ACCAGTTCGTAAGAAATACCAAGAAGCCTTTCTATCACTCAATAATATC
CTCATGGTTGCGCCTGACGTTATGATTGGTGCTAGCTTCTTGATTCTCTT
TACCCAACTCAAGTTTTCACTTGGCTTTTTGACCGTTCTATCTAGTCACG
TGGCCTTCTCCATTCCTATCGTGGTCTTGATGGTCTTGCCTCGACTCAAG
GAAATGAATGGCGACATGATTCATGCGGCCTATGACTTGGGAGCTAGTCA
ATTTCAGATGTTCAAGGAAATCATGCTTCCTTACCTGACTCCGTCTATCA
TTACTGGTTATTTCATGGCCTTCACCTATTCGTTAGATGACTTTGCCGTG
ACCTTCTTTGTAACAGGAAATGGCTTTTCAACCCTATCAGTCGAGATTTA
CTCTCGTGCTCGCAAGGGGATTTCCTTAGAAATCAATGCCCTGTCTGCTC
TAGTCTTTCTCTTTAGTATTATCCTAGTTGTAGGTTATTACTTTATCTCT
CGTGAGAAGGAGGAGCAAGCATGA (SEQ ID NO: 100)
MKKFANLYLGLVFLVLYLPIFYLIGYAFNAGDDMNSFTGFSWTHFETMFG
DGRLMLILAQTFFLAFLSLIATIIGTFGAIYIYQSRKKYQEAFLSLNNI
LMVAPDVMIGASFLILFTQLKFSLGFLTVLSSHVAFISPIVVLMVLPRLK
EMNGDMIHAAYDLGASQFQMFKEIMLPYLTPSIITGYFMAFTYSLDDFAV
TFFVTGNGFSTLSVEIYSRARKGISLEINALSALVFLFSIILVVGYYFIS
REKEEQA

ID59 1071 bp (SEQ ID NO: 101)
ATGAAAAAAATCTATTCATTTTTAGCAGGAATTGCAGCGATTATCCTTGT
CTTGTGGGAATTGCGACTCATTTAGATAGTAAAATCAATAGTCGAGATAG
TCAAAAATTGGTTATCTATAACTGGGGAGACTATATCGATCCTGAACTCT
TGACTCAGTTTACAGAAGAAACAGGAATTCAAGTTCAGTACGAGACTTTT
GACTCCAACGAAGCCATGTACACTAAGATAAAGCAGGGTGGAACGACCTA
CGATATTGCCATTCCAAGTGAATATATGATTAACAAGATGAAGGACGAAG
ACCTCTTGGTTCCGCTTGATTATTCAAAAATTGAAGGAATCGAAAATATC
GGACCAGAGTTTCTCAACCAGTCCTTTGACCCAGGTAATAAATTCTCCAT
CCCTTACTTCTGGGGAACCTTAGGAATTGTCTACAACGAAACCATGGTAG
ATGAAGCGCCTGAGCATTGGGATGACCTTTGGAAGCCGGAGTATAAGAAT
TCTATCATGCTCTTTGATGGGGCGCGTGAGGTGCTGGGACTAGGACTCAA
TTCCCTCGGCTACAGCCTCAACTCCAAGGATCTGCAGCAGTTGGAAGAGA
CAGTGGATAAGCTCTACAAACTGACTCCAAATATCAAGGCTATCGTTGCG
GACGAGATGAAGGGCTATATGATTCAGAATAATGTTGCAATCGGCGTGAC
CTTCTCTGGTGAAGCCAGCCAAATGTTAGAAAAAATGAAAATCTACGTT
ATGTGGATACCGACAGAGGCCAGCAATCTTTGGTTTGACAATATGGTCATT
CCCAAAACAGTTAAAAACCAAAACTCAGCCTATGCCTTTATCAACTTTAT
GTTGAAACCTGAAAATGCTCTCCAAATGCGGAGTATGTCGGCTATTCAAC
ACCAAACCTACCAGCGAAGGAATTGCTCCCAGAGGGAAACAAAGGAAGATA
AGGCCTTCTATCCCGATGTTGAAACCATGAAACACCTAGAAGTTTATGAG
AAATTTGACCATAAAATGGACAGGGAAATATAGCGACCTCTTCCTACGTT
TAAAATGTATCGGAAGTAG
```

(SEQ ID NO: 102)
MKKIYSFLAGIAAIILVLWGIATHLDSKINSRDSQKLVIYNWGDYIDPEL
LTQFTEETGIQVQYETFDSNEAMTKIKQGGTTYDIAIPSEYMINKMKDED
LLVPLDYSKIEGIENIFEFLNQSFDPGNKFSIPYFWGTLGIVYNETMVDE
APEHWDDLWKPEYKNSIMLFDGAREVLGLGLNSLGYSLNSKDLQQLEETV
DKLYKLTPNIKAIVADEMKGYMIQNNVAIGVTFSGEASQMLEKNENLRYV
VPTEASNLWFDNMVIPKTVKNQNSAYAFINFMLKPENALQNAEYVGYSTP
NLPAKELLPEETKEDKAFYPDVETMKHLEVYEKFDHKWTGKYSDLFLQFK
MYRK

ID61 1851 bp (SEQ ID NO: 103)
ATGAATAAAAACTAACAGATTATGTGATTGATCTGGTGGAAATTTTAAA
TAAACAACAAAAGCAGGTTTCTGGGGAATATTTGATATTTTCAGTATGGT
GGTTTCCATCATTGTATCTTATATTTTTATTTTATGGGCTGATTAATCCAG
CACCTGTTGACTACATTATCTATACGAGTTTGGCCTTCCTGTTCTATCAA
TTGATGATTGGTTTTGGGGGTTGAACGCGAGCATTAGTCGTTACAGCAA
GATTACGGATTTCATGAAAATCTTTTTGGTGTGACTGCTAGCAGTGTCT
TGTCATATAGTATCTGTTATGCCTTCTTGCCACTCTTCTCCATCCGTTTC
ATCATTCTCTTTATCCTTGTTGAGTACCTTCTTGATTTATTGCCACGGAT
TACTTGGCAGTTAATCTACTCCAGACGCAAAAAAGGTAGTGGTGATGGAG
AACACCGTCGGACCTTCTTGATTGGTGCCGGTGATGGTGGGGCTCTTTTT
ATGGATAGTTACCAACATCCAACCAGTGAATTAGAACTGGTCGGTATTTC
GGATAAGGATTCTAAGAAAAAGGGTCAAAAACTTGGTGGTATTCCTGTTT
TGGGCTCTTATGACAATCTGCCTGAATTAGCCAAACGCCATCAAATCGAG
CGTGTCATCGTTGCGATTCCGTCGCTGGATCCGTCAGAATATGAGCGTAT
CTTGCAGATGTGTAATAAGCTGGGTGTCAAATGTTACAAGATGCCTAAGG
TTGAAACTGTTGTTCAGGGCGTTCACCAAGCAGGTACTGGCCTCCAAAAA
ATTGATATTACGGACCTTTGGGTCGTCAGGAAATCCGTCTTGACGAATC
GCGTCTGGGTGCAGAACTGACAGGTAAGACCATCTTAGTCACAGGAGCTG
GAGGTTCAATCGGTTCTGAAATCTGTCGTCAAGTTAGTCGCTTCAATCCT
GAACGCATTGTTCTTCTCGGTCATGGGGAAAACTCAATCTACCTTGTTTAT
CATGAATTGATTCGTAAGTTCCAAGGGATTGATTATGTACCTGTGATTGC
GGACATTCAAGACTATGATCGTTTGTTGCAAGTCTTTGAGCAGTACAAAC
CTGCTATTGTTTATCATGCGGCAGCCCACAAGCATGTTCCTATGATGGAG
CGCAATCCAAAAGAAGCCTTCAAAAACAATATCCGTGGAACTTACAATGT
TGCTAAGGCTGTTGATGAAGCTAAAGTGTCTAAGATGGTTATGATTTCGA
CAGATAAGGCAGTCAATCCACCAAATGTTATGGGAGCAACCAAGCGCGTG
GCGGAGTTGATTGTCACTGGCTTTAACCAACGTAGCCAATCAACCTACTG
TGCAGTTCGTTTTGGGAATGTTCTTGGTAGCCGTGGTAGTGTCATTCCAA
TCTTTGAACGTCAGATTGCTGAAGGTGGGCCTGTAACGGTGACAGACTTC
CGTATGACCCGTTACTTTATGACCATTCCAGAAGCTAGCCGTCTGGTTAT
CCATGCTGGTGCTTATGCCAAAGATGGGGAAGTCTTTATCCTTGATATGG
GCAAACCAGTCAAGATTTATGACTTGGCCAAGAAGATGGTGCTTCTAAGT
GGCCACACTGAAAGTGAAATTCCAATCGTTGAAGTTGGAATCCGCCCAGG
TGAAAAACTCTACGAAGAACTCTTGGTATCAACCGAACTCGTTGATAATC
AAGTTATGGATAAGATTTTCGTTGGTAAGGTTAATGTCATGCCTTTAGAA
TCCATCAATCAAAAGATTGGAGAGTTCCGCACTCTCAGTGGAGATGAGTT
GAAGCAAGCTATTATCGCCTTTGCTAATCAAACAACCCCACATTGAATAA (SEQ ID NO: 104)
MNKKLTDYVIDLVEILNKQQKQVFWGIFDIFSMVVSIIVSYILFYGLINP
APVDYIIYTSLAFLFYQLMIGFWGLNASISRYSKITDFMKIFFGVTASSV
LSYSICYAFLPLFSIRFIILFILLSTFLILLPRITWQLIYSRRKKGSGDG
EHRRTFLIGAGDGGALFMDSYQHPTSELELVGILDKDSKKKGQKLGGIPV
LGSYDNLPELAKRHQIERVIVAIPSLDPSEYERILQMCNKLGVKCYHMPK
VETVVQGLHQAGTGFQKIDITDLLGRQEIRLDESRLGAELTGKTILVTGA
GGSIGSEICRQVSRFNPERIVLLGHGENSIYLVYHELIRKFQGIDYVPAV
IADIQDYDRLLQVFEQYKPAIVYHAAAHKHVPMMERNPKEAFKNNIRGTY
NVAKAVDEAKVSKMVMISTDKAVNPPNVMGATKRVAELIVTGFNQRSQST
YCAVRFGNVLGSRGSVIPVFERQIAEGGPVTDFRMTRYFMTIPEASRL
VIHAGAYAKDGEVFILDMGKPVKIYDLAKKMVLLSGHTESEIPIVEVGIR
PGETLYEELLVSTELVDNQVMDKIFVGKVNVMPLESINQKIFEFRTLSGD
ELKQAIIAFANQTTHIE

ID101 1338 bp (SEQ ID NO: 105)
ATGATTGAACTTTATGATAGTTACAGTCAAGAAAGTCGAGATTTACATGA
AAGTCTAGTCGCTACTGGTCTTTCTCAACTTGGAGTGGTCATCGATGCAG
ATGGTTTTCTGCCTGATGGTCTGCTTTCTCCTTTTACCTATTATCTAGGT
TACGAGGATGGAAAACCTCTCTATTTTAATCAAGTTCCCGTTTCAGATTT
TTGGGAAATTTTAGGAGATAATCAGTCTGCTTGTATTGAAGATGTGACC
AGGAGAGGGCTGTCATTCATTATGCTGATGAATGCAGGCTCGCTTGGTT
AAACAGGTAGACTGGAAAGACCTAGAAGGTCGAGTACGTCAGGTTGACCA
CTACAATCGCTTCGGAGCTTGTTTTGCTACAACGACTTATAGCGCAGATA
GCGAGCCGATTATGACAGTTTACCAAGATGTCAATGGTCAACAAGTTTTA
CTGGAAACCATGTGACGGGTGATATCTTATTGACTTTGCCAGGTCAGTC
```

TABLE 2-continued

CATGCGTTACTTTGCAAATAAAGTTGAATTTATCACCTTCTTTTTGCAAG
ATTTGGAAATAGATACCAGTCAGCTTATCTTTAATACTCTAGCGACTCCT
TTCTTGGTTTCCTTCCATCATCCAGATAAATCTGGCTCGGATGTCTTGGT
ATGGCAGGAACCTCTCTATGATGCCATTCCAGGTAATATGCAGTTGATTT
TGGAAAGTGATAATGTGCGTACTAAGAAGATCATCATTCCAAATAAGGCG
ACTTATGAGCGCGCTTTAGAGTTAACTGACGAGAATACCATGATCAGTTT
GTGCACTTGGGTTATCATTACCCAGTTCAAACGTGATAATTTCCTAAGAC
GAGATGCCTTAATCTTGACCAATTCAGATCAGATTGAGCAAGTAGAAGCA
ATCGCAGGAGCCTTGCCTGATGTCACTTTCCGTATTGCAGCGGTGACAGA
GATGTCTTCTAAGCTCTTAGACATGCTTTGCTATCCTAATGTGGCCCTTT
ACCAGAACGCTAGTCCACAGAAGATTCAGGAGCTGTATCAACTGTCGGAT
ATTTACTTGGATATAAACCACAGTAATGAGTTGCTACAGGCAGTGCGTCA
GGCCTTTGAGCACAATCTCTTGATTCTTGGCTTTAATCAGACGGTGCACA
ATAGACTTTATATCCGCTCCAGACCATCTATTTGAAAGTAGTGAAGTTGC
TGCTTTGGTTGAGACCATTAAATTGGCCCTTTCAGATGTTGATCAAATGC
GTCAGGCACTTGGCAAACAAGGCCAACATGCAAATTATGTTGACTTGGTG
AGATATCAGGAAACCATGCAAACTGTTTTAGGAGGCTAA (SEQ ID NO: 106)
MIELYDSYSQESRDLHESLVATGLSQLGVVIDADGFLPDGLLSPFTYYLG
YEDGKPLYFNQVPVSDFWEILGDNQSACIEDVTQERAVIHYADGMQARLV
KQVDWKDLEGRVRQVDHYNRFGACFATTTYSADSEPIMTVYQDVNGQQVL
LENHVTGDILLTLPGQSMRYFANKVEFITFFLQDLEIDTSQLIFNTLATP
FLVSFHHPDKSGSDVLVWQEPLYDAIPGNMQLILESDNVRTKKIIIPNKA
TYERALELTDEKYHDQFVHLGYHYQFKRDNFLRRDALILTNSDQIEQVEA
IAGALPDVTFRIAAVTEMSSKLLDMLCHYQFKRDNFLRRDALILTNSDQI
EQVEAIAGALPDVTFRIAAVTEMSSKLLDMLCTPNVALYQNASPQKIQEL
YQLSDIYLDINGSNELLQAVRQAFEHNLLILGFNQTVHNRLYIAPDHLFE
SSEVAALVETIKLALSDVDQMRQALGKQGQHANYVDLVRYQETMQTVLGG

ID102 1512 bp (SEQ ID NO: 107)
ATGACAATTTACAATATAAATTTAGGAATTGGTTGGGCTAGTAGCGGTGT
TGAATACGCTCAAGCCTATCGTGCTGGTGTTTTTCGGAAATTAAATCTGT
CCTCTAAGTTTATCTTTACAGATATGATTTTAGCGCTGATAATATTCAGCAC
TTAACAGCCAATATTGGTTTTGATGATAATCAGGTTATCTGGCTTTATAA
TCATTTCACAGATATCAAAATTGCACCTACTAGCGTGACAGTGGATGATG
TCTTGGCTTACTTTGGTGGTGAAGAAAGTCACAGAGAAAAAAATGGCAAG
GTTTTACGTGTATTCTTTTTTGACCAAGATAAGTTTGTAACCTGTTATTT
GGTTGATGAGAACAAGGACTTGGTTCAACATGCCGAGTATGTTTTTAAGG
GAAACCTGATTCGGAAGGATTACTTTTCTTATACGCGTTATTGTAGCGAG
TATTTTGCTCCCAAGGACAATGTTGCAGTCTTATACCAACGAACTTTTTA
TAATGAAGACGGGACTCCAGTCTATGTATATCTTGATGAATCAAGGGAAGG
AAGAGTTTATCATTTCGATGATAAGATTTTCTATGGAAAGCAAGCTTTT
GTGCGTGCCTTTATGAAATCTTTGAATTTGAATAAGTCTGATTGGTCAT
CTCGATAGGGACAGGTATTGGACAGGTTGTGTTTGAGGAAGCACAGA
CAGCACATCTAGCGGTAGTTGTTCATGCGGAGCATTATAGTGAAAATGCT
ACAAATGAGGACTATATCCTTTGGAATAACTATTATGACTATCAGTTTAC
CAATGCAGTAAAGGTTGACTTGTTTTATCGTGTCTACTGATAGACAAATG
AAGTTCTACAAGAGCAATTTGCCAAATATACTCAGCATCAGCCAAAGATT
GTTACCATTCCTGTAGGCAGTATTGATTCCTTGACAGATTCAAGTCAAGG
GCGCAAACCATTTTCATTGATTACGGCTTCACGTCTTGCCAAAGAAAAGC
ACATTGATTGGCTTGTGAAAGCTGTGATTGAAGCTCATAAGGAGTTACCG
AACTAACCTTTGATATCTATGGTAGTGGTGGAGAAGATTCTCTGCTTAG
AGAAATTATTGCAAATCATCAGGCAGGACTATATCCAACTCAAGGGGC
ATGCGGAACTTTCTCGAGATTTATAGCCAGTATGAGGTCTACTTAACGGCT
TCTACCAGCGAAGGATTGGTCTGACCTTGATGGAAGCTATTGGTTCAGG
TCTACCTCTAATTGGTTTTGATGTGCCTTATGGTAATCAGACCTTTATAG
AGGATGGGCAAATGGTTATTTGATTCCAAGTTCATCTGACCATGTAGAA
GACCAAATCAAGCAAGCTTATGCCGCTAAGATTTGTCAATTGTATCAAGA
AAATCGTTTGGAAGCTATGCGTGCCTATTCTTACCAAATTGCAGAAGGCT
TCTTGACCAAAGAAATTTTAGAAAAGTGGAAGAAAACAGTAGAGGAGGTG
CTCCATGATTGA (SEQ ID NO: 108)
MTIYNINLGIGWASSGVEYAQAYRAGVFRKLNLSSKFIFTDMILADNIQH
LTANIGFDDNQVIWLYNHFTDIKIAPTSVTVDDVLAYFGGEESHREKNGK
VLRVFFFDQDKFVTCYLVDENKDLVQHAEYVFKGNLIRKDYFSYTRYCSE
YFAPKDNVAVLYQRTFYNEDGTPVYDILMNQGKEEVYHFKDKIFYGKQAF
VRAFMKSLNLNKSDLVILDRETGIGQVVFKEEAQTAHLAVVVHAEHYSENA
TNEDYILWNNYYDYQFTNADKVDFFIVSTDRQNEVLQEQFAKYTQHQPKI
VTIPVGSIDSLTDSSQGRKPFSLITASRLAKEKHIDWLVKAVIEAHKELP
ELTFDIYGSGGEDSLLREIIANHQAEDYIQLKGHAELSQIYSQYEVYLTA
STSEGFGLTLMEAIGSGLPLIGFDVPYGNQTFIEDGQNGYLIPSSSDHVE
DQIKQAYAAKICQLYQENRLEAMRAYSYQIAEFGLTKEILEKWKKTVEEV
LHD

ID103 2292 bp (SEQ ID NO: 109)
ATGTCCTCTCTTTCGGATCAAGAATTAGTAGCTAAAACAGTAGAGTTTCG
TCAGCGTCTTTCCGAGGGAGAAAGTCTAGACGATATTTTGGTTGAAGCTT
TTGCTGTGGTGCGTGAAGCAGATAAGCGGATTTTAGGGATGTTTCCTTAT
GATGTTCAAGTCATGGGAGCTATTGTCATGCACATGCATGGAAATGTTGCTGA
GATGAATACGGGGGAAGGTAAGACCTTGACAGCTACCATGCCTGTCTATT
TGAACGCTTTTTCAGGAGAAGGAGTGATGGTTGTGACTCCTAATGAGTAT
TTATCAAAGCGTGATGCCGAGGAAATGGGTCAAGTTTATCGTTTTCTAGG
ATTGACCATTGGTGTACCATTTACGGAAGATCCAAAGAAGGAGATGAAAG
CTGAAGAAAAGAAGCTTATCTATGCTTCGGATATCATCTACACAACCAAT
AGTAATTTAGGTTTTGATTATCTAAATGATAACCTAGCCTCGAATGAAGA
AGGTAAGTTTTTACGACCGTTTAACTATGTGATTATTGATGAAATTGATG
ATATCTTGCTTGATAGTGCACAAACTCCTCTGATTATTGCGGGTTCTCCT
CGTGTTCAGTCTAATTACTATGCGATCATTGATACACTTGTAACAACCTT
GGTCGAAGGAGAGGATTATACTTTAAGAGGAGAAAGAGGAGGTTTGGCT
CACTACTAAGGGGGCCAAGTCTGCTGAGAATTTCCTAGGGATTGATAATT
TATACAAGGAAGAGCATGCGTCTTTTGCTCGTCATTTGGTTTATGCGATT
CGAGCTCATAAGCTCTTTACTAAAGATAAGGACTATATCATTCGTGGAAA
TGAGATGGTACTGGTTGATAAGGGACACAGGGCGTCTAATGGAAATGACTA
AACTTCAAGGAGGTCTCCATCAGGCTATTGAAGCCAAGGAACATGTCAAA
TTATCTCCTGAGACGCGGGCTATGGCCTCGATCACCTATCAGAGTCTTTT
TAAGATGTTTAATAAGATATCTGGTATGACAGGGACAGGTAAGGTGCGTG
AAAAAGAGTTTATTGAAACTTACAATATGTCTGTAGTACGCATTCCAACC
AATCGTCCGAGACAACGGATTGACATATCCAGATAATCTATATATCACTTT
ACCTGAAAAAGTGTATGCATCCTTGGAGTACATCAAGCAATACCATGCTA
AGGGAAATCCTTTACTCGTTTTTGTAGGCTCAGTTGAAATGTCTCAACTC
TATTCGTCTCTTGTTTCGTGAAGGGATTGCCCATAATGTCCTAATGCT
AATAATGCGGCGCGTGAGGCTCAGATTATCTCCGAGTCAGGTCAGATGGG
GGCTGTGACAGTGGCTACCTCTATGGCAGGACGTGGTACGGATATCAAGC
TTGGGTAAAGGAGCTCGCAGAGCTTGGGGGCTTGATTGTTATTGGGACTGA
GCGGATGGAAAGTCAGCGGATCGACCTACAAATTCGTGGCCGTTCTGGTC
GTCAGGGAGATCCTGGTATGAGTAAATTTTTTGTATCCTTAGAGGATGAT
GTTATCAAGAAATTTGGTCCATCTTGGGTGCATAAAAAGTACAAGGACTA
TCAGGTTCAAGATATGACTCAACCGGAAGTATTGAAAGGTCGTAAATACC
GGAAACTAGTCGAAAAGGCTCAGCATGCCAGTGATAGTGCTGGACGTTCAG
CACGTCGTCAGACTCTGGAGTATGCTGAAAGTATGAATACAACGGGAT
ATAGTCTATAAAGAGAGAAATCGTCTAATAGATGGTTCTCGTGACTTAGA
GGATGTTGTTGTGGATATCATTGAGAGATATACAGAAGAGGTAGCGGCTG
ATCACTATGCTAGTCGTGAATTATTGTTTCACTTTATTGTGACCAATTAT
AGTTTTCATGTTAAAGAGGTTCCAGATATATGAGATGTAACTGACAAAAC
TGCAGTTCGTAGCTTTATGAAGCAGGTGATTGATAAAGAACTTTCTGAAA
AGAAAGAATTACTTAATCAACATGACTTATATGAACAGTTTTTACGACTT
TCACTGCTTAAAGCCATTGATGACAACTGGGTAGAGCAGGATTACTATCT
ACAACAGCTATCCATGGCTATCGGTGGTCAATCCTAGTCAGAAAATC
CAATCGTAGAGTACTATCAAGAAGCCTACGCGGGCTTTGAAGCTATGAAA
GAACAGATTCATGCGGATATGGTGCGTAATCTCCTGATGGGGCTGGTTGA
GGTCACTCCAAAAGGTGAAATCGTGACTCATTTTCCATAA (SEQ ID NO: 110)
MSSLSDQELVAKTVEFRQRLSEGESLDDILVEAFAVVREADKRILGMFPY
DVQVMGAIVMHYGNVAEMNTGEGKTLTATMPVYLNAFSGEGVMVVTPNEY
LSKRDAEEMGQVYRFLGLTIGVPFTEDPKKEMKAEEKKLIYASDIIYTTN
SNLGFDYLNDNLASNEEGKFLRPFNYVIIDEIDDILLDSAQTPLIIAGSP
RVQSNYYAIIDTLVTTLVEGEDYIFKEEKEEVWLTTKGAKSAENFLGIDN
LYKEEHASFARHLVYAIRAHKLFTKDKDYIIRGNEMVLVDKGTGRLMEMT
KLQGGLHQAIEAKEHVKLSPETRAMASITYQSLFKMFNKISGMTGTGKVA
EKEEFIETYNMSVVRIPTNRPRQRIDYPDNLYITLPEKVYASLEYIKQYHA
KGNPLLVFVGSVEMSQLYSSLLFREGIAHNVLNANNAAREAQIISESGQM
GAVTVATSMAGRGTDIKLGKGVAELGGLIVIGTERMESQRIDLQIRGRSG
RQGDPGMSKFFVSLEDDVIKKFGPSWVHKKYKDYQVQDMTQPEVLKGRKY
RKLVEKAQHASDSAGRSARRQTLEYAESMNIQRDIVYKERNRLIDGSRDL
EDVVVDIIERYTEEVAADHYASRELLFHFIVTNISFHVKEVPKYIDVTDK
TAVRSFMKQVIDKELSEKKELLNQHDLYEQFLRLSLLKAIDDNWVEQVDY
LQQLSMAIGGQSASQKNPIVEYYQEAYAGREAMKEQIHADMVRNLLMGLV
EVTPKGEIVTHFP

ID104 879 bp (SEQ ID NO: 111)
ATGAAACAAGAATGGTTTGAAAGTAATGATTTTGTAAAAACAACAAGCAA
GAACAAGCCTGAAGAGCAAGCTCAAGAGGTTGCAGACAAGGCTGAAGAAA
GGATACCCGATCTCGATACACCAATTGAAAAAAATACTCAGTTAGAGGAG
GAAGTCTCTCAAGCTGAAGTCGAATTGGAAAGCCAGCAAGAAGAAAAT
TGAAGCTCCTGAAGACAGTCAAGCGAGAACAGAAATAGAAGAAAAGAAGG
CATCTAATTCTACTGAAGAAGAGCCAGACCTTTCTAAAGAAACAGAAAAA
GTCACTATAGCTGAAGAGAGCCAAGAAGCTCTTCCTCAGCAAAAAGCAAC
CACGAAAGAGCCACTTCTTATCAGTAAATCTTTAGAAAGTCCTTATATCC

TABLE 2-continued

```
CCGACCAAGCTCCAAAATCTAGGGATAAATGGAAAGAGCAAGTGCTTGAT
TTTTGGTCTTGGCTAGTGGAAGCGATCAAATCTCCTACAAGTAAGTTGGA
AACAAGTATCACACACAGTTACACAGCCTTTCTCTTGCTCATTCTGTTTC
TGCATCTTCCTTTTTCTTTAGTATCTATCACATCAAACATGCTTACTATG
GACATATAGCAAGCATTAACAGTCGCTTCCCTGAGCAGCTAGCTCCTTTA
ACTCTTTTTTCTATCATCTCTATCCTAGTAGCGACAACACTCTTCTTCTT
TTCATTCCTCTTGGGTAGTTTCGTTGTGAGACGATTTATCCACCAGGAAA
AGGACTGGACGCTAGACAAGGTTCTCCAACAATATAGTCAACTCTTGGCA
ATTCCAATCTCCTCACTGCTATTGCTAGTTTCTTTGCTTTCTTTGATAGC
CTACGATTTACAGCCCTCTTGTGTGTGA (SEQ ID NO: 112)
MKQEWFESNDFVKTTSKNKPEEQAQEVADKAEERIPDLDTPIEKNTQLEE
EVSQAEVELESQQEEKIEAPEDSEARTEIEEKKASNSTEEEPDLSKTEKV
TIAEEEESQEALPQQKATTKEPLLISKSLESPYIPDQAPKSRDKWKEQVLD
FWSWLVEAIKSPTSKLETSITHSYTAFLLLILFSASSFFFSIYHIKHAYY
GHIASINSRFPEQLAPLTLFSIISILVATTLFFFSFLLGSFVVRRFIHQE
KDWTLDKVLQQYSQLLAIPISSLLLLVSLLSLIAYDLQPSCV

ID106 327 bp (SEQ ID NO: 113)
ATGTACTTTCCAACATCCTCTGCCTTGATTGAATTTCTCATCTTGGCTGT
ACTGGAGCAGGGTGATTCTTATGGTTATGAGATTAGCCAAACCATTAAGC
TGATCGCTAATATCAAAGAATCCACACTCTATCCCATTCTCAAAAAATTG
GAAGGCAATAGCTTTCTGACACCTATTCTAGAGAGTTCCAAGGTCGCAT
GCGCAAATACTACTCCTTGACAAACGGTGGTATAGAGCAGCTCTTGACCC
TAAAAGATGAATGGGCACTCTATACAGACACCATCAATGGCATCATAGAA
GGGAGTATCCGCCATGACAAGAACTGA (SEQ ID NO: 114)
MYFPTSSALIEFLILAVLEQGDSYGYEISQTIKLIANIKESTLYPILKKL
EGNSFLTTYSREFQGRMRKYYSLTNGGIEQLLTLKDEWALYTDTINGIIE
GSIRHDKN

ID108 954 bp (SEQ ID NO: 115)
ATGGATTTTGAAAAAATTGAACAAGCTTATATCTATTTACTAGAGAATGT
CCAAGTCATCCAAAGTGATTTGGCGACCAACTTTTATGACGCCTTGGTGG
AGCAAAATAGCATCTATCTGGATGGTGAAACTGAGCTAAACCAGGTCAAA
GACAACAATCAGGCCCTTAAGCGTTTAGCACTCAGGAAAGAAGAATGCT
CAAGACCTACCAGTTTCTCTTGATGAAGGCTGGGCAAACAGAACCCTTGC
AGGCCAATCACCAGTTTACACCGGATGCTATTGCTTTGCTTTTGGTGTTT
ATTGTGAAGAGTTGTTTAAAGAGGAGGAAATTACTATCCTCGAAATGGG
TTCTGGGATGGGAATTCTAGGAATGGGAAGTGGATGATTTGCTGATTGATCTGGCAG
CTAGCATGGCAGATGTAATTGGTTTGCAGGCTGGCTTTGTCCAAGGAGAT
GCCGTTCGCCCACAAATGCTCAAAGAAAGCGATGTGGTCATCAGTGACTT
GCCTGTCGGCTATTATCGATGATGCCGTTGCGTCGCGCCATCAAGTTG
CTTCTAGCCAAGAACATACTTACGCCCATCACTTGCTCATGAACAAGG
CTTAAGTACCTCAAGTCAGACGGATACGCTATTTTTCTAGCTCCGAGTGA
TTGTTGACCAGTCCTCAAAGTGATTTGTTAAAAGAATGGCTGAAAGAAGA
GGCAGCTCTGGTTGCTATGATTAGTCTGCCTGAAAATCTCTTTGCTAATG
CCAAACAATCTAAGACTATTTTTATCTTACAGAAGAAAAATGAAATAGCA
GTAGAGCCTTTTGTTTATCCACTTGCTAGCTTGCAAGATGCAAGTGTTTT
AATGAAATTTAAAGAAAATTTTCAAAATGGACTCAAGGTACTGAAATAT
AA (SEQ ID NO: 116)
MDFEKIEQAYIYLLENVQVIQSDLATNFYDALVEQNSIYLDGETELNQVK
DNNQALKRLALRKEEWLKTYQFLLMKAGQTEPLQANHQFTPDAIALLLVF
IVEELFKEEEITILEMGSGMGILGAGFVQGDAVRPQMLKESDVVISDLPVGYYPDDAVASRHQV
ASSQEHTYAHHLLMEQGLKYLKSDGYAIFLAPSDLLTSPQSDLLKEWLKE
EASLVAMSLPENLFANAKQSKTIFILQKKNEIAVEPFVYPLASLQDASVL
MKFKENFQKWTQGTEI

ID110 1902 bp (SEQ ID NO: 117)
ATGATTATTTTACAAGCTAATAAAATTGAACGTTCTTTTGCAGGAGAGGT
TCTTTTTGATAATATCAACCTGCAGGTTGATGAACGAGATCGGATTGCTC
TTGTTGGGAAAAATGGTGCAGGTAAGTCTACTCTTTTGAAGATTTTAGTT
GGAGAAGAGGAGCCAACTAGCGGAGAAATCAATAAAAAGGATATCTCTTT
GTCTTACCTAGCCCAAGATAGCCGTTTTGAGTCTGAAAATACCATCT
ACGATGAAATGCTTCATGTCTTTAATGATTTGCGTCGGACGGAGAGACAA
CTGCGTCAGATGGAGCTGGAGATGGGTGAAAAGTCTGGTGAGGATTTGGA
TAAAATGACTGTCAGATTATGACCGCTTATCTGAGAATTTTCGCCAAGCAG
GTGGCTTTACCTATGAAGCTGATATTCGAGCGATTTTGAATGGATTCAAG
```

```
TTTGACGAGTCTATGTGGCAGATGAAAATTGCTGAGCTTTCTGGTGGTCA
AAATACTCGTTTGGCACTTGCCAAAATGCTCCTTGAAAAGCCCAATCTCT
TGGTCTTGGACGAGCCAACTAACCACTTGGATATTGAAACCATCGCCTGG
CTAGAAAATTACTTGGTAAACTATAGCGGTGCCCTCATTATCGTCAGCCA
CGACCGTTATTTCTTGGACAAGGTTGCGACAATTACGCTAGATTTGACCA
AGCATTCCTTGGATCGCTATGTGGGAATTACTCGTTTTGTCGAATTGA
AGGAGCAAAAGCTAGTTACTGAGGCAAAAACATATGAAAAGCAACAGAAG
GAATCGCTGCTCTGGAAGACTTTGTCAATCGCAATCTAGTTCGTGCTTC
AACGACTAAACGTGCTCAATCTCGCCGTAAACAACTAGAAAAAATGGAGC
GTTTGGACAAGCTCGAAGCTGGCAAGAAAGCAGCCAACATGACCTTCCAG
TCTGAAAAACGTCGGGCAATGTTGTTTTGACTGTTGAAATGCAGCTGT
TGGCTATGACGGGGAAGTCTTGTCACAACCTATCAACCTAGATCTTCGTA
AGATGAATGCTGTCGCTATCGTTTGGTCCAAATGGTATCCGGCAAGTCAACC
TTTATCAAGTCTATTGTGACCAGATTCCTTTTATCAAGGGAGAAAAGCG
CTTTGGCGCTAATGTTGAGGTTGGTTACTATGACCAAACCCAAAGCAAGC
TGACACCAAGTAATACGGTGCTGGATGAACTCTGGAATGATTTCAAACTG
ACACCAGAAGTTGAAATCCGCAACCGTCTTGGAGCCTTCCTTTTCTCAGG
AGATGATGTTAAAAATCAGTCGGCATGCTATCTGGTGGCGAAAAAGCTC
GTTTGCTTTTAGCTAAATTGTCTATGGAAAACATAACTTTTGATTCTG
ATGAGCCGACCAACCCACTTGGATATTGATAGTAAGGAAGTGCTAGAAAA
TGCCTTGACTTTGATGGAACCTTGCTGTTTGTCAGTCATGATCGTT
ACTTTATCAATCGTGTGGCAACTCATGTTTTGGAATTGTCTGAGAATGGT
TCAACTCTCTACCTTGGAGATTACGACTACTATGTTGAGAAGAAGCAAC
AGCAGAAATGAGTCAGACTGAGGAAGCTTCAACTAGCAATCAAGCAAAGG
AAGCAAGTCCAGTCAATGACTATCAGGCCCAGAAAGAAAGTCAAAAAGAA
GTTCGCAAACTCATGCGACAAATCGAAAGTCTAGAAGCTGAAATTGAAGA
GCTAGAAAGTCAAAGCCAAGCCATTTCTGAACAAATGTTGGAAACAAACG
ATGCCGACAAACTCATGGAATTACAGGCTGAGCTGGACAAAATCAGCCAT
CGTCAGGAAGAAGCTATGCTTGAGTGGGAAGAATTATCAGAGCAGGTGTA
A (SEQ ID NO: 118)
MIILQANKIERSFAGEVLFDNINLQVDERDRIALVGKNGAGKSTLLKILV
GEEEPTSGEINKKKDISLSYLAQDSRFESENTIYDEMLHVFNDLRRTERQ
LRQMELEMGEKSGEDLDKLMSDYDRLSENFRQAGGFTYEADIRAILNGFK
FDESMWQMKIAELSGGQNTRLALAKMLLEKPNLLVLDEPTNHLDIETIAW
LENYLVNYSGALIIVSHDRYFLDKVATITLDLTKHSLDRYVGNYSRFVEL
KEQKLVTEAKNYEKQQKEIAALEDFVNRNLVRASTTKRAQSRRKQLEKME
RLDKPEAGKKAANMTFQSEKTSGNVVLTVENAAVGYDGEVLSQPINLDLR
KMNAVAIVGPNGIGKSTFIKSIVDQIPFIKGEKRFGANVEVGYYDQTQSK
LTPSNTVLDELWNDFKLTPEVEIRNRLGAFLFSGDDVKKSVGMLSGGEKA
RLLLAKLSMENNNFLILDEPTNHLDIDSKEVLENALIDFDGTLLFVSHDR
YFINRVATHVLELSENGSTLYLGDYDYYVEKKATAEMSQTEEASTSNQAK
EASPVNDYQAQKESQKEVRKLMRQIESLEAEIEELESQSQAISEQMLETN
DADKLMELQAELDKISHRQEEAMLEWEELSEQV

ID111 1179 bp (SEQ ID NO: 119)
ATGAATCGCTATGCAGTGCAGTTGATTAGCCGTGGGGCTATCAATAAAAT
GGGAAATATGCTCTATGATTATGGAAATAGTGTCTGGTTGGCTTCTATGG
GGACTATAGGACAGACAGTTTTAGGAATGTATCAGATTTCTGAGCTCGTC
ACATCTATTCTCGTCAATCCCTTTGGCGGAGTTATTTCAGACCGTTTTTC
TCGTCGTAAGATTTAATGACGGCAGATCTTGTTTGTGGGATTCTTTGTCT
GGCTATTTCTTCATAAGGAATAGCTGGATGATTGGCGCTTGATTGT
TGCTAACATTGTGCAGGCTATTGCTTTTGCCTTTTCTCGCACAGCCAATA
AAGCTATCATAACTGAAGTGGTGGAGAAAGATGAGATTGTGATCTATAAT
TCTCGCTTAGAGCTGGTTTTGCAGGTTGTAGGTGTTAGCTCCTGTTCT
TTCCTTCCTTGTTTTACAGTTTGCAAGTCTCCATATGACGACTACTGCTA
GACTCGCTGACTTTTTTCATTGCTTTTGTTCTAGTGGCTTTCCTTCCAAA
AGAGGAAGCAAAAGTTCAAGAGAAAAAGGCTTCAGTGGCTTTCCTTCCA
AAAGAGGAAGCAAAAGTTCAAGAGAAAAAGGCTTTTACTGGGAGAGATAT
TTTTGTAGATATCAAGGATGGGTTACACTATATCTGGCATCAGCAAGAAA
TTTTCTTCCTTTTGCTGGTAGCTTCCAGCGTTAATTTCTTTTTTGCAGCT
TTTGAATTTCTACTTCCCTTTTCGAATCAGCTTTACGGGTCAGAAGGAGC
CTATGCAAGTATTTTAACTATGGGGCTATTGGTTCCATCATTGGGGCTC
TTCTAGCTGATAAATTAAAGCTAATATTATAATCTTTTGATTTTAATC
GCTTTGACAGGTGTCGGAGTTTTTATGATGGGATTACCACTTCCAACTT
TCTTTCCTTTTCTGGAAATTTAGTTTGTGAATTGTTTATGACGATTTTTA
ATATTCACTTTTTTACTCAAGTACAAACCAAGGTTGAGAGCGAATTTCTT
GGAAGAGTACTAGATTCTTACCTTAGCTATTCTATTTATTGCCTAT
TGCAAAAGGATTTATGACAGTCTTGCCAAGTGTCCATCTTTATTCTTTCT
TGATTATTGGACTTGGAGTTGTAGCCTTATATTTCTTAGCTCTCGGATAT
GTTCGAACTCATTTTGAAAAATTGATATAA (SEQ ID NO: 120)
MNRYAVQLISRGAINKMGNMLYDYGNSVWLASMGTIGQTVLGMYQISELV
TSILVNPFGGVISDRFSRRKILMTADLVCGILCLAISFIRNDSWMIGALI
VANIVQAIAFAFSRTANKAIITEVVEKDEIVIYNSRLELVLQVVGVSSPV
LSFLVLQFASLHMTLLLDSLTFFIAFVLVAFLPKEEAKVQEKKAFTGRDI
```

TABLE 2-continued

FVDIKDGLHYIWHQQEIFFLLLVASSVNFFFAAFEFLLPFSNQLYGSEGA
YASILTMGAIGSIIGALLASKIKANIYNLLILLALTGVGVFMMGLPLPTF
LSFSGNLVCELFMTIFNIFFTQVQTKVESEFLGRVLSTIFTLAILFMPIA
KGFMTVLPSVHLYSFLIIGLGVVALYFLALGYVRTHFEKLI

ID113 2466 bp (SEQ ID NO: 121)
ATGCAAAATCAATTAAATGAATTAAAACGAAAAATGCTGGAATTTTTCCA
GCAAAAACAAAAAAATAAAAAATCAGCTAGACCTGGCAAGAAAGGTTCAA
GTACCAAAAAATCTAAAACCTTAGATAAGTCAGCCATTTTCCCAGCTATT
TTACTGAGTATAAAAGCCTTATTTAACTTACTCTTTGTACTCGGTTTTCT
AGGAGGAATGTTGGGAGCTGGGATTTGCTTTGGGATACGGAGTGGCCTTAT
TTGACAAGGTTCGGGTGCCTCAGACAGAAGAATTGGTGAATCAGGTCAAG
GACATCTCTTCTATTTCAGAGATTACCTATTCGGACGGGACGGTGATTGC
TTCCATAGAGAGTGATTTGTTGCGCACTTCTATCTCATCTGAGCAAATTT
CGGAAAAATCTGAAGAAGGCTATCATTGCGACAGAAGATGAACACTTTAA
GAACATAAGGGTGTAGTACCCAAGGCGGTGATTCGTGCGACCTTGGGGAA
ATTTGTAGGTTTGGGTTCCTCAGTGGGGGTTCAACCTTGACCCAGCAAC
TAATTAAACAGCAGGTGGTTGGGGATGCGCCGACCTTGGCTCGTAAGGCG
GCAGAGATTGTGGATGCTCTTGCCTTGGAACGCGCCATGAATAAAGATGA
GATTTTAACGACCTATCTCAATGTGGCTCCCTTTGGCGAAATAATAAGGG
ACAGAATATTGCAGGGGCTCGGCAAGCAGCTGAGGGAATTTTCGGTGTAG
ATGCCAGTCAGTTGACTGTTCCTCAAGCAGCATTTTTAGCAGGACTTCCA
CAGAGTCCATTACTTACTCTCCTTATGAAAATACTGGGGAGTTGAAGAGT
GATGAAGACCTAGAAATTGGCTTAAGACGGGCTAAGGCAGTTCTTTACAG
TATGTATCGTACAGGTGCATTAAGCAAAGACGAGTATTCTCAGTACAAGG
ATTATGACCTTAAACAGGACTTTTTACCATCGGGCACGGTTACAGGAATT
TCACGAGACTATTTATACTTTACAACTTTGGCAGAAGCTCAAGCATGTAT
GTATGACTATCTAGCTCAGAGAGACAATGTCTCCGCTAAGGAGTTGAAAA
ATGAGGCAACTCAGAAGTTTTATCGAGATTTGGCAGCCAAGGAAATTGAA
AATGGTGGTATAAGATTACTACTACCATAGATCAGAAAATTCATTCTGCC
ATGCAAAGTGCGGTTGCTGATTATGGCTATCTTTTAGACGATGGAACAGG
TCGTGTAGAAGTAGGGAATGTCTTGATGGATAACCAAACAGGTGCTATTC
TAGGCTTTGTAGGTGGTCGTAATTATCAAGAAATCAAAATAATCATGCC
TTTGATACCAAACGTTCGCCAGCTTCTACTACCAAGCCCTTGCTGGCCTA
CGGTATTGCTATTGACCAGGGCTTGATGGGAAGTGAAACGATTCTATCTA
ACTATCCAACAAACTTTGCTAATGGCAATCCGATTATGTATGCTAATAGC
AAGGGAACAGGAATGATGACCTTGGGAGAAGCTCTGAACTATTCATGGAA
TATCCCTGCTTACTGGACCATCGTATGCTCCGTGAAAAGGGTGTTGATG
TCAAGGGTTATATGAAAAGATGGGTTACGAGATTCCTGAGTACGGTATT
GAGAGCTTGCCAATGGGTGGTGTATTGAAGTCACAGTTGCCCAGCATAC
CAATGGCTATCAGACCTTAGCTAATAATGGAGTTTTATCATCAGAAGCATG
TGATTTCAAAGATTGAAGCAGCAGATGGTAGAGTGGTGTATGAGTATCAG
GATAAACCGGTTCAAGTCTATTCAAAAGCTACTGCGACGATTATGCAGGG
ATTGCTACGAGAAGTTCTATCCTCTGTGACAACAACCTTCAAGTCTAAA
CTGACTTCTTTAAATCCTACTCTGGCTAATGCAGATTGGATTGGGAAGAC
TGGTACAACCAACCAAGACGAAAATATGTGGCTCATGCTTTCGACACCTA
GATTAACCCTAGGTGGCTGGATTGGGCATGATGATAATCATTCATTGTCA
CGTAGAGCAGGTTATTCTAATAACTCTAATTACATGGCTCATCTGGTAAA
TGCGATTCAGCAAGCTTCCCCAAGCATTTGGGGGAACGAGCGCTTTGTT
TAGATCCTAGTGTAGTGAAATCGGAAGTCTTTGAAATCAACAGGTCAAAAA
CCAGAGAAGGTTTCTGTTGAAGGAAAAGAAGTCTTGAAATCAACAGGTCA
AAAACCAGAGAAGGTTTCTGTTGAAGGAAAAGAAGTAGAGGTCACAGGTT
CGCTGTTACCAGCTATTGGGCTAATAAGTCAGGAGCGCCAGCGACAAGTT
ATCGCTTTGCTATTGGCGGAAGTGATGCGGATTATCAGAATGCTTGGTCT
AGTATTGTGGGGAGTCTACCAACTCCATCCAGCTCCAGCAGTTCAAGTAG
TAGTTCTAGCAGTAGCAGTAACTCAAGTACTACTACACGACCTTCTTCTT
CAAGGGCGAGACGATAA (SEQ ID NO: 122)
MQNQLNELKRKMLEFFQQKQKNKKSARPGKKGSSTKKSKTLDKASAIFPA
ILLSIKALFNLLFVLGFLGGMLGAGIALGYGVALFDKVRVPQTEELVNQV
KDISSISEITYSDGTVIASIESDLLRTSISSEQISENLKKAIIATEDEHF
KEHKGVVPKAVIRATLGKFVGLGSSSGGSTLTQQLIKQQVVGDAPTLARK
AAEIVDALALERAMNKDEILTTYLNVAPFGRNNKGQNIAGARQAAEGIFG
VDASQLTVPQAAFLAGLPQSPITYSPYENTGELKSDEDLEIGLRRAKAVL
YSMYRTGALSKDEYSQYKDYDLKQKFLPSGTVTGIRSDYLYFTTLAEAQE
RMYDYLAQRDNVSAKELKNEATQKFYRDLAAKEIENGGYKITTTIDQKIH
SAMQSAVADYGYLLDDGTGRVEVGNVLMDNQTGAILGFVGGRNYQENQNN
HAFDTKRSPASTTKPLLAYGIADQGLMGSETILSNYPTNFANGNPIMYAN
SKGTGMMTLGEALNYSWNIPAYWTYRMLREKGVDVKGYMEKMGYEIPEYG
IESLPMGGGIEVTVAQHTNGYQTLANNGVYHQKHVISKIEAADGRVVYEY
QDKPVQVYSKATATIMQGLLREVLSSRVTTTFKSNLTSLNPTLANADWIG
KTGTTNQDENMWLMLSTPRLTLGGWIGHDDNHSLSRRAGYSNNSNYMAHL
VNAIQQASPSIWGNERFALDPSVVKSEVLKSTGQKPEKVSVEGKEVEVTG
STVTSYWANKSGAPATSYRFAIGGSDADYQNAWSSIVGSLPTPSSSSSSS
SSSSDSSNSSTTRPSSSRARR

ID114 1974 bp (SEQ ID NO: 123)
ATGAAAAAATTTTATGTAAGTCCAATTTTTCCTATTCTAGTAGGATTGAT
TGCGTTTGGAGTCTTATCCACTTTCATTATTTTTGTTAATAATAATCTGT
TGACGGTTTTAATTTTGTTTCTTTTTGTAGGAGGCTATGTTTTTTTATTT
AAGAAACTGAGAGTGCATTATACAAGGAGTGATGTAGAACAGATACAGTA
TGTAAACCACCAAGCGGAAGAAAGTTTGACAGCTCTATTGGAACAGATGC
CTGTAGGTGTTATGAAATTGAATTTATCTTCTGGAGAGGTTGAGTGGTTT
AATCCCTATGCTGAATTGATTTTGACCAAGGAAGATGGTGATTTTGATTT
AGAAGCTGTTCAAACGATTATCAAGGCTTCAGTAGGAAATCCGTCTACTT
ATGCCAAGCTTGGTGAGAAGCGTTATGCTGTTCATATGGATGCTTCTTCC
GGTGTTTTGTATTTTGTAGATGTATCCAGGGAACAAGCCATAACAGATGA
ATTGGTAACAAGTAGACCAGTGATTGGGATTGTCTCTGTGGATAATTATG
ATGATTGGAGGATGAAACTTCTGAGTCAGATATTAGTCAAATCAATAGTT
TTGTAGCTAATTTTTATATCAGAGTTTTCAGAAAACACATGATGTTTTCT
CGTCGGGTAAGTATGGATCGATTTTATCTATTTACTGACTACACGGTGCT
TGAGGGCTTGATGAATGATAAATTTTCTGTTATTGATGCTTTCAGAGAAG
AGTCGAAACAGAGACAGTTGCCCTTGACCTTAAGTATGGGATTTTCTTAT
GGCGATGGAAATCATGATGAGATAGGGAAAGTTGCTTTGCTCAATTTGAA
CTTGGCTGAAGTACGTGGTGGCGACCAGGTGGTTGTTAAGGAAAACGACG
AAACGAAAAATCCAGTTTATTTTGGTGGTGGGTCTGCTGCTTCAATCAAG
CGTACACGGACTCGTACGCGCGCTATGATGACAGCTATTTCAGATAAGAT
TCGGAGTGTAGATCAGGTTTTTGTAGTCGGTCACAAAATTTAGACATGGA
TGCTTTGGGCTCTGCTGTAGGTATGCAGTTGTTCGCCAGCAATGTGATTG
AAAAATAGCTATGCTCTTATGATGAAGAACAAATGTCTCCAGATATTGAAC
GAGCTGTTCATTCATAGAAAAGAAGGAGTTACGAAGTTGTTGTCTGTTA
AGGATGCAATGGGGATGGTGACCAATCGTTCTTTGTTGATTCTTGTAGAC
CATTCAAAGACAGCCTTAACATTACTCAAAAGAATTTTTATGATTTATTTAC
CCAAACCATTGTTATTGACCACCATAGAAGGGATCAGGATTTTCCAGATA
ATGCGGTTATTACTTATATCGAAAGTGGTGCAAGTAGTGCCAGTGAGTTG
GTAACGGAATTCATTCAGTTCCAGAATTCTAAGAAAAATCGTTTGAGTCG
TATGCAAGCAAGTGTCTTGATGGCTGGTATGATGTTGGATACTAAAAATT
TCAACCTCGCGAGTAACTAGTCGGACATTTGATGTTGCTAGCTATCTCAGA
ACGCGCGGAAGTGATAGTATTGCTATCCAGGAAATCGCTGCGACAGATTT
TGAAGAATATCGTGAGGTCAATGAACTTATTTTACAGGGCGTAAATTGA
GTTCAGATGTACTAATAGCAGAGGCTAAGGACATGAAATGCTATGATACA
GTTGTTATTAGTAAGGCAGCAGATGCCATGTTAGCCATGTCAGGTATTGA
AGCGAGTTTTGTTCTTGCGAAGAATACAACAAGGATTTATCTCTATCTCAG
CTCGAAGTCGTAGTAAACTGAATGTACAACGGATTATGGAAGAGTTAGGC
GGTGGAGGCCACTTTAATTTGGCAGCAGCTCAAATTAAAGATGTAACCTT
GTCAGAAGCAGGTGAAAAACTGACAGAAATTGTATTAAATGAAATGAAGG
AAAAGGAGAAAGAAGAATGA (SEQ ID NO: 124)
MKKFYVSPIPILVGLIAFGVLSTFIIFVNNNLLTVLILFLFVGGYVFLF
KKLRVHYTRSDVEQIQYVNHQAEESLTALLEQMPVGVMKLNLSSGEVEWF
NPYAELILTKEDGDFDLEAVQTIIKASVGNPSTYAKLGEKRYAVHMDASS
GVLYFVDVSTRQAITDELVTSRPVIGIVSVDNYDDLEDETSESDISQINS
FVANFISEFSEKHMMFSRRVSMDRFYLFTDYTVLEGLMNDKFSVIDAFRE
ESKQRQLPLTLSMGFSYGDGNHEIGKVALLNLNLAEVRGGDQVVVKENDE
TKNPVYFGGGSAASIKRTRTRTRAMMTAISDKIRSVDQVFVVGHKNLDMD
ALGSAVGMQLFASNVIENSYALYDEEQMSPDIERAVSFIEKEGVTKLLSV
KDAMGMVTNRSLLILVDHSKTALTLSKEFYDLFTQTIVIDHHRRDQDFPD
NAVITYIESGASSASELVTELIQFQNSKKNRLSRMQASVLMAGMMLDTKN
FTSRVTSRTFDVASYLRTRGSDSIAIQEIAATDFEEYREVNELILQGRKL
GSDVLIAEAKDMKCYDTVVISKAADAMLAMSGIEASFVLAKNTQGFISIS
ARSRSKLNVQRIMEELGGGGHFNLAAAQIKDVTLSEAGEKLTEIVLNEMK
EKEKEE

ID115 663 bp (SEQ ID NO: 125)
ATGAAGTGCTTGTTATGTGGGCAGACTATGAAGACTGTTTTAACTTTTAG
TAGTCTCTTACTTCTGAGGAATGATGACTCTTGTCTTTGTTCAGACTGTG
ATTCTACTTTTGAAAGAATTGGGGAAGAGAACTGTCCAAATTGTATGAAA
ACAGAGTTGTCAACAAAGTGTCAAGATTGTCAACTTTGGTGTAAAGAGGG
AGTTGAAGTCAGTCATAGAGCGATTTTTACTTACAATCAAGCTATGAAGG
ATTTTTTCAGTCGGTATAAGTTTGATGGAGACTTCCTGTTAAGAAAAGTT
TTCGCTTCATTTTTAAGTGAGGAGTTGAAAAAGTACAAAGAGTATCAATT
TGTTGTAATTCCCCTAAGTCCTGATAAGATGCTAATAGAGGATTTAAAT
AGGTTGAGGGCTTGGTAGAGGCAGCAGGCTTTGAGTATCTGGATTTATTA
GAGAAAAGAGAAGAGAGAGCCAGTTCTTCTAAAAATCGTTCAGAGCGCTT
GGGGACAGAACTTCCTTTCTTTATTAAAAGTGGAGTCACTATTCCTAAAA
AAATCCTACTTATAGATGATATCTATACTACAGGAGCAACTATAAATCGT
GTTAAGAAACTGTTGGAAGAAGCTGGTGCTAAGGATGTAAAAACATTTCC
CTTGTAAGATGA

TABLE 2-continued (SEQ ID NO: 126)
MKCLLCGQTMKTVLTFSSLLLLRNDDSCLCSDCDSTFERIGEENCPNCMK
TELSTKCQDCQLWCKEGVEVSHRAIFTYNQAMKDFFSRYKFDGDFLLRKV
FASFLSEELKKYKEYQFVVIPLSPDRYANRGFNQVEGLVEAAGFEYLDLL
EKREERASSSKNRSERLGTELPFFIKSGVTIPKKILLIDDIYTTGATINR
VKKLLEEAGAKDVKTFSLVR ID116 1299 bp (SEQ ID NO: 127)
ATGAAAGTAAATTTAGATTATCTCGGTCGTTTATTTACTGAGAATGAATT
AACAGAAGAAGAACGTCAGTTGGCGGAGAAACTTCCAGCAATGAGAAAGG
AGAAGGGGAAACTTTTCTGTCAACGCTGTAATAGTACTATTCTAGAAGAA
TGGTATTTGCCCATCGGTGCTTACTATTGTCGAGAGTGCTTGCTGATGAA
GCGAGTCAGAAGTGATCAAACTTTATACTATTTTCCGCAGGAGGATTTTC
CAAAGCAAGATGTTCTCAAATGGCGCGGCCAATTAACTCCTTTTCAAGAG
AAGGTGTCAGAGGGATTGCTTCAAGTAGTAGACAAGCAAAAGCCAACCTT
AGTTCATGCGGTAACAGGAGCTGGAAAGACAGAAATGATTTATCAAGTAG
TGGCTAAAGTGATCAATGCGGGTGGTGCAGTGTGTTTGGCTAGTCCTCGC
ATAGATGTTTGTTTGGAGCTGCATGTACAAGCGCCTGCAACAGGATTTTCTTG
CGGGATAGCTTTGCTACATGGAGAATCGGAACCTTATTTTCGAACACCAC
TAGTTGTTGCAACAACCCATCAGTTATTGAAGTTTTATCAAGCTTTTGAT
TGCTGATAGTGGATGAAGTAGATGCTTTTCCTTATGTTGATAATCCCATG
CTTTACCACGCTGTCAAATAATAGTGTAAAGGAGAATGGATTGAAGATCT
TTTTAACAGCGACTTCGACCAATGAGTTAGATAAAAAGGTTCCGTTTAGGA
GAACTAAAAAGACTGAATTTACCGAGACGGTTTCATGGAAATCCGTTGAT
TATTCCAAAACCAATTTGGTTATCGGATTTTAATCGCTACTTAGACAAGA
ATCGTTTGTCACCAAAGTTAAAGTCCTATATTGAGAAGCAGAAAAGACA
GCTTATCCGTTACTCATTTTTGCTTCAGAAATTAAGAAAGGGGAGCAGTT
AGCAGAAATCTTACAGGAGCAATTTCCAAATGAGAAAATTGGCTTTGTAT
CTTCTGTAACAGAGGATCGATTAGAGCAAGTACAAGCTTTTCGAGATGGA
GAACTGACAATCTTATCAGTACGACAATCTTGGAGCGCGGAGTTACCTT
CCCTTGTGGATGTTTTCGTAGTAGAGGCCAATCATCGTTTGTTTACCAAG
TCTAGTTTGATTCAGATTGGTGGACGAGTTGGACGAAGCATGGATAGACC
GACAGGAGATTTGCTTTTCTTCCATGATGGGTTAAATGCTTCAATCAAGA
AGGCGATTAAGGAAATTCAGATGATGAATAAGGAGGCTGGTCTATGA (SEQ ID NO: 128)
MKVNLDYLGRLFTENELTEEERQLAEKLPAMRKEKGKLFCQRCNSTILEE
WYLPIGAYYCRECLLMKRVRSDQTLYYFPQEDFPKQDVLKWRGQLTPFQE
KVSEGLLQVVDKQKPTLVHAVTGAGKTEMIYQVVAKVINAGGAVCLASPR
IDVCLELYKRLQQDFSCGIALLHGESEPYFRTPLVVATTHQLLKFYQAFD
LLIVDEVDAFPYVDNPMLYHAVKNSVKENGLRIFLTATSTNELDKKVRLG
ELKRLNLPRRFHGNPLIIPKPIWLSDFNRYLDKNRLSPKLKSYIEKQRKT
AYPLLIFASEIKKGEQLAEILQEQFPNEKIFGVSSVTEDRLEQVQAFRDG
ELTILISTTILERGVTFPCVDVGVVEANHRLFTKSSLIQIGGRVGRSMDR
PTGDLLFFHDGLNASIKKAIKEIQMMNKEAGL ID117 870 bp (SEQ ID NO: 129)
ATGCAAATTCAAAAAGTTTTAAGGGGCAGTCTCCCTATGGCAAGCTGTA
TCTAGTGGCAACGCCGATTGGCAATCTAGATGATATGACTTTTCGTGCTA
TCCAGACCTTGAAAGAAGTGGACTGGATTGCTGCTGAGGATACGCGCAAT
ACAGGGCTTTTGCTCAAGCATTTTGACATTTCCACCAAGCAGATCAGTTT
TCATGAGCACAATGCCAAGGAAAAAATTCCTGATTTGATTTGGTTTCTTGA
AAGCAGGGCAAAGTATTGCTCAGGTCTCTGATGCGGTTTGCCTAGCATT
TCAGACCCTGGTCATGATTTAGTTAAGGCAGCTATTGAGGAAGAAATTG
AGTTGTGACAGTTCCAGGTGCCTCTGCAGGAATTTCTGCCTTGATTGCCA
GTGGTTTAGCGCCACAGCCACATATCTTTTACGGTTTTTTACCGAGAAAA
TCAGGTCAGCAGAAGCAATTTTTTGGCTTGAAAAAAGATTATCCTGAAGA
ACAGATTTTTTATGAATCACCTCATCGTGTAGCAGACACGTTGGAAAATA
TGTTAGAAGTCTACGGTGACCGCTCCGTTGTCTTGGTCAGGGAATTGACC
AAAATCTATGAAGAATACCAACGAGGTACTATCTCTGAGTTATTAGAAAG
CATTGCTGAAACGCCACTCAAGGGCGAATGTCTTCTCATTGTTGAGGGTG
CCAGTCAGGGTGTGGAGGAAAAGGACGAGGAAGACTTGTTCGTGAAATT
CAAACCCGCATCCAGCAAGGTGTGAAGAAAAAACCAAGCTATCAAGGAAGT
CGCTAAGATTACCAGTGGAATAAAAGTCAGCTCTACGCTGCCTACCACGA
CTGGGAAGAAAACAATAA (SEQ ID NO: 130)
MQIQKSFKGQSPYGKLYLVATPIGNLDDMTFRAIQTLKEVDWIAAEDTRN
TGLLLKHFDISTKQISGHEHNAKEKIPDLIGFLKAGQSIAQVSDAGLPSI
SDPGHDLVKAAIEEEIAVVTVPGASAGISALIASGLAPQPHIFYGFLPRK
SGQFFGLKKDYPETQIFYESPHRVADTLENMLEVYGDRSVVLVRELTKIY
EEYQRGTISELLESIAETPLKGECLLIVEGASQGVEEKDEEKLFVEIQTR
IQQGVKKNQAIKEVAKIYQWNKSQLYAAYHDWEEKQ ID118 345 bp (SEQ ID NO: 131)
ATGATAAAGAAAGGGAAAGGGCTGTTTTATGGACAAAAAGAATTATTTGA
CGCGCTGGATGATTTTTCCCAACAATTATTGGTAACCTTAGCCGATGTGG
AAGCCATCAAGAAAAATCTCAAGAGCCTGGTAGAGGAAATACAGCTCTT
CGCTTTGGAAAATAGTAAGTTGCGAGAACGCTTGGGTGAGGTGGAAGCAG
ATGCTCCTGTCAAGGCCAAGCATGTTCGCGAAAGTGTCCGTCGTATTTAC
CGTGATGGATTTCACGTATGTAATGATTTTTATGGACAACGTCGAGAGCA
GGACGAAGAATGTATGTTTTGTGACGAGTTGTTATACAGGGAGTAA (SEQ ID NO: 132)
MIKKGKGCFMDKKELFDALDDFSQQLLVTLADVEAIKKNLKSLVEENTAL
RLENSKLRERLGEVEADAPVKAKHVRESVRRIYRDGFHVCNDFYGQRREQ
DEECMFCDELLYRE ID119 639 bp (SEQ ID NO: 133)
ATGTCAAAAGGATTTTTAGTCTCTCTTGAGGGACCAGAGGGAGCAGGCAA
GACCAGTGTTTTAGAGGCTCTGCTACCAATTTTAGAGGAAAAAGGAGTAG
AGGTGTTGACGACCCGTGAACCTGGCGGAGTCTTGATTGGGGAGAAGATT
CGGGAAGTGATTTTGGATCCAAGTCATACTCAGATGGATGCTAAAACAGA
GCTACTTCTCTATATTGCCAGTCGCAGACAGCATTTGGTGGAAAAGTCTT
TTCCAGCCCTTGAAGCTGGCAAGTTGGTCATCATGGATCGTTTTATCGAT
AGTTCTGTTGCCTATCAGGGATTTGGTCGTGGCTTAGATATTGAAGCCAT
TGACTGGCTCAATCAGTTTGCGACAGATGGCCTCAAACCCGATTTGACAC
TCTATTTTGACATCGAGGTGGAAGAAGGGCTGGCTCGTATTGCTGCTAAT
AGTGACCGCGAGGTTAATCGTTTGGAATTTGGAAGGGTTGGACTTGACTAA
AAAAGTTCGTCAAGGCTACCTTCTCTTCTGGATAAAGAGGGAAATCGCAT
TGTCAAGATTGATGCTAGTCTCCCTTTGGAGCAAGTTGTGGAAACTACCA
AGGCTGTCTTGTTGACGGAATGGGCTTGGCCAAATGA (SEQ ID NO: 134)
MSKGFLVSLEGPEGAGKTSVLEALLPILEEKGVEVLTTREPGGVLIGEKI
REVILDPSHTQMDAKTELLLYIASRRQHLVEKVLPALEAGKLVIMDRFID
SSVAYQGFGRGLDIEAIDWLNQFATDGLKPDLTYFDIEVEEGLARIAAN
SDREVNRLDLEGLDLHKKVRQGYLSLLDKEGNRIVKIDASLPLEQVVETT
KAVLFDGMGLAK ID120 408 bp (SEQ ID NO: 135)
ATGGTAGAACAAAGAAAATCAATTACCATGAAAGATGTTGCTTTAGAAGC
AGGAGTTAGTGTTGGAACTGTTTCACGTGTAATTAATAAAGAAAAGGCAT
TAAAGAAGTAACTTTGAAAAAAGTGGAACAAGCGATTAAAACTTTGAATT
ACATTCCAGATTACTACGCTAGAGGAATGAAAAAAAATCGAACAGAAACG
ATTGCAATCATTGTACCAAGTATCTGGCATCCCTTCTTTTCAGAATTTGC
TATGCATGTGGAAATGAAGTCTATAAGAGAAATAACAAATTACTCTTATG
TTCTATCAATGGTACAAATAGAGAGCAAGACTATCTGGAGATGTTGCGTC
ATAATAAAGTTGATGGAGTGGTTGCCATTACCTATAGGCCAATTGAACAT
TACTTGACGTCAGGAATTCCCTTTGTTAGTATTGACCGCACATACTCAGA
GATTGCCATTCCTTGTGTTTCA (SEQ ID NO: 136)
MVEQRKSITMKDVALEAGVSVGTVSRVINKEKGIKEVTLKKVEQAIKTLN
YIPDYYARGMKKNRTETIAIIVPSIWHPFFSEFAMHVENEVYKRNNKLLL
CSINGTNREQDYLEMLRHNKVDGVVAITYRPIEHYLTSGIPFVSIDRTYS
EIAIPCVS ID121 285 bp (SEQ ID NO: 137)
ATGAATATATTTAGAACAAAGAATGTTAGTTTAGATAAAACAGAGATGCA
TAGGCATTTGAAGTTATGGGATCTGATTTTGCTGGGTATCGGAGCCATGG
TAGGGACAGGCGTTCTTTACAATCACAGGTACTGCAGCTGCAACACTTGCT
GGCCCAGCCCTAGTGATTTCAATCGTTATTTCTGCCTTGTGTGTGGGATT
ATCAGCCTCTTTTTTGCAGAATTTGCCTCGCGAGTACCCGCTACAGGAGG
TGCCTATAGTTACCTCTATGCTATCTTAGGAGAATTCCCTGCCTGGTTGG
CTGGTTGGTTAACCATGATGGAGTTCATGACAGCCATATCAGGCGTAGCT
TCGGGTTGGGCAGCTTATTTTAA (SEQ ID NO: 138)
MNIFRTKNVSLDKTEMHRHLKLWDLILLGIGAMVGTGVFTITGTAAATLA
GPALVISIVISALCVGLSALFFAEFASRVPATGGAYSYLYAILGEFPAWL
AGWLTMMEFMTAISGVASGWAAYF TABLE 2-continued ID124 1311 bp (SEQ ID NO: 139)
ATGAAATCAAGAGTAAAGGAAACGAGTATGGATAAAATTGTGGTTCAAGG
TGGCGATAATCGTCTGGTAGGAAGCGTGACGATCGAGGGAGCAAAAAATG
CAGTCTTACCCTTGTTGGCAGCGACTATTCTAGCAAGTGAAGGAAAGACC
GTCTTGCAGAATGTTCCGATTTTGTCGGATGTCTTTATTATGAATCAGGT
AGTTGGTGGTTTGAATGCCAAGGTTGACTTTGATGAGGAAGCTCATCTTG
TCAAGGTGGATGCTACTGGCGACATCACTGAGGAAGCCCCTTACAAGTAT
GTCAGCAAGATGCGCGCCTCCATCGTTGTATTAGGGCCAATCCTTGCCCG
TGTCGGTCATGCCAAGGTATCCATGCCAGGTGGTTGTACGATTGGTAGCC
GTCCTATTGATCTTCATTTGAAAGGTCTGGAAGCTATGGGGTTAAGATT
AGTCAGACAGCTGGTTACATCGAAGCCAAGGCAGAACGCTTGCATGGTGC
TCATATCTATATGGACTTTCCAAGTGTTGGTGCAACGCAGAACTTGATGA
TGGCAGCGACTCTGGCTGATGGGGTACAGTGATTGAGAATGCTGCGCGTG
AGCCTGAGATTGTTGACTTAGCCATTCTCCTTAATGAAATGGGAGCCAAG
GTCAAAGGTGCTGGTACAGAGACTATAACCATTACTGGTGTTGAGAAACT
TCATGGTACGACTCACAATGTAGTCCAAGACCGTATCGAAGCAGGAACCT
TTATGGTAGCTGCTGCCATGACTGGTGGTGATGTCTTGATTCGAGACGCT
GTCTGGGAGCACAACCGTCCCTTGACTTGCCAGTTACTTGAAATGGGTGT
TGAAGTAATTGAAGAAGACGAAGGAATTCGTGTTCGTTCTCAACTAGAAA
TCTAAAAGCTGTTCATGTGAAAACCTTGCCCCACCCAGGATTTCCAACAG
ATATGCAGGCTCAATTTACAGCCTTGATGACAGTTGCAAAAGGCGAATCA
ACCATGGTGGAGACAGTTTTCGAAATCGTTTCCAAACCTAGAAGAGATGC
GCCGCATGGGCTTGCATTCTGAGATTATCCGTGATACAGCTCGTATTGTT
GGTGGACAGCCTTTGCAGGGAGCAGAAGTTCTTTCAACTGACCTTCGTGC
CAGTGCGGCCTTGATTTTGACAGGTTTGGTAGCACAGGGAGAAACTGTGG
TCGGTAAATTGGTTCACTTGGATAGAGGTTACTACGGTTCCATGAGAAG
TTGGCGCAGCTAGGTGCTAAGATTCAGCGGATTGAGGCAAGTGATGAAGA
TGAATAA (SEQ ID NO: 140)
MKSRVKETSMDKIVVQGGDNRLVGSVTIEGAKNAVLPLLAATILASEGKT
VLQNVPILSDVFIMNQVVGGLNAKVDGDEEAHLVKVDATGDITEEAPYKY
VSKMRASIVVLGPILARVGHAKVSMPGGCTIGSRPIDLHLKGLEAMGVKI
SQTAGTYIEAKAERLHGAHIYMDFPSVGATQNLMAATLADGVTIENAA
REPEIVDLAILLNEMGAKVKGAGTETITITGVEKLHGTTHNVVQDRIEAG
TFMVAAAMTGGDVLIRDAVWEHNRPLIAKLLEMGVEVIEEDEGIRVRSQL
ENLKAVHVKTLPHPGFPTDMQAQFTALMTVAKGESTMVETVFENRGQHLE
EMRRMGLHSEIIRDTARIVGGQPLQGAEVLSTDLRASAALILTGLVAQGE
TVVGKLVHLDRGYYGFHEKLAQLGAKIQRIEASDEDE ID125 1101 bp (SEQ ID NO: 141)
ATGTTATTAGCGTCAACAGTAGCCTTGTCATTTGCCCCAGTATTGGCAAC
TCAAGCAGAAGAAGTTCTTTGGACTGCACGTAGTGTTGAGCAAATCCAAA
ACGATTTGACTAAAACGGACAACAAAACAAGTTATACCGTACAGTATGGT
GATACTTTGAGCACCATTGCAGAAGCCTGGGTGTAGATGTCACAGTGCTT
GCGAATCTGAACAAAATCACTAATATGGACTTGATTTTCCCAGAAACTGT
TTTGACAACGACTGTCAATGAAGCAGAAGAAGTAACAGAAGTTGAAATCC
AAACACCTCAAGCAGACTCTAGTGAAGAAGTGACAACTGCGACAGCAGAT
TTGACCACTAATCAAGTGACCGTTGATGATCAAACTGTTCAGGTTGCAGA
CCTTTCTCAACCAATTGCAGAAGTTACAAAGACAGTGATTGCTTCTGAAG
AAGTGGCACCATCTACGGGCACTTCTGTCCCAGAGGAGCAAACGACCGAA
ACAACTCGCCCAGTTGCAGAAGAAGCTCCTCAGGAAACGACTCCAGCTGA
GAAGCAGGAAACACAAACAAGCCCTCAAGCTGCATCAGCAGTGGAAGCAA
CTACAACAAGTTCAGAAGCAAAAGAAGTAGCATCATCAAATGGAGCTACA
GCAGCAGTTCTACTTATCAACCAGAAGAAACGAAAGTAATTCAACAACTT
ACGAGGCTCCAGCTGCGCCCGATTATGCTGGACTTGCAGTAGCAAAATCT
GAAAATGCAGGTCTTCAACCACAAACAGCTGCCTTTAAWGAAGAAATGCA
TAACTGTTGGCATTACATCCTTTAGTGGTTATCGTCCAGGAGACAGTGGA
GATCACGGAAAAGGTTTGGCTATCGACTTTATGGTACCAGAACGTTCAGA
ATTAGGGGATAAGATTGCGAATATGCTATTCAAAATATGGCCAGCCGTG
GCATTAGTTACACATCTGGAAACAACGTTTCTATGCTCCATTCGATAGCA
AATATGGGCCAGCTAACACTTGGAACCCAATGCCAGACCGTGGTAGTGTG
ACAGAAAATCACATATGATCACGTTCACGTTTCAATGAATGGATAA (SEQ ID NO: 142)
MLLASTVALSFAPVLATQAEEVLWTARSVEQIQNDLTKTDNKTSYTVQYG
DTLSTIAEALGVDVTVLANLNKITNMDLIFPETVLTTTVNEAEEVTEVEI
QTPQADSSEEVTTATADLTTNQVTVDDQTVQVADLSQPIAEVTKTVIASE
EVAPSTGTSVPEEQTTETTRPVAEEAPQETTPAEKQETQTSPQAASAVEA
TTTSSEAKEVASSNGATAAVSTYQPEETKVISTTYEAPAPDYAGLAVAK
SENAGLQPQTAAFKKKLLTCLALHPLVVIVQETVEITEKVWLSTLWYQNV
QNZGIRLRNMLFKIWPAVALVTSSGNNVSMLHSIANMGQLTLGTQCQTVV
VZQKITMITFTFQZMD ID126 1281 bp (SEQ ID NO: 143)
TTGTTTAAGAAAAATAAAGACATTCTTAATATTGCATTGCCAGCTATGGG
TGAAAACTTTTTGCAGATGCTAATGGGAATGGTGGACAGTTATTTGGTTG
CTCATTTAGGATTGATAGCTATTTCAGGGGTTTCAGTAGCTGGTAATATT
ATCACCATTTATCAGGCGATTTTCATCGCTCTGGGAGCTGCTATTTCCAG
TGTTATTCAAAAAGCATAGGGCAGAAAGACCAGTCGAAGTTGGCCTATC
ATGTGACTGAGGCGTTGAAGATTACCTTACTATTAAGTTTCCTTTTAGGA
TTTTTGTCCATCTTCGCTGGGAAAGAGATGATAGGACTTTTGGGGACGGA
GAGGGATGTAGCTGAGAGTGGTGGACTGTGTATCTATCTTTGGTAGGCGGAT
CGATTGTTCTCTTAGGTTTAATGACTAGTCTAGGAGCCTTGATTCGTGCA
ACGCATAATCCACGTCTGCCCTCTCTATGTTAGTTTTTTTATCCAATGCCTT
GAATATTCTTTTTTTCAAGTCTAGCTATTTTTGTTCTGGATATGGGGATAG
CTGGTGTTGCTTGGGGACAATTGTGTCTCGTTTGGTTGGTCTTGTGATT
TTGTCGTTCACAATTAAAACTGCCTTATGGGAAGCCAACTTTTGGTTTAGA
TAAGGAACTGTTGACCTTGGCTTTACCAGCAGCTGGAGAGCGACTTATGA
TGAGGCTGGAGATGTAGTGATCATTGCCTTGGTCGTTTCTTTGGGACGG
AGGCAGTTGCTGGGAATGCAATCGGAGAAGTCTTGACCCAGTTTAACTAT
ATGCCTGCCTTTGGCGTCGTACGGCAACGGTCATGCTGTTGGCCCGAGC
AGTTGGAGAGGATGATTGGAAAGAGTTGCTAGTTTGAGTAAACAAACCT
TTTGGCTTCTCTGTTCCTCATGTTGCCCCTGTCCTTTAGTATATATGTCT
TGGGTGTACCATTAACTCATCTCTATACGACTGATTCTCAGCGGTGGAG
GCTAGTGTCTAGTGACACTGTTTTCACTACTTGGGACCCCTATGACGAC
AGGAACAGTCATCTATACGCAGTCTGGCAGGGATTAGGAAATGCACGCC
TCCCTTTTTATGCGACAAGTATAGGAATGGTGTATCCGCATTGGGACA
GGATATCTGATGGGATTGTGCTTGGTTGGGGCTTGCCTGGTATTTGGGC
AGGGTCTCTCTTGGATAATGGTTTTCGCTGGTTATTTCTACGCTATCGTT
ACCAGCGCTATATGAGCTTGAAAGGATAG (SEQ ID NO: 144)
LFKKNKDILNIALPAMGENFLQMLMGMVDSYLVAHLGLIAISGVSVAGNI
ITIYQAIFALGAAISSVISKSIGQKDQSKLAYHVTEALKITLLLSFLLGF
LLGFLSIFAGKEMIGLLGTERDVAESGGLYLSLVGGSIVLLGLMTSLGAL
IRATHNPRLPLYVSFLSNALNILFSSLAIFVLDMGIAGVAWGTIVSRLVG
LVILWSQLKLPYGKPTFGLDKELLTLALPAAGERLMMRAGDVVIIALVVS
FGTEAVAGNAIGEVLTQFNYMPAFGVATAVMLLARAVGEDDWKRVASLS
KQTFWLSLFLMLPLSFSIYVLGVPLTHLYTTDSLAVEASVLVTLFSLLGT
PMTTGTVIYTAVWQGLGNARLPFYATSIGMWCIRIGTGYLMGIVLGWGLP
GIWAGSLLDNGFRWLFLRYRYQRYMSLKG ID127 894 bp (SEQ ID NO: 145)
GTGGGAAGAATTATCAGAGCAGGTGTAAAGATGGAACATCTTGGAAAAGT
ATTTCGTGAATTTCGAACAAGTGGAAATTATTCTTTAAAGGAAGCAGCAG
GCGAATCCTGCTCTACCTCTCAGTTATCTCGCTTTGAGCTTGGGGAGTCT
GACTGGCAGTCTCCCGTTTCTTTGAGATTTTGGATAACATTCATGTAACA
ATCGAAAATTTCATGGATAAGGCAAGGAATTTTCATAATCATGAACATGT
GTCTATGATGGCACAGATTATCCCACTTTACTATTCAAACGATATTGCAG
GTTTTCAAAAGCTTCAAAGAGAACAACTTGAAAAGTCTAAGAGTTCGACG
ACTCCCCCTTTATTTTGAGCTGAACTGGATTTTGCTACAAGGTCTGATTTG
TCAAAGAGATGCGAGTTATGATATGAAGCAGGATGATTTGGGTAAAGTGT
CAGATTATCTCTTCAAAACAGAAGAATGGACCATGTATGAGTTGATTCTT
TTCGGTAACCTCTATAGTTTTCTACGATGTAGACTCACTCGGATTGGTAG
AGAAGTTATGGAGAGGGAGGAATTTTACCAAGAGATTAGTCGCCATAAGA
GATTAGTGTTGATTTTGGCCCTCAATTGTTACCAGCATTGTTTAGAGCAT
TCTTCTTTTTTATAATGCCAACTATTTGAGGCTTATACAGAAGAAGATTATT
GACAAAGGTATTAAGCTTTATGAGCGTAATGTTTTCCATTATTTAAAGG
TTTTGCCTTATATCAAAAAGGACAGTGTAAGAAGGCTGTAAGCAGATGCA
AGAGGCCATGCATATTTTTGATGTGTTAGGTCTTCCAGAGCAAGTAGCCT
ATTATCAGGACACTACTACGAAAATTTGTCAAAAGTTAA (SEQ ID NO: 146)
VGRIIRAGVKMEHLGKVFREFRTSGNYSLKEAAGESCSTSQLSRFELGES
DLAVSRFFEILDNIGVTIENFMDKARNFHNHEHVSMMAQIIPLYYSNDIA
GFQKLQREQLEKSKSSTTPLYFELNWILLQGLICQRDASYDMKQDDLGKV
ADYLFKTEEWTMYELILFGNLYSFYDVDYVTRIGREVMEREEFYQEISRH
KRLVLILALNCYQHCLEHSSFYNANYFEAYTEKIIDKGIKLYERNVFHYL
KGRALYQKGQCKEGCKQMEAMHIFDVLGLPEQVAYYQEHYEKFVKS

TABLE 3

ID1 1068 bp (SEQ ID NO: 147)
ATGTCTAACATTCAAAACATGTCCCTGGAGGACATCATGGGAGAGCGCTT

TABLE 3-continued

```
TGGTCGCTACTCCAAGTACATTATTCAAGACCGGGCTTTGCCAGATATTC
GTGATGGGTTGAAGCCGGTTCAGCGCCGTATTCTTTATTCTATGAATAAG
GATAGCAGGGTTGAAGCCGGTTCAGCGCCGTATTCTTTATTCTATGAATA
AGGATAGCAATACTTTTGACAAGGCTACCGTAAGTCGGCCAAGTCAGTC
GGGAACATCATGGGGAATTTCCACCCACACGGGGATTCTTCTATCTATGA
TGCCATGGTTCGTATGTCACAGAACTGGAAAAATCGTGAGATTCTAGTTG
AAATGCACGGTAATAACGGTTCTATGGACGGAGATCCTCCTGCGGCTATG
CGTTATACTGAGGCACGTTTGTCTGAAATTGCAGGCTACCTTCTTCAGGA
TATCGAGAAAAAGACAGTTCCTTTTGCATGGAACTTTGACGATACGGAGA
AGAACCAACGGTCTTGCCAGCAGCCTTTCCAAACCTCTTGGTCAATGGT
TCGACTGGGATTTCGGCTGGTTATGCCACAGACATTCCTCCCCATAATTT
AGCTGAGGTCATAGATGCTGCAGTTTACATGATTGACCACCCAACTGCAA
AGATTGATAAACTCATGGAATTCTTGCCTGGACCAGACTTCCTACAGGGG
CTATTATTCAGGGTCGTGATGAAATCAAGAAACTTATGAGACTGGGAAA
GGGCGCGTGGTTGTTCGTTCCAAGACTGAAATTGAAAAGCTAAAAGGTGG
TAAGGAACAAATCGTTATTATTGAGATTCCTTATGAAATCAATAAGGCCA
ATCTAGTCAAGAAAATCGATGATGTTCGTGTTAATAACAAGGTAGCTGGG
ATTGCTGAGGTTCGTGATGAGTCTGACCGTGATGGTCTTCGTATCGCTAT
CGAACTTAAGAAAGACGCTAATACTGAGCTTGTTCTCAACTACTTATTTA
AGTACACCGACCTACAAATCAACTACAACTTTAATATGGTGGCGATTGAC
AATTTCACACCTCGTCAGGTTGGATTGTTCCAATCCTGTCTAGCTATATC
GCTCACCGTCGAGAAGTGA
```

(SEQ ID NO: 148)
MSNIQNMSLEDIMGERFGRYSKYIIQDRALPDIRDGLKPVQRRILYSMNK
DSNTFDKSYRKSAKSVGNIMGNFHPHGDSSIYDAMVRMSQNWKNREILVE
MHGNNGSMDGDPPAAMRYTEARLSEIAGYLLQDIEKKTVPFAWNFDDTEK
EPTVLPAAFPNLLVNGSTGISAGYATDIPPHNLAEVIDAAVYMIDHPTAK
IDKLMEFLPGPDFPTGAIIQGRDEIKKAYETGKGRVVVRSKTEIEKLKGG
KEQIVIIEIPYEINKANLVKKIDDVRVNNKVAGIAEVRDESDRDGLRIAI
ELKKDANTELVLNYLFKYTDLQINYNFNMVAIDNFTPRQVGLFQSCLAIS
TLVEK

ID12 684 bp (SEQ ID NO: 149)
ATGCCGACATTAGAAATAGCACAAAAAAAACTGGAGTTCATTAAGAAGGC
AGAAGAATATTACAATGCCTTGTGTACAAATATACAGTTGAGCGGAGATA
ACTAAAAGTAATTTCCGTTACTTCTGTTAACCCTGGGGAAGGAAAAACAA
CTACTCGATGGCGATACTGAAATTCAGTTATGTTAGGAGTTTTTAAATC
TCGTGAAAAAATTACAGGGCTAACAGAATTTTTATCTGGGACAGCTGATT
TATCTCACGGTTTATGTGATACAAATATTGAAAATTTATTTGTAGTTCAA
TCGGGATCTGTATCACCCAAACCCTACAGCCTTGTTACAAAGTAAAAATTT
TAATGATATGATTGAAACATTGCGTAAATATTTTGATTATATCATTATTG
ATACACCGCCTATTGGAATTGTTATTGATGCGGCAATTATCACTCAAAAG
TGTGATGCGTCCATCTTGGTAACGACAACAGGTGAGGCGAATAAACGTAA
TATCCAAAAAGCGAAACAACAATTAAAACAAACAGGGAAACTGTTCCTAG
GAGTTGTTTTAAATAAATTGGATATCTCGGTTAATAAGTATGGAGTTTAC
GGTTCCTATGGAAATTATGGTAAAAAATAAATAA (SEQ ID NO: 150)
MPTLEIAQKKLEFIKKAEEYYNALCTNIQLSGDKLKVISVTSVNPGEGKT
TTSINIAWSFARAGYKTLLIDGDTRNSVMLGVFKSREKITGLTEFLSGTA
DLSHGLCDTNIENLFVVQSGSVSPNPTALLQSKNFNDMIETLRKYFDYII
IDTPPIGIVIDAAIITQKCDASILVTATGEANKRDIQKAKQQLKQTGKLF
LGVVLNKLDISVNKYGVYGSYGNYGKK

ID13 1182 bp (SEQ ID NO: 151)
ATGGAGGCAAATATGAAACATCTAAAAACATTTACAAAAAATGGTTTCAA
TTATTAGTCGTTATCGTCATTAGTTTTTTAGTGGAGCCTTGGGTAGTTT
TTCAATAACTCAACTAACTCAAAAAGTAGTGTAAACAACTCTAACAACAA
TAGTACTATTACACAAACTGCCTATAAGAACGAAAATTCAACAACACAGG
CTGTTAACAAAGTAAAGATGCTGTTGTTTCTGTTATTACTTATTCGGCAA
ACAGACAAAATAGCGTATTTGGCAATGATGATACTGACACAGATTCTCAG
CGAATCTCTAGTGAAGGATCTGGAGTTATTTATAAAAAGAATGATAAAGA
AGCTTACATCGTCACCAACAATCACGTTATTAATGGCAGCAGCAAAGTAG
ATATTCGATTGTCAGATGGGACTAAAGTACCTGGAGAAATTGTCGGAGCT
GACACTTTCTCTGATATTGCTGTCGTCAAAATCTCTTCAGAAAAAGTGAC
AACAGTAGCTGAGTTTGGTGATTCTAGTAAGTTAACTGTAGGAGAAACTG
CTATTGCCATCGGTAGCCCGTTAGGTTCTGAATATGCAAATACTGTCACT
CAAGGTATGCTATCCAGTCTCAATAGAAATGTATCCTTAAAATCGGAAGA
TGGACAAGCTATTTCTACAAAAGCCATCCAAACTGATACTGCTATTAACC
CAGGTAACTCTGGCGGCCCACTGATCAATATTCAAGGGCAGGTTATCGGA
ATTACCTCAAGTAAAATTGCTACAAATGGAGGAACATCTGTAGCCGGTCT
TGGTTTCGCAATTCCTGCAAATGATGCTATCAATATTATTGAACAGTTAG
AAAAAAACGGAAAAGTGACGCGTCCAGCTTTGGGAATCCAGATGGTAATT
```

TATCTAATGTGAGTACAAGCGACATCAGAAGACTCAATATTCCAAGTAAT
GTTACATCTGGTGTAATTGTTCGTTCGGTACAAAGTAATATGCCTGCCAA
TGGTCACCTTGAAAAATACGATGTAATTACAAAAGTAGATGACAAAGAGA
TTGCTTCATCAACAGACTTACAAAGTGCTCTTTACAACCATTCTATCGGA
GACACCATTAAGATAACCTACTATCGTAACGGGAAGAAGAAACTACCTC
TATCAAACTTAACAAGAGTTCAGGTGATTTAGAATCTAA (SEQ ID NO: 152)
MEANMKHLKTFYKKWFQLLVVIVISFFSGALGSFSITQLTQKSSVNNSNN
NSTITQTAYKNENSTTQAVNKVKDAVVSVITYSANRQNSVFGNDDTDTDS
QRISSEGSGVIYKKNDKEAYIVTNNHVINGASKVDIRLSDGTKVPGEIVG
ADTFSDIAVVKISSEKVTTVAEFGDSSKLTVGETAIAIGSPLGSEYANTV
TQGIVSSLNRNVSLKSEDGQAISTKAIQTDTAINPGNSGGPLINIQGDVI
GITSSKIATNGGTSVEGLGFAIPANDAINIIEQLEKNGKVTRPALGIQMV
NLSNVSTSDIRRLNIPSNVTSGVIVRSVQSNMPANGHLEKYDVITKVDDK
EIASSTDLQSALYNHSIGDTIKITYYRNGKEETTSIKLNKSSGDLES

ID15 939 bp (SEQ ID NO: 153)
ATGGCAGAAATTTATCTAGCAGGTGGTTGTTTTTGGGGCCTAGAGGAATA
TTTTTCACGCATTTCTGGAGTGCTAGAAACCAGTGTTGGCTACGCTAATG
GTCAAGTCGAAACGACCAATTACCAGTTGCTCAAGGAAACAGACCATGCA
GAAACGGTCCAAGTGATTTACGATGAGAAGGAAGTGTCACTCAGAGAGAT
TTTACTTTATTATTCCGAGTTATCGATCCTCTATCTAATCAATCAACAAG
GGAATGACCGTGGTCGCCAATATCGAACTGGGATTTATTATCAGGATGAA
GCAGATTTGCCAGCTATCTACACAGTGGTCGAGGAGCAGGAACGCATGCT
GGGTCGAAAGATTGCAGTAGAAGTGGAGCAATTACGCCACTACATTCTGG
CTGAAGACTACCACCAAGACTATCTCAGGAAGAATCCTTCAGGTTACTGT
CATATCGATGTGACCGATGCTGATAAGCCATTGATTGATGCAGCAAACTA
TGAAAAGCCTAGTCAAGAGGTGTTGAAGGCCAGTCTATCTGAAGAGTCTT
ATCGTGTCACACAAGAAGCTGCTACAGAGGCTCCATTTACCAATGCCTAT
GACCAAACCTTTGAAGAGGGGATTTATGTAGATATTACGACAGGTGAGCC
ACTCTTTTTTTGCCAAGGATAAGTTTGCTTCAGGTTGTGGTTGGCAAGTT
TTAGCCGTCCGATTTCCAAAGAGTTGATTCATTATTACAAGGATCTGAGC
CATGGAATGGAGCGAATTGAAGTTCGTTCTCGTTCAGGCAGTGCTCACTT
GGGTCATGTTTTCACAGATGGACCGCGGGAGTTAGGCGGCCTCCGTTACT
GTATCAATTCTGCTTCTTTACGCTTTGTGGCCAAGGATGAGATGGAAAAA
GCAGGATATGGCTATCTATTGCCTTACTTAAACAAATAA (SEQ ID NO: 154)
MAEIYLAFFCFWGLEEYFSRISGVLETSVGYANGQVETTNYQLLKETDHA
ETVQVIYDEKEVSLRIELLYYFRVIDPLSINQQGNDRGRQYRTGIYYQDE
ADLPAIYTVVQEQERMLGRKIAVEVEQLRHYILAEDYHQDYLRKNPSGYC
HIDVTDADKPLIDAANYEKPSQEVLKASLSEESYRVTQEAATEAPFTNAY
DQTFEEGIYVDITTGEPLFFAKDKFASGCGWPSFSRPISKELIHYYKDLS
HGMERIEVRSRSGSAHLGHVFTDGPRELGGLRYCINSASLRFVAKDEMEK
AGYGYLLPYLNK

ID17 870 bp (SEQ ID NO: 155)
ATGAAGATTATTGTACCTGCAACCAGTGCCAATATCGGGCCAGGTTTTGA
CTCGGTCGGTGTAGCTGTAACCAAGTATCTTCAAATTGAGGTCTGCGAAG
AACGAGATGAGTGGCTGATTGAACACCAGATTGGCAAATGGATTCCACAT
GACGAGCGTAATCTCTTGCTCAAAAGCGCTTTGCAAATTGTACCAGACTT
GCAACCAAGACGCTTGAAAATGACCAGTGATGTCCCTTTGGCGCGCGGTT
TGGGGTTCTTCCAGCTCGGTTATCGTTGCTGGGATTGAACTAGCCAACCA
CTGGGTCAACTCAACTTATCAGACCATGAAAATTGCAGTTAGCGACCAA
GATTGAAGGGCATCCTGACAATGTGGCTCCAGCCATTTATGGTAATCTCG
TTATTGCAAGTTCTGTTGAAGGGCAAGTCTCTGCTATCGTAGCAGACTTT
CCAGAGTGTGATTTTCTAGCTTACATCCCAAACTATGAATTACGTACTCG
CGACAGCCGTAGTCTTCCTAAAAAATTGTCTTATAAGGAAGCTGTTG
CTGCAAGTTCTATCGCAATGTAGCGGTTGCTGCCTTGTTGGCAGGAGAC
ATGGTGACCGCTGGGCAAGCAATCGAGGGAGACCTCTTCCATGAGCGCTA
TCGTCAGGACTTGGTAAGAGAATTTGCGATGATTAAGCAAGTGACCAAAG
AAAATGGGGCTATCGAACCTACCTTTCTGGTGCGGGCCGACAGTTATG
GTTCTGGCTTCTCATGACAAGATGCCAACAATTAAGGCAGAATTGGAAAA
GCAACCTTTCAAGGGAAAACTGCATGACTTGAGAGTTGATACCCAAGGTG
TCCGTGTAGAAGCAAAATAA (SEQ ID NO: 156)
MKIIVPATSANIGPGFDSVGVAVTKYLQIEVCEERDEWLIEHQIGKWIPH
DERNLLLKIALQIVPDLQPRRLKMTSDVPLARGLGSSSSVIVAGIELANQ
LGQLNLSDHEKLQLATKIEGHPDNVAPAIYGNLVIASSVEGQVSAIVADF
PECDFLAYIPNYELRTRDSRSVLPKKLSYKEAVAASSIANVAVAALLAGD
MVTAGQAIEGKLFHERYRQDLVREFAMIKQVTKENGAYATYLSGAGPTVM
VLASHDKMPTIKAELEKQPFKGKLHDLRVDTQGVRVEAK

TABLE 3-continued

ID20 564 bp (SEQ ID NO: 157)
ATGAAATATCACGATTACATCTGGGATTTAGGTGGAACTTTACTGGATAA
TTATGAAACTTCAACAGCTGCATTTGTTGAAACATTGGCACTGTATGGTA
TCACACAAGACCATGACAGTGTCTATCAAGCTTTAAAGGTTTCTACTCCT
TTTGCGATGAGACATTCGCTCCCAATTTAGAGAATTTTTTAGAAAAGTAC
AAGGAAAATGAAGCCAGAGAGCTTGAACACCCGATTTTATTTGAAGGAGT
TTCTGACCTATTGGAAGACATTTCAAATCAAGGTGGCCGTCATTTTTGG
TCTCTCATCGAAATGATCAGGTTTTGGAAATTTTAGAAAAAACCTCTATA
GCAGCTTATTTTACAGAAGTGGTGACTTCTAGCTCAGGCTTTAAGAGAAA
GCCAAATCCCGAATCCATGCTTTATTTAAGAGAAAAGTATCAGATTAGCT
CTGGTCTTGTCATTGGTGATCGGCCGATTGATATCGAAGCAGGTCAAGCT
GCAGGACTTGATACCCACTTGTTTACCAGTATCGTGAATTTAAGACAAGT
ATTAGACATATAA (SEQ ID NO: 158)
MKYHDYIWDLGGTLLDNYETSTAAFVETLALYGITQDHDSVYQALKVSTP
FAIETFAPNLNENFLEKYKENEARELEHPILFEGVSDLLEDISNQGGRHFL
VSHRNDQVLEILEKTSIAAYFTEVVTSSSGFKRKPNPESMLYLREKYQIS
SGLVIGDRPIDIEAGQAAGLDTHLFTSIVNLRQVLDI

ID21 1875 bp (SEQ ID NO: 159)
ATGACAGAAGAAATCAAAAATCTGCAGGCACAGGATTATGATGCCAGTCA
AATTCAAGTTTTAGAGGGCTTAGAGGCTGTTCGTATGCGTCCAGGGATGT
ACATTGGATCAACCTCAAAAGAAGGTCTTCACCATCTAGTCTGGGAAATT
GTTGATAACTCAATTGACGAGGCCTTGGCAGGATTTGCCAGCCATATTCA
AGTTTTTATTGAGCCAGATGATTCCGATTACTGTTGTGGATGATGGGCGTG
GTATCCCAGTCGATATTCAGGAAAAAACAGGCCGTCCTGCTGTTGAGACC
GTCTTTACAGTCCTTCACGCTGGAGGAAAGTTCGGCGGTGGTGGATAAA
GGTTTCAGGTGGTCTTCACGGGGTGGGGTCGTCAGTAGTAATGCCCTTT
CCACTCAATTAGACGTTCATGTTCACAAAAATGGTAAGATTCATTACCAA
GAATACCGTCGTGGTCATGTTGTCGCAGATCTTGAAATAGTTGGAGATAC
GGATAAAACAGGAACAACTGTTCACTTCACACCGGACCCAAAATCTTCA
CTGAAACAACATCTTTGATTTTGATAAATTAAATAAACGGATTCAAGAG
TTGGCCTTTCTAAATCGCGGTCTTCAAATTCAATTACAGATAAGCGCCAA
GGTTTGGAACAAACCAAGCATTATCATTATGAAGGTGGGATTGCTAGTTA
CGTTGAATATATCAACGAGAACAAGGATGTAATCTTTGATACACCAATCT
ATACAGACGGTGAGATGGATGATATCACAGTTGAGGTAGCCATGCAGTAC
ACAACTGGTTACCATGAAAATGTCATGAGTTCGCCAATAATATTCATACC
CATGAAGGTGGAACACATGAACAAGGTTTCCGTACAGCCTTGACACGTGT
TATCAACGATTATGCTCGTAAAAATAAGTTACTGAAAGACAATGAAGATA
ATTTAACAGGGGAAGATGTTCACGAAGGCTTAACTGCAGTTATCTCAGTT
AAACACCCCAAATCCACAGTTTGAAGGACAAACCAAGACCAAATTGGGAAA
TAGCGAAGTGGTCCAAGATTACCAATCGCCTCTTCAGTGAAGCTTTCTCCG
ATTTCCTCATGGAAAATCCACAGATTGCCAAACGTATCGTAGAAAAAGGA
ATTTTGGCTGCCAAGGCTCGTGTGGCTGCCAAGCGTGCGCGTGAAGTCAC
ACGTAAAAAATCTGGTTTGGAAATTTCCAACCTTCCAGGGAAACTAGCAG
ACTGTTCTTCTAATAACCCTGCTGAAACAGAACTCTTCATCGTCGAAGGA
GACTCAGCTGGTGGATCAGCCAATCTGGTCGTAACCGTGAGTTTCAGGC
TATCCTTCCAATTCGCGGTAAGATTTTGAACGTTGAAAAAGCAAGTATGG
ATAAGATTCTAGCCAACGAAGAAATTCGTAGTCTTTTCACACGCCATGGGA
ACAGGATTTGGCGCAGAATTTGATGTTTGAAAGCCCGTTACCAAAAACT
CGTTTTGATGACCGATGCCGATGTCGATGGAGCCCACATTCGTACCCTTC
TTTTAACCTTGATTTATCGTTATATGAAACCAATCCTAGAAGCTGGTTAT
GTTTATATTGCCCAACCACCAATCTATGTGTCAAGGTTGGAAGCGAGAT
TAAAGAATATATCCAGCCGGGTGCAGATCAAGAAATCAAACTCCAAGAAG
CTTTAGCCCGTTATAGTGAAGGTCGTACCAAACCGACTATTCAGCGTTAT
AAGGGGCTAGGTGAAATGGACGATCATCAGCTGTGGGAAACAACCATGGA
TCCCGAACATCGCTTGATGGCTAGAGTTTCTGTAGATGATGTGCAGAAGC
AGATAAAATCTTTGATATGTTGA (SEQ ID NO: 160)
MTEEIKNLQAQDYDASQIQVLEGLEAVRMRPGMYIGSTSKEGLHHLVWEI
VDNSIDEALAGFASHIQVFIEPDDSITVVDDGRGIPVDIQEKTGRPAVET
VFTVLHAGGKFGGGGYKVSGGLHGVGSSVVNALSTQLDVHVHKNGKIHYQ
EYRRGHVVADLEIVDGTDKTGTTVHFTPDPKIFTETTIFDFDKLNKRIQE
LAFLNRGLQISITDKRQGLEQKTKHYHYEGGIASYVEYINENKDVIFDTPI
YTDGEMDDITVEVAMQYTTGYHENVMSFANNIGTHEGGTHEQGFRTALTR
VINDYARKNKLLKDNEDNLTGEDVREGLTAVISVKHPNPQFEGQTKTKLG
NSEVVKITNRLFSEAFSDFLMENPQIAKRIVEKGILAAKARAVAAKRARE
VTRKKSGLEISNLPGKLADCSSNNPAETELFIVEGDSAGGSAKSGRNREF
QAILPIRGKILNVEKASMDKILANEEIRSLFTAMGTGFGAEFDVSKARYQ
KLVLMTDADVDGAHIRTLLLTIYRYMKPILEAGYVYIAQPPIYGVKVGS
EIKEYIQPGADQEIKLQEALARYSEGRTKPTIQRYKGLGEMDDHQLWETT
MDPEHRLMARVSVDDVQKQIKSLIC

ID54 1446 bp (SEQ ID NO: 161)
ATGAGTAGACGTTTTAAAAAATCACGTTCACAGAAAGTGAAGCGAAGTGT
TAATATAGTTTTGCTGACTATTTATTTATTGTTAGTTTGTTTTTTATTGT
TCTTAATCTTTAAGTACAATATCCTTGCTTTTAGATATCTTAATCTAGTG
GTAACTGCCTACTAGTTGCCTTGGTAGGGCTACTCTTGATTAT
CTATAAAAAAGCTGAAAAGTTTACTATTTTTCTGTTGGTGTTCTCTATCC
TTGTCAGCTCTGTGTCGCTCTTTGCAGTACAGCAGTTTGTTGGACTGACC
AATCGTTTAAATGCGACTTCTAATTACTCAGAATATTCAATCAGTGTCGC
TGTTTTAGCAGATAGTGAGATCGAAAATGTTACGCAACTGACGAGTGTGA
CAGCACCGACTGGGACTAATAATGAAAATATTCAGAAATTACTAGCTGAT
ATCAAGTCAAGTCAGAATACCGATTTGACGGTCAACCAGAGTTCGTCTTA
CTTGGCAGCTTACAAGAGTTTGATTGCAGGGGAGACTAAGGCCATTGTCC
TAAATAGTGTCTTTGAAACATCATCGAGTCAGAGTATCCAGACTACGCA
TCGAAGATAAAAAAGATTATACTAAGGGATTCACTAAAAAAGTAGAAGCT
CCTAAGACGCTAAGAGTCAGTCTTTCAATATCTATGTTAGTGGAATTGA
CACCTATGGTCCTATTAGTTCGGTGTCGCGATCAGATGTCAACATCCTGA
TGACTGTCAATCGAGATACCAAGAAAATCCTCTTGACCACAACGCCACGT
GATGCCTATGTACCAATCGCAGATGGTGGAAATAATCAAAAGATAAATT
GACTCATGCGGGCATTTATGGAGTTGATTCGTCCATTCACACCTTAGAAA
ATCTCTATGGAGTGGATATCAATTACTATGTGCGATTGAACTTCACTTCG
AGAATTTACTGCCCATACGAATGGAAAGTATTACCCTGCAGGCAATGTTC
ATCTTGATTCAGAACAGGCTCTCGGTTTTGTTCGTGAGCGCTACTCCCTA
GCAGATGGCGATCGTGACCGCGGGCGCCATCAACAAAGGTGATTGTGGC
TATCCTTCAAAAATTAACGTCAACCGAAGTGCTGAAAAATTATAGTACGA
TCATTAGCTTGCAAGATTCTATCCAAACAAATATGCCACTTGAGACC
ATGATAAATTTGGTCAATGCTCAGTTAGAAAGTGGAGGGAATTATAAAGT
AAATTCTCAAGATTTAAAAGGGACAGGTCGGATGGATCTTCCTTCTTATG
CAATGCCAGACAGTAACCTCTATGTGATGGAAATAGATGATAGTAGTTTA
GCTGTAGTTAAAGCAGCTATACAGGATGTGATGGAGGGTAGATGA (SEQ ID NO: 162)
MSRRFKKSRSQKVKRSVNIVLLTIYLLLVCFLLFLIFKYNILAFRYLNLV
VTALVLLVALVGLLLIIYKKAKFTIFLLVFSILVSSVSLFAVQQFVGLTN
RLNATSNYSEYSISVAVLADSEIENVTQLTSVTAPTGTNNENIQKLLADI
KSSQNTDLTVNQSSSYLAAYKSLIAGETKAIVLNSVFENIIESEYPDYAS
KIKKIYTKGFTKKVEAPKTSKSQSFNIYVSGIDTYGPISSVSRSDVNILM
TVNRDTKKILLTTTPRDAYVPIADGGNNQKDKLTHAGIYGVDSSIHTLEN
LYGVDINYYVRLNFTSFLKLIDLLGGIDVYNDQEFTAHTNGKYYPAGNVH
LDSEQALGFVRERYSLADGDRDRGRHQQKVIVAILQKLTSTEVLKNYSTI
INSLQDSIQTNMPLETMINLVNAQLESGGNYKVNSQDLKGTGRMDLPSYA
MPDSNLYVMEIDDSSLAVVKAAIQDVMEGR

ID55 732 bp (SEQ ID NO: 163)
ATGATAGACATCCATTCGCATATCGTTTTGATGTAGATGACGGTCCCAAG
TCAAGAGAGGAAAGCAAGGCTCTCTTGGCAGAATCCTACAGACAGGGGGT
GCGAACCATTGTTTCTACCTCTCACCGTCGCAAGGGCATGTTTGAAACTC
CGGAAGAGAAGATAGCAGAAAACTTTCTTCAGGTTCGGGAAATAGCTAAG
GAAGTGGCGAGTGACTTGGTCATTGCTTACGGGGCTGAAATTTATTACAC
ACCAGATGTTCTGGATAAGCTGGAAAAAAAGCGGATTCCGACCCTCAATG
ATAGTCGTTATGCCTTGATAGAGTTTAGTATGAACACTCCTTATCGCGAT
ATTCATAGCGCCTTGAGCAAGATCTTGATGTTGGGAATTACTCCAGTCAT
TGCCCACATTGAGCGCTATGATGCTCTTGAAAATAATGAAAAACGCGTTC
GAGAACTGATCGATATGGGCTGTTACACGCAAGTAAATAGTTCACATGTC
CTCAAACCCAAACTTTTTGGGCGAACGTTATAAATTCATGAAAAAAAGAG
CTCAGTATTTTTTAGAGCAGGATTTGGTTCATGTCATTGCAAGTGATATG
CACAATCTAGACGGTAGACCTCCTCATATGGCAGAAGCATATGACCTTGT
TACCCAAAAATACGGAGAAGCGAAGGCTCAGGAACTTTTTATAGACAATC
CTCGAAAAATTGTAATGGATCAACTAATTTAG (SEQ ID NO: 164)
MIDIHSHIVFDVDDGPKSREESKALLAESYRQGVRTIVSTSHRRKGMFET
PEEKIAENFLQVREIAKEVASKLVIAYGAEIYYTPDVLDKLEKKRIPTLN
DSRYALIEFSMNTPYRDIHSALSKILMLGITPVIAHIERYDALENNEKRV
RELIDMGCYTQVNSSHVLKPKLFGERYKFMKKRAQYFLEQDLVHVIASDM
HNLDGRPPHMAEAYDLVTQKYGEAKAQELFIDNPRKIVMDQLI

ID58 3990 bp (SEQ ID NO: 165)
TTGATTTATATAATCGCTATCAATATAACAATGCAATCAGGAGGTTTTGC
AATGAAACATGAAAACAACAGCGTTTTCTATTCGTAAATACGCTGTAG
GAGCAGCTTCTGTTCTAATTGGATTTGCCTTCCAAGCACAGACTGTTGCA
GCCGATGGAGTTACTCCTACTACTACAGAAAACCAACCGACCATCCTAC
GGTTTCTGATTCCCCTCAATCATCCGAAATCGGACTGAGGAAACACCTAA

TABLE 3-continued

```
AGCAGTGCTTCAACCAGAAGCTCCAAAAACTGTAGAAACAGAAACTCCAG
CTACTGATAAGGTAGCTAGTCTTCCAAAAACAGAAGAAAAACCACAAGAG
GAAGTTAGTTCAACTCCTAGTGATAAAGCAGAAGTGGTAACTCCAACTTC
TGCTGAAAAAGAAACTGCTAATAAAAAGGCAGAAGAAGCTAGCCCTAAAA
AGGAAGAAGCGAAAGAGGTTGATTCTAAAGAGTCAAATACAGACAAGACT
GACAAGGATAAACCAGCTAAAAAAGATGAAGCGAAAGCAGAGGCTGACAA
ACCGGCAACAGAGGCAGGAAAGGAACGTGCTGCAACTGTAAATGAAAAAC
TAGCGAAAAAGAAAATTGTTTCTATTGATGCTGGACGTAAATATTTCTCA
CCAGAACAGCTCAAGGAAATCATCGATAAAGCGAAACATTATGGCTACAC
TGATTTACACCTATTAGTCGGAAATGATGGACTCCGTTTCATGTTGGACG
ATATGAGCATCACAGCTAACGGCAAGACCTATGCCAGTGACGATGTCAAA
CGCGCCATTGAAAAAGGTACAAATGATTATTACAACGATCCAAACGGCAA
TCACTTAACAGAAAGTCAAATGACAGATCTGATTAACTATGCCAAAGATA
AAGGTATCGGTCTCATTCCGACAGTAAATAGTCCTGGACACATGGATGCG
ATTCTCAATGCCATGAAAGAATTGGGAATCCAAAACCCTAACTTTAGCTA
TTTTGGGAAGAAATCAGCCCGTACTGTCGATCTTGACAACGAACAAGCTG
TCGCTTTTACAAAAGCCCTTATCGACAAGTATGCTGCTTATTTCGCGAAA
AAGACTGAAATCTTCAACATCGGACTTGATGAATATGCCAATGATGCGAC
AGATGCTAAAGGTTGGAGTGTGCTTCAAGCTGATAAATACTATCCAAACG
AAGGCTACCCTGTAAAAGGCTATGAAAAATTTATTGCCTACGCCAATGAC
CTCGCTCGTATTGTAAAATCGCACGGTCTCAAACCAATGGCTTTTAACGA
CGGTATCTACTACAATAGCGACAAGCTTTGGTAGTTTTGACAAAGACA
TCATCGTTTCTATGTGGACTGGTGGTTGGGAGGCTACGATGTCGCTTCT
TCTAAACTACTAGCTGAAAAAGGTCACCAAATCCTTAATACCAATGATGC
TTGGTACTACGTTCTTGGACGAAACGCTGATGGCCAAGGCTGGTACAATC
TCGATCAGGGGCTCAATGGTATTAAAAACACACCAATCACTTCTGTACCA
AAAACAGAAGGAGCTGATATCCCAATCATCGGTGGTATGGTAGCTGCTTG
GGCTGACACTCCATCTGCACGTTATTCACCATCACGCCTCTTCAAACTA
TGCGTCATTTTGCAAATGCCAACGCTGAATACTTCGCAGCTGATTATGAA
TCTGCAGAGCAAGCACTTAACGAGGTACCAAAAGACCTGAACCGTTATAC
TGCAGAAAGCGTCACGGCCGTAAAGAAGCTGAAAAAGCTATTCGCTCTCT
CGATAGCAACCTTAGCCGTGCCCAACAAGATCGATTGATCAAGCCATTG
CTAAACTTCAAGAAACTGTCACCAACTTGACCCTCACGCCTGAAGCTCAA
AAAGAAGAAGAGCTAAACGTGAGGTTGAAAAACTTGCCAAAAACAAGGT
AATCTCAATCGATGCTGGACGCAAATACTTTACTCTGAACCAGCTCAAAC
GCATCGTAGACAAGGCCAGTGAGCTCGGATATTCTGATGTCCATCTCCTT
CTAGGAAATGACGGACTTCGCTTTCTACTCGATGATATGACCATTACTGC
CAACGGGAAAACCTATGCTAGTGATGACGTTAAAAAAGCTATTATCGAA
GGAACTAAAGCTTACTACGACGATCCAAACGGTACTGCACTAACACAGGC
AGAAGTAACAGAGCTAATTGAATACGCTAAATCTAAGGACATCGGTCTCA
TCCCAGCTATTAACAGTCCAGGTCACATGGATGCTATGCTGGTTGCCATG
GAAAAATTAGGTATTAAAAATCCTCAAGCCCACTTTGATAAAGTTTCAAA
AACAACTATGGACTTGAAAAACGGAGAAGCGATGAACTTTGTAAAAGCCC
TCATCGGTAATACATGGACTCTTTGCAGGTAAAACAAAGATTTTCAACT
TTGGTACTGACGAATACGCCAACGATGCGACTAGTGCCCAAGGCTGGTAC
TACCTCAAGTGGTATCAACTCTATGGCAAATTTGCCGAATATGCCAACAC
CCTCGCAGCTATGGCCAAAGAAAGAGGGCTTAACCAATGGCCTTCAACG
ATGGCTTCTACTATGAAGCAAGGCGATGTTCAGTTTGACAAAGATGTC
TTGATTTCTTACTGGTCTAAAGGCTGGTGGGATATAACCTCGCATCACC
TCAATACCTAGCAAGCAAAGGCTATAAAATTCTTGAATACCAACGGTGACT
GGTACTACATTCTTGGTCAAAAACCAGAAGATGGTGGTGTTTCCTCAAG
AAAGCTATTGAGAATACTGGAAAAACACCATTCAATCAACTAGCTTCTAC
CAAATATCCTGAAGTAGATCTTCCAACAGTCGGAAGTATGCTTTCAATCT
GGGCAGATAGACCAAGCGCTGAATACAAGGAAGAGGGAAATCTTTGAACTC
ATGACTGCCTTTGCAGACCACAACAAAGACTACTTTGTGCTAATTATAA
TGCTCTCCGCGAAGAAATAGCTAAAATTCCTACAAACTTAGAAGGATATA
GTAAAGAAAGTCTTGAGGCCCTTGACGCAGCTAAACAGCTCTAAATTACA
ACCTCAACCGTAATAAACAAGCTGAGCTTGACACGCTTGTAGCCAACCTA
AAAGCCGCTCTTCAAGGCCTCAAACCAGCTGTAACTCATTCAGGAAGCCT
AGATGAAAATGAAGTGGCTGCCAATGTTGAAACCAGACCAGAACTCATCA
CAAGAACTGAAGAAATTCCATTTGAAGTTATCAAGAAAGAAAATCCTAAC
CTCCCAGCCGGTCAGGAAAATATTCACAGCAGGAGTCAAAGGTGAACTG
AACTCATTACATCTCTGTACTCACTGAAAATGGAAAAACAACAGAAACAG
TCCTTGATAGCCAGGTAACCAAAGAAGTTATAAACCAAGTGGTTGAAGTT
GGCGCTCCTGTAACTCACAAGGGTGATGAAGTGGTCTTGCACCAACTAC
TGAGGTAAAAACTAGACTGGATATCCAAGAAGAAGAAAATTCCATTTACCA
CAGTGACTTGTGAAAATCCACTCTTACTCAAAGGAAAAACCAAGTCATT
ACTAAGGGCGTCAATGGACATCGTAGCAACTTCTACTCTGTGAGCACTTC
TGCCGATGGTAAGGAAGTGAAAACACTTGTAAATAGTGTCGTAGCACAGG
AAGCCGTTACTCAAATAGTCGAAGTCGGAACTATGGTAACACATGTAGGC
GATGAAAACGGACAAGCGCTATTGCTGAAGAAAACCAAACTAGAAAT
CCCAAGCCAACCAGCTCCATCAACTGCTCCTGCTGAGGAAAGCAAAGTTC
TTCCTCAAGATCCAGCTCCTGTGGTAACAGAGAAAAACTTGCCAACACAG
GAACTCACGATTCTGCAGGACTAGTAGTCGCAGGACTCATGTCCCACACTA
GCAGCCTATGGACTCACTAAAAGAAAAGAAGACTAA
```

(SEQ ID NO: 166)
MIYIIAINITMQSGGFAMKHEKQQRFSIRKYAVGAASVLIGFQAQTVAAD
GVTPTTTENQPTIHTVSDSPQSSENRTEETPKAVLQPEAPKTVETETPAT
DKVASLPKTEEKPQEEVSSTPSDKAEVVTPTSAEKETANKKAEEASPKKE
EAKEVDSKESNTDKTKDKDKPAKKDEAKAEADKPATEAGKERAATVNEKL
AKKKIVSIDAGRKYFSPEQLKEIIDKAKHYGYTDLHLLVGNDGLRFMLDD
MSITANGKTYASDDVKRAIEKGTNDYYNDPNGNHLTESQMTDLINYAKDK
GIGLIPTVNSPGHMDAILNAMKELGIQNPNFSYFGKKSARTVDLDNEQAV
AFTKALIDKYAAYFAKKTEIFNIGLDEYANDATDAKGWSVLQADKYYPNE
GYPVKGYEKFIAYANDLARIVKSHGLKPMAFNDGIYYNSDTSFGSFDKDI
IVSMWTGGWGGYDVASSKLLAEKGHQILNTNDAWYYVLGRNSDTSFGSFD
KDIIVSMWTGGWGGYDVASSKLLAEKGHQILNTNDAWYYVLPSRLFKMRH
FANANAEYFAADYESAEQALNEVPKDLNRYTAESVTAVKEAEKAIRSLDS
NLSRAQQDTIDQAIAKLQETVNNLTLTPEAQKEEEAKREVEKLAKNKVIS
IDAGRKYFTLNQLKRIVDKASELGYSDVHLLLGNDGLRFLLDDMTITANG
KTYASDDVKKAIIEGTKAYYDDPNGTALTQAEVTELIEYAKSKDIGLIPA
INSPGHMDAMLVAMEKLGIKNPQAHFDKVSKTTMDLKNEEAMNFVKALIG
KYMDFFAGKTKIFNFGTDEYANDATSAQGWYYLKWYQLYGKFAEYANTLA
AMAKERGLQPMAFNDGFYYEDKDDVQFDKDVLISYWSKGWWGYNLASPQY
LASKGYKFLNTNGKWYYILGQKPEDGGGFLKKAIENTGKTPFNQLASTKY
PEVDLPTVGSMLSIWADRPSAEYKEEEIFELMTAFADHNKDYFRANYNAL
REELAKIPTNLEGYSKESLEALDAAKTALNYNLRNKQAELDTLVANLKA
ALQGLKPAVTHSGSLDENEVAANVETRPELITRTEEIPPFEVIKKENPNLP
AGQENIITAGVKKGETTHYISVLTENGKTTETVLDSQVTKEVINQVVEVG
APVTHKGDESGLAPTTEVKPRLDIQEEEIPFTTVTCENPLLLKGKTQVIT
KGVNGHRSNFYSVSTSADGKEVKTLVNSVVAQEAVTQIVEVGTMVTHVGD
ENGQAAIAEEKPKLEIPSQPAPSTAPAEESKVLPQDPAPVVTEKKLPETG
THDSAGLVVAGLMSTLAAYGLTKRKED

ID122 825 bp (SEQ ID NO: 167)
ATGAACAAAAAACAAGACAGACACTAATCGGACTGCTAGTGTTATTGCT
TTTGTCTACAGGGAGCTATTATATCAAGCAGATGCCGTCGGCACCTAATA
GTCCCAAAACCAATCTTAGTCAGAAAAACAAGCGTCTGAAGCTCCTAGT
CAAGCATTGGCAGAGAGTGTCTTAACAGACGCAGTCAAGAGTCAAATAAA
GGGGAGTCTGGAGTGGAATGGCTCAGGTGCTTTTATCGTCAATGGTATAA
AACAAATCTAGATGCCAAGGTTTCAAGTAAGCCCTACGCTGACAATAAAA
CAAAGACAGTGGGCAAGGAAACTGTTCCAACCGTAGCTAATGCCCTCTTG
TCTAAGGCCACTCGTCAGTACAAGAATCGTAAAGAAACTGGGAATGGTTC
AACTTCTTGGACTCCTCCAGGTTGGCATCAGGTCAAGAATCTAAAGGGCT
CTTATACCCATGCAGTCGATAGAGGTCATTTGTTAGGCTATGCCTTATCG
GTGGGTTTGGATGGTTTTGATGCCTCAACAAGCAATCCTAAAAACATTGCT
GTTCAGACAGCCTGGGCAAATCAGGCACAAGCCGAGTATTCGACTGGTCA
AAACTACTATGAAAGCAAGGTGCGTAAAGCCTTGGACCAAAAACAAGCGTG
CCGTTACCGTGTAACCCTTTACTACGCTTCAAACGAGGATTTAGTTCCCT
CAGCTTCACAGATTGAAGCCAAGTCTTCGGATGGAGAATTGGAATTCAAT
GTTCTAGTTCCCAATGTTCAAAAGGGACTTCAACTGGATTACCGAACTGG
AGAAGTAACTGTAACTCAGTAA (SEQ ID NO: 168)
MNKKTRQTLIGLLVLLLLSTGSYYIKQMPSAPNSPKTNLSQKKQASEAPS
QALAESVLTDAVKSQIKGSLEWNGSGAFIVNGNKTNLDAKVSSKPYADNK
TKTVGKETVPTVANALLSKATRQYKNRKETGNGSTSWTPPGWHQVKNLKG
SYTHAVDRGHLLGYALIGGLDGFDASTSNPKNIAVQTAWANQAQAEYSTG
QNYYESKVRKALDQNKRVRYRVTLYYASNEDLVPSASQIEAKSSDGELEF
NVLVPNVQKGLQLDYRTGEVTVTQ

ID123 225 bp (SEQ ID NO: 169)
GTGCTAAGATTCAGCGGATTGAGGCAAGTGATGAAGATGAATAAGAAATC
AAGCTACGTAGTCAAGCGTTTACTTTTAGTCATCATAGTCTGATTTTAGG
TACTCTGGCTCTAGGAATCGGTTTAATGGTAGGTTATGGAATCTTGGGCA
AGGGTCAAGATCCATGGGCTATCCTGTCTCCAGCAAAATGGCAGGAATTG
ATTCATAAATTTACAGGAAATTAG (SEQ ID NO: 170)
VLRFSGLRQVMKMNKKSSYVVKRLLLVIIVLILGTLALGIGLMVGYGILG
KGQDPWAILSPAKWQELIHKFTGN
```

The invention claimed is:

1. An isolated *Streptococcus pneumoniae* surface associated polypeptide comprising the amino acid sequence of SEQ ID NO: 4 or an amino acid sequence that is at least 90% identical to the amino acid sequence of SEQ ID NO: 4.

2. The polypeptide of claim 1, wherein said polypeptide is in a substantially pure form.

3. The isolated polypeptide of claim 1, wherein said polypeptide is at least 95% identical to the amino acid sequence of SEQ ID NO: 4.

4. A composition comprising the polypeptide of claim 1.

5. The vaccine composition of claim 4, wherein said composition further comprises one or more additional components selected from excipients, diluents, and/or adjuvants.

6. The polypeptide of claim 1, wherein said polypeptide is at least 99% identical to the amino acid sequence of SEQ ID NO: 4.

7. The polypeptide of claim 6, wherein said polypeptide consists of the amino acid sequence of SEQ ID NO: 4.

8. The composition of claim 4, wherein said polypeptide is at least 95% identical to the amino acid sequence of SEQ ID NO: 4.

9. The composition of claim 8, wherein said polypeptide is at least 99% identical to the amino acid sequence of SEQ ID NO: 4.

10. The composition of claim 9, wherein said polypeptide comprises the amino acid sequence of SEQ ID NO: 4.

11. A fusion protein comprising an isolated *Streptococcus pneumoniae* surface associated polypeptide comprising the amino acid sequence of SEQ ID NO: 4 or an amino acid sequence that is at least 90% identical to the amino acid sequence of SEQ ID NO: 4.

12. The fusion protein of claim 11, wherein said amino acid sequence is at least 95% identical to the amino acid sequence of SEQ ID NO: 4.

13. The fusion protein of claim 12, wherein said amino acid sequence is at least 99% identical to the amino acid sequence of SEQ ID NO: 4.

14. An isolated *Streptococcus pneumoniae* polypeptide comprising (a) the amino acid sequence of SEQ ID NO: 4 or (b) an amino acid sequence that is at least 90% identical to the amino acid sequence of SEQ ID NO: 4, and wherein said polypeptide of (b) is antigenic.

15. The polypeptide of claim 14, wherein said polypeptide is at least 95% identical to the amino acid sequence of SEQ ID NO: 4, and wherein said polypeptide is antigenic.

16. The polypeptide of claim 15, wherein said polypeptide is at least 99% identical to the amino acid sequence of SEQ ID NO: 4, and wherein said polypeptide is antigenic.

17. An antigenic composition comprising the polypeptide of claim 14.

18. The composition of claim 17, wherein said composition further comprises one or more additional components selected from excipients, diluents, and/or adjuvants.

19. The composition of claim 17, wherein said polypeptide is at least 95% identical to the amino acid sequence of SEQ ID NO: 4, and wherein said polypeptide is antigenic.

20. The composition of claim 19, wherein said polypeptide is at least 99% identical to the amino acid sequence of SEQ ID NO: 4, and wherein said polypeptide is antigenic.

21. A fusion protein comprising an isolated *Streptococcus pneumoniae* polypeptide comprising (a) the amino acid sequence of SEQ ID NO: 4 or (b) an amino acid sequence that is at least 90% identical to the amino acid sequence of SEQ ID NO: 4, and wherein said polypeptide is antigenic.

22. The fusion protein of claim 21, wherein said amino acid sequence is at least 95% identical to the amino acid sequence of SEQ ID NO: 4, and wherein said polypeptide is antigenic.

23. The fusion protein of claim 22, wherein said amino acid sequence is at least 99% identical to the amino acid sequence of SEQ ID NO: 4, and wherein said polypeptide is antigenic.

* * * * *